United States Patent
Simov et al.

(10) Patent No.: US 12,030,872 B2
(45) Date of Patent: Jul. 9, 2024

(54) N-HETEROARYL INDAZOLE DERIVATIVES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: Vladimir Simov, South Boston, MA (US); William P. Kaplan, Boston, MA (US); John J. Acton, III, Cranford, NJ (US); Michael J. Ardolino, Arlington, MA (US); Joanna L Chen, Braintree, MA (US); Peter H. Fuller, Ashland, MA (US); Hakan Gunaydin, Somerville, MA (US); Derun Li, Roxbury, MA (US); Ping Liu, Westfield, NJ (US); Kaitlyn Marie Logan, Boston, MA (US); Joey Methot, Westwood, MA (US); Gregori J. Morriello, Randolph, NJ (US); Santhosh F. Neelamkavil, Edison, NJ (US); Luis Torres, Norwood, MA (US); Xin Yan, Newton, MA (US); Hua Zhou, Acton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 690 days.

(21) Appl. No.: 17/286,870

(22) PCT Filed: Oct. 25, 2019

(86) PCT No.: PCT/US2019/057981
§ 371 (c)(1),
(2) Date: Apr. 20, 2021

(87) PCT Pub. No.: WO2020/092136
PCT Pub. Date: May 7, 2020

(65) Prior Publication Data
US 2021/0395236 A1 Dec. 23, 2021

Related U.S. Application Data

(60) Provisional application No. 62/753,474, filed on Oct. 31, 2018.

(51) Int. Cl.
*C07D 405/14* (2006.01)
*C07D 401/14* (2006.01)
(Continued)

(52) U.S. Cl.
CPC ......... *C07D 405/14* (2013.01); *C07D 401/14* (2013.01); *C07D 403/04* (2013.01); *C07D 409/14* (2013.01); *C07D 413/04* (2013.01); *C07D 413/14* (2013.01); *C07D 417/04* (2013.01); *C07D 417/14* (2013.01)

(58) Field of Classification Search
None
See application file for complete search history.

(56) References Cited

U.S. PATENT DOCUMENTS

| 4,166,452 A | 9/1979 | Generales, Jr. |
| 4,256,108 A | 3/1981 | Theeuwes |

(Continued)

FOREIGN PATENT DOCUMENTS

| WO | 2007149798 A2 | 12/2007 |
| WO | 2011019780 A1 | 2/2011 |

(Continued)

OTHER PUBLICATIONS

Aasly, J.O. et al., Clinical Features of LRRK2-Associated Parkinson's Disease in Central Norway, American Neurological Association, 2005, 762-765, 57(5).

(Continued)

*Primary Examiner* — Jeffrey S Lundgren
*Assistant Examiner* — Anthony Joseph Seitz
(74) *Attorney, Agent, or Firm* — Sylvia A. Ayler; Catherine D. Fitch

(57) ABSTRACT

The present invention is directed to substituted certain N-heteroaryl indazole derivatives of Formula (I): and pharmaceutically acceptable salts thereof, wherein $R^1$, $R^2$, $R^3$, X, Y, and Z are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of diseases, such as Parkinson's disease, in which LRRK-2 kinase is involved.

(I)

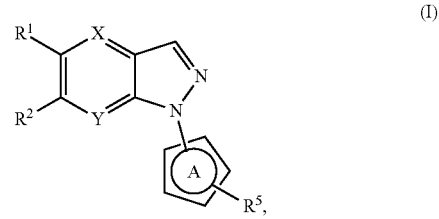

15 Claims, No Drawings

(51) Int. Cl.
  C07D 403/04    (2006.01)
  C07D 409/14    (2006.01)
  C07D 413/04    (2006.01)
  C07D 413/14    (2006.01)
  C07D 417/04    (2006.01)
  C07D 417/14    (2006.01)

(56)  References Cited

U.S. PATENT DOCUMENTS

| | | | |
|---|---|---|---|
| 4,265,874 | A | 5/1981 | Bonsen et al. |
| 9,738,648 | B2* | 8/2017 | Liu-Bujalski ........ A61K 31/519 |
| 11,161,854 | B2* | 11/2021 | Candito ............... C07D 405/14 |
| 2016/0159804 | A1 | 6/2016 | Liu-bujalski et al. |
| 2018/0127411 | A1 | 5/2018 | Siu et al. |
| 2022/0259188 | A1* | 8/2022 | Zhou ................... C07D 471/18 |

FOREIGN PATENT DOCUMENTS

| | | | | |
|---|---|---|---|---|
| WO | WO-2016036586 | A1 * | 3/2016 | ............ A61P 25/16 |
| WO | 2017012576 | A1 | 1/2017 | |
| WO | WO-2017012576 | A1 * | 1/2017 | ......... A61K 31/4545 |

OTHER PUBLICATIONS

Adams, J.R. et al., PET in LRRK2 mutations: comparison to sporadic Parkinson's disease and evidence for presymptomatic compensation, Brain, 2005, 2777-2785, 128.

Agalliu, I. et al., Higher Frequency of Certain Cancers in LRRK2 G2019S Mutation Carriers With Parkinson Disease, JAMA Neurology, 2015, 58-65, 72(1).

Bailey, R.M. et al., LRRK2 phosphorylates novel tau epitopes and promotes tauopathy, Acta Neuropathol, 2013, 809-827, 126.

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1q32 and STAT3 with Ankylosing Spondylitis Suggests Genetic Overlap with Crohn's Disease, PLoS Genetics, 2010, 1-5, 6(12):e1001195.

Engel, P. et al., Therapeutic Targeting of B Cells for Rheumatic Autoimmune Diseases, Pharmacological Reviews, 2011, 127-156, 63(1).

Gilks, W.P. et al., A common LRRK2 mutation in idiopathic Parkinson's disease, Lancet, 2005, 415-416, 365.

Goedert, M. et al., Mutations causing neurodegenerative tauopathies, Biochimica et Biophysica Acta, 2005, 240-250, 1739.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Ibrahim, H. et al., A Review: The Use of Rituximab in Neuromuscular Diseases, Journal of Clinical Neuromuscular Disease, 2010, 91-102, 12(2).

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS One, 2012, 1-9, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G BAC transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, 2006, 1-9, 1:17.

Zimprich, A. et al., Mutations in LRRK2 Cause Autosomal-Dominant Parkinsonism with Pleomorphic Pathology, Neuron, 2004, 601-607, 44(4).

* cited by examiner

N-HETEROARYL INDAZOLE DERIVATIVES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2019/057981 filed Oct. 25, 2019, which claims priority from U.S. Ser. No. 62/753,474 filed Oct. 31, 2018.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al, Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al, Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al, Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32): 19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11): 1990-3).

Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and Parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., JNeurosci. 2012 Feb. 1; 32(5): 1602-11). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1): 127-56; Homam et al., Homam et al., Clin Neuromuscluar disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4): 1439-44).

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain N-heteroaryl indazoles derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of Formula (I), exhibit excellent LRRK2 inhibitory activity. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

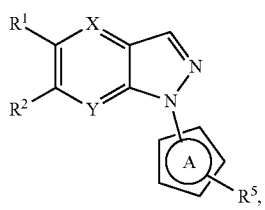
(I)

or a pharmaceutically acceptable salt thereof, wherein:
X is selected from N, C—H, C—F, and C—Cl;
Y is selected from N, C—H, C—F, and C—Cl;
$R^1$ is selected from H, F, Cl, CN, —($C_1$-$C_3$)alkyl, —O($C_1$-$C_3$)alkyl, —($C_1$-$C_3$)haloalkyl, —O($C_1$-$C_3$)haloalkyl, and —($C_3$-$C_6$)cycloalkyl;
$R^2$ is a moiety selected from:

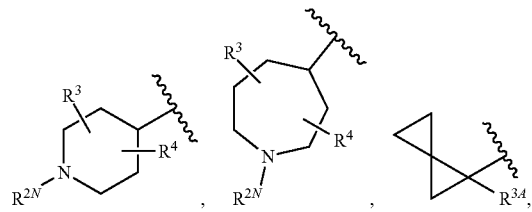

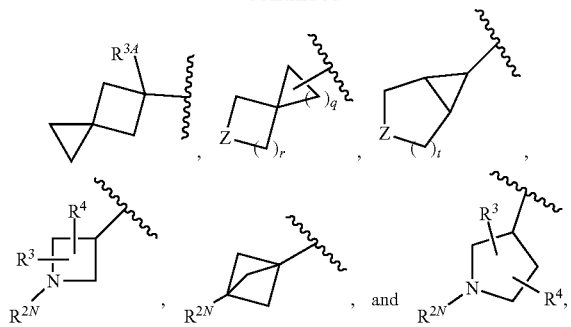

wherein:
q is 1, 2, or 3;
r is 1 or 2;
t is 1 or 2;
Z is selected from O and N($R^{2N}$);
$R^{2N}$ is selected from H, ($C_1$-$C_6$)alkyl, —($C_1$-$C_6$)haloalkyl, ($C_1$-$C_6$)alkyl-OH, ($C_1$-$C_6$)alkyl-CN, —S(O)$_2$($C_1$-$C_6$)alkyl, —($C_1$-$C_6$)alkyl-S(O)$_2$($C_1$-$C_6$)alkyl, C(O)O($C_1$-$C_6$)alkyl, C(O)NH$_2$, C(O)NH($C_1$-$C_6$)alkyl, —C(O)N(($C_1$-$C_6$)alkyl)$_2$, ($C_1$-$C_6$)alkyl-O—($C_1$-$C_6$)alkyl, oxetanyl which is optionally substituted with $R^{2A}$, furanyl which is optionally substituted with 1 or 2 groups selected from OH and $R^{2A}$, pyranyl which is optionally substituted with 1 or 2 groups selected from OH and $R^{2A}$, and

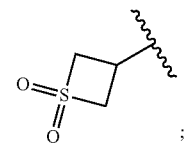 [SMILES: *C1CS(=O)(=O)C1]

each $R^{2A}$ is independently selected from H and —($C_1$-$C_4$)alkyl;
$R^3$ is selected from H, F, Cl, ($C_1$-$C_4$)alkyl, ($C_1$-$C_6$)haloalkyl, and ($C_1$-$C_6$)alkyl-OH;
$R^{3A}$ is selected from H and CN;
$R^4$ is selected from H, F, Cl, ($C_1$-$C_4$)alkyl, ($C_1$-$C_6$)haloalkyl, and ($C_1$-$C_6$)alkyl-OH;
ring A is 5-membered heteroaryl group comprising 1, 2, or 3 ring heteroatoms selected from N, O, and S;
$R^5$ is selected from H, ($C_1$-$C_6$)alkyl, ($C_1$-$C_6$)haloalkyl, ($C_3$-$C_6$)cycloalkyl, ($C_3$-$C_6$)cycloalkyl substituted with ($C_1$-$C_4$)alkyl, S(O)$_2$($C_3$-$C_6$)cycloalkyl, C(O)N($R^{5A}$)$_2$, C(O)O$R^{5A}$, phenyl, heteroaryl, heterocycloalkyl and

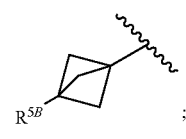

and
each $R^{5A}$ is independently selected from H and —($C_1$-$C_4$)alkyl; and
$R^{5B}$ is selected from H, ($C_1$-$C_4$)alkyl, ($C_1$-$C_4$)haloalkyl, ($C_1$-$C_4$)alkyl-O—($C_1$-$C_4$)alkyl, CN, S(O)$_2$($C_3$-$C_6$)cycloalkyl, C(O)N($R^{5A}$)$_2$, and C(O)O$R^{5A}$.
In another embodiment, in Formula (I):

X is selected from C—H, C—F, and C—Cl; and
Y is selected from C—H, C—F, and C—Cl.
In another embodiment, in Formula (I):
X is selected from C—H, C—F, and C—Cl;
Y is selected from C—H, C—F, and C—Cl; and
R¹ is selected from H, Cl, —CH₃, and CN.
In another embodiment, in Formula (I):
X is C—H; and
Y is C—H.
In another embodiment, in Formula (I):
X is C—H;
Y is C—H; and
R¹ is selected from H, Cl, —CH₃, and CN.
In another embodiment, in Formula (I):
X is N; and
Y is selected from C—H, C—F, and C—Cl.
In another embodiment, in Formula (I):
X is N;
Y is selected from C—H, C—F, and C—Cl; and
R¹ is selected from H, Cl, —CH₃, and CN.
In another embodiment, in Formula (I):
X is N; and
Y is C—H.
In another embodiment, in Formula (I):
X is N;
Y is C—H; and
R¹ is selected from H, Cl, —CH₃, and CN.
In another embodiment, in Formula (I):
X is N; and
Y is C—F.
In another embodiment, in Formula (I):
X is N;
Y is C—F; and
R¹ is selected from H, Cl, —CH₃, and CN.
In another embodiment, in Formula (I):
X is N; and
Y is C—Cl.
In another embodiment, in Formula (I):
X is N;
Y is C—Cl; and
R¹ is selected from H, Cl, —CH₃, and CN.
In another embodiment, in Formula (I):
X is selected from C—H, C—F, and C—Cl; and
Y is selected from N.
In another embodiment, in Formula (I):
X is selected from C—H, C—F, and C—Cl;
Y is selected from N; and
R¹ is selected from H, Cl, —CH₃, and CN.
In another embodiment, in Formula (I):
X is C—H; and
Y is N.
In another embodiment, in Formula (I):
X is C—H;
Y is N; and
R¹ is selected from H, Cl, —CH₃, and CN.
In another embodiment, in Formula (I):
X is C—F; and
Y is N.
In another embodiment, in Formula (I):
X is C—F;
Y is N; and
R¹ is selected from H, Cl, —CH₃, and CN.
In another embodiment, in Formula (I):
X is C—Cl; and
Y is N.
In another embodiment, in Formula (I):
X is C—Cl;
Y is N; and
R¹ is selected from H, Cl, —CH₃, and CN.
In another embodiment, in Formula (I):
X is N; and
Y is N.
In another embodiment, in Formula (I):
X is N;
Y is N; and
R¹ is selected from H, Cl, —CH₃, and CN.
In an alternative of each of the preceding embodiments, in Formula (I):
R² is:

wherein:
$R^{2N}$ is selected from H,

—(C₁-C₆)alkyl, —(C₁-C₆)haloalkyl, —(C₁-C₆)alkyl-OH, —(C₁-C₆)alkyl-CN, —S(O)₂(C₁-C₆)alkyl, —(C₁-C₆)alkyl-S(O)₂(C₁-C₆)alkyl, —C(O)NH₂, —C(O)NH(C₁-C₆)alkyl, —C(O)N((C₁-C₆)alkyl)₂, and —(C₁-C₆)alkyl-O—(C₁-C₆)alkyl;
$R^{2A}$ is selected from H and —(C₁-C₄)alkyl:
$R^{2B}$ is selected from H and OH;
R³ is selected from H, F, Cl, (C₁-C₄)alkyl, (C₁-C₆)haloalkyl, and (C₁-C₆)alkyl-OH; and
R⁴ is selected from H, F, Cl, —(C₁-C₄)alkyl, —(C₁-C₆)haloalkyl, and —(C₁-C₆)alkyl-OH.
In an alternative of the immediately preceding embodiment, $R^{2B}$ is H.
In an alternative of each of the preceding embodiments, in Formula (I):
R² is:

wherein:
$R^{2N}$ is selected from H, CH₃, CH₂CH₃, CF₃, CH₂CHF₂, CH₂CF₃, CH₂CH₂OH, CH₂CH₂CN, CH₂CH₂—S(O)₂CH₃, S(O)₂CH₃, S(O)₂CH₂CH₃, C(O)NH₂, C(O)NHCH₃, C(O)NCH₃, CH₂CH₂—O—CH₃,

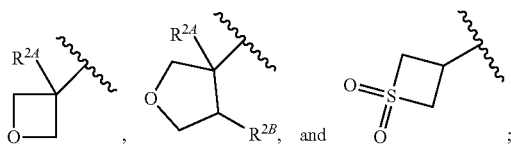

$R^{2A}$ is selected from H, —CH$_3$, and —CH$_2$CH$_3$;

$R^{2B}$ is selected from H and OH;

$R^3$ is selected from H, F, Cl, CH$_3$, CH$_2$CH$_3$, CF$_3$, CH$_2$CHF$_2$, CH$_2$CF$_3$, CH$_2$OH, CH$_2$CH$_2$OH; and $R^4$ is selected from H, F, Cl, CH$_3$, CH$_2$CH$_3$, CF$_3$, CH$_2$CHF$_2$, CH$_2$CF$_3$, and CH$_2$CH$_2$OH.

In an alternative of the immediately preceding embodiment, $R^{2B}$ is H.

In an alternative of each of the preceding embodiments, in Formula (I):

$R^2$ is:

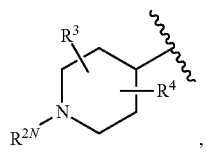

wherein:

$R^{2N}$ is selected from

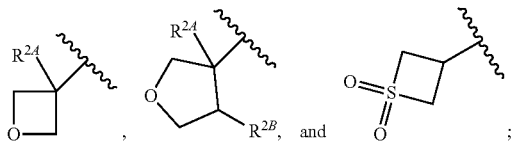

$R^{2A}$ is selected from H, —CH$_3$, and —CH$_2$CH$_3$;

$R^{2B}$ is selected from H and OH;

$R^3$ is selected from H, F, Cl, CH$_3$, CH$_2$CH$_3$, CF$_3$, CH$_2$CHF$_2$, CH$_2$CF$_3$, CH$_2$OH, and CH$_2$CH$_2$OH; and $R^4$ is selected from H, F, Cl, CH$_3$, CH$_2$CH$_3$, CF$_3$, CH$_2$CHF$_2$, CH$_2$CF$_3$, and CH$_2$CH$_2$OH.

In an alternative of the immediately preceding embodiment, $R^{2B}$ is H.

In an alternative of each of the preceding embodiments, in Formula (I):

$R^2$ is:

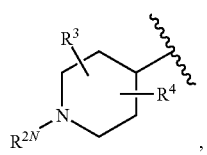

wherein:

$R^{2N}$ is

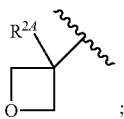

$R^{2A}$ is selected from H and —CH$_3$;

$R^3$ is selected from H, F, Cl, CH$_3$, CH$_2$CH$_3$, CF$_3$, CH$_2$CHF$_2$, CH$_2$CF$_3$, CH$_2$OH, and CH$_2$CH$_2$OH; and $R^4$ is selected from H, F, Cl, CH$_3$, CH$_2$CH$_3$, CF$_3$, CH$_2$CHF$_2$, CH$_2$CF$_3$, and CH$_2$CH$_2$OH.

In an alternative of each of the preceding embodiments, in Formula (I):

$R^2$ is:

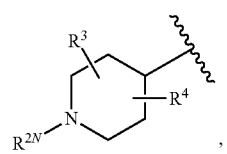

wherein:

$R^{2N}$ is

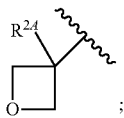

$R^{2A}$ is selected from H and —CH$_3$;

$R^3$ is selected from H, F, Cl, CH$_3$, CH$_2$CH$_3$, CF$_3$, CH$_2$CHF$_2$, CH$_2$CF$_3$, CH$_2$OH, and CH$_2$CH$_2$OH; and $R^4$ is selected from H, F, Cl, CH$_3$, CH$_2$CH$_3$, CF$_3$, CH$_2$CHF$_2$, CH$_2$CF$_3$, and CH$_2$CH$_2$OH.

In an alternative of each of the preceding embodiments, in Formula (I):

$R^2$ is:

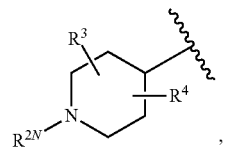

wherein:

$R^{2N}$ is

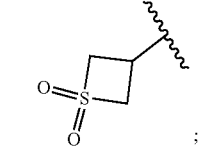 [SMILES: *C1CS(=O)(=O)C1]

$R^3$ is selected from H, F, and CH$_3$; and $R^4$ is selected from H, F, and CH$_2$CH$_2$OH.

In an alternative of each of the preceding embodiments, in Formula (I):

$R^2$ is a moiety selected from:

wherein R³ᴬ is H.

In an alternative of the immediately preceding embodiment, R³ᴬ is CN.

In an alternative of each of the preceding embodiments, in Formula (I):

R² is:

wherein:
R²ᴺ is selected from

H, —(C₁-C₆)alkyl, —(C₁-C₆)haloalkyl, (C₁-C₆)alkyl-OH, (C₁-C₆)alkyl-CN, S(O)₂(C₁-C₆)alkyl, (C₁-C₆)alkyl-S(O)₂(C₁-C₆)alkyl, C(O)NH₂, —C(O)NH(C₁-C₆)alkyl, C(O)N((C₁-C₆)alkyl)₂, and (C₁-C₆)alkyl-O—(C₁-C₆)alkyl; R²ᴬ is selected from H and (C₁-C₆)alkyl; R²ᴮ is selected from H and OH;

R³ is selected from H, F, Cl, (C₁-C₄)alkyl, (C₁-C₆)haloalkyl, and (C₁-C₆)alkyl-OH; and R⁴ is selected from H, F, Cl, (C₁-C₄)alkyl, (C₁-C₆)haloalkyl, and (C₁-C₆)alkyl-OH.

In an alternative of each of the preceding embodiments, in Formula (I):

R² is:

wherein:
R²ᴺ is selected from H, CH₃, CH₂CH₃, CF₃, CH₂CHF₂, CH₂CF₃, CH₂CH₂OH, CH₂CH₂CN, CH₂CH₂—S(O)₂CH₃, S(O)₂CH₃, S(O)₂CH₂CH₃, C(O)NH₂, C(O)NHCH₃, C(O)NCH₃₂, CH₂CH₂—O—CH₃, R²ᴬ is selected from H, CH₃, and CH₂CH₃;
R²ᴮ is selected from H and OH;
R³ is selected from H, F, Cl, CH₃, CH₂CH₃, CF₃, CH₂CHF₂, CH₂CF₃, CH₂OH, and CH₂CH₂OH; and
R⁴ is selected from H, F, Cl, —CH₃, CH₂CH₃, CF₃, CH₂CHF₂, CH₂CF₃, and CH₂CH₂OH.

In an alternative of each of the preceding embodiments, in Formula (I):

R² is:

wherein:
R²ᴺ is selected from

R²ᴬ is selected from H, —CH₃, and CH₂CH₃;
R²ᴮ is selected from H and OH;
R³ is selected from H, F, Cl, —CH₃, CH₂CH₃, CF₃, CH₂CHF₂, CH₂CF₃, CH₂OH, and CH₂CH₂OH; and
R⁴ is selected from H, F, Cl, —CH₃, CH₂CH₃, CF₃, CH₂CHF₂, CH₂CF₃, and CH₂CH₂OH.

In an alternative of each of the preceding embodiments, in Formula (I):

R² is:

wherein:
R²ᴺ is

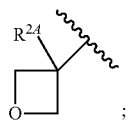

R$^{2A}$ is selected from H and —CH$_3$;
R$^3$ is selected from H, F, Cl, CH$_3$, CH$_2$CH$_3$, CF$_3$, CH$_2$CHF$_2$, CH$_2$CF$_3$, CH$_2$OH, and CH$_2$CH$_2$OH; and
R$^4$ is selected from H, F, Cl, CH$_3$, CH$_2$CH$_3$, CF$_3$, CH$_2$CHF$_2$, CH$_2$CF$_3$, and CH$_2$CH$_2$OH.

In an alternative of each of the preceding embodiments, in Formula (I):
R$^2$ is:

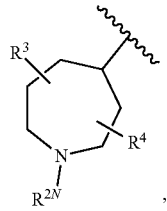

wherein:
R$^{2N}$ is

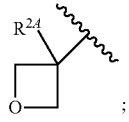

R$^{2A}$ is selected from H and —CH$_3$;
R$^3$ is selected from H, F, and CH$_3$; and
R$^4$ is selected from H, F, and CH$_2$CH$_2$OH.

In an alternative of each of the preceding embodiments, in Formula (I):
R$^2$ is a moiety selected from:

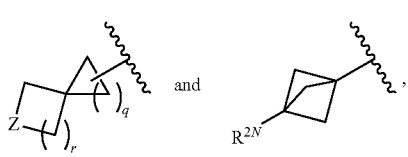

wherein:
q is 1, 2, or 3;
r is 1 or 2;
Z is O or NR$^{2N}$;
R$^{2N}$ is selected from

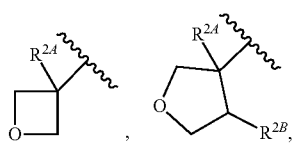

H, (C$_1$-C$_6$)alkyl, (C$_1$-C$_6$)haloalkyl, (C$_1$-C$_6$)alkyl-OH, (C$_1$-C$_6$)alkyl-CN, S(O)$_2$(C$_1$-C$_6$)alkyl, (C$_1$-C$_6$)alkyl-S(O)$_2$(C$_1$-C$_6$)alkyl, C(O)O(C$_1$-C$_6$)alkyl, C(O)NH$_2$, C(O)NH(C$_1$-C$_6$)alkyl, C(O)N((C$_1$-C$_6$)alkyl)$_2$, and (C$_1$-C$_6$)alkyl-O—(C$_1$-C$_6$)alkyl;
R$^{2A}$ is selected from H and (C$_1$-C$_4$)alkyl; and
R$^{2B}$ is selected from H and OH.

In an alternative of each of the preceding embodiments, in Formula (I):
R$^2$ is a moiety selected from:

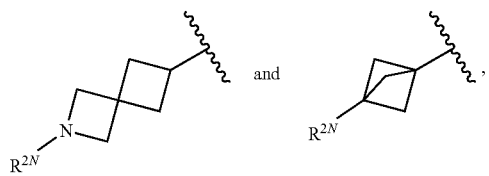

wherein:
R$^{2N}$ is selected from

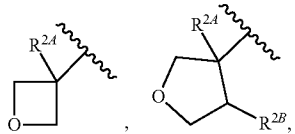

H, (C$_1$-C$_6$)alkyl, (C$_1$-C$_6$)haloalkyl, (C$_1$-C$_6$)alkyl-OH, (C$_1$-C$_6$)alkyl-CN, S(O)$_2$(C$_1$-C$_6$)alkyl, (C$_1$-C$_6$)alkyl-S(O)$_2$(C$_1$-C$_6$)alkyl, C(O)NH$_2$, C(O)NH(C$_1$-C$_6$)alkyl, C(O)N((C$_1$-C$_6$)alkyl)$_2$, and (C$_1$-C$_6$)alkyl-O—(C$_1$-C$_6$)alkyl;
R$^{2A}$ is selected from H and (C$_1$-C$_4$)alkyl; and
R$^{2B}$ is selected from H and OH.

In an alternative of each of the preceding embodiments, in Formula (I):
R$^2$ is a moiety selected from:

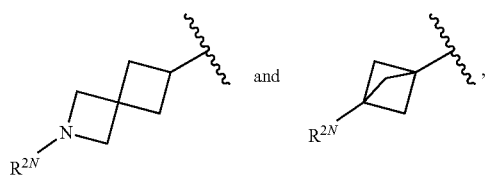

wherein:
R$^{2N}$ is selected from

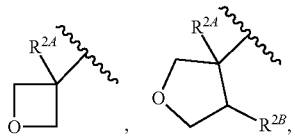

H, (C$_1$-C$_6$)alkyl, (C$_1$-C$_6$)haloalkyl, (C$_1$-C$_6$)alkyl-OH, (C$_1$-C$_6$)alkyl-CN, S(O)$_2$(C$_1$-C$_6$)alkyl, (C$_1$-C$_6$)alkyl-S(O)$_2$(C$_1$-C$_6$)alkyl, C(O)NH$_2$, C(O)NH(C$_1$-C$_6$)alkyl, C(O)N((C$_1$-C$_6$)alkyl)$_2$, and (C$_1$-C$_6$)alkyl-O—(C$_1$-C$_6$)alkyl;
R$^{2A}$ is selected from H and (C$_1$-C$_4$)alkyl; and
R$^{2B}$ is selected from H and OH.

In an alternative of each of the preceding embodiments, in Formula (I):

R² is a moiety selected from:

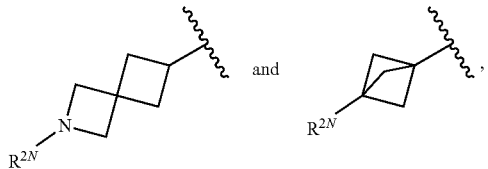

wherein:

R²ᴺ is selected from H, CH₃, CH₂CH₃, CF₃, CH₂CHF₂, CH₂CF₃, CH₂CH₂OH, CH₂CH₂CN, CH₂CH₂—S(O)₂CH₃, S(O)₂CH₃, S(O)₂CH₂CH₃, C(O)NH₂, C(O)NHCH₃, C(O)NCH₃₂, CH₂CH₂—O—CH₃,

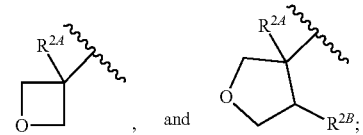

R²ᴬ is selected from H, —CH₃, and —CH₂CH₃; and
R²ᴮ is selected from H and OH.

In an alternative of each of the preceding embodiments, in Formula (I):

R² is a moiety selected from:

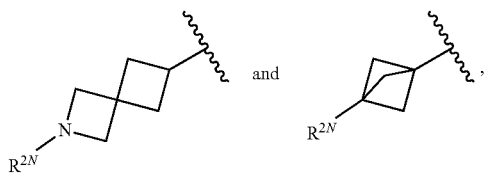

wherein:

R²ᴺ is selected from

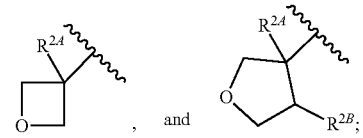

R²ᴬ is selected from H, —CH₃, and —CH₂CH₃; and
R²ᴮ is selected from H and OH.

In an alternative of each of the preceding embodiments, in Formula (I):

R² is a moiety selected from:

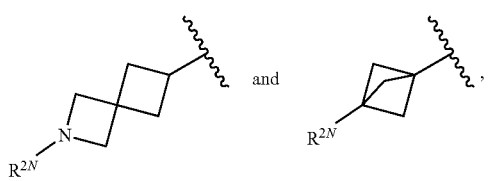

wherein:

R²ᴺ is

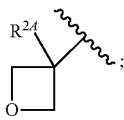

and

R²ᴬ is selected from H and —CH₃.

In an alternative of each of the preceding embodiments, in Formula (I):

R² is a moiety selected from:

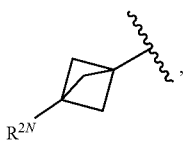

wherein:

R²ᴺ is

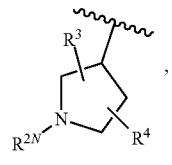

and

R²ᴬ is selected from H and —CH₃.

In an alternative of each of the preceding embodiments, in Formula (I):

R² is a moiety selected from:

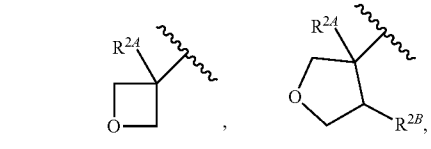

wherein:

R²ᴺ is selected from

H, (C₁-C₆)alkyl, (C₁-C₆)haloalkyl, (C₁-C₆)alkyl-OH, (C₁-C₆)alkyl-CN, S(O)₂(C₁-C₆)alkyl, (C₁-C₆)alkyl-S(O)₂(C₁-C₆)alkyl, C(O)NH₂, C(O)NH(C₁-C₆)alkyl, C(O)N((C₁-C₆)alkyl)₂, and (C₁-C₆)alkyl-O—(C₁-C₆)alkyl;

R²ᴬ is selected from H and (C₁-C₄)alkyl;
R²ᴮ is selected from H and OH;

R³ is selected from H, F, Cl, (C₁-C₄)alkyl, (C₁-C₆)haloalkyl, and (C₁-C₆)alkyl-OH; and
R⁴ is selected from H, F, Cl, (C₁-C₄)alkyl, (C₁-C₆)haloalkyl, and (C₁-C₆)alkyl-OH.

In an alternative of each of the preceding embodiments, in Formula (I):
R² is a moiety selected from:

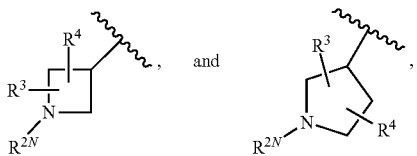

wherein:
R²ᴺ is selected from

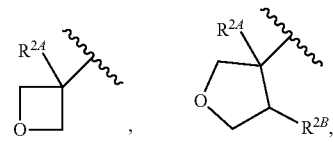

H, (C₁-C₆)alkyl, (C₁-C₆)haloalkyl, (C₁-C₆)alkyl-OH, (C₁-C₆)alkyl-CN, S(O)₂(C₁-C₆)alkyl, (C₁-C₆)alkyl-S(O)₂(C₁-C₆)alkyl, C(O)NH₂, C(O)NH(C₁-C₆)alkyl, C(O)N((C₁-C₆)alkyl)₂, and (C₁-C₆)alkyl-O—(C₁-C₆)alkyl;
R²ᴬ is selected from H and (C₁-C₄)alkyl;
R²ᴮ is selected from H and OH;
R³ is selected from H, F, Cl, (C₁-C₄)alkyl, (C₁-C₆)haloalkyl, and (C₁-C₆)alkyl-OH; and
R⁴ is selected from H, F, Cl, (C₁-C₄)alkyl, (C₁-C₆)haloalkyl, and (C₁-C₆)alkyl-OH.

In an alternative of each of the preceding embodiments, in Formula (I):
R² is a moiety selected from:

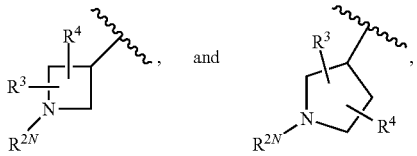

wherein:
R²ᴺ is selected from H, —CH₃, —CH₂CH₃, —CF₃, —CH₂CHF₂, —CH₂CF₃, —CH₂CH₂OH, —CH₂CH₂CN, —CH₂CH₂—S(O)₂CH₃, —S(O)₂CH₃, —S(O)₂CH₂CH₃, —C(O)NH₂, —C(O)NHCH₃, —C(O)NCH₃₂, —CH₂CH₂—O—CH₃,

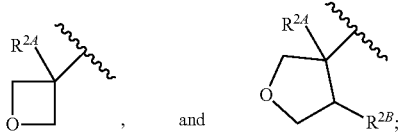

R²ᴬ is selected from H, —CH₃, and —CH₂CH₃;
R²ᴮ is selected from H and OH;

R³ is selected from H, F, Cl, CH₃, CH₂CH₃, CF₃, CH₂CHF₂, CH₂CF₃, CH₂OH, and CH₂CH₂OH; and
R⁴ is selected from H, F, Cl, CH₃, CH₂CH₃, CF₃, CH₂CHF₂, CH₂CF₃, CH₂OH, and CH₂CH₂OH.

In an alternative of each of the preceding embodiments, in Formula (I):
R² is a moiety selected from:

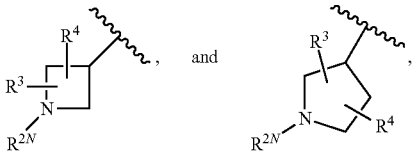

wherein:
R²ᴺ is selected from

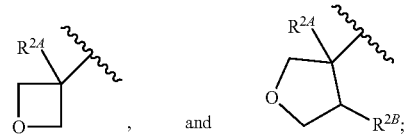

R²ᴬ is selected from H, —CH₃, and —CH₂CH₃;
R²ᴮ is selected from H and OH;
R³ is selected from H, F, Cl, CH₃, CH₂CH₃, CF₃, CH₂CHF₂, CH₂CF₃, CH₂OH, and CH₂CH₂OH; and
R⁴ is selected from H, F, Cl, —CH₃, CH₂CH₃, CF₃, CH₂CHF₂, CH₂CF₃, and CH₂CH₂OH.

In an alternative of each of the preceding embodiments, in Formula (I):
R² is a moiety selected from:

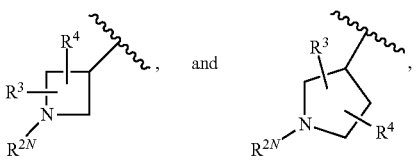

wherein:
R²ᴺ is

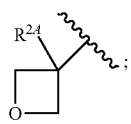

R²ᴬ is selected from H and —CH₃;
R³ is selected from H, F, Cl, CH₃, CH₂CH₃, CF₃, CH₂CHF₂, CH₂CF₃, CH₂OH, and CH₂CH₂OH; and
R⁴ is selected from H, F, Cl, CH₃, CH₂CH₃, CF₃, CH₂CHF₂, CH₂CF₃, and CH₂CH₂OH.

In an alternative of each of the preceding embodiments, in Formula (I):
R² is a moiety selected from:

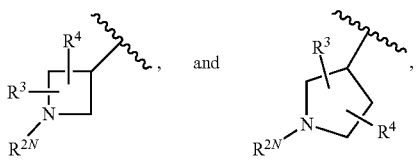

wherein:
R$^{2N}$ is

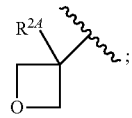

R$^{2A}$ is selected from H and —CH$_3$;
R$^3$ is selected from H, F, and CH$_3$; and
R$^4$ is selected from H, F, and CH$_2$CH$_2$OH.

In an alternative of each of the preceding embodiments, in Formula (I):
R$^2$ is:

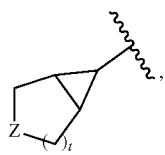

wherein:
t is 1 or 2;
Z is selected from O and NR$^{2N}$.

In an alternative of each of the preceding embodiments, in Formula (I):
R$^2$ is:

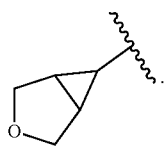 [SMILES: *C1C2COCC12]

In an alternative of each of the preceding embodiments, in Formula (I):
ring A is selected from pyrazolyl, triazolyl, thiazolyl, oxazolyl, and oxadiazolyl; and
R$^5$ is selected from H, (C$_1$-C$_6$)alkyl, (C$_1$-C$_6$)haloalkyl, (C$_3$-C$_6$)cycloalkyl, (C$_3$-C$_6$)cycloalkyl substituted with (C$_1$-C$_4$)alkyl, S(O)$_2$(C$_3$-C$_6$)cycloalkyl, C(O)N(R$^{5A}$)$_2$, C(O)OR$^{5A}$, phenyl, heteroaryl, and heterocycloalkyl; and
R$^{5A}$ is selected from H and —(C$_1$-C$_4$)alkyl.

In an alternative of each of the preceding embodiments, in Formula (I):
ring A is selected from pyrazolyl, triazolyl, thiazolyl, oxazolyl, and oxadiazolyl; and
R$^5$ is selected from H, (C$_1$-C$_6$)alkyl, (C$_1$-C$_6$)haloalkyl, (C$_3$-C$_6$)cycloalkyl, (C$_3$-C$_6$)cycloalkyl substituted with —(C$_1$-C$_4$)alkyl. C(O)N(R$^{5A}$)$_2$, and heteroaryl; and
R$^{5A}$ is selected from H and —(C$_1$-C$_4$)alkyl.

In an alternative of each of the preceding embodiments, in Formula (I):
ring A is a moiety selected from:

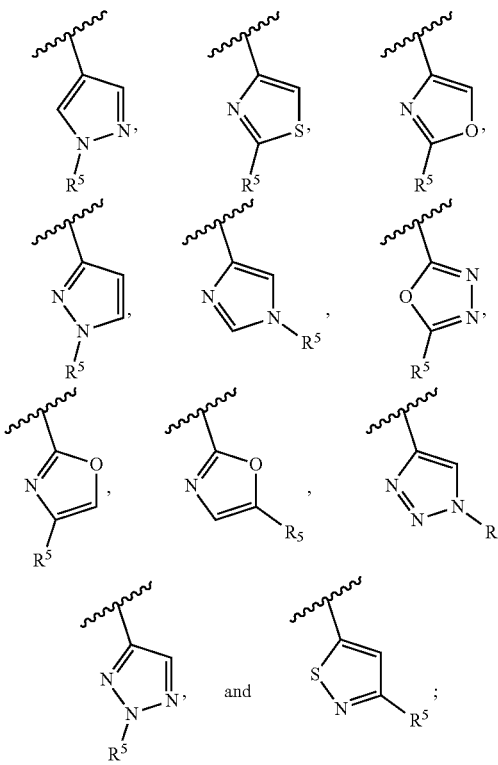

R$^5$ is selected from H, (C$_1$-C$_6$)alkyl, (C$_1$-C$_6$)haloalkyl, (C$_3$-C$_6$)cycloalkyl, (C$_3$-C$_6$)cycloalkyl substituted with (C$_1$-C$_4$)alkyl, S(O)$_2$(C$_3$-C$_6$)cycloalkyl, C(O)N(R$^{5A}$)$_2$, C(O)OR$^{5A}$, phenyl, heteroaryl, heterocycloalkyl and R

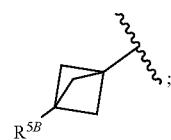

and
each R$^{5A}$ is independently selected from H and —(C$_1$-C$_4$)alkyl; and
R$^{5B}$ is selected from H, (C$_1$-C$_4$)alkyl, (C$_1$-C$_4$)haloalkyl, (C$_1$-C$_4$)alkyl-O—(C$_1$-C$_4$)alkyl, CN, S(O)$_2$(C$_3$-C$_6$)cycloalkyl, C(O)N(R$^{5A}$)$_2$, and C(O)OR$^{5A}$.

In an alternative of each of the preceding embodiments, in Formula (I):
ring A is a moiety selected from:

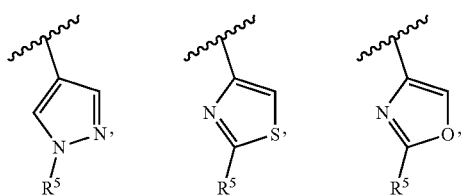

-continued

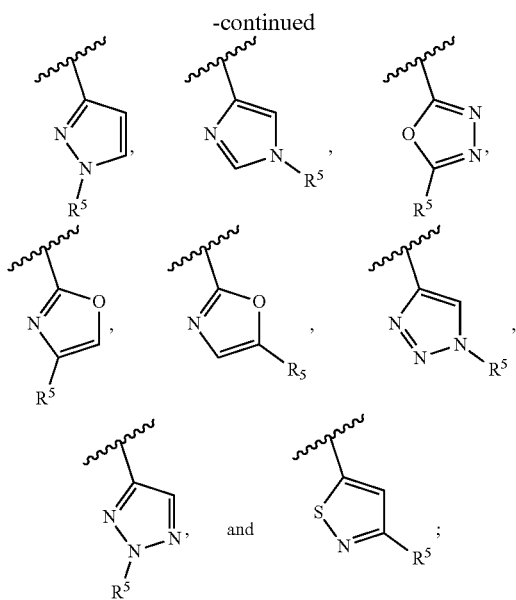

$R^5$ is selected from H, $CH_3$, $CH_2CH_3$, $CF_3$, $CH_2CHF_2$, $CH_2CF_3$, cyclopropyl, cyclobutyl, cyclopentyl, cyclohexyl, $C(O)N(R^{5A})_2$, pyrimidinyl, and

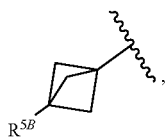

wherein each said cyclopropyl, cyclobutyl, cyclopentyl, and cyclohexyl is unsubstituted or substituted with 1 or 2 groups selected from —$CH_3$ and —$CH_2CH_3$;
$R^{5A}$ is selected from H and —$(C_1$-$C_3)$alkyl; and
$R^{5B}$ is selected from H, $(C_1$-$C_4)$alkyl, $(C_1$-$C_4)$haloalkyl, $(C_1$-$C_4)$alkyl-O—$(C_1$-$C_4)$alkyl, CN, $C(O)N(R^{5A})_2$, and $C(O)OR^{5A}$.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below. —

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl —$CH_2C(O)$— groups (keto forms) may undergo tautomerism to form hydroxyl —CH═C(OH)— groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showed, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"($C_1$-$C_6$)Alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halogen atom. As appreciated by those of skill in the art, "halo" or "halogen" as used herein is intended to include chloro (Cl), fluoro (F), bromo (Br) and iodo (I). Chloro (Cl) and fluoro(F) halogens are generally preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

Preparative Examples

The compounds of the invention can be prepared according to the following schemes and specific examples, or modifications thereof, using readily available starting materials, reagents and conventional synthesis procedures. In these reactions, it is also possible to make use of variants which are themselves known to those of ordinary skill in this art but are not mentioned in detail. General procedures for making the compounds claimed in this invention can be readily understood and appreciated by one skilled in the art from viewing the following Schemes and descriptions. Abbreviations used in the preparative examples below may include, but are not limited to the following:

| | |
|---|---|
| AcOH | Acetic Acid |
| AdBrettPhos-Pd-G3 | Di-Ad-BrettPhos-G3-Palladacycle, [2-(Di-1-adamantylphosphino)-2',4',6'-triisopropyl-3,6-dimethoxybiphenyl][2-(2'-amino-1,1'-biphenyl)]palladium(II) methanesulfonate (MFCD27952546) |

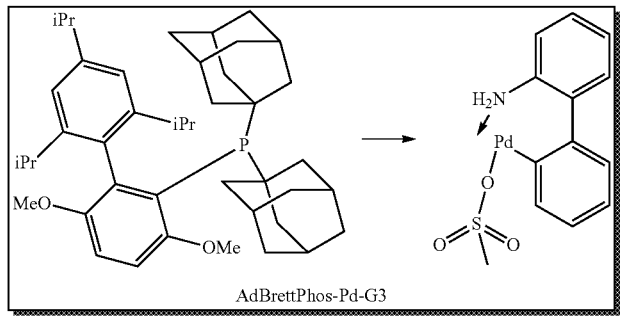

AdBrettPhos-Pd-G3

| | |
|---|---|
| aq | Aqueous |
| BHT | 3,5-Di-tert-4-butylhydroxytoluene |
| CPME | Cyclopentyl methyl ester |
| Cy | Cyclohexyl |
| DAST | Diethylaminosulfur trifluoride |
| DCE | Dichloroethane |
| DCM | Dichloromethane |
| DIC | N,N'-Diisopropylcarbodiimide |
| DIPA | N,N-Diisopropylamine |
| DIPEA | N,N-Diisopropylethylamine |
| DMA | Dimethylacetamide |
| DMEA | Dimethylethylamine |
| DMF | Dimethylformamide |
| DMSO | Dimethyl sulfoxide |
| EtOAc | Ethyl acetate |
| ESI | Electrospray ionization |
| h | Hours |
| HPLC | High performance liquid chromatography |
| IPA | Isopropyl alcohol |
| Josiphos-SL-J009-1-Pd-G3 | {(R)-1-[(Sp)-2-(Dicyclohexylphosphino)ferrocenyl]ethyl-ditert-butylphosphine}[2-(2'-amino-1,1'-biphenyl)]palladium(II) methanesulfonate (MFCD27978424) |

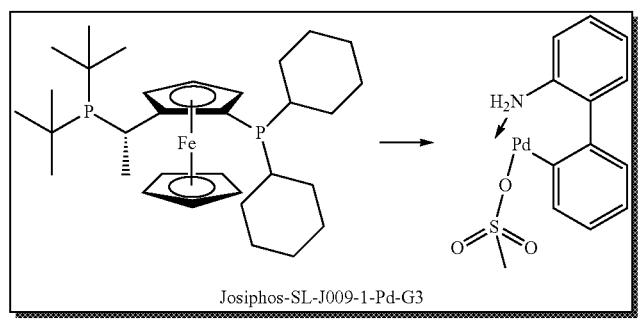

Josiphos-SL-J009-1-Pd-G3

| | |
|---|---|
| LCMS | Liquid chromatography-mass spectrometry |
| LiHMDS | Lithium bis(trimethylsilyl)amide |
| MeCN | Acetonitrile |
| MeOH | Methanol |
| MS | Mass spectrometry |
| NiXantPhos | 4,6-Bis(diphenylphosphino)-10H-phenoxazine, 4,6-Bis(diphenylphosphino)phenoxazine (MFCD03788937) |

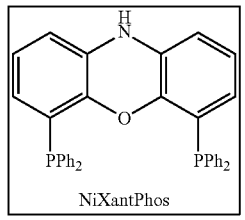
NiXantPhos-Pd-G3      MFCD28144626
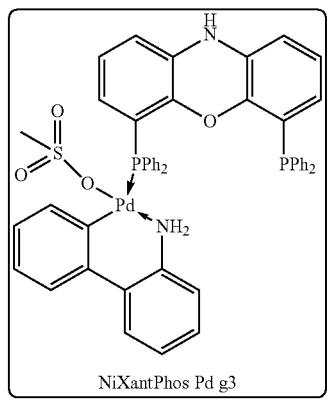
| | |
|---|---|
| NMP | N-Methyl-2-pyrrolidine |
| Pd$_2$dba$_3$ | Tris(dibenzylideneacetone)dipalladium(0) |
| Pd/C | Palladium on Carbon |
| PE | Petroleum Ether |
| psi | Pounds per square inch |
RockPhos Pd G3
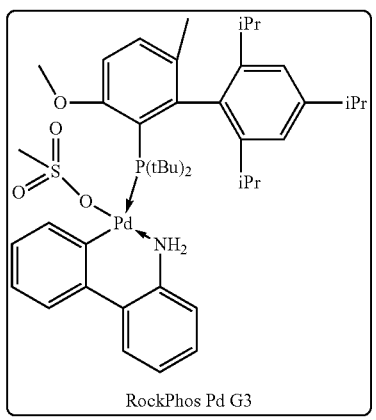
| | |
|---|---|
| RT | Retention time |
| rt | Room temperature |
| SFC | Supercritical Fluid Chromatography |
| TFA | Trifluoroacetic acid |
| THF | Tetrahydrofuran |
| TLC | Thin Layer Chromatography |

Xphos Pd G3

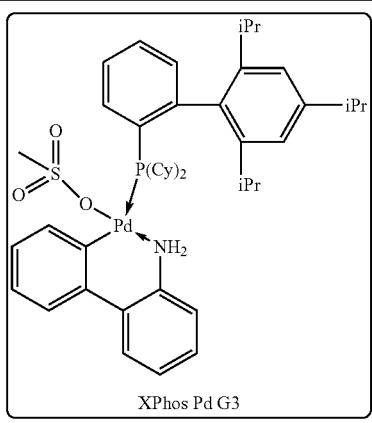

XPhos Pd G3

General Experimental Information:

Unless otherwise noted, all reactions are magnetically stirred.

Unless otherwise noted, when diethyl ether is used in the experiments described below, it is Fisher ACS certified material and is stabilized with BHT.

Unless otherwise noted, "concentrated" means evaporating the solvent from a solution or mixture using a rotary evaporator or vacuum pump.

Unless otherwise noted, proton nuclear magnetic resonance ($^1$H NMR) spectra and proton-decoupled carbon nuclear magnetic resonance ($^{13}$C{$^1$H} NMR) spectra were recorded on a 600 MHz, 500 MHz, or 400 MHz NMR spectrometer at ambient temperature. All chemical shifts (δ) are reported in parts per million (ppm). Proton resonances are referenced to residual protium in the NMR solvent. Carbon resonances are referenced to the carbon resonances of the NMR solvent. Data are represented as follows: chemical shift, multiplicity (br=broad, br s=broad singlet, s=singlet, d=doublet, dd=doublet of doublets, ddd=doublet of doublet of doublets, t=triplet, q=quartet, m=multiplet), coupling constants (J) in Hertz (Hz), integration.

Unless otherwise noted, flash chromatography was carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase Aqueous solutions were concentrated on a Genevac or were lyophilized. Reverse phase prep-HPLC conditions are described as follows.

Reverse Phase Prep-HPLC Conditions:

Method A:

Isolation of material from the reaction mixture was carried out under reverse-phase purification using an Agilent 1200 HPLC-MSD system consisting of a 6130B single quadrupole mass-selective detector (MSD), G1315B diode array detector (DAD), G2258A autosampler, two G1361A preparative pumps, one G1379A quaternary pump with degasser, one G1312A binary pump, and three G1364B fraction collectors from Agilent Technologies (Agilent Technologies, Palo Alto, CA). System control and data analysis were performed using Agilent's ChemStation software, revision B.04.03. A Waters SunFire C18 OBD Prep Column, 100 Å, 5 μm, 19 mm×150 mm column was used as the stationary phase (Waters Corporation, Milford, MA, USA). Gradient elution was carried out using water (solvent A) and acetonitrile (solvent B) as a mobile phase. A 10% trifluoroacetic acid solution was teed into the mobile phase as a modifier using a static mixer prior to the column, pumped at 1% of the total mobile phase flowrate. Electrospray (ESI) Mass-triggered fraction collected was employed using positive ion polarity scanning to monitor for the target mass.

HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Method B:

Isolation of material from the reaction mixture was carried out under reverse-phase purification using an Agilent 1200 HPLC-MSD system consisting of a 6130B single quadrupole mass-selective detector (MSD), G1315B diode array detector (DAD), G2258A autosampler, two G1361A preparative pumps, one G1379A quaternary pump with degasser, one G1312A binary pump, and three G1364B fraction collectors from Agilent Technologies (Agilent Technologies, Palo Alto, CA). System control and data analysis were performed using Agilent's ChemStation software, revision B.04.03. A Waters XBridge C18 OBD Prep Column, 100 Å, 5 μm, 19 mm×150 mm column was used as the stationary phase (Waters Corporation, Milford, MA, USA). Gradient elution was carried out using water (solvent A) and acetonitrile (solvent B) as a mobile phase. A 10% Ammonium Hydroxide solution was teed into the mobile phase as a modifier using a static mixer prior to the column, pumped at 1% of the total mobile phase flowrate. Electrospray (ESI) Mass-triggered fraction collected was employed using positive ion polarity scanning to monitor for the target mass.

HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |

| Time (min) | % Acetonitrile | Mobile Phase Flowrate (mL/Min) | Modifier Flowrate (mL/min) |
|---|---|---|---|
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Unless otherwise noted, all LRRK2 IC$_{50}$ data presented in tables refers to the LRRK2 G2019S Km ATP LanthaScreen™ Assay that is described in the Biological Assay section.

Synthesis of Common Intermediates

Synthesis of Common Intermediates A.1, A.1-1, (R)-(1-(1H-indazol-6-yl)spiro[2.2]pentane-1-carbonitrile), and A.1-2, (S)-(1-(1H-indazol-6-yl)spiro[2.2]pentane-1-carbonitrile)

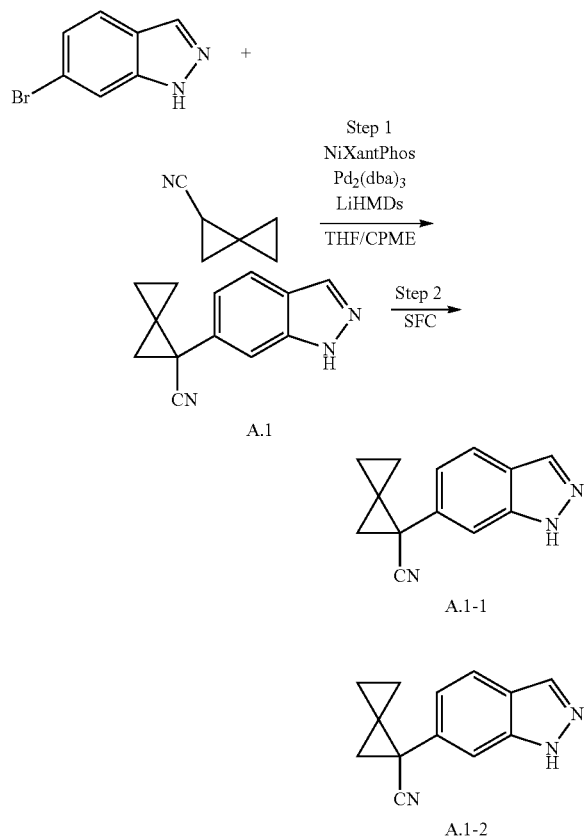

Step 1—Synthesis of Intermediate A.1, (R and S)-(1-(1H-indazol-6-yl)spiro[2.2]pentane-1-carbonitrile)

A 5000-mL 4-necked round-bottom flask was purged with nitrogen and maintained under an inert atmosphere. The vessel was charged with THF (2800 mL), and sparged with nitrogen for 10 min. Pd$_2$(dba)$_3$ (45.78 g, 50.12 mmol) and NiXantPhos (55.35 g, 100.24 mmol) were charged in the vessel and the resulting solution was stirred for 20 min at room temperature. Another 10-L 4-necked round-bottom flask was purged with nitrogen and maintained under an inert atmosphere. The vessel was charged with CPME (2800 mL), and sparged with nitrogen for 10 min. The vessel was then charged with 6-bromo-1H-indazole (197.5 g, 1002.4 mmol) and spiro[2.2]pentane-1-carbonitrile (140 g, 1503 mmol). The resulting solution was stirred for 10 min at room temperature. The solution of catalyst was then added to the substrate solution under nitrogen and the solution was placed in a cool water bath (20° C.). LiHMDS (1M THF, 3000 ml, 3000 mmol) was added dropwise over 30 min under nitrogen, keeping the temperature of the solution below 25° C. The resulting solution was stirred for 2 hours at 80° C. The reaction mixture was cooled to 20° C. with a water/ice bath and quenched by the addition of aqueous saturated ammonium chloride solution (10 L). The resulting solution was extracted with ethyl acetate (2×2000 mL), dried over anhydrous sodium sulfate and concentrated. The crude material was purified by silica gel column chromatography (33% EtOAc/petroleum ether) to provide intermediate A.1, (R and S)-1-(1H-indazol-6-yl)spiro[2.2]pentane-1-carbonitrile. MS (ESI) in z calc'd for C$_{13}$H$_{12}$N$_3$ [M+H]$^+$ 210. found 210.

Step 2—Resolution of A.1, (R and S)-(1-(1H-indazol-6-yl)spiro[2.2]pentane-1-carbonitrile)

Intermediate A.1 (152 g, 0.73 mmol) was resolved by CHIRAL-Prep-SFC [Column: CHIRALPAK AD-H, 5 cm×25 cm (5 μm); 50% MeOH/CO$_2$; Flow rate: 170 mL/min; 220 nm; RT1:4.29 min (A.1-1); RT2: 6.69 min (A.1-2)].

Common Intermediate A.1-1, (R)-1-(1H-indazol-6-yl)spiro[2.2]pentane-1-carbonitrile MS (ESI) m/z calc'd for C$_{13}$H$_{12}$N$_3$ [M+H]$^+$ 210. found 210. $^1$H NMR (400 MHz, CDCl$_3$) δ 8.08 (s, 1H), 7.74-7.72 (d, 1H), 7.59 (s, 1H), 7.01-6.99 (d, 1H), 2.31-2.29 (d, 1H), 1.86-1.85 (d, 1H), 1.37-1.02 (m, 4H).

Common Intermediate A.1-2, (S)-1-(1H-indazol-6-yl)spiro[2.2]pentane-1-carbonitrile MS (ESI) m/z calc'd for C$_{13}$H$_{12}$N$_3$ [M+H]$^+$ 210. found 210. $^1$H NMR (400 MHz, CDCl$_3$) δ 8.08 (s, 1H), 7.74-7.71 (d, 1H), 7.59 (s, 1H), 7.01-6.98 (d, 1H), 2.30-2.29 (d, 1H), 1.86-1.85 (d, 1H), 1.37-1.05 (m, 4H).

Synthesis of Common Intermediates B.6 (5-chloro-6-(piperidin-4-yl)-1H-indazole) and B.7 (5-chloro-6-(1-(oxetan-3-yl)piperidin-4-yl)-1H-indazole)

Scheme B

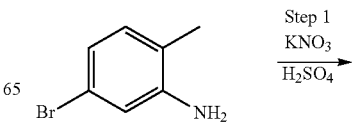

Step 1
KNO$_3$
H$_2$SO$_4$

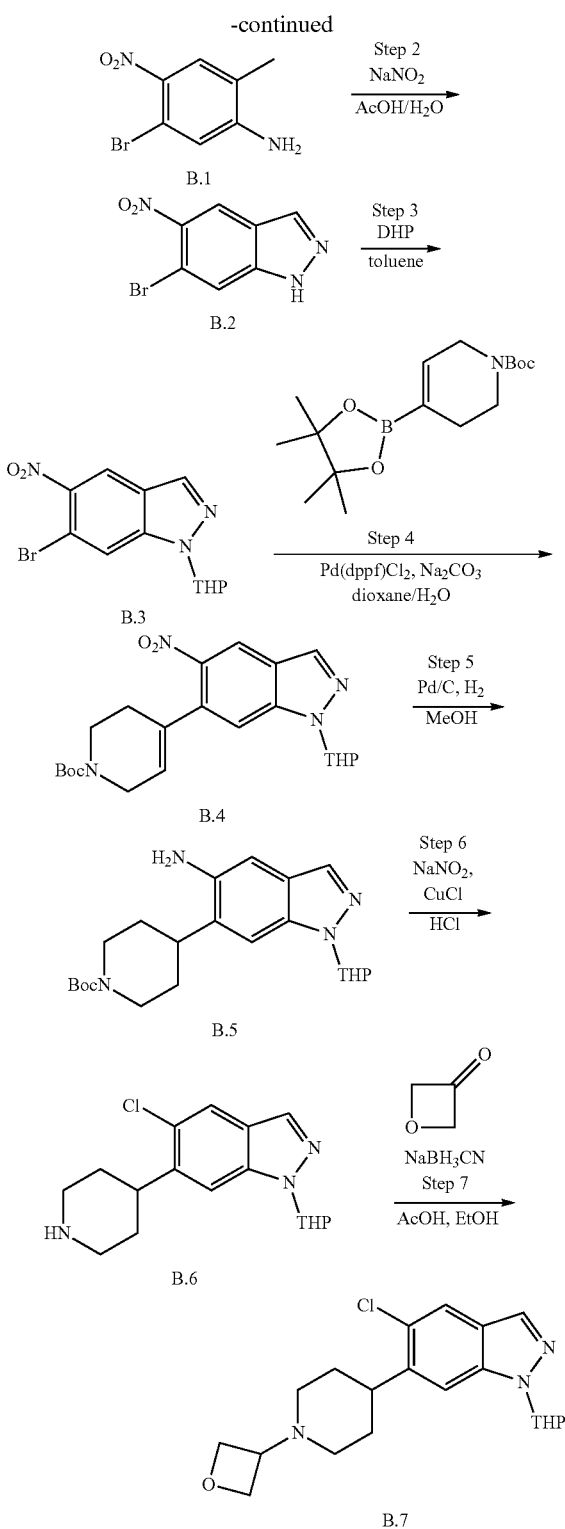

KNO$_3$ (135.8 g, 1.34 mol). The solution was stirred at 20° C. for 3 hours. The crude reaction was then added to 10 L of ice water and a solid precipitated. The solid was filtered off to afford intermediate B.1, (5-bromo-2-methyl-4-nitroaniline after combining material from the duplicate reactions. The crude material was used directly for subsequent steps without additional purification.

Step 2—Synthesis of Intermediate B.2, 6-bromo-5-nitro-1H-indazole

Two duplicate reactions were carried out in parallel: To a 3-necked 3 L flask was added intermediate B.1 (170 g, 0.73 mol) and acetic acid (1.1 L). Then, a solution of NaNO$_2$ (55.8 g, 0.81 mol) in H$_2$O (170 mL) was added. The reaction was stirred at 100° C. for 12 hours. The duplicate reactions were then combined, the solvent was removed and the crude residue was diluted with saturated NaHCO$_3$ (10 L) and the aqueous phase was extracted with EtOAc (2 L×3). The organic phase was washed with brine (2 L), and the solvent was removed to afford crude intermediate B.2, 6-bromo-5-nitro-1H-indazole. The crude material was used directly for the next step without additional purification.

Step 3—Synthesis of Intermediate B.3, 6-bromo-5-nitro-1-(tetrahydro-2H-pyran-2-yl)-1H-indazole Two duplicate reactions were carried out in parallel: Into a 3-necked 3 L flask was added intermediate B.2 (170 g, 0.70 mol) and toluene (1.1 L). Then, trifluoroacetic acid (24.0 g, 0.21 mol), and 3,4-dihydro-2H-pyran (88.6 g, 1.05 mol) were added to the solution. The reaction was stirred at 80° C. for 12 hours. Afterward, the duplicate reactions were combined, the solvent was removed and the crude residue was purified by silica gel chromatography (gradient elution of 1% to 9% EtOAc/petroleum ether) to afford intermediate B.3, 6-bromo-5-nitro-1-(tetrahydro-2H-pyran-2-yl)-1H-indazole. $^1$HNMR: (400 MHz, CDCl$_3$) δ: 8.37 (s, 1H), 8.15 (s, 1H), 8.01 (s, 1H), 5.73 (dd, J=9.2, 2.8 Hz, 1H), 4.00-0.04 (m, 1H), 3.76-3.81 (m, 1H), 2.49-2.51 (m, 1H), 2.11-2.18 (m, 2H), 1.71-1.79 (m, 3H).

Step 4—Synthesis of Intermediate B.4, tert-butyl 4-(5-nitro-1-(tetrahydro-2H-pyran-2-yl)-1H-indazol-6-yl)-3,6-dihydropyridine-1(2H)-carboxylate Two duplicate reactions were carried out in parallel: To a 3-necked 2 L flask was added intermediate B.3 (90.0 g, 0.27 mol), dioxane (450 mL), and H$_2$O (360 mL). Next, tert-butyl 4-(4,4,5,5-tetramethyl-1,3,2-dioxaborolan-2-yl)-3,6-dihydropyridine-1(2H)-carboxylate (89.6 g, 0.29 mol) was added followed by Na$_2$CO$_3$ (87.7 g, 0.83 mol). Then, Pd(dppf)Cl$_2$ (10.1 g, 0.014 mol) was added to the reaction. The solution was allowed to stir at 80° C. for 12 hours under a nitrogen atmosphere. Afterward, the duplicate reactions were combined and the solution was extracted with EtOAc (500 mL×3), and the organic layers were combined and washed with brine (500 mL). The organic layer was concentrated and the crude residue was purified by silica gel column chromatography (gradient elution of 1% to 17% EtOAc/petroleum ether) to afford intermediate B.4, tert-butyl 4-(5-nitro-1-(tetrahydro-2H-pyran-2-yl)-1H-indazol-6-yl)-3,6-dihydropyridine-1(2H)-carboxylate. $^1$HNMR: (400 MHz, CDCl$_3$) δ: 8.49 (s, 1H), 8.17 (s, 1H), 7.44 (s, 1H), 5.69-5.76 (m, 2H), 4.04-4.16 (m, 3H), 3.69-3.82 (m, 3H), 2.52-2.55 (m, 1H), 2.18-2.36 (m, 2H), 2.09-2.18 (m, 2H), 1.56-1.82 (m, 3H), 1.52 (s, 9H).

Step 1—Synthesis of Intermediate B.1, 5-bromo-2-methyl-4-nitroaniline

Two duplicate reactions were carried out in parallel: To a 3-necked 3 L flask was added H$_2$SO$_4$ (1.25 L). The flask was cooled to 0° C. Then, 5-bromo-2-methylaniline (250 g, 1.34 mol) was added followed by the portion-wise addition of

Step 5—Synthesis of Intermediate B.5, tert-butyl 4-(5-amino-1-(tetrahydro-2H-pyran-2-yl)-1H-indazol-6-yl)piperidine-1-carboxylate Two duplicate reactions were carried out in parallel: To a 2 L flask was added intermediated B.4 (85.0 g, 0.20 mol) and MeOH (560 mL) followed by Pd/C (15 g). The solution was stirred at 50° C. under an atmosphere of hydrogen gas (15 psi) for 12 hours. Afterward, the solution was filtered, and the filtrate was concentrated to afford crude intermediate B.5, tert-butyl 4-(5-amino-1-(tetrahydro-2H-pyran-2-yl)-1H-indazol-6-yl)piperidine-1-carboxylate after combining the material from the duplicate reactions. The crude material was used directly for the next step without additional purification. MS (ESI) m/z calc'd for $C_{22}H_{33}N_4O_3$ [M+H]$^+$ 401. found 401.

Step 6—Synthesis of Common Intermediate B.6, 5-chloro-6-(piperidin-4-yl)-1H-indazole Two duplicate reactions were carried out in parallel: To a 3-necked 2 L flask was added intermediate B.6 (75.0 g, 187.3 mmol) along with HCl (525 mL) and the flask was cooled to 0° C. Then, NaNO$_2$ (14.2 g, 206.0 mmol) and H$_2$O (525 mL) was added dropwise. The solution was stirred at 0° C. for 15 minutes. Into a separate 3-necked 5 L flask was added CuCl (33.4 g, 337.1 mmol) and H$_2$O (350 mL), and the solution was heated to 60° C. The solution containing intermediate B.6, HCl, NaNO$_2$, and H$_2$O at 0° C. was then added to the flask containing CuCl and H$_2$O at 60° C. The resulting mixture was stirred at 60° C. for 1 hour. Then, the duplicate reactions were combined and saturated NaHCO$_3$ was added until the mixture reached pH=7. Then, saturated NH$_4$OH (10 L) was added to the solution and it was extracted with EtOAc (2 L×4). The organic layers were combined, washed with brine (2 L), and concentrated. The crude residue was diluted into EtOAc (5 L), and washed with saturated NH$_4$OH (3 L). The organic phase was collected and concentrated until a precipitate was formed. The solid precipitate was filtered off to afford common intermediate B.6, 5-chloro-6-(piperidin-4-yl)-1H-indazole. The material was used directly without further purification. MS (ESI) m/z calc'd for $C_{12}H_{15}ClN_3$ [M+H]$^+$ 236. found 236.

Step 7—Synthesis of Intermediate B.7, 5-chloro-6-(1-(oxetan-3-yl)piperidin-4-yl)-1H-indazole To a 3-necked 1 L flask was added intermediate B.6 (30.0 g, 127.3 mmol), oxetan-3-one (18.3 g, 254.5 mmol), and EtOH (280 mL). Then, AcOH (15.3 g, 254.5 mmol) and MgSO$_4$ (30.6 g, 254.5 mmol) was added. Next, NaBH$_3$CN (16.0 g, 254.5 mmol) was added portionwise and the solution was stirred at 90° C. for 2 hours. Afterward, the reaction solution was added to saturated NaHCO$_3$ (200 ml) and the mixture was extracted with 2:1 CHCl$_3$:iPrOH (300 mL×3). The combined organic phases were washed with brine (200 mL) and then concentrated. The crude residue was purified by silica gel column chromatography (eluent 9% MeOH/DCM). The resulting material was then mixed with MeCN (100 mL) and stirred for 20 minutes. The suspended solid is then filtered off to afford common intermediate B.7, 5-chloro-6-(1-(oxetan-3-yl)piperidin-4-yl)-1H-indazole. MS (ESI) m/z calc'd for $C_{15}H_{19}ClN_3O$ [M+H]$^+$ 292. found 292. $^1$HNMR: (400 MHz, CD$_3$OD) δ: 7.97 (s, 1H), 7.82 (s, 1H), 7.51 (s, 1H), 4.73 (t, J=6.8 Hz, 2H), 4.65 (t, J=6.4 Hz, 2H), 3.58 (q, J=6.4 Hz, 1H), 3.15-3.31 (m, 1H), 2.96-2.99 (m, 2H), 1.97-2.09 (m, 4H), 1.80-1.85 (m, 2H).

Synthesis of Common Intermediates C.4, (5-methyl-6-(piperidin-4-yl)-1H-indazole) and C.5, (5-methyl-6-(1-(oxetan-3-yl)piperidin-4-yl)-1H-indazole)

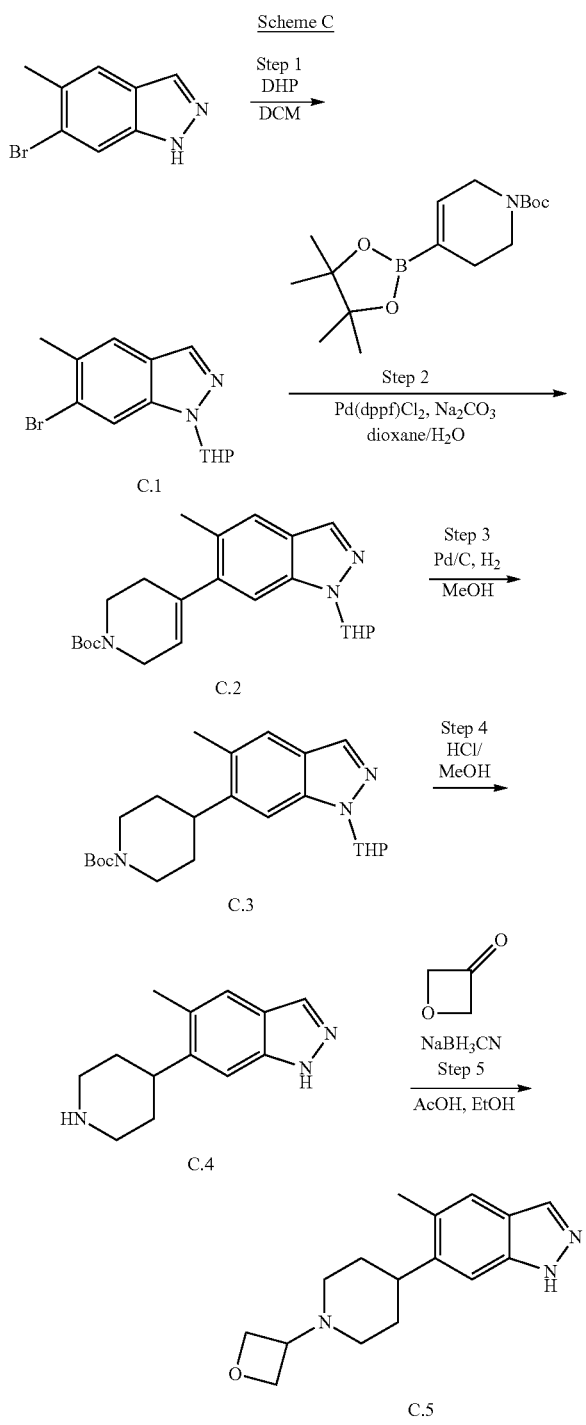

Step 1—Synthesis of Intermediate C.1, 6-bromo-5-methyl-1-(tetrahydro-2H-pyran-2-yl)-1H-indazole Two duplicate reactions were carried out in parallel: To a 3-necked 3 L flask was added 6-bromo-5-methyl-1H-indazole (215 g, 1.02 mol) and DCM (1.4 L) followed by TsOH·H$_2$O (38.7 g, 203.7 mmol) and 3,4-dihydro-2H-pyran (171.4 g, 2.04 mol). The solution was stirred at room temperature for 1 hour. Then, the reaction was quenched with saturated NaHCO$_3$ until the solution reached pH=8. The mixture was extracted with DCM (1 L×2), and the organic phases were combined and concentrated to give a crude solid. The crude material was mixed with petroleum ether (1 L) and stirred for 1 hour. The resulting solid was filtered off and washed with additional petroleum ether (200 mL×2) to afford intermediate C.1, 6-bromo-5-methyl-1-(tetrahydro-2H-pyran-2-yl)-1H-indazole after combining the material from the duplicate reactions. The material was carried on without further purification.

Step 2—Synthesis of Intermediate C.2, tert-butyl 4-(5-methyl-1-(tetrahydro-2H-pyran-2-yl)-1H-indazol-6-yl)-3,6-dihydropyridine-1(2H)-carboxylate Three duplicate reactions were carried out in parallel: To a 3-necked 3 L flask was added intermediate C.1 (160.0 g, 542.0 mmol) and dioxane (800 mL) followed by H$_2$O (640 ml), tert-butyl 4-(4,4,5,5-tetramethyl-1,3,2-dioxaborolan-2-yl)-3,6-dihydropyridine-1(2H)-carboxylate (176.0 g, 569.1 mmol), Pd(dppf)Cl$_2$ (19.83 g, 27.1 mmol), and Na$_2$CO$_3$ (172.3 g, 1.63 mol). The resulting solution was warmed to 80° C. and stirred for 12 hours under an atmosphere of nitrogen. Afterward, the reaction was cooled, all three duplicate reactions were combined and the resulting mixture was diluted with H$_2$O (3 L). The mixture was extracted with EtOAc (2 L×3), and the organic phases were combined and washed with brine (2 L). The organic phase was then concentrated and the crude residue was purified by silica gel chromatography (gradient elution of 1% to 9% EtOAc/petroleum ether) to afford intermediate C.2, tert-butyl 4-(5-methyl-1-(tetrahydro-2H-pyran-2-yl)-1H-indazol-6-yl)-3,6-dihydropyridine-1(2H)-carboxylate. $^1$HNMR: (400 MHz, CDCl$_3$) δ: 7.93 (s, 1H), 7.49 (s, 1H), 7.29 (s, 1H), 5.64-5.69 (m, 2H), 4.05-4.12 (m, 3H), 3.65-3.78 (m, 3H), 2.36-2.60 (m, 7H), 2.05-2.18 (m, 2H), 1.57-1.80 (m, 4H), 1.52 (s, 9H).

Step 3—Synthesis of Intermediate C.3, tert-butyl 4-(5-methyl-1-(tetrahydro-2H-pyran-2-yl)-1H-indazol-6-yl)piperidine-1-carboxylate Six duplicate reactions were carried out in parallel: To a 2 L hydrogenation bottle was added intermediate C.2 (100 g, 251.6 mmol) and MeOH (700 mL). Then, Pd/C (20 g) was added. The solution was degassed under vacuum and purged with H$_2$ gas several times. The reaction solution was stirred at 50° C. for 12 hours under an atmosphere of H$_2$ (15 psi). Then, all six duplicate reactions were combined, and the resulting solution was filtered. The filtrate was concentrated to afford crude intermediate C.3, tert-butyl 4-(5-methyl-1-(tetrahydro-2H-pyran-2-yl)-1H-indazol-6-yl)piperidine-1-carboxylate. The crude material was used directly for the next step without additional purification. MS (ESI) m/z calc'd for C$_{23}$H$_{34}$N$_3$O$_3$ [M+H]$^+$ 400. found 400.

Step 4—Synthesis of Intermediate C.4, 5-methyl-6-(piperidin-4-yl)-1H-indazole Three duplicate reactions were carried out in parallel: To a 3-necked 3 L flask was added intermediate C.3 (185.0 g, 463.0 mmol) and MeOH (900 mL). Then, HCl/MeOH (740 mL) was added dropwise at 0° C. The solution was stirred at 20° C. for 12 hours. Afterward, all three duplicate reactions were combined and the solvent was evaporated to give a crude solid. The crude residue was combined with H$_2$O (2 L) and the pH was adjusted to 10 using NH$_3$·H$_2$O (28%). The mixture was extracted with 2:1 CHCl$_3$:iPrOH (500 mL×3). The combined organic phase was washed with brine (500 mL) and then concentrated to give a solid. The resulting solid was triturated with MeCN (300 mL) and the solid was filtered off and collected to afford intermediate C.4, 5-methyl-6-(piperidin-4-yl)-1H-indazole. The material was used directly for the next step without additional purification. MS (ESI) m/z calc'd for C$_{13}$H$_{18}$N$_3$ [M+H]$^+$ 216. found 216.

Step 5—Synthesis of Common Intermediate C.5, 5-methyl-6-(1-(oxetan-3-yl)piperidin-4-yl)-1H-indazole To a 3-necked 1 L flask was added intermediate C.4 (50.0 g, 232.2 mmol) and EtOH (500 mL). Then, AcOH (27.9 g, 464.5 mmol) was added followed by MgSO$_4$ (55.9 g, 464.5 mmol) and oxetan-3-one (33.47 g, 464.5 mmol). Next, NaBH$_3$CN (29.2 g, 464.5 mmol) was added portionwise at 20° C. The solution was warmed to 90° C. and stirred for 2 hours. Afterward, the reaction was quenched with saturated NaHCO$_3$ until the reaction solution reached a pH of 8. The solution was filtered, and the filtrate was concentrated to a crude residue. The residue was extracted with 2:1 CHCl$_3$:iPrOH (100 mL×3) and the combined organic phase was washed with brine (100 mL) and concentrated. The resulting residue was purified by silica gel column chromatography (eluent 25% EtOAc/EtOH) to afford common intermediate C.5, 5-methyl-6-(1-(oxetan-3-yl)piperidin-4-yl)-1H-indazole. MS (ESI) m/z calc'd for C$_{16}$H$_{22}$N$_3$O [M+H]$^+$ 272. found 272. $^1$HNMR: (400 MHz, DMSO) δ: 7.88 (s, 1H), 7.52 (s, 1H), 7.41 (s, 1H), 4.72-4.85 (m, 2H), 4.65-4.68 (m, 2H), 3.59-3.64 (m, 1H), 2.89-3.00 (m, 3H), 2.43 (s, 3H), 2.06-2.10 (m, 2H), 1.85-1.89 (m, 4H).

Synthesis of Common Intermediate D.2, 5-chloro-6-(1-(3-methyloxetan-3-yl)piperidin-4-yl)-1H-indazole Scheme D

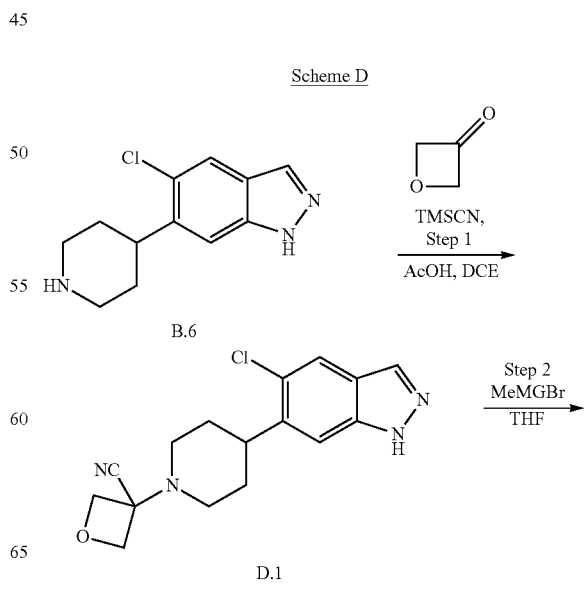

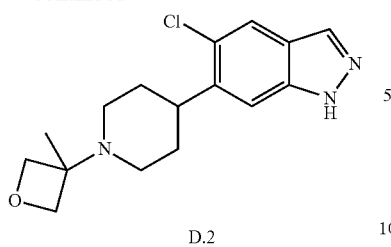

D.2

Step 1—Synthesis of Intermediate D.1, 3-(4-(5-chloro-1H-indazol-6-yl)piperidin-1-yl)oxetane-3-carbonitrile Intermediate B.6 (85.00 g, 360.61 mmol) was solvated in DCE (560 mL) and oxetan-3-one (28.59 g, 396.67 mmol) was added followed by the dropwise addition of AcOH (25.99 g, 432.73 mmol) at 25° C. The solution was warmed to 50° C. for 30 minutes. Then, TMSCN (35.77 g, 360.61 mmol) was added to the mixture. The reaction was stirred at 50° C. for 12 hours. Afterward, the reaction solution was added to H$_2$O (600 mL), and the resulting solution was extracted with 2:1 CHCl$_3$:iPrOH (2 L×1, 1 L×2). The combined organic phases were washed with brine (200 mL) and concentrated. The crude residue was then purified by silica gel chromatography (gradient elution EtOAc/petroleum ether 1% to 9%) to afford intermediate D.1, 3-(4-(5-chloro-1H-indazol-6-yl)piperidin-1-yl)oxetane-3-carbonitrile. $^1$HNMR: (400 MHz, CDCl$_3$) δ: 10.41 (s, 1H), 8.01 (s, 1H), 7.80 (s, 1H), 7.41 (s, 1H), 4.85 (d, J=6.8 Hz, 2H), 4.72 (d, J=6.4 Hz, 2H), 3.21-3.25 (m, 1H), 2.79-2.82 (m, 2H), 2.35-2.40 (m, 2H), 2.05-2.09 (m, 2H), 1.79-1.86 (m, 2H).

Step 2—Synthesis of Common Intermediate D.2, 5-chloro-6-(1-(3-methyloxetan-3-yl)piperidin-4-yl)-1H-indazole To a solution of intermediate D.1 (25.00 g, 78.92 mmol) in THF (250 mL) was added MeMgBr (3.0 M, 131.53 mL) at 0° C. under an atmosphere of nitrogen. The evolution of gas was observed. The resulting solution was stirred at 60° C. for 3 hours. Afterward, the reaction was quenched with H$_2$O and extracted with DCM (400 mL×1,200 mL×1, 100 ml×1). The combined organic phases were dried over Na$_2$SO$_4$, filtered, and concentrated. The crude residue was then purified by silica gel chromatography (gradient elution of 2% to 9% EtOAc/petroleum ether). The resulting product was triturated with DCM (100 mL) and the solid was filtered off and washed with additional DCM (20 mL) to afford common intermediate D.2, 5-chloro-6-(1-(3-methyloxetan-3-yl)piperidin-4-yl)-1H-indazole. MS (ESI) m/z calc'd for C$_{16}$H$_{21}$ClN$_3$O [M+H]$^+$ 306. found 306. $^1$HNMR: (400 MHz, CDCl$_3$) δ: 10.31 (s, 1H), 8.00 (s, 1H), 7.78 (s, 1H), 7.45 (s, 1H), 4.65 (d, J=5.6 Hz, 2H), 4.29 (d, J=5.6 Hz, 2H), 3.08-3.12 (m, 1H), 2.68-2.71 (m, 2H), 2.30-2.36 (m, 2H), 1.98-2.01 (m, 2H), 1.73-1.98 (m, 2H), 1.44 (s, 3H).

Synthesis of Common Intermediated E.2, 5-chloro-6-(1-(3-methyloxetan-3-yl)piperidin-4-yl)-1-(1H-pyrazol-4-yl)-1H-indazole Scheme E

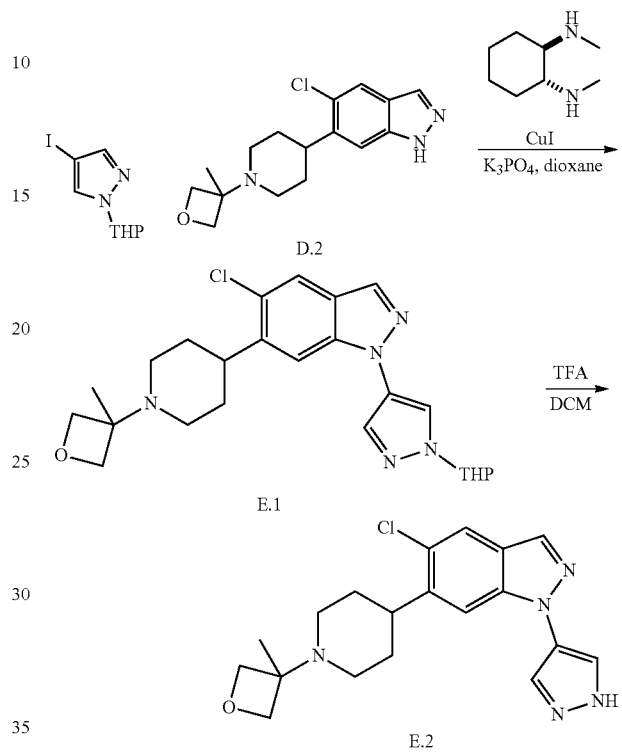

Step 1—Synthesis of Intermediate E.1, 5-chloro-6-(1-(3-methyloxetan-3-yl)piperidin-4-yl)-1-(1-(tetrahydro-2H-pyran-2-yl)-1H-pyrazol-4-yl)-1H-indazole Into a dry microwave vial was added intermediate D.2 (1.0 g, 3.27 mmol), 4-iodo-1-(tetrahydro-2H-pyran-2-yl)-1H-pyrazole (1.364 g, 4.91 mmol), (trans)-N1,N2-dimethylcyclohexane-1,2-diamine (0.233 g, 1.635 mmol), potassium phosphate tribasic (2.082 g, 9.81 mmol), and copper(I) iodide (0.187 g, 0.981 mmol). The vial was sealed and purged with nitrogen gas. Then, degassed 1,4-dioxane (12 mL) was added. The reaction was warmed to 90° C. and stirred overnight. Afterward, the crude reaction was cooled and diluted with EtOAc and saturated NaHCO$_3$. The resulting biphasic mixture was extracted twice with EtOAc. The resulting organic layers were combined, dried over Na$_2$SO$_4$, filtered, and concentrated to afford crude intermediate E.1, 5-chloro-6-(1-(3-methyloxetan-3-yl)piperidin-4-yl)-1-(1-(tetrahydro-2H-pyran-2-yl)-1H-pyrazol-4-yl)-1H-indazole. The crude material was used directly for the next step without additional purification. MS (ESI) m/z calc'd for C$_{24}$H$_{31}$ClN$_5$O$_2$ [M+H]$^+$ 456. found 456.

Step 2—Synthesis of Common Intermediate E.2, 5-chloro-6-(1-(3-methyloxetan-3-yl)piperidin-4-yl)-1-(1H-pyrazol-4-yl)-1H-indazole Intermediate E.1 (1.491 g, 3.27 mmol) was solvated in DCM (2.5 mL) in a 2 dram vial. Then, trifluoroacetic acid (7.46 g, 65.4 mmol) was added. The resulting solution was warmed to 37° C. and stirred for 2 hours. Afterward, the reaction was slowly quenched with saturated NaHCO$_3$. The crude material was then filtered and concentrated. The resulting residue was purified by silica gel column chromatography (gradient elution 0% to 100% (3:1 EtOAc:EtOH) in hexanes) to afford common intermediate E.2, 5-chloro-6-(1-(3-methyloxetan-3-yl)piperidin-4-yl)-1-(1H-pyrazol-4-yl)-1H-indazole. MS (ESI) m/z calc'd for C$_{19}$H$_{23}$N$_5$O [M+H]$^+$ 372. found 372. $^1$H NMR (499 MHz, DMSO-d$_6$) δ 8.43 (s, 1H), 8.22 (s, 1H), 7.96 (s, 2H), 7.55 (s, 1H), 4.43 (d, J=5.5 Hz, 2H), 4.14 (d, J=5.5 Hz, 2H), 3.05-2.95 (m, 1H), 2.64 (d, J=11.1 Hz, 2H), 2.25-2.17 (m, 2H), 1.89-1.74 (m, 5H), 1.31 (s, 3H).

Synthesis of Common Intermediate F.4, 6-bromo-5-chloro-1-(1-methyl-1H-pyrazol-4-yl)-1H-indazole

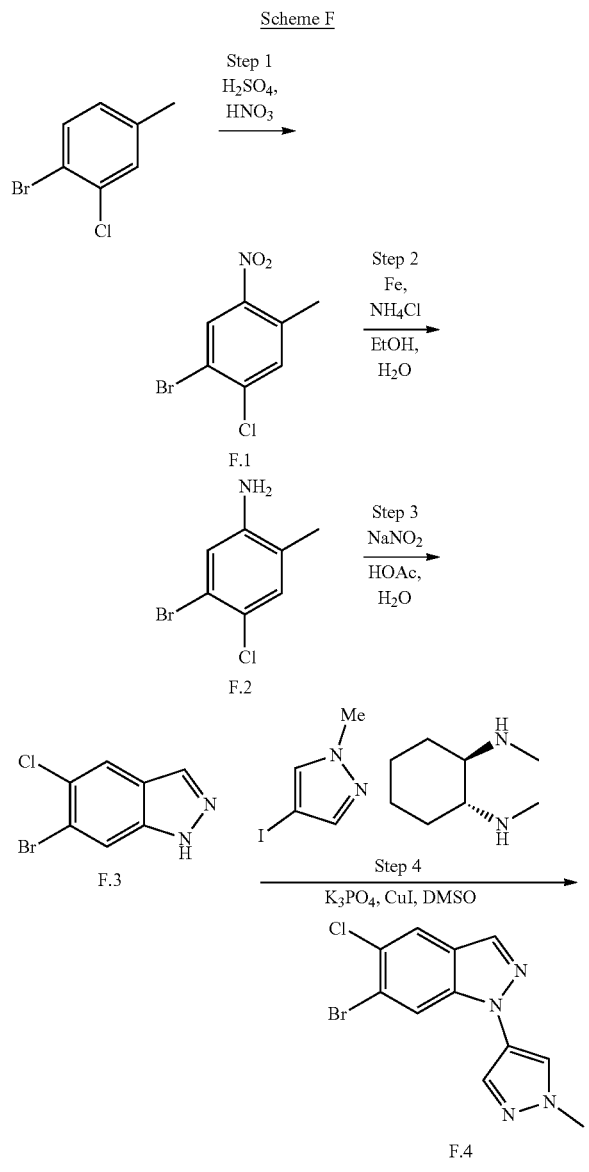

Step 1—Synthesis of Intermediate F.1, 1-bromo-2-chloro-4-methyl-5-nitrobenzene

To a stirred solution of 1-bromo-2-chloro-4-methylbenzene (1000 g, 4866.7 mmol, 1 equiv.) in H$_2$SO$_4$ (conc.) (3.25 L) was added HNO$_3$ (conc.) (700 mL) dropwise at 0° C. under a nitrogen atmosphere. The resulting mixture was stirred for 5 min at room temperature. The resulting mixture was then poured into ice-water (25 L). The resulting mixture was filtered, and the filter cake was washed with water (500 mL×2) and dried to afford intermediate F.1, 1-bromo-2-chloro-4-methyl-5-nitrobenzene. The crude material was used directly for the next step without additional purification.

Step 2—Synthesis of Intermediate F.2, 5-bromo-4-chloro-2-methylaniline

To a stirred mixture of intermediate F.1 (900 g, 3593.1 mmol, 1 equiv.) and Fe (1003.28 g, 17965.5 mmol, 5 equiv.) in EtOH (6.3 L) was added a solution of NH$_4$Cl (576.60 g, 10779.3 mmol, 3 equiv.) in water (2.7 L). The resulting mixture was stirred for 3 hours at 80° C. The solid was filtered out. The resulting filtrate was poured into ice-water (30 L). The resulting mixture was filtered, and the filter cake was washed with water (500 mL×2) and dried to afford intermediate F.2, 5-bromo-4-chloro-2-methylaniline. The crude material was used directly for the next step without additional purification.

Step 3—Synthesis of Intermediate F.3, 6-bromo-5-chloro-1H-indazole

To a stirred solution of intermediate F.2 (500 g, 2267.7 mmol, 1 equiv.) in AcOH (5 L) was added a solution of NaNO$_2$ (164.28 g, 2381.1 mmol, 1.05 equiv.) in water (500 mL). The resulting mixture was stirred for 2 hours at 100° C. The mixture was then allowed to cool down to room temperature. The resulting mixture was poured into ice-water (30 L) and then filtered. The resulting filter cake was washed with water (500 mL×2) and dried to afford intermediate F.3, 6-bromo-5-chloro-1H-indazole. The crude material was used directly for the next step without additional purification.

Step 4—Synthesis of Common Intermediate F.4, 6-bromo-5-chloro-1-(1-methyl-1H-pyrazol-4-yl)-1H-indazole Into a 4-necked 5 L round-bottom flask was added intermediate F.3 (200 g, 864.0 mmol, 1 equiv.), 4-iodo-1-methyl-1H-pyrazole (269.57 g, 1296.0 mmol, 1.50 equiv.), (trans)-N1,N2-dimethylcyclohexane-1,2-diamine (61.45 g, 432.003 mmol, 0.50 equiv.), CuI (32.91 g, 172.801 mmol, 0.20 equiv.), K$_3$PO$_4$ (550.20 g, 2592.017 mmol, 3.00 equiv.) and DMSO (2 L). The resulting mixture was stirred for 5 hours at 90° C. under a nitrogen atmosphere. The mixture was then allowed to cool down to room temperature. The resulting mixture was diluted with water (5 L) and then extracted with EtOAc (3 L×3). The combined organic layers were washed with brine (3 L), dried over anhydrous Na$_2$SO$_4$, and concentrated under reduced pressure. The crude residue was purified by silica gel column chromatography (eluent 50% EtOAc/petroleum ether) to afford common intermediate F.4, 6-bromo-5-chloro-1-(1-methyl-1H-pyrazol-4-yl)-1H-indazole. MS (ESI) m/z calc'd for C$_{11}$H$_9$BrClN$_4$ [M+H]$^+$ 312.9.

found 312.9. $^1$H NMR: (400 MHz, DMSO-d$_6$) δ 8.40 (s, 1H), 8.32-8.27 (m, 1H), 8.16 (s, 1H), 8.15-8.10 (m, 1H), 7.92 (s, 1H), 3.94 (s, 3H).

Synthesis of Common Intermediate G.2, 1-(bicyclo[1.1.1]pentan-1-yl)-4-iodo-1H-pyrazole

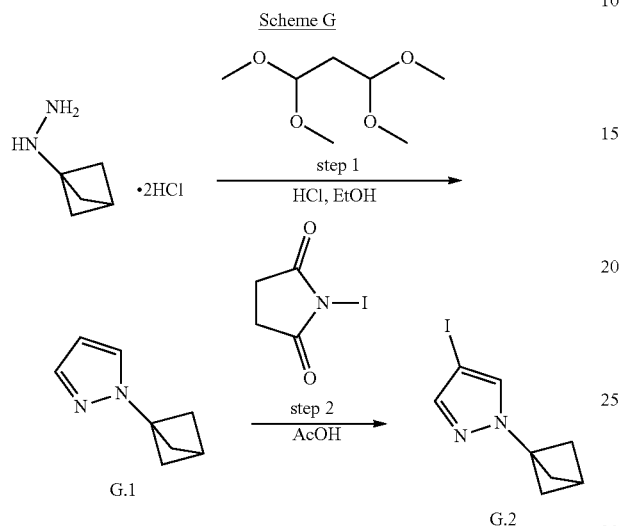

Step 1—Synthesis of Intermediate G.1, 1-(bicyclo[1.1.1]pentan-1-yl)-1H-pyrazole

A 30-mL round-bottomed vial with stir bar was charged with bicyclo[1.1.1]pentan-1-ylhydrazine dihydrochloride (600 mg, 3.51 mmol), followed by ethanol (4.38 mL). Then, 1,1,3,3-tetramethoxypropane (576 mg, 3.51 mmol) and hydrochloric acid (1106 mg, 11.22 mmol) were added. The vial was sealed and heated to 80° C. overnight. The reaction was heated for another 14 hours after that. The mixture was cooled, extracted twice with ethyl acetate, and then twice with DCM. The organic layers were combined, dried, and concentrated. The resulting crude material was purified by silica gel chromotography using a gradient of 0-60% of 3:1 EtOAc:EtOH in hexanes to afford intermediate G.1, 1-(bicyclo[1.1.1]pentan-1-yl)-1H-pyrazole. MS (ESI) in z calc'd for C$_8$H$_{11}$N$_2$ [M+H]$^+$ 135. found 135.

Step 2—Synthesis of Common Intermediate G.2, 1-(bicyclo[1.1.1]pentan-1-yl)-4-iodo-1H-pyrazole A 30-mL round-bottomed vial was charged with intermediate G.1 (290 mg, 2.161 mmol), acetic acid (10.81 mL), and N-iodosuccinimide (535 mg, 2.377 mmol). The vial was sealed and heated to 80° C. overnight. The reaction was then concentrated under reduced pressure, and the crude oil was directly purified via silica gel column chromotography using a gradient of 0-60% of 3:1 EtOAc:EtOH in hexanes to afford common intermediate G.2, 1-(bicyclo[1.1.1]pentan-1-yl)-4-iodo-1H-pyrazole. MS (ESI) m/z calc'd for C$_8$H$_{10}$IN$_2$ [M+H]$^+$ 261. found 261. $^1$H NMR (600 MHz, DMSO-d$_6$) δ 7.98 (s, 1H), 7.54 (s, 1H), 2.60 (s, 1H), 2.20 (s, 6H).

EXAMPLES

Preparation of Example 1.1, (S)-1-(1-(1-methyl-1H-pyrazol-4-yl)-1H-indazol-6-yl)spiro[2.2]pentane-1-carbonitrile

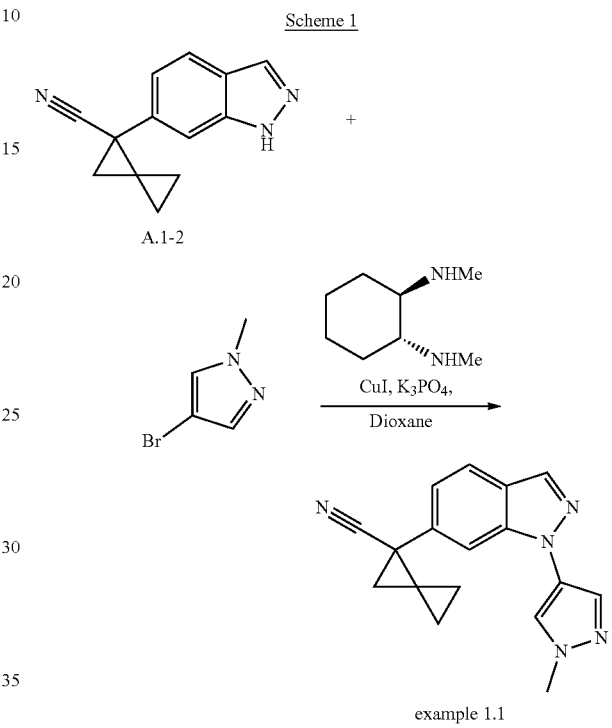

(trans)-N1,N2-dimethylcyclohexane-1,2-diamine (3.77 μl, 0.024 mmol) was added to a stirring solution of intermediate A.1-2 (S)-1-(1H-indazol-6-yl)spiro[2.2]pentane-1-carbonitrile (25 mg, 0.119 mmol), 4-bromo-1-methyl-1H-pyrazole (37.0 μl, 0.358 mmol), CuI (2.3 mg, 0.012 mmol) and potassium phosphate tribasic (76 mg, 0.358 mmol) in dioxane (600 μl). The reaction was sealed and heated overnight at 90° C. Upon completion, saturated aqueous NaHCO$_3$ was added to the cooled reaction and the separated aqueous layer extracted with EtOAc (3×). The combined organic layer was dried over MgSO$_4$, filtered, and concentrated to dryness. The crude residue was purified using reverse phase prep-HPLC (Method A), followed by SFC re-purification (Column: BiPhenyl, 21×250; Modifier: MeOH w/0.25% DMEA; RT (min): 3.6; Instrument: Sepiatec) to afford example 1.1, (S)-1-(1-(1-methyl-1H-pyrazol-4-yl)-1H-indazol-6-yl)spiro[2.2]pentane-1-carbonitrile. MS (ESI) m/z calc'd for C$_{17}$H$_{16}$N$_5$ [M+H]$^+$ 290. found 290. $^1$H NMR (499 MHz, DMSO-d$_6$) δ 8.30 (s, 1H), 8.28 (s, 1H), 7.91 (s, 1H), 7.88 (d, J=8.4 Hz, 1H), 7.52 (s, 1H), 7.14 (d, J=8.4 Hz, 1H), 3.95 (s, 3H), 2.30 (d, J=5.2 Hz, 1H), 2.18 (d, J=5.2 Hz, 1H), 1.26-1.20 (m, 3H), 1.04 (m, 1H). LRRK2 IC$_{50}$ 14.4 nM Compounds in Table 1 below were prepared from common intermediate A.1-2 using the method described in Scheme 1.

TABLE 1

| Example | Structure Name | Observed m/z [M + H]+ | LRRK2 IC50 (nM) |
|---|---|---|---|
| 1.2 | (S)-1-(1-(1-phenyl-1H-pyrazol-4-yl)-1H-indazol-6-yl)spiro[2.2]pentane-1-carbonitrile, TFA salt | 352 | 19.9 |
| 1.3 | (S)-1-(1-(1-(oxetan-3-yl)-1H-pyrazol-4-yl)-1H-indazol-6-yl)spiro[2.2]pentane-1-carbonitrile | 332 | 80.1 |
| 1.4 | (S)-1-(1-(1-phenyl-1H-imidazol-4-yl)-1H-indazol-6-yl)spiro[2.2]pentane-1-carbonitrile, TFA salt | 352 | 12.9 |
| 1.5 | (S)-1-(1-(1-methyl-1H-pyrazol-3-yl)-1H-indazol-6-yl)spiro[2.2]pentane-1-carbonitrile, TFA salt | 290 | 7.4 |

TABLE 1-continued

| Example | Structure Name | Observed m/z [M + H]+ | LRRK2 IC50 (nM) |
|---|---|---|---|
| 1.6 | (S)-1-(1-(5-methyloxazol-2-yl)-1H-indazol-6-yl)spiro[2.2]pentane-1-carbonitrile, TFA salt | 291 | 57.6 |
| 1.7 | (S)-1-(1-(3-methylisothiazol-5-yl)-1H-indazol-6-yl)spiro[2.2]pentane-1-carbonitrile, TFA salt | 307 | 12.2 |
| 1.8 | (S)-1-(1-(2-methylthiazol-4-yl)-1H-indazol-6-yl)spiro[2.2]pentane-1-carbonitrile, TFA salt | 307 | 11.8 |

Preparation of Example 2.1, 5-chloro-1-(1-methyl-1H-pyrazol-4-yl)-6-(1-(oxetan-3-yl)piperidin-4-yl)-1H-indazole Scheme 2

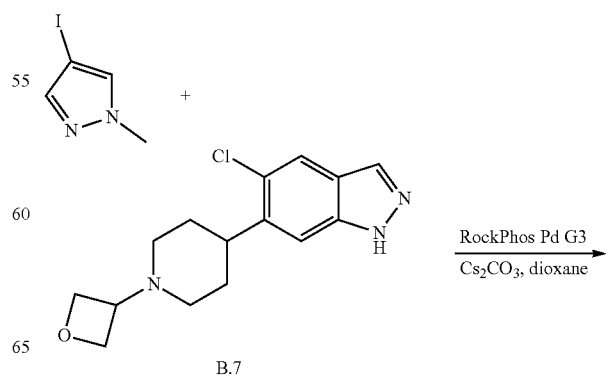

B.7

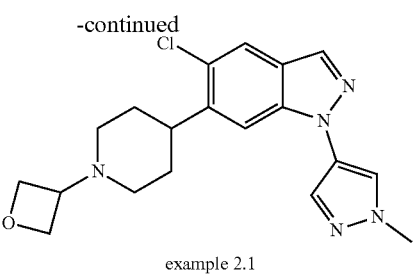

example 2.1

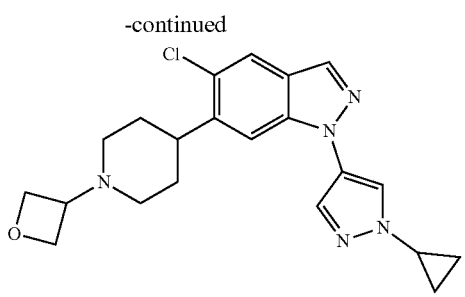

example 2.2

Intermediate B.7 (400 mg, 1.371 mmol), cesium carbonate (1650 mg, 5.06 mmol), 4-iodo-1-methyl-1H-pyrazole (570 mg, 2.74 mmol), and RockPhos Pd G3 (240 mg, 0.286 mmol) were combined in a dry 50 mL microwave vial with a magnetic stir bar. The vial was sealed and purged with nitrogen gas. Then, 1,4-dioxane (12 mL) was added via syringe. The solution was warmed to 105° C. and stirred overnight. The next day, the crude material was cooled to room temperature, filtered through a plug of Celite® (diatomaceous earth) using EtOAc as eluent, and concentrated. The resulting residue was purified by silica gel chromatography (gradient elution of 0-100% of (3:1 EtOAc:EtOH) in hexanes, with 1% triethylamine by volume) to provide example 2.1, 5-chloro-1-(1-methyl-1H-pyrazol-4-yl)-6-(1-(oxetan-3-yl)piperidin-4-yl)-1H-indazole. MS (ESI) m/z calc'd for $C_{19}H_{23}ClN_5O$ [M+H]$^+$ 372. found 372. $^1$H NMR (499 MHz, DMSO-$d_6$) δ 8.41 (s, 1H), 8.22 (s, 1H), 7.96 (s, 1H), 7.91 (s, 1H), 7.58 (s, 1H), 4.62-4.52 (m, 2H), 4.49-4.41 (m, 2H), 3.96 (s, 3H), 3.50-3.39 (m, 1H), 3.09-2.98 (m, 1H), 2.91-2.82 (m, 2H), 2.02-1.74 (m, 6H). LRRK2 IC$_{50}$ 2.4 nM.

Preparation of Example 2.2, 5-chloro-1-(1-cyclopropyl-1H-pyrazol-4-yl)-6-(1-(oxetan-3-yl)piperidin-4-yl)-1H-indazole To a solution of 1-cyclopropyl-4-iodo-1H-pyrazole (64.2 mg, 0.274 mmol) in anhydrous dioxane (5 ml) was added common intermediate B.7 (40 mg, 0.137 mmol), (trans)-N1,N2-dimethylcyclohexane-1,2-diamine (3.90 mg, 0.027 mmol), potassium phosphate (87 mg, 0.411 mmol) and CuI (2.61 mg, 0.014 mmol). The resulting mixture was stirred at 90° C. under N$_2$ protection for 16 hours. LCMS showed the starting material was consumed. After filtration and concentration, the crude product was purified by reverse phase pre-HPLC (TFA) to give example 2.2, 5-chloro-1-(1-cyclopropyl-1H-pyrazol-4-yl)-6-(1-(oxetan-3-yl)piperidin-4-yl)-1H-indazole, TFA salt. MS (ESI) m/z calc'd for $C_{21}H_{25}ClN_5O$ [M+H]$^+$ 378. found 378. $^1$H NMR (400 MHz, CD$_3$OD) δ 8.20 (s, 1H), 8.14 (s, 1H), 7.92 (s, 1H), 7.85 (s, 1H), 7.47 (s, 1H), 4.88-4.90 (m, 5H), 4.35-4.57 (m, 1H), 4.35-4.35 (m, 1H), 3.67-3.85 (m, 1H), 3.45-3.67 (m, 3H), 3.01-3.19 (m, 2H), 2.25 (d, J=13.9 Hz, 2H), 2.01-2.18 (m, 2H), 1.07-1.35 (m, 4H). LRRK2 IC$_{50}$<0.625 nM.

Compounds in Table 2 below were prepared from common intermediate B.7 using the method described in Scheme 2 or Scheme 3.

Scheme 3

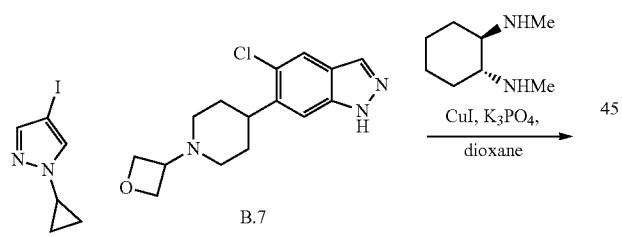

TABLE 2

| Example | Structure Name | Observed m/z [M + H]+ | LRRK2 IC50 (nM) |
|---|---|---|---|
| 2.3 | 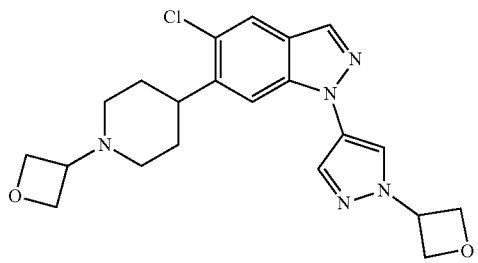 5-chloro-1-(1-(oxetan-3-yl)-1H-pyrazol-4-yl)-6-(1-(oxetan-3-yl)piperidin-4-yl)-1H-indazole, TFA salt | 414 | 5.2 |
| 2.4 | 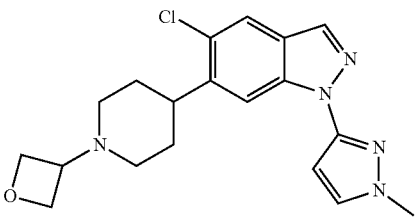 5-chloro-1-(1-methyl-1H-pyrazol-3-yl)-6-(1-(oxetan-3-yl)piperidin-4-yl)-1H-indazole, TFA salt | 372 | 28.9 |
| 2.5 | 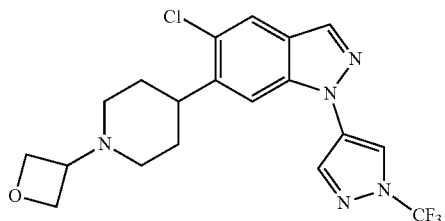 5-chloro-6-(1-(oxetan-3-yl)piperidin-4-yl)-1-(1-(trifluoromethyl)-1H-pyrazol-4-yl)-1H-indazole, TFA salt | 426 | 10.4 |
| 2.6 | 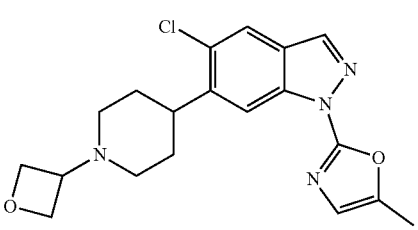 2-(5-chloro-6-(1-(oxetan-3-yl)piperidin-4-yl)-1H-indazol-1-yl)-5-methyloxazole, TFA salt | 373 | 3.7 |
| 2.7 | 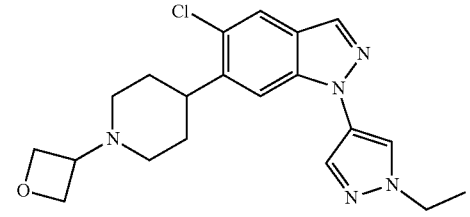 5-chloro-1-(1-ethyl-1H-pyrazol-4-yl)-6-(1-(oxetan-3-yl)piperidin-4-yl)-1H-indazole, TFA salt | 386 | 2.3 |
| 2.8 | 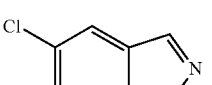 | 412 | 0.9 |

Preparation of Examples 3.2, 5-chloro-1-(1-cyclopropyl-1H-1,2,3-triazol-4-yl)-6-(1-(oxetan-3-yl)piperidin-4-yl)-1H-indazole, and example 3.3, 5-chloro-1-(2-cyclopropyl-2H-1,2,3-triazol-4-yl)-6-(1-(oxetan-3-yl)piperidin-4-yl)-1H-indazole

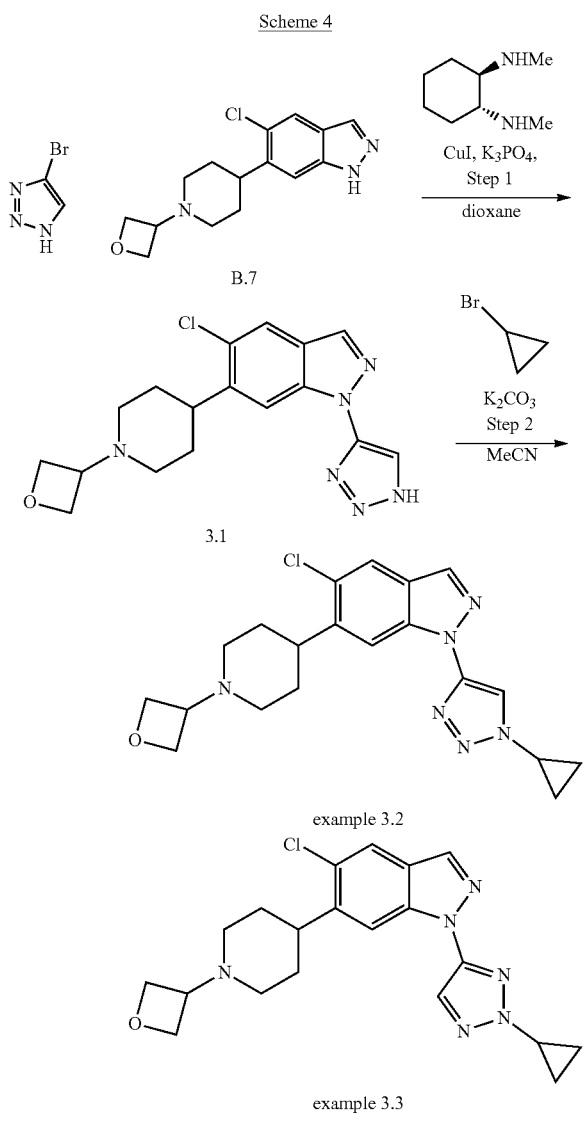

Step 1—Synthesis of Intermediate 3.1, 5-chloro-6-(1-(oxetan-3-yl)piperidin-4-yl)-1-(1H-1,2,3-triazol-4-yl)-1H-indazole To a solution of 4-bromo-1H-1,2,3-triazole (22.82 mg, 0.154 mmol) in anhydrous dioxane (5 ml) was added common intermediate B.7 (30 mg, 0.103 mmol), (trans)-N1,N2-dimethylcyclohexane-1,2-diamine (2.93 mg, 0.021 mmol), potassium phosphate (65.5 mg, 0.308 mmol) and CuI (1.958 mg, 10.28 μmol). The resulting mixture was stirred at 90° C. under $N_2$ protection for 16 hours. After cooling to room temperature, the reaction solution was filtered and concentrated. The crude residue was purified by pre-HPLC (TFA) to intermediate 3.1, give 5-chloro-6-(1-(oxetan-3-yl)piperidin-4-yl)-1-(1H-1,2,3-triazol-4-yl)-1H-indazole, TFA salt. MS (ESI) m/z calc'd for $C_{17}H_{20}ClN_6O$ $[M+H]^+$ 359. found 359.

Step 2—Synthesis of Examples 3.2 5-chloro-1-(1-cyclopropyl-1H-1,2,3-triazol-4-yl)-6-(1-(oxetan-3-yl)piperidin-4-yl)-1H-indazole, and Example 3.3 5-chloro-1-(2-cyclopropyl-2H-1,2,3-triazol-4-yl)-6-(1-(oxetan-3-yl)piperidin-4-yl)-1H-indazole A mixture of 5-chloro-6-(1-(oxetan-3-yl)piperidin-4-yl)-1-(1H-1,2,3-triazol-4-yl)-1H-indazole (30 mg, 0.084 mmol), $K_2CO_3$ (23.11 mg, 0.167 mmol), and bromocyclopropane (40.5 mg, 0.334 mmol) in MeCN (5 ml) was stirred at 80° C. for 4 hours. LCMS showed the starting material was consumed. After filtration and concentration, the crude product was purified by pre-HPLC (TFA) to give example 3.2, 5-chloro-1-(1-cyclopropyltriazol-4-yl)-6-[1-(oxetan-3-yl)piperidin-1-ium-4-yl]indazole, TFA salt, and example 3.3, 5-chloro-1-(2-cyclopropyltriazol-4-yl)-6-[1-(oxetan-3-yl)piperidin-1-ium-4-yl]indazole, TFA salt.

Example 3.2, 5-chloro-1-(1-cyclopropyl-1H-1,2,3-triazol-4-yl)-6-(1-(oxetan-3-yl)piperidin-4-yl)-1H-indazole MS (ESI) m/z calc'd for $C_{20}H_{24}ClN_6O$ $[M+H]^+$ 399. found 399. $^1$H NMR (400 MHz, $CD_3OD$) δ 8.31-8.40 (m, 1H), 8.19-8.31 (m, 2H), 7.92-8.01 (m, 1H), 5.28-5.46 (m, 2H), 5.13 (m, 2H), 4.88-4.98 (m, 5H), 4.37-4.51 (m, 1H), 4.37-4.51 (m, 1H), 4.37-4.51 (m, 1H), 3.54-3.69 (m, 3H), 3.02-3.22 (m, 2H), 2.32 (m, 2H), 2.01-2.19 (m, 2H). LRRK2 $IC_{50}$ 4.3 nM.

Example 3.3, 5-chloro-1-(2-cyclopropyl-2H-1,2,3-triazol-4-yl)-6-(1-(oxetan-3-yl)piperidin-4-yl)-1H-indazole MS (ESI) m/z calc'd for $C_{20}H_{24}ClN_6O$ $[M+H]^+$ 399. found 399. $^1$H NMR (400 MHz, $CD_3OD$) δ 8.30 (s, 1H), 8.21-8.26 (m, 2H), 8.01 (s, 1H), 7.98 (s, 1H), 6.18 (m, 1H), 5.27-5.37 (m, 2H), 5.14 (m, 2H), 4.88-4.99 (m, 5H), 4.43-4.50 (m, 1H), 3.56-3.70 (m, 3H), 3.13 (m, 2H), 2.33 (m, 2H), 1.96-2.23 (m, 3H). LRRK2 $IC_{50}$ 9.1 nM.

Preparation of Example 4.1, 5-chloro-6-(1-(oxetan-3-yl)piperidin-4-yl)-1-(1H-pyrazol-4-yl)-1H-indazole and Example 4.2, 5-chloro-6-(1-(oxetan-3-yl)piperidin-4-yl)-1-(1-(pyrimidin-2-yl)-1H-pyrazol-4-yl)-1H-indazole Scheme 5

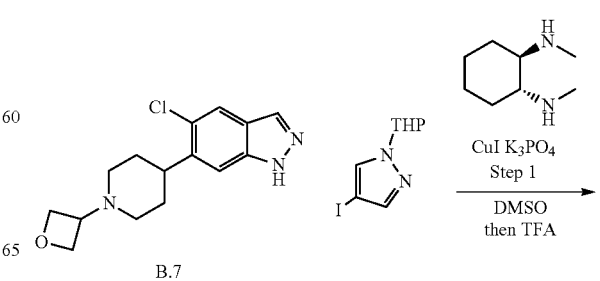

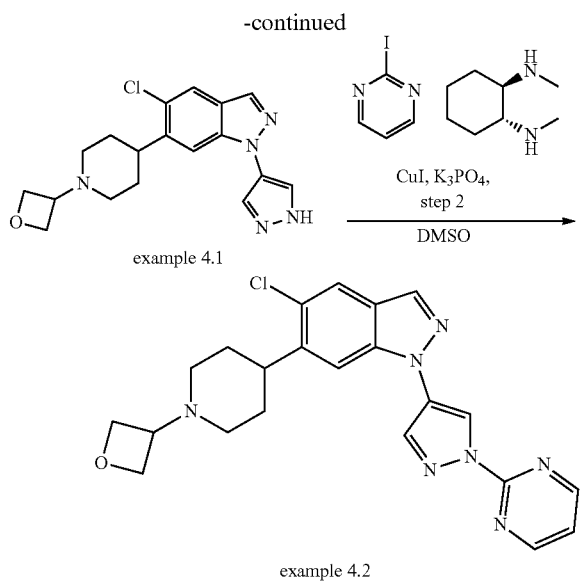

example 4.1 example 4.2

Step 1—Synthesis of Example 4.1, 5-chloro-6-(1-(oxetan-3-yl)piperidin-4-yl)-1-(1H-pyrazol-4-yl)-1H-indazole In an inert atmosphere glovebox, a 20 mL vial with stir bar was charged with copper(I) iodide (38.1 mg, 0.200 mmol) and (trans)-N1,N2-dimethylcyclohexane-1,2-diamine (71.1 mg, 0.500 mmol), which were dissolved in dimethyl sulfoxide (3.33 mL) and stirred for 5 min to form a pale blue solution. A 30 mL microwave vial was then charged with potassium phosphate (637 mg, 3.00 mmol), common intermediate B.7 (292 mg, 1 mmol) and 4-iodo-1-(tetrahydro-2H-pyran-2-yl)-1H-pyrazole (417 mg, 1.500 mmol), and the dimethyl sulfoxide catalyst solution was then added to this vial, which was then sealed, removed from the glovebox and heated to 70° C. After 14 hours, the vial was cooled, diluted with 10 mL water and 10 mL ethyl acetate, poured into a separatory funnel, the layers separated, and the aqueous layer extracted twice with 30 mL portions ethyl acetate. The organics were then combined, dried over sodium sulfate, and condensed. The crude material was purified by silica gel column chromatography (gradient elution of 0-60% (3:1 EtOAc:EtOH)/hexanes) to provide 5-chloro-6-(1-(oxetan-3-yl)piperidin-4-yl)-1-(1-(tetrahydro-2H-pyran-2-yl)-1H-pyrazol-4-yl)-1H-indazole. This material was then dissolved in dichloromethane (3.60 mL) and cooled to 0° C. with stirring. Trifluoroacetic acid (0.554 ml, 7.20 mmol) was then added drop wise and the resulting reaction gradually warmed to room temperature overnight. After 14 hours, additional trifluoroacetic acid (0.554 mL, 7.20 mmol) was added, and the reaction stirred an additional 2 hours. The crude reaction was then diluted with 10 mL dichloromethane and 10 mL water, and the aqueous layer carefully neutralized with saturated sodium bicarbonate. The layers were poured into a separatory funnel and extracted 3× with 10 mL portions of dichloromethane. The organics were combined, dried over sodium sulfate, filtered and condensed. The crude material was purified by silica gel column chromatography (gradient elution of 0-100% (3:1 EtOAc:EtOH)/hexanes), and the resulting solid obtained was slurried in 30 mL hexanes, filtered and dried under vacuum to give example 4.1, 5-chloro-6-(1-(oxetan-3-yl)piperidin-4-yl)-1-(1H-pyrazol-4-yl)-1H-indazole. MS (ESI) m/z calc'd for $C_{16}H_{18}ClN_5$ [M+H]$^+$ 316. found 316. $^1$H NMR (499 MHz, DMSO-d$_6$) δ 8.43 (s, 1H), 8.29-8.12 (m, 1H), 7.97 (d, J=6.1 Hz, 2H), 7.57 (s, 1H), 4.56 (t, J=6.5 Hz, 2H), 4.45 (t, J=6.1 Hz, 2H), 3.44 (p, J=6.8 Hz, 1H), 3.10-2.94 (m, 1H), 2.85 (d, J=11.0 Hz, 2H), 2.07-1.67 (m, 6H). LRRK2 IC$_{50}$ 1.4 nM.

Step 2—Synthesis of Example 4.2, 5-chloro-6-(1-(oxetan-3-yl)piperidin-4-yl)-1-(1-(pyrimidin-2-yl)-1H-pyrazol-4-yl)-1H-indazole Compound example 4.1 (20 mg, 0.056 mmol), copper(I) iodide (3.2 mg, 0.017 mmol), potassium phosphate (35.6 mg, 0.168 mmol), (trans)-N1,N2-dimethylcyclohexane-1,2-diamine (4.4 μl, 0.028 mmol), and 2-iodopyrimidine (17.27 mg, 0.084 mmol) in DMSO (0.5 mL) were heated to 90° C. for 2 hours under an atmosphere of nitrogen. The mixture was cooled, diluted with water (5 mL) and extracted with EtOAc (3×5 mL). The combined organic fractions were washed with brine (10 mL), dried over MgSO$_4$, filtered, and concentrated. The residue was filtered and purified by reverse phase prep-HPLC (Method A) to afford example 4.2, 5-chloro-6-(1-(oxetan-3-yl)piperidin-4-yl)-1-(1-(pyrimidin-2-yl)-1H-pyrazol-4-yl)-1H-indazole, TFA salt. MS (ESI) m/z calc'd for $C_{22}H_{23}ClN_7O$ [M+H]$^+$ 436. found 436. $^1$H NMR (499 MHz, DMSO-d$_6$) δ 10.49 (s, 1H), 9.15 (s, 1H), 8.96 (d, J=4.8 Hz, 2H), 8.42 (s, 1H), 8.38 (s, 1H), 8.09 (s, 1H), 7.65-7.49 (m, 2H), 4.78 (m, 4H), 4.40 (m, 1H), 3.61-3.33 (m, 3H), 3.08 (s, 2H), 2.26-1.98 (m, 4H). LRRK2 IC$_{50}$<0.625 nM.

Preparation of Example 5.1, 4-(5-chloro-6-(1-(oxetan-3-yl)piperidin-4-yl)-1H-indazol-1-yl)-N-methyl-1H-pyrazole-1-carboxamide Scheme 6

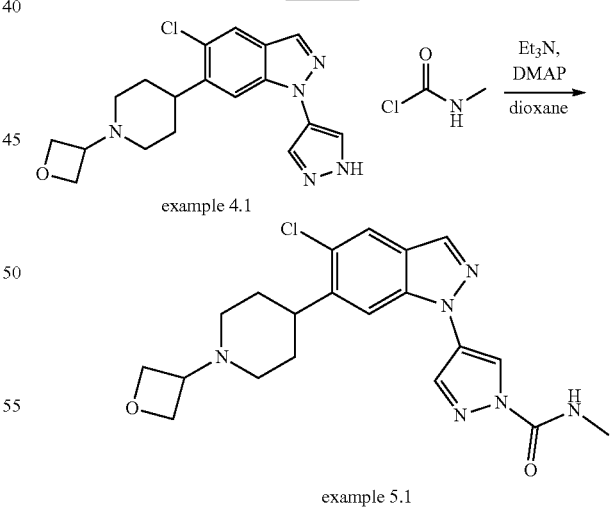

example 4.1 example 5.1

To a stirred solution of compound example 4.1 (22 mg, 0.061 mmol), 4-dimethylaminopyridine (4 mg, 0.033 mmol), and methylcarbamic chloride (11.50 mg, 0.123 mmol), dioxane (0.5 ml) and triethylamine (25 μl, 0.179 mmol) were added. The reaction was stirred at 40° C. for 3 hours. A few drops of saturated aqueous NaHCO$_3$ was added and the reaction was diluted with DMSO and filtered. The reaction mixture was purified by reverse phase prep-HPLC (Method A) to afford example 5.1, 4-(5-chloro-6-(1-(oxetan-3-yl)piperidin-4-yl)-1H-indazol-1-yl)-N-methyl-1H-pyrazole-1-carboxamide, TFA salt. MS (ESI) in z calc'd for $C_{20}H_{24}ClN_6O_2$ [M+H]$^+$ 415. found 415. $^1$HNMR (499 MHz, DMSO-$d_6$) δ 10.45 (s, 1H), 8.83 (s, 1H), 8.64 (m, 1H), 8.34 (s, 1H), 8.29 (s, 1H), 8.06 (s, 1H), 7.52 (s, 1H), 4.76 (m, 4H), 4.40 (m, 1H), 3.66-3.45 (m, 3H), 3.08 (m, 2H), 2.87 (d, J=4.7 Hz, 3H), 2.27-1.92 (m, 4H). LRRK2 IC$_{50}$ 0.9 nM.

Compounds in Table 3 below were prepared from compound example 4.1 using the method described in Scheme 6.

5-methyl-1-(1-methyl-1H-pyrazol-4-yl)-6-(1-(oxetan-3-yl)piperidin-4-yl)-1H-indazole. MS (ESI) in z calc'd for $C_{20}H_{26}N_5O$ [M+H]$^+$ 351. found 351. $^1$H-NMR (500 MHz, CDCl$_3$) δ 8.00 (s, 1H), 7.82 (s, 1H), 7.73 (s, 1H), 7.53 (s, 1H), 7.42 (s, 1H), 4.66-4.71 (m, 4H), 4.02 (s, 3H), 3.51-3.57 (m, 1H), 2.92 (m, 2H), 2.85 (m, 1H), 2.45 (s, 3H), 1.97-2.02 (m, 2H), 1.87 (m, 4H). LRRK2 IC$_{50}$ 1.1 nM.

TABLE 3

| Example | Structure Name | Observed m/z [M + H]$^+$ | LRRK2 IC$_{50}$ (nM) |
| --- | --- | --- | --- |
| 5.2 | methyl 4-(5-chloro-6-(1-(oxetan-3-yl)piperidin-4-yl)-1H-indazol-1-yl)-1H-pyrazole-1-carboxylate, TFA salt | 416 | 1.4 |

Preparation of Example 6.1, 5-methyl-1-(1-methyl-1H-pyrazol-4-yl)-6-(1-(oxetan-3-yl)piperidin-4-yl)-1H-indazole Preparation of Example 7.1, 5-chloro-1-(1-methyl-1H-pyrazol-4-yl)-6-(1-(3-methyloxetan-3-yl)piperidin-4-yl)-1H-indazole

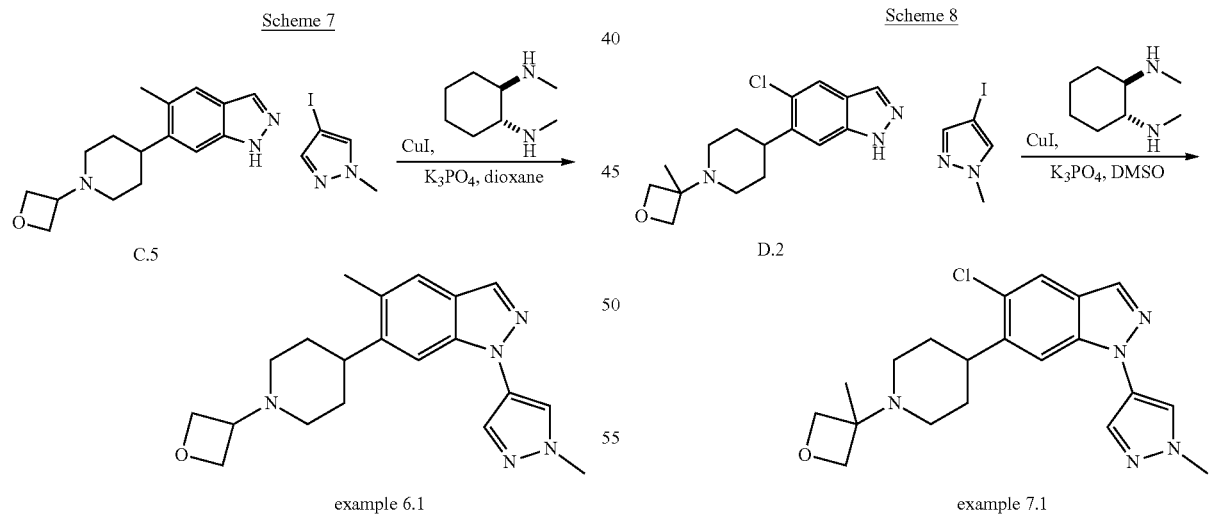

To a solution of 3-iodo-1-methyl-1H-pyrazole (20 mg, 0.096 mmol) and intermediate C.5 (20 mg, 0.074 mmol) in anhydrous 1,4-Dioxane (1 ml) was added (trans)-N1,N2-dimethylcyclohexane-1,2-diamine (5 mg, 0.035 mmol), CuI (5 mg, 0.026 mmol) and K$_3$PO$_4$ (50 mg, 0.236 mmol). The resulting mixture was stirred at 90° C. for 16 hours. After filtering and concentrating the reaction solution, the residue was purified by prep-HPLC (basic) to afford example 6.1, To a solution of 4-iodo-1-methyl-1H-pyrazole (10.20 mg, 0.049 mmol) in anhydrous DMSO (5 ml) was added common intermediate D.2 (10 mg, 0.033 mmol), (trans)-N1,N2-dimethylcyclohexane-1,2-diamine (0.930 mg, 6.54 µmol), potassium phosphate (20.82 mg, 0.098 mmol) and CuI (0.623 mg, 3.27 µmol). The resulting mixture was stirred at 90° C. under N$_2$ atmosphere for 12 hours. LCMS showed the starting material was consumed. After filtration and concentration, the crude product was purified by pre-HPLC (TFA) to give example 7.1, 5-chloro-1-(1-methyl-1H-pyrazol-4-yl)-6-(1-(3-methyloxetan-3-yl)piperidin-4-yl)-1H-indazole, TFA salt. MS (ESI) m/z calc'd for $C_{20}H_{25}ClN_5O$ [M+H]$^+$ 386. found 386. $^1$H NMR (400 MHz, CD$_3$OD) δ 8.15 (s, 1H), 8.13 (s, 1H), 7.94 (s, 1H), 7.86 (s, 1H), 7.50 (s, 1H), 4.92 (m, 3H), 4.49 (d, J=7.83 Hz, 2H), 4.01 (s, 3H), 3.52-3.66 (m, 1H), 3.38-3.48 (m, 3H), 3.33 (br s, 1H), 2.30 (m, 2H), 2.08-2.18 (m, 2H), 1.79 (s, 3H). LRRK2 IC$_{50}$ 1.4 nM.

Preparation of Example 7.2-5, 5-chloro-1-(1-(3-(methoxymethyl)bicyclo[1.1.1]pentan-1-yl)-1H-pyrazol-4-yl)-6-(1-(3-methyloxetan-3-yl)piperidin-4-yl)-1H-indazole

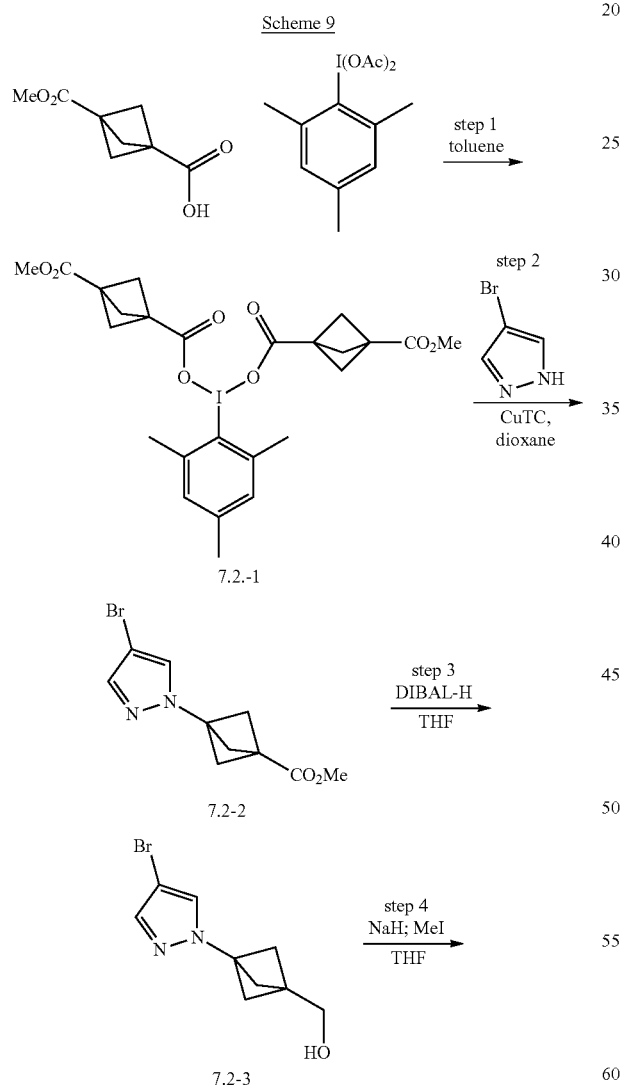

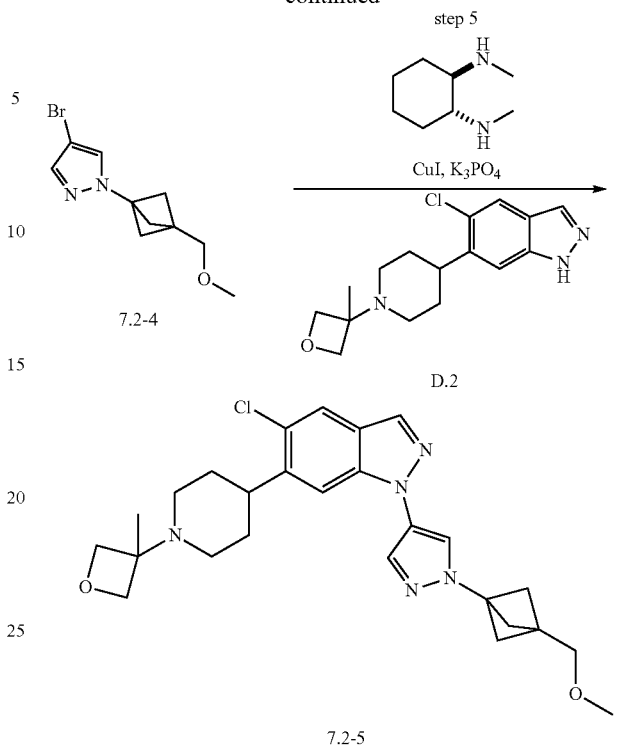

Step 1—Synthesis of Intermediate 7.2-1, O$^{r1}$,O$^1$-(mesityl-λ$^3$-iodanediyl) 3,3'-dimethyl bis(bicyclo[1.1.1]pentane-1,3-dicarboxylate)

A 500 mL round-bottom flask was charged with iodomesitylene diacetate (2.86 g, 7.80 mmol), 3-(methoxycarbonyl)bicyclo[1.1.1]pentane-1-carboxylic acid (2.86 g, 16.22 mmol), and 150 mL toluene. The flask was attached to a rotary evaporator with the water bath heated to 55° C. and the solvent (and the generated acetic acid) was removed over a time period of ~20 min. A second 100 mL aliquot of toluene was added to the flask and the evaporation step was repeated. Repeat the evaporation step for two more times with 50 mL toluene each time. After further removal of residual toluene under high-vac, intermediate 7.2-1, O$^{r1}$,O$^1$-(mesityl-λ$^3$-iodanediyl) 3,3'-dimethyl bis(bicyclo[1.1.1]pentane-1,3-dicarboxylate) was acquired. $^1$HNMR: (500 mHz, CDCl3): δ 7.10 (s, 2H), 3.68 (s, 6H), 2.70 (s, 6H), 2.39 (s, 3H), 2.20 (s, 12H).

Step 2—Synthesis of Intermediate 7.2-2, methyl 3-(4-bromo-1H-pyrazol-1-yl)bicyclo[1.1.1]pentane-1-carboxylate To a solution of 4-bromo-1H-pyrazole (1.0 g, 2.69 mmol), 4,7-diphenyl-1,10-phenanthroline (805 mg, 2.42 mmol), and intermediate 7.2-1 (3.0 g, 5.35 mmol) in anhydrous 1,4-dioxane (25 mL) in a 40 mL scintillation vial was added CuTC (307.5 mg, 1.52 mmol) with no extrogenous base (reaction done in nitrogen glovebox). The dark brown reaction mixture was then stirred at room temperature for 2 hrs. The mixture change to a clear greenish-blue mixture. The reaction was taken out of the glovebox and opened to air for 15 minutes. The material was then transferred to a 100 mL round bottom flask and concentrated to dryness under reduced pressure. The residue was taken up with DCM (5 mL) and purification was via silica gel column chromotography using a gradient eluant of 0-30% ethyl acetate in hexane to afford intermediate 7.2-2, methyl 3-(4-bromo-1H-pyrazol-1-yl)bicyclo[1.1.1]pentane-1-carboxylate. MS (ESI) m/z calc'd for $C_{10}H_{12}ClN_2O_2$ [M+H]$^+$ 271. found 271.

Step 3—Synthesis of Intermediate 7.2-3, (3-(4-bromo-1H-pyrazol-1-yl)bicyclo[1.1.1]pentan-1-yl) methanol To a solution of intermediate 7.2-2 (325 mg, 1.20 mmol) in anhydrous THF (3.75 mL) cooled to 0° C. via ice/water bath was added via syringe 1.0 M DiBAL-H in hexane (3.60 mL, 3.60 mmol) and the resulting solution stirred at 0° C. for 2 hrs. LCMS proved all starting material was consumed. The reaction was quenched by slowly pouring it into aqueous NH$_4$Cl solution (10 mL) and allowed to stir vigorously at room temperature. A slurry forms and the material is then filtered thru celite removing all the aluminum by-products. The organic was then separated and dried over sodium sulfate, filtered, and concentrated to dryness under reduced pressure. The residue was taken up in into 1 mL of DCM and purified via silica gel column chromatography using a gradient eluant of 0-80% ethyl acetate in hexane to afford intermediate 7.2-3, (3-(4-bromo-1H-pyrazol-1-yl)bicyclo[1.1.1]pentan-1-yl)methanol. MS (ESI) m/z calc'd for $C_9H_{12}ClN_2O$ [M+H]$^+$ 243. found 243.

Step 4—Synthesis of Intermediate 7.2-4, 4-bromo-1-(3-(methoxymethyl)bicyclo[1.1.1]pentan-1-yl)-1H-pyrazole To a solution of intermediate 7.2-3 (280 mg, 1.15 mmol) in anhydrous THF (5.5 mL) cooled to 0° C. via ice/water bath was added, in portions over 5 minutes, NaH (55.3 mg, 1.38 mmol) and the resulting solution stirred for 30 minutes at 0° C. Iodomethane (0.14 mL, 2.30 mmol) was then added via syringe dropwise and the solution stirred for an additional 2 hrs allowing to warm to room temperature. LCMS of the reaction proved that the major peak present was product. The reaction was quenched with aqueous ammonium chloride (5 mL) and diluted with ethyl acetate (5 mL). The organic was separated, dried over sodium sulfate, filtered and the filtrate concentrated to dryness under reduced pressure. The residue was taken up into 10 mL DCM and purified by silica gel column chromatography using a gradient eluant of 0-50% ethyl acetate in hexane to afford intermediate 7.2-4, 4-bromo-1-(3-(methoxymethyl)bicyclo[1.1.1]pentan-1-yl)-1H-pyrazole. MS (ESI) m/z calc'd for $C_{10}H_{14}ClN_2O$ [M+H]$^+$ 257. found 257.

Step 5—Synthesis of Example 7.2-5, 5-chloro-1-(1-(3-(methoxymethyl)bicyclo[1.1.1]pentan-1-yl)-1H-pyrazol-4-yl)-6-(1-(3-methyloxetan-3-yl)piperidin-4-yl)-1H-indazole A 2-5 mL microwave vial with small magnetic stirrer was charged with (in order) common intermediate D.2 (80 mg, 0.262 mmol), CuI (5 mg, 0.026 mmol), potassium phosphate tri-basic (167 mg, 0.785 mmol) and tram-N1,N2-dimethylcyclohexane-1,2-diamine (7.44 mg, 0.052 mmol) and then was capped. The material was set under nitrogen (3× vacuum follow by N2) and then intermediate 7.2-4 (81 mg, 0.314 mmol) in 2.5 mL of anhydrous dioxane was added via syringe to the dry solids. The reaction was purged again (2× vacuum followed by N2) and then heated to 110° C. and stirred overnight. LCMS proved the reaction was complete with all starting material consumed. The reaction was filtered off and the solids washed with ethyl acetate (10 mL). The solvent was removed under reduced pressure and the residue taken up into 1.5 mL DCM. Purification was done via silica gel column chromatography with a gradient eluent of 0-100% 3:1 ethyl acetate:ethanol in hexane. The tubes containing the product were combined and the solvent removed under reduced pressure. The residue was then taken up into 1 mL acetonitrile and 0.4 mL water. The solution was passed thru a syringe filter and collected into an 1 dram pre-tared, labeled vial. The material was frozen via dry ice/acetone bath and placed onto the Lyophilizer overnight to afford example 7.2-5, 5-chloro-1-(1-(3-(methoxymethyl)bicyclo[1.1.1]pentan-1-yl)-1H-pyrazol-4-yl)-6-(1-(3-methyloxetan-3-yl)piperidin-4-yl)-1H-indazole. MS (ESI) m/z calc'd for $C_{26}H_{33}ClN_5O_2$ [M+H]$^+$ 482. found 482. $^1$HNMR: (500 mHz, DMSO-d6): δ 8.42 (s, 1H), 8.23 (s, 1H), 8.03 (s, 1H), 7.97 (s, 1H), 7.56 (s, 1H), 4.44 (d, J=5.4 Hz, 2H), 4.15 (d, J=5.5 Hz, 2H), 3.57 (s, 2H), 3.32 (s, 6H), 3.04-2.96 (m, 1H), 2.66 (d, J=11.0 Hz, 2H), 2.25 (s, 3H), 2.21 (d, J=10.6 Hz, 2H), 1.84 (s, 3H), 1.79 (d, J=11.4 Hz, 1H), 1.32 (s, 3H). LRRK2 IC$_{50}$<0.625 nM Compounds in Table 4 below were prepared from common intermediate D.2 using the method described in Schemes 8 or 9.

TABLE 4

| Example | Structure Name | Observed m/z [M + H]$^+$ | LRRK2 IC$_{50}$ (nM) |
|---|---|---|---|
| 7.3 | 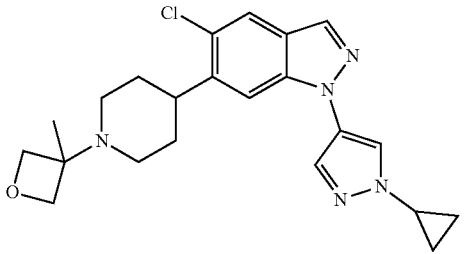 [SMILES: CC1(N2CCC(c3cc4c(cnn4-c4cnn(C5CC5)c4)cc3C#N)CC2)COC1]<br>5-chloro-1-(1-cyclopropyl-1H-pyrazol-4-yl)-6-(1-(3-methyloxetan-3-yl)piperidin-4-yl)-1H-indazole | 412 | 1.6 |

TABLE 4-continued

| Example | Structure Name | Observed m/z [M + H]+ | LRRK2 IC50 (nM) |
|---|---|---|---|
| 7.4 | 5-chloro-1-(1-ethyl-1H-pyrazol-4-yl)-6-(1-(3-methyloxetan-3-yl)piperidin-4-yl)-1H-indazole | 400 | 0.8 |
| 7.5 | 5-chloro-1-(1-(difluoromethyl)-1H-pyrazol-4-yl)-6-(1-(3-methyloxetan-3-yl)piperidin-4-yl)-1H-indazole | 422 | 10.1 |
| 7.6 | 2-(5-chloro-6-(1-(3-methyloxetan-3-yl)piperidin-4-yl)-1H-indazol-1-yl)-5-methyloxazole, TFA salt | 387 | 5.7 |
| 7.7 | 5-chloro-1-(1-(1-methylcyclopropyl)-1H-pyrazol-4-yl)-6-(1-(3-methyloxetan-3-yl)piperidin-4-yl)-1H-indazole | 426 | 11.4 |
| 7.8 | | 388 | 7.1 |

Preparation of Example 8.1, 4-(5-chloro-6-(1-(3-methyloxetan-3-yl)piperidin-4-yl)-1H-indazol-1-yl)-N-methyl-1H-pyrazole-1-carboxamide Scheme 10

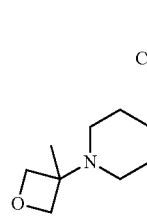

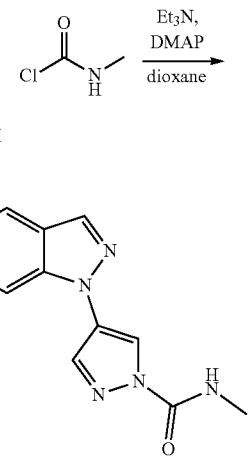

example 8.1

To a one dram vial containing common intermediate E.2 (15 mg, 0.040 mmol), 4-dimethylaminopyridine (4 mg, 0.033 mmol), and methylcarbamic chloride (7.54 mg, 0.081 mmol), dioxane (0.5 ml) and triethylamine (20 µl, 0.143 mmol) were added. The reaction was stirred at room temperature for 2 hours and then at 40° C. for an additional hour. A few drops of saturated aqueous NaHCO₃ was added and the reaction was diluted with DMSO and filtered. The reaction mixture was purified by reverse phase prep-HPLC (Method A) to obtain example 8.1, 4-(5-chloro-6-(1-(3-methyloxetan-3-yl)piperidin-4-yl)-1H-indazol-1-yl)-N-methyl-1H-pyrazole-1-carboxamide, TFA salt. MS (ESI) in z calc'd for $C_{21}H_{26}ClN_6O_2$ [M+H]⁺ 429. found 429. ¹H NMR (499 MHz, DMSO-d₆) δ 10.44 (s, 1H), 8.82 (s, 1H), 8.67 (q, J=4.7 Hz, 1H), 8.35 (s, 1H), 8.29 (s, 1H), 8.07 (s, 1H), 7.52 (s, 1H), 4.84 (d, J=7.5 Hz, 2H), 4.41 (d, J=7.5 Hz, 2H), 3.50 (m, 2H), 3.46-3.15 (m, 4H), 2.88 (d, J=4.7 Hz, 3H), 2.11 (m, 4H), 1.67 (s, 3H). LRRK2 IC₅₀ 2.9 nM

Preparation of Example 8.2, 4-(5-chloro-6-(1-(3-methyloxetan-3-yl)piperidin-4-yl)-1H-indazol-1-yl)-N-ethyl-1H-pyrazole-1-carboxamide Scheme 11

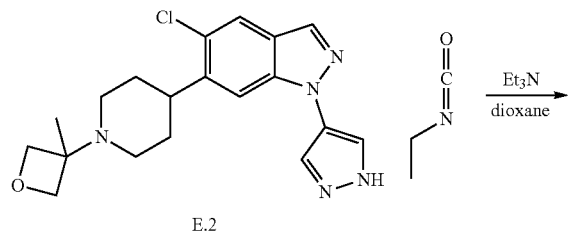

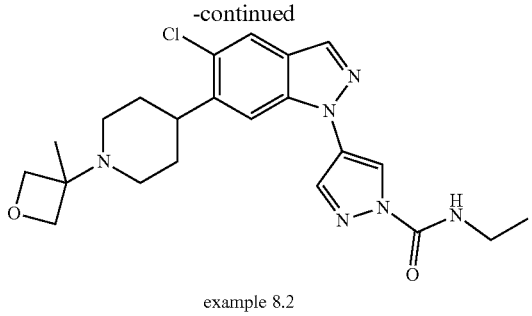

example 8.2

To a one dram vial containing common intermediate E.2 (20 mg, 0.054 mmol) isocyanoethane (30 mg, 0.422 mmol), dioxane (0.4 ml) and triethylamine (0.1 mL, 0.717 mmol)) were added. The reaction was stirred at room temperature for 30 minutes. A few drops of saturated aqueous NaHCO₃ was added and the reaction was diluted with DMSO and filtered. The reaction mixture was purified by reverse phase prep-HPLC (Method A) to obtain example 8.2, 4-(5-chloro-6-(1-(3-methyloxetan-3-yl)piperidin-4-yl)-1H-indazol-1-yl)-N-ethyl-1H-pyrazole-1-carboxamide, TFA salt. MS (ESI) m/z calc'd for $C_{22}H_{28}ClN_6O_2$ [M+H]⁺ 443. found 443. ¹H NMR (499 MHz, DMSO-d₆) δ 10.43 (s, 1H), 8.82 (s, 1H), 8.78 (t, J=5.9 Hz, 1H), 8.35 (s, 1H), 8.28 (s, 1H), 8.07 (s, 1H), 7.51 (s, 1H), 4.84 (d, J=7.6 Hz, 2H), 4.40 (d, J=7.6 Hz, 2H), 3.50 (m, 1H), 3.38-3.30 (m, 4H), 3.24 (m, 2H), 2.09 (m, 4H), 1.67 (s, 3H), 1.17 (t, J=7.2 Hz, 3H). LRRK2 IC₅₀ 4.6 nM.

Preparation of Example 9.1, 5-chloro-1-(1-(cyclopropylsulfonyl)-1H-pyrazol-4-yl)-6-(1-(3-methyloxetan-3-yl)piperidin-4-yl)-1H-indazole Scheme 12

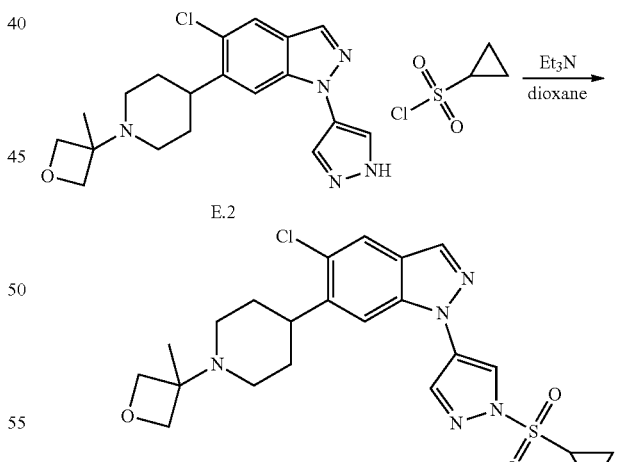

example 9.1

To a one dram vial containing common intermediate E.2 (19 mg, 0.050 mmol) and cyclopropanesulfonyl chloride (31 mg, 0.22 mmol), a solution of triethylamine in dioxane (0.8 mL, 0.4 M) was added. The reaction was stirred at 40° C. for 3 hours. A few drops of saturated aqueous NaHCO₃ was added and the reaction was diluted with DMSO and filtered. The reaction mixture was purified by reverse phase prep- HPLC (Method A) to afford example 9.1, 5-chloro-1-(1-(cyclopropylsulfonyl)-1H-pyrazol-4-yl)-6-(1-(3-methyloxetan-3-yl)piperidin-4-yl)-1H-indazole, TFA salt. MS (ESI) m/z calc'd for $C_{22}H_{27}ClN_5SO_3$ [M+H]$^+$ 476. found 476. $^1$H NMR (499 MHz, DMSO-d$_6$) δ 8.89 (s, 1H), 8.52 (s, 1H), 8.37 (s, 1H), 8.07 (s, 1H), 7.53 (s, 1H), 4.79 (m, 2H), 4.40 (m, 2H), 3.32-3.96 (m, 3H), 2.15-2.00 (m, 5H), 1.65 (s, 3H), 1.45-1.20 (m, 6H). LRRK2 IC$_{50}$ 2.7 nM.

Preparation of Example 10.1, 5-chloro-6-(1-(3-methyloxetan-3-yl)piperidin-4-yl)-1-(1-(pyrimidin-2-yl)-1H-pyrazol-4-yl)-1H-indazole

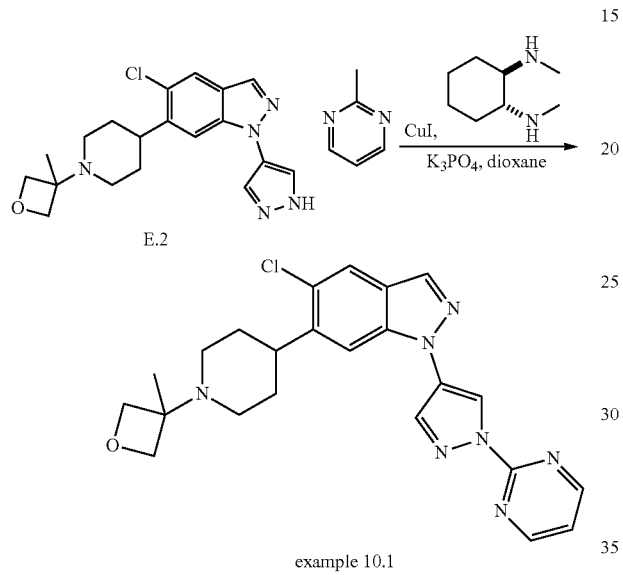

example 10.1

Common intermediate E.2 (80 mg, 0.215 mmol), copper (I) iodide (12.3 mg, 0.065 mmol), potassium phosphate (137 mg, 0.645 mmol), (trans)-N1,N2-dimethylcyclohexane-1,2-diamine (0.017 mL, 0.108 mmol), and 2-iodopyrimidine (66.5 mg, 0.323 mmol) in DMSO (2 mL) were heated to 90° C. for 1 hour under an atmosphere of nitrogen. The mixture was cooled, diluted with water (5 mL) and extracted with EtOAc (3×5 mL). The combined organic fractions were washed with brine (10 mL), dried over MgSO$_4$, filtered, and concentrated. The reaction mixture was purified via silica gel column chromatography (gradient elution of 0% to 100% (3:1 EtOAC/EtOH) in DCM). The product was further purified by reverse phase prep HPLC (Method A). The resulting salt was neutralized using saturated aqueous NaHCO$_3$ (pH>7 was obtained) and extracted 4× with 3:1 CHCl$_3$:iPrOH (20 mL). The combined organic layers were dried over Na$_2$SO$_4$, filtered, and concentrated to provide example 10.1, 5-chloro-6-(1-(3-methyloxetan-3-yl)piperidin-4-yl)-1-(1-(pyrimidin-2-yl)-1H-pyrazol-4-yl)-1H-indazole. MS (ESI) in z calc'd for $C_{23}H_{25}ClN_7O$ [M+H]$^+$ 450. found 450. $^1$H NMR (499 MHz, DMSO-d$_6$) δ 9.26 (s, 1H), 8.97 (d, J=4.8 Hz, 2H), 8.44 (s, 1H), 8.33 (s, 1H), 8.01 (s, 1H), 7.76 (s, 1H), 7.57 (t, J=4.8 Hz, 1H), 4.44 (d, J=5.6 Hz, 2H), 4.15 (d, J=5.6 Hz, 2H), 3.03 (m, 1H), 2.67 (m, 2H), 2.23 (m, 2H), 1.96-1.80 (m, 4H), 1.32 (s, 3H). LRRK2 IC$_{50}$<0.625 nM.

Preparation of Example 11.1, 5-chloro-1-(1-(2,2-difluoroethyl)-1H-pyrazol-4-yl)-6-(1-(3-methyloxetan-3-yl)piperidin-4-yl)-1H-indazole Scheme 14

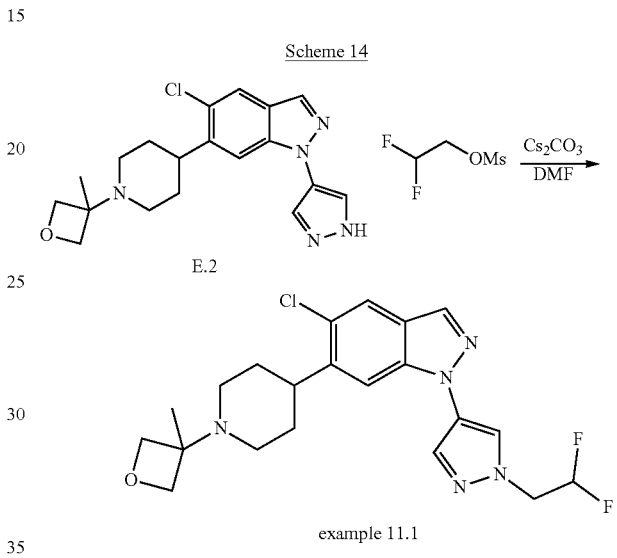

example 11.1

Common intermediate E.2 (25 mg, 0.067 mmol) and cesium carbonate (77 mg, 0.235 mmol) were solvated in DMF (1.0 mL) in a dry 1 dram vial with stir bar. Then, 2,2-difluoroethyl methanesulfonate (21.53 mg, 0.134 mmol) was added. The reaction was warmed to 80° C. and stirred for 2 hours. Aftward, the reaction was cooled, diluted with DMSO, and filtered. The crude residue was purified by reverse phase prep-HPLC (Method A) to afford example 11.1, 5-chloro-1-(1-(2,2-difluoroethyl)-1H-pyrazol-4-yl)-6-(1-(3-methyloxetan-3-yl)piperidin-4-yl)-1H-indazole, TFA salt. MS (ESI) m/z calc'd for $C_{21}H_{25}ClF_2N_5O$ [M+H]$^+$ 436. found 436. $^1$H NMR (499 MHz, DMSO-d$_6$) δ 10.47 (s, 1H), 8.41 (s, 1H), 8.29 (s, 1H), 8.07 (s, 1H), 8.05 (s, 1H), 7.48 (s, 1H), 6.60-6.35 (m, 1H), 4.89-4.80 (m, 2H), 4.80-4.71 (m, 2H), 4.44-4.37 (m, 2H), 3.49 (s, 1H), 3.38-3.18 (m, 4H), 2.10 (s, 4H), 1.67 (s, 3H). LRRK2 IC$_{50}$ 3.4 nM.

Compounds in Table 5 below were prepared from common intermediate E.2 using the method

TABLE 5

| Example | Structure Name | Observed m/z [M + H]+ | LRRK2 IC$_{50}$ (nM) |
|---|---|---|---|
| 11.2 | 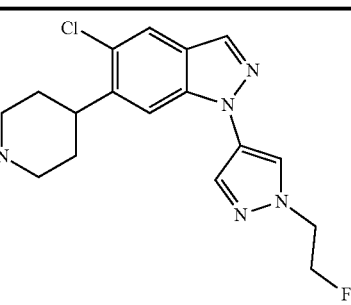<br>5-chloro-1-(1-(2-fluoroethyl)-1H-pyrazol-4-yl)-6-(1-(3-methyloxetan-3-yl)piperidin-4-yl)-1H-indazole, TFA salt | 418 | 0.9 |
| 11.3 | 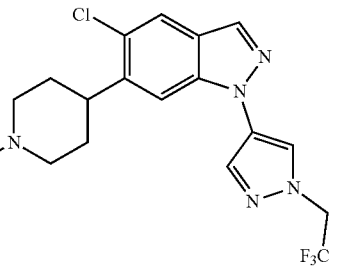<br>5-chloro-6-(1-(3-methyloxetan-3-yl)piperidin-4-yl)-1-(1-(2,2,2-trifluoroethyl)-1H-pyrazol-4-yl)-1H-indazole, TFA salt | 454 | 1.3 |
| 11.4 | 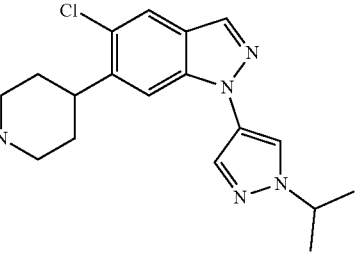<br>5-chloro-1-(1-isopropyl-1H-pyrazol-4-yl)-6-(1-(3-methyloxetan-3-yl)piperidin-4-yl)-1H-indazole, TFA salt | 414 | 0.9 |
| 11.5 | 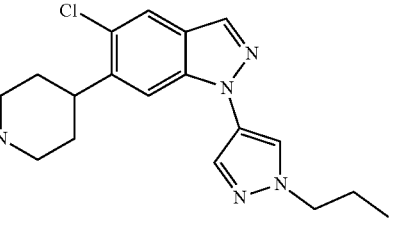<br>5-chloro-6-(1-(3-methyloxetan-3-yl)piperidin-4-yl)-1-(1-propyl-1H-pyrazol-4-yl)-1H-indazole, TFA salt | 414 | 3.3 |

Preparation of Example 12.1, 1-(1-methyl-1H-pyrazol-4-yl)-6-(1-(3-methyloxetan-3-yl)piperidin-4-yl)-1H-indazole-5-carbonitrile

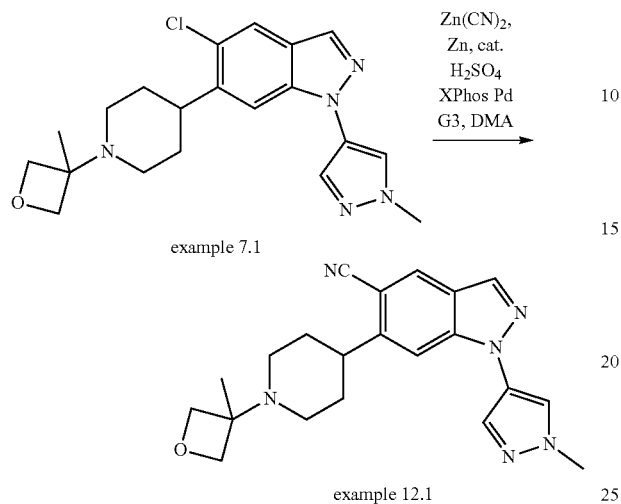

example 7.1 example 12.1

XPhos Pd G3 precatalyst (9.6 µmol) was added to a septum-topped microwave vial, followed by DMA (800 µl) and sulfuric acid, 98% (0.256 µl, 4.80 µmol). Zinc cyanide (6.7 mg, 0.058 mmol), zinc dust (0.31 mg, 4.8 µmol) and compound example 7.1, 5-chloro-1-(1-methyl-1H-pyrazol-4-yl)-6-(1-(3-methyloxetan-3-yl)piperidin-4-yl)-1H-indazole (37 mg, 0.096 mmol) were next added, then the reaction was sealed under nitrogen and heated at 120° C. overnight. Upon completion, the reaction was diluted with ethyl acetate (3×), the organic layer was washed with aqueous sodium hydrogen carbonate, dried ($Na_2SO_4$), filtered, and the solvent was evaporated under reduced pressure. The crude product was purified by reverse phase prep-HPLC (Method A) to afford example 12.1, 1-(1-methyl-1H-pyrazol-4-yl)-6-(1-(3-methyloxetan-3-yl)piperidin-4-yl)-1H-indazole-5-carbonitrile, TFA salt. MS (ESI) in z calc'd for $C_{21}H_{25}N_6O$ [M+H]$^+$ 377. found 377. $^1$H NMR (499 MHz, DMSO-d$_6$) δ 8.55 (s, 1H), 8.49 (s, 1H), 8.38 (s, 1H), 7.95 (s, 1H), 7.50 (s, 1H), 4.85 (d, J=7.7 Hz, 2H), 4.46 (d, J=7.7 Hz, 2H), 3.40 (m, 1H), 3.33 (m, 4H), 3.25 (m, 4H), 2.15 (s, 3H), 1.70 (s, 3H). LRRK2 IC$_{50}$ 6.3 nM.

Compounds in Table 6 below were prepared from the indicated compound example number using the method described in Scheme 15.

TABLE 6

| Example | Prepared from example number | Name | Observed m/z [M + H]$^+$ | LRRK2 IC$_{50}$ (nM) |
|---------|------------------------------|------|--------------------------|----------------------|
| 12.2 | Example 2.2 | 1-(1-cyclopropyl-1H-pyrazol-4-yl)-6-(1-(oxetan-3-yl)piperidin-4-yl)-1H-indazole-5-carbonitrile | 389 | 0.8 |

TABLE 6-continued
| Example | Prepared from example number | Structure Name | Observed m/z [M + H]+ | LRRK2 IC$_{50}$ (nM) |
|---|---|---|---|---|
| 12.3 | Example 7.2 | 1-(1-cyclopropyl-1H-pyrazol-4-yl)-6-(1-(3-methyloxetan-3-yl)piperidin-4-yl)-1H-indazole-5-carbonitrile | 403 | <0.625 |
Preparation of Example 13.2, 5-chloro-1-(1-cyclopropyl-1H-pyrazol-4-yl)-6-(1-(3-ethyloxetan-3-yl)piperidin-4-yl)-1H-indazole
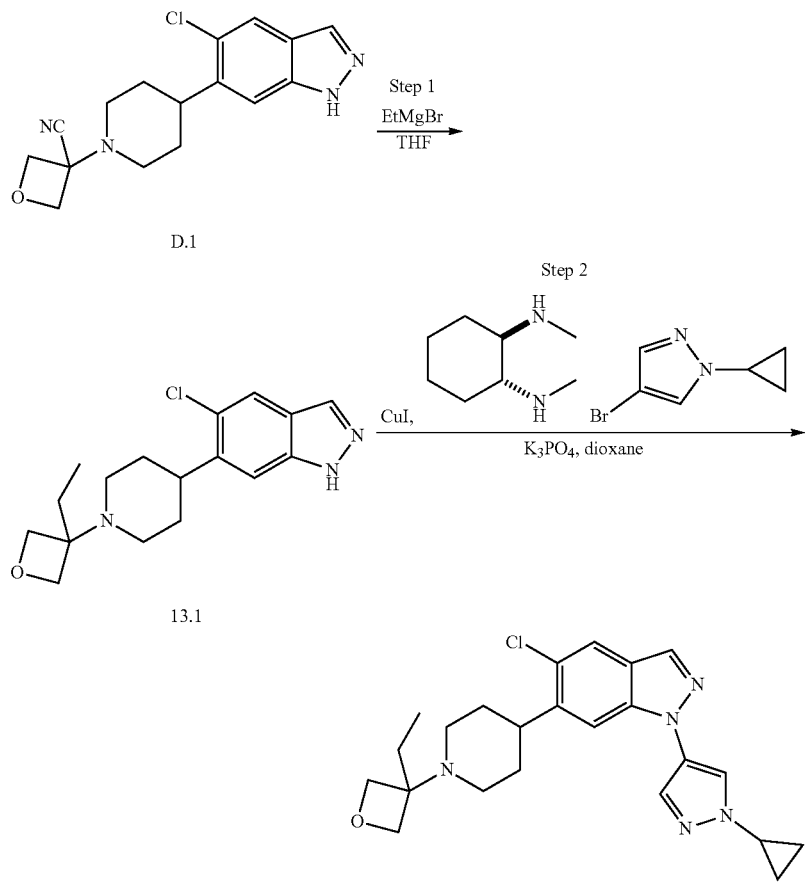

Step 1—Synthesis of Intermediate 13.1, 5-chloro-6-(1-(3-ethyloxetan-3-yl)piperidin-4-yl)-1H-indazole Common intermediate D.1 (100 mg, 0.316 mmol) was solvated in THF (2 mL) in a 2 dram vial with stir bar under an atmosphere of nitrogen. Then, 3.4 M ethylmagnesium bromide in 2-MeTHF (0.464 mL, 1.578 mmol) was added slowly via syringe. The reaction was warmed to 50° C. and stirred for 3 hours. Afterward, the crude reaction was carefully quenched by the addition of saturated NaHCO$_3$. The mixture was diluted and extracted with EtOAc (2×). The organic layers were combined, dried over Na$_2$SO$_4$, filtered, and concentrated to give intermediate 13.1, 5-chloro-6-(1-(3-ethyloxetan-3-yl)piperidin-4-yl)-1H-indazole, which was used as is for the next step without any additional purification. MS (ESI) m/z calc'd for C$_{17}$H$_{23}$Cl N$_3$O [M+H]$^+$ 320. found 320.

Step 2—Synthesis of Example 13.2, 5-chloro-1-(1-cyclopropyl-1H-pyrazol-4-yl)-6-(1-(3-ethyloxetan-3-yl)piperidin-4-yl)-1H-indazole Into a dry microwave vial with stir bar was added intermediate 13.1 (60 mg, 0.188), potassium phosphate tribasic (119 mg, 0.563 mmol), (trans)-N1,N2-dimethylcyclohexane-1,2-diamine (13.34 mg, 0.094 mmol), 4-bromo-1-cyclopropyl-1H-pyrazole (70.2 mg, 0.375 mmol), and copper(I) iodide (10.72 mg, 0.056 mmol). The vial was sealed, purged with nitrogen gas, and dioxane (2 mL) was added. The resulting reaction mixture was warmed to 85° C. and stirred overnight. The next day, the crude reaction mixture was filtered through a plug of Celite® (diatomaceous earth) with EtOAc. The filtrate was concentrated and then purified by reverse phase prep-HPLC (Method B) to afford example 13.2, 5-chloro-1-(1-cyclopropyl-1H-pyrazol-4-yl)-6-(1-(3-ethyloxetan-3-yl)piperidin-4-yl)-1H-indazole. MS (ESI) m/z calc'd for C$_{23}$H$_{29}$ClN$_5$O [M+H]$^+$ 426. found 426. $^1$H NMR (499 MHz, DMSO-d$_6$) δ 8.47 (s, 1H), 8.21 (s, 1H), 7.96 (s, 1H), 7.91 (s, 1H), 7.55 (s, 1H), 4.45 (d, J=6.0 Hz, 2H), 4.28 (d, J=6.0 Hz, 2H), 3.91-3.83 (m, 1H), 3.05-2.96 (m, 1H), 2.82-2.74 (m, 2H), 2.40-2.30 (m, 2H), 1.88-1.67 (m, 6H), 1.20-1.14 (m, 2H), 1.10-1.01 (m, 5H). LRRK2 IC$_{50}$ 2.7 nM.

Preparation of Examples 14.2-1, (R or S)-5-chloro-1-(1-methyl-1H-pyrazol-4-yl)-6-(1-(tetrahydrofuran-3-yl)piperidin-4-yl)-1H-indazole and 14.2-2 (R or S)-5-chloro-1-(1-methyl-1H-pyrazol-4-yl)-6-(1-(tetrahydrofuran-3-yl)piperidin-4-yl)-1H-indazole Scheme 17

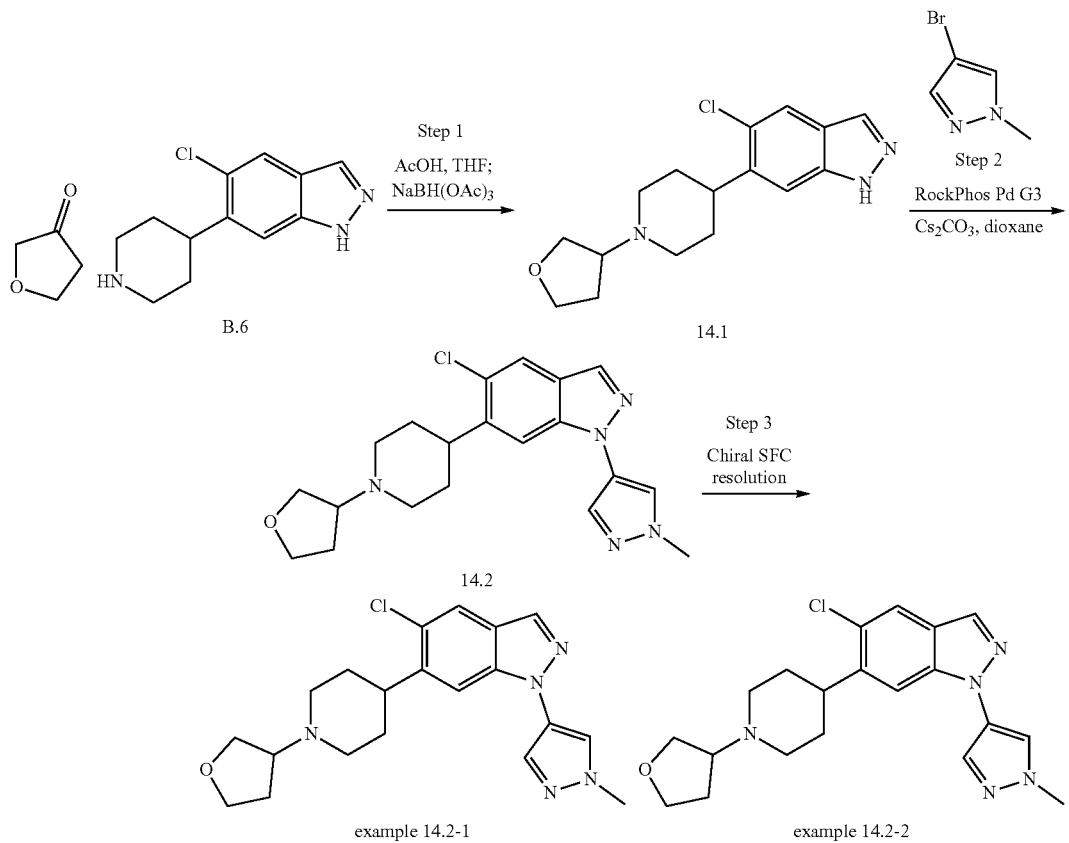

Step 1—Synthesis of Intermediate 14.1, (R and S)-5-chloro-6-(1-(tetrahydrofuran-3-yl)piperidin-4-yl)-1H-indazole Common intermediate B.6 (300 mg, 1.273 mmol) and acetic acid (92 mg, 1.527 mmol) were solvated in THF (9 mL) in a 100 mL RBF with stir bar. Then, dihydrofuran-3 (2H)-one (438 mg, 5.09 mmol) was added via syringe. The solution was stirred at room temperature for 15 minutes. Then, NaBH(OAc)$_3$ (1.079 g, 5.09 mmol) was added in a single portion. After 15 minutes, the crude reaction was quenched with saturated NaHCO$_3$ and diluted with EtOAc. The organic layer was dried over Na$_2$SO$_4$, filtered, and concentrated. The crude residue was purified by silica gel chromatography (gradient elution of 0% to 100% of (3:1 EtOAc:EtOH) in hexanes with 2% triethylamine by volume) to afford intermediate 14.1, (R and S)-5-chloro-6-(1-(tetrahydrofuran-3-yl)piperidin-4-yl)-1H-indazole. MS (ESI) m/z calc'd for C$_{16}$H$_{21}$ClN$_3$O [M+H]$^+$ 306. found 306.

Step 2—Synthesis of Intermediate 14.2, (R and S)-5-chloro-1-(1-methyl-1H-pyrazol-4-yl)-6-(1-(tetrahydrofuran-3-yl)piperidin-4-yl)-1H-indazole Intermediate 14.1 (50 mg, 0.164 mmol), cesium carbonate (186 mg, 0.572 mmol), 4-bromo-1-methyl-1H-pyrazole (52.6 mg, 0.27 mmol), and RockPhos Pd G3 (20.56 mg, 0.025 mmol) were combined in a dry microwave vial with stir bar. The vessel was sealed and purged with nitrogen gas. Then, dioxane (2.5 mL) was added. The reaction was heated to 105° C. and stirred overnight. The next day, the crude reaction was filtered through a plug of Celite® (diatomaceous earth) with EtOAc. The filtrate was concentrated and the residue purified by reverse phase prep-HPLC (Method A) to afford intermediate 14.2, (R and S)-5-chloro-1-(1-methyl-1H-pyrazol-4-yl)-6-(1-(tetrahydrofuran-3-yl)piperidin-4-yl)-1H-indazole, TFA salt. MS (ESI) m/z calc'd for C$_{20}$H$_{25}$ClN$_5$O [M+H]$^+$ 386. found 386.

Step 3—Chiral SFC Resolution of Intermediate 14.2, (R and S)-5-chloro-1-(1-methyl-1H-pyrazol-4-yl)-6-(1-(tetrahydrofuran-3-yl)piperidin-4-yl)-1H-indazole to Afford Examples 14.2-1, (R or S)-5-chloro-1-(1-methyl-1H-pyrazol-4-yl)-6-(1-(tetrahydrofuran-3-yl)piperidin-4-yl)-1H-indazole and 14.2-2, (R or S)-5-chloro-1-(1-methyl-1H-pyrazol-4-yl)-6-(1-(tetrahydrofuran-3-yl)piperidin-4-yl)-1H-indazole Intermediate 14.2, (R and S)-5-chloro-1-(1-methyl-1H-pyrazol-4-yl)-6-(1-(tetrahydrofuran-3-yl)piperidin-4-yl)-1H-indazole was resolved by chiral-prep-SFC (Column: IG, 21 mm×250 mm; 40% (iPrOH/0.1% NH$_4$OH)/CO$_2$; Flow rate: 70 ml/min; 220 nm; RT: 3.7 min (example 14.2-1), 4.8 min (example 14.2-2).

Example 14.2-1, (R and S)-5-chloro-1-(1-methyl-1H-pyrazol-4-yl)-6-(1-(tetrahydrofuran-3-yl)piperidin-4-yl)-1H-indazole MS (ESI) m/z calc'd for C$_{20}$H$_{25}$ClN$_5$O [M+H]$^+$ 386. found 386. LRRK2 IC$_{50}$ 1.2 nM.

Example 14.2-2, (R and S)-5-chloro-1-(1-methyl-1H-pyrazol-4-yl)-6-(1-(tetrahydrofuran-3-yl)piperidin-4-yl)-1H-indazole MS (ESI) m/z calc'd for C$_{20}$H$_{25}$ClN$_5$O [M+H]$^+$ 386. found 386. LRRK2 IC$_{50}$ 2.8 nM. Preparation of examples 15.3-1 (R or S)-5-chloro-1-(1-cyclopropyl-1H-pyrazol-4-yl)-6-(1-(3-methyltetrahydrofuran-3-yl)piperidin-4-yl)-1H-indazole and 15.3-2 (R or S)-5-chloro-1-(1-cyclopropyl-1H-pyrazol-4-yl)-6-(1-(3-methyltetrahydrofuran-3-yl)piperidin-4-yl)-1H-indazole.

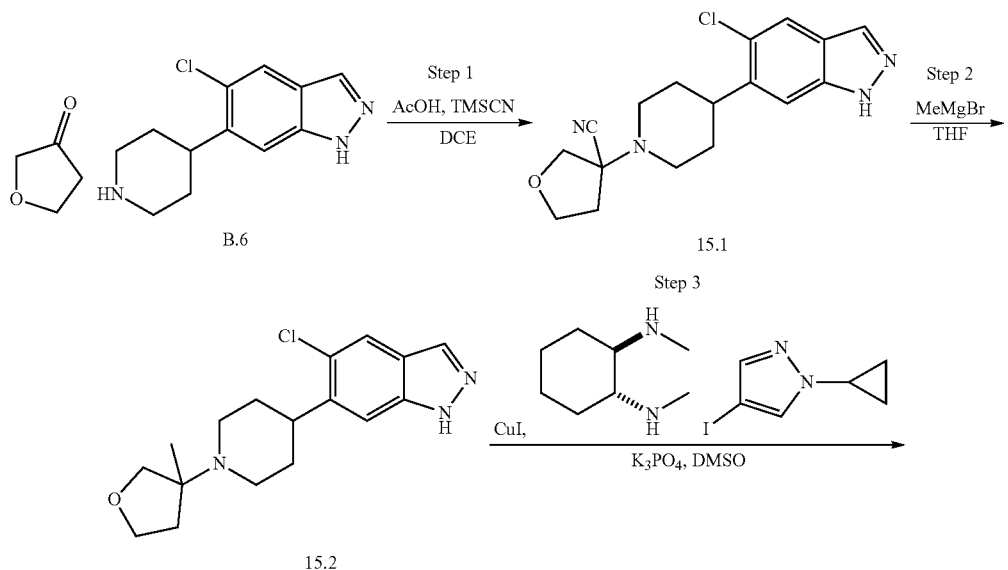

Scheme 18

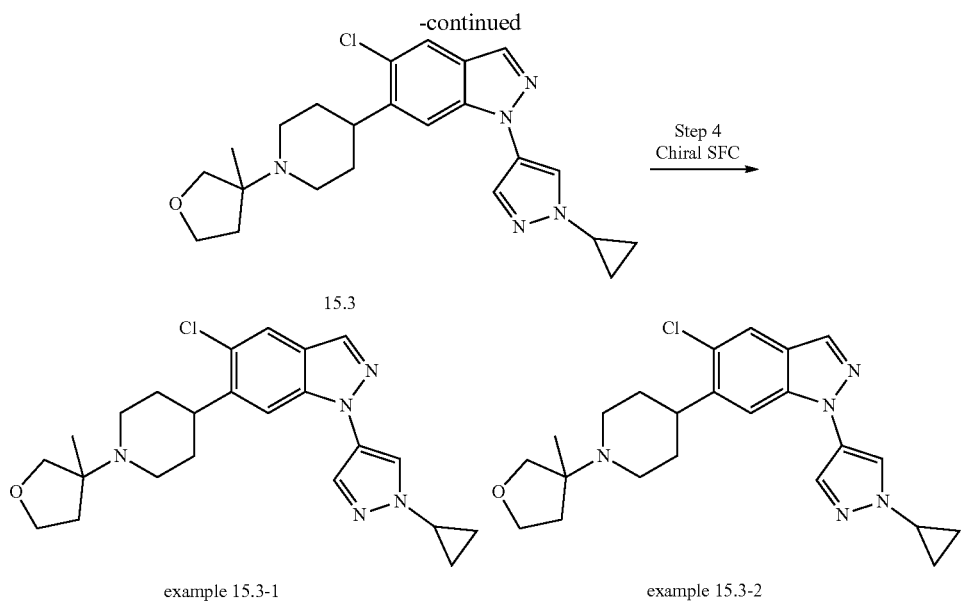

example 15.3-1 example 15.3-2

Step 1—Synthesis of Intermediate 15.1, (R and S)-5-chloro-1-(1-cyclopropyl-1H-pyrazol-4-yl)-6-(1-(3-methyltetrahydrofuran-3-yl)piperidin-4-yl)-1H-indazole Common intermediate B.6 (1.0 g, 4.24 mmol) was suspended in DCE (14 ml) with 1 gram of 4 angstrom molecular sieves, and acetic acid (0.364 ml, 6.36 mmol) was added while stirring the mixture. Then, dihydrofuran-3(2H)-one (0.548 g, 6.36 mmol) was added via syringe. After 10 minutes of stirring at room temp, trimethylsilanecarbonitrile (0.796 ml, 6.36 mmol) was added carefully via syringe. The reaction was then heated to 60° C. After 3 hours, the crude reaction was quenched with saturated NaHCO$_3$ and diluted with DCM. The organic layer was extracted 2×, then dried over Na$_2$SO$_4$, filtered, and concentrated to give intermediate 15.1, (R and S)-5-chloro-1-(1-cyclopropyl-1H-pyrazol-4-yl)-6-(1-(3-methyltetrahydrofuran-3-yl)piperidin-4-yl)-1H-indazole. The material was used directly for the next step without additional purification. MS (ESI) in z calc'd for C$_{16}$H$_{19}$Cl N$_3$O [M-CN]$^+$304. found 304.

Step 2—Synthesis of Intermediate 15.2, 5-chloro-6-(1-(3-methyltetrahydrofuran-3-yl)piperidin-4-yl)-1H-indazole Intermediate 15.1 (1.2 g, 3.63 mmol) was solvated in THF (13 mL) under an atmosphere of nitrogen. Then, 3.0 M methylmagnesium bromide in diethyl ether (4.84 mL, 14.51 mmol) was added slowly via syringe. The reaction was warmed to 50° C. After 3 hours, the crude reaction was carefully quenched with saturated NaHCO$_3$ and diluted with EtOAc. The organic layer was extracted 2×, dried over Na$_2$SO$_4$, filtered, and concentrated to afford intermediate 15.2, 5-chloro-6-(1-(3-methyltetrahydrofuran-3-yl)piperidin-4-yl)-1H-indazole. The crude product was used directly for the next step without additional purification. MS (ESI) m/z calc'd for C$_{17}$H$_{23}$Cl N$_3$O [M+H]$^+$ 320. found 320.

Step 3—Synthesis of Intermediate 15.3, (R and S)-5-chloro-1-(1-cyclopropyl-1H-pyrazol-4-yl)-6-(1-(3-methyltetrahydrofuran-3-yl)piperidin-4-yl)-1H-indazole Into a dry microwave vial with stir bar was added intermediate 15.2 (200 mg, 0.625 mmol), potassium phosphate tribasic (398 mg, 1.876 mmol), (trans)-N1,N2-dimethylcyclohexane-1,2-diamine (44.5 mg, 0.313 mmol), 1-cyclopropyl-4-iodo-1H-pyrazole (293 mg, 1.251 mmol), and copper (I) iodide (35.7 mg, 0.188 mmol). The vial was sealed and purged with nitrogen. Then, DMSO (3.5 mL) was added and the solution was heated to 80° C. overnight. The next day, the crude material was filtered through a plug of Celite® (diatomaceous earth) using EtOAc. The filtrate was concentrated and purified by reverse phase prep-HPLC (Method A) to afford intermediate 15.3, (R and S)-5-chloro-1-(1-cyclopropyl-1H-pyrazol-4-yl)-6-(1-(3-methyltetrahydrofuran-3-yl)piperidin-4-yl)-1H-indazole, TFA salt. MS (ESI) m/z calc'd for C$_{23}$H$_{28}$Cl N$_5$O [M+H]$^+$ 426. found 426.

Step 4—Chiral Resolution of Intermediate 15.3, (R and S)-5-chloro-1-(1-cyclopropyl-1H-pyrazol-4-yl)-6-(1-(3-methyltetrahydrofuran-3-yl)piperidin-4-yl)-1H-indazole to Afford Examples 15.3-1, (R or S)-5-chloro-1-(1-cyclopropyl-1H-pyrazol-4-yl)-6-(1-(3-methyltetrahydrofuran-3-yl)piperidin-4-yl)-1H-indazole and 15.3-2, (R or S)-5-chloro-1-(1-cyclopropyl-1H-pyrazol-4-yl)-6-(1-(3-methyltetrahydrofuran-3-yl)piperidin-4-yl)-1H-indazole Intermediate 15.3, (R and S)-5-chloro-1-(1-cyclopropyl-1H-pyrazol-4-yl)-6-(1-(3-methyltetrahydrofuran-3-yl)piperidin-4-yl)-1H-indazole was resolved by chiral-prep-SFC (Column: CCA, 21 mm×250 mm; 15% (MeOH/0.1% NH$_4$OH)/CO$_2$; Flow rate: 70 ml/min; 220 nm; RT: 5.6 min (example 15.3-1), 6.5 min (example 15.3-2).

Example 15.3-1, (R or S)-5-chloro-1-(1-cyclopropyl-1H-pyrazol-4-yl)-6-(1-(3-methyltetrahydrofuran-3-yl)piperidin-4-yl)-1H-indazole MS (ESI) m/z calc'd for C$_{23}$H$_{28}$ClN$_5$O [M+H]$^+$ 426. found 426. $^1$H NMR (499 MHz, DMSO-d$_6$) δ 8.47 (s, 1H), 8.21 (s, 1H), 7.95 (s, 1H), 7.90 (s, 1H), 7.54 (s, 1H), 3.89-3.77 (m, 3H), 3.56 (d, J=7.7 Hz, 1H), 3.48 (d, J=7.7 Hz, 1H), 3.04-2.90 (m, 2H), 2.70-2.62 (m, 1H), 2.47-2.34 (m, 2H), 1.93-1.73 (m, 6H), 1.19-1.14 (m, 2H), 1.10 (s, 3H), 1.06-0.99 (m, 2H). LRRK2 IC$_{50}$<0.625 nM.

Example 15.3-2, (R or S)-5-chloro-1-(1-cyclopropyl-1H-pyrazol-4-yl)-6-(1-(3-methyltetrahydrofuran-3-yl)piperidin-4-yl)-1H-indazole MS (ESI) m/z calc'd for C$_{23}$H$_{28}$ClN$_5$O [M+H]$^+$ 426. found 426. $^1$H NMR (499 MHz, DMSO-d$_6$) δ 8.47 (s, 1H), 8.21 (s, 1H), 7.95 (s, 1H), 7.90 (s, 1H), 7.54 (s, 1H), 3.89-3.77 (m, 3H), 3.56 (d, J=7.7 Hz, 1H), 3.48 (d, J=7.7 Hz, 1H), 3.04-2.90 (m, 2H), 2.70-2.62 (m, 1H), 2.47-2.34 (m, 2H), 1.93-1.73 (m, 6H), 1.19-1.14 (m, 2H), 1.10 (s, 3H), 1.06-0.99 (m, 2H). LRRK2 IC$_{50}$ 3.5 nM.

Compounds in Table 7 below were prepared through intermediate 15.2 using the method described in Scheme 18. Purification was carried out using silica gel column chromatography or reverse phase prep-HPLC (Method A), followed by chiral prep-SFC resolution (Column: CCA, 21 mm×250 mm; 15% (MeOH/0.1% NH$_4$OH)/CO$_2$; Flow rate: 70 ml/min; 220 nm; RT: 5.8 min (example 15.4-1), 7.0 min (example 15.4-2).

Preparation of Example 16.1, 5-chloro-1-(1-methyl-1H-pyrazol-4-yl)-6-(piperidin-4-yl)-1H-indazole and Example 16.2, 5-chloro-1-(1-methyl-1H-pyrazol-4-yl)-6-(1-(2-(methylsulfonyl)ethyl)piperidin-4-yl)-1H-indazole Scheme 19

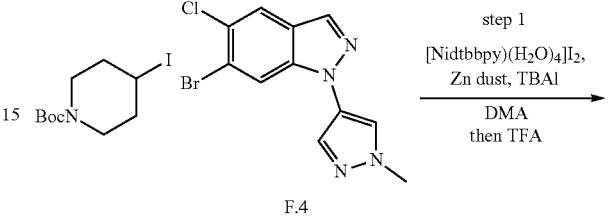

F.4

TABLE 7

| Example | Structure Name | Observed m/z [M + H]$^+$ | LRRK2 IC$_{50}$ (nM) |
|---|---|---|---|
| 15.4-1 | (R or S)-5-chloro-1-(1-methyl-1H-pyrazol-4-yl)-6-(1-(3-methyltetrahydrofuran-3-yl)piperidin-4-yl)-1H-indazole | 400 | <0.625 |
| 15.4-2 | (R or S)-5-chloro-1-(1-methyl-1H-pyrazol-4-yl)-6-(1-(3-methyltetrahydrofuran-3-yl)piperidin-4-yl)-1H-indazole | 400 | 3.5 | step 2

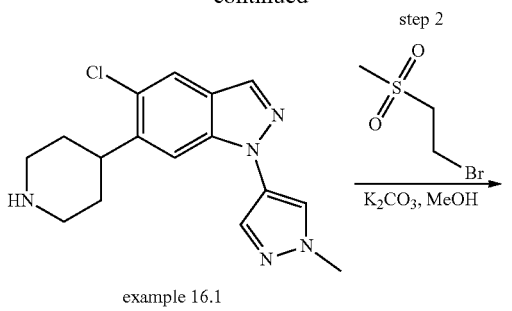

example 16.1

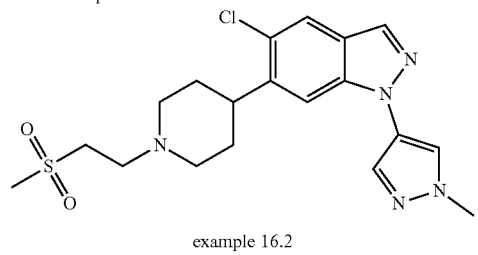

example 16.2

Step 1—Synthesis of Example 16.1, 5-chloro-1-(1-methyl-1H-pyrazol-4-yl)-6-(piperidin-4-yl)-1H-indazole In an inert-atmosphere glovebox, an 8 mL vial with stir bar was charged with tetrabutylammonium iodide (32.3 mg, 0.088 mmol), tert-butyl 4-iodopiperidine-1-carboxylate (218 mg, 0.700 mmol), common intermediate F.4 (109 mg, 0.35 mmol), [Ni(dtbbpy)(H$_2$O)$_4$]I$_2$ (18.31 mg, 0.035 mmol), and freshly activated zinc (45.8 mg, 0.700 mmol), the solids were then dissolved in DMA (1.75 mL). The vial was sealed, removed from the glovebox and heated to 60° C. overnight. The reaction was then cooled, diluted in ethyl acetate and filtered through a plug of Celite® (diatomaceous earth) with ethyl acetate. The crude material was purified by silica gel column chromatography (gradient elution of 0-40% (3:1 EtOAc:EtOH)/hexanes) to provide tert-butyl 4-(5-chloro-1-(1-methyl-1H-pyrazol-4-yl)-1H-indazol-6-yl)piperidine-1-carboxylate. This material was then dissolved in dichloromethane (1.1 mL) and cooled to 0° C. with stirring. Trifluoroacetic acid (167 µl, 2.16 mmol) was then added dropwise, and the resulting reaction warmed to room temperature overnight. After 14 h, the reaction was diluted with water and dichloromethane, and the aqueous layer carefully neutralized with saturated sodium bicarbonate. The layers were transferred to a separatory funnel and the aqueous layer extracted 3× with dichloromethane. The organics were then combined, dried over sodium sulfate, and condensed. The crude material was slurried in 10 mL isopropyl acetate with a few drops of hexane for 5 hours, then the solids were filtered on fritted Buchner and dried overnight under vacuum to give example 16.1, 5-chloro-1-(1-methyl-1H-pyrazol-4-yl)-6-(piperidin-4-yl)-1H-indazole. MS (ESI) m/z calc'd for C$_{19}$H$_{20}$ClN$_5$O [M+H]$^+$ 358. found 358. $^1$H NMR (600 MHz, DMSO-d$_6$) δ 8.31 (s, 1H), 8.26 (s, 1H), 8.03 (s, 1H), 7.91 (s, 1H), 7.43 (s, 2H), 3.96 (s, 3H), 3.40 (dd, J=18.7, 12.4 Hz, 2H), 3.12 (t, J=11.8 Hz, 2H), 2.02 (d, J=13.6 Hz, 2H), 1.89 (d, J=12.1 Hz, 2H). LRRK2 IC$_{50}$ 6.9 nM.

Step 2—Synthesis of Example 16.2, 5-chloro-1-(1-methyl-1H-pyrazol-4-yl)-6-(1-(2-(methylsulfonyl)ethyl)piperidin-4-yl)-1H-indazole In a microwave vial, 1-bromo-2-(methylsulfonyl)ethane (15.9 mg, 0.085 mmol), potassium carbonate (29.4 mg, 0.213 mmol) and compound example 16.1 (15 mg, 0.043 mmol) were combined and dissolved in MeCN (1 ml). The vial was sealed, and stirred at 60° C. for 12 h. Upon completion, the reaction was diluted in iPrOH/chloroform (1:3 v/v) and saturated aqueous sodium bicarbonate. The separated organic layer was filtered through a phase separator, concentrated and purified by reverse phase prep-HPLC (Method A) to afford example 16.2, 5-chloro-1-(1-methyl-1H-pyrazol-4-yl)-6-(1-(2-(methylsulfonyl)ethyl)piperidin-4-yl)-1H-indazole. TFA salt. MS (ESI) m/z calc'd for C$_{19}$H$_{25}$ClN$_5$O$_2$S [M+H]$^+$ 422. found 422. $^1$H NMR (499 MHz, DMSO-d$_6$) δ 8.30 (s, 1H), 8.25 (s, 1H), 8.02 (s, 1H), 7.91 (s, 1H), 7.46 (s, 1H), 3.91 (s, 3H), 3.80-3.50 (m, 5H), 3.39 (m, 2H), 3.26 (m, 2H), 3.18 (s, 3H), 2.10 (m, 2H), 2.02 (m, 2H). LRRK2 IC$_{50}$<0.625 nM.

Compounds in Table 8 below were prepared from example 16.1 using the method described in Scheme 19.

TABLE 8

| Example | Structure Name | Observed m/z [M + H]$^+$ | LRRK2 IC$_{50}$ (nM) |
| --- | --- | --- | --- |
| 16.3 | | 360 | 3.7 |

Preparation of Example 17.1, 4-(5-chloro-1-(1-methyl-1H-pyrazol-4-yl)-1H-indazol-6-yl)-N-methylpiperidine-1-carboxamide Preparation of Example 18.2, 5-chloro-6-(1-(2,2-difluoroethyl)piperidin-4-yl)-1-(1-methyl-1H-pyrazol-4-yl)-1H-indazole

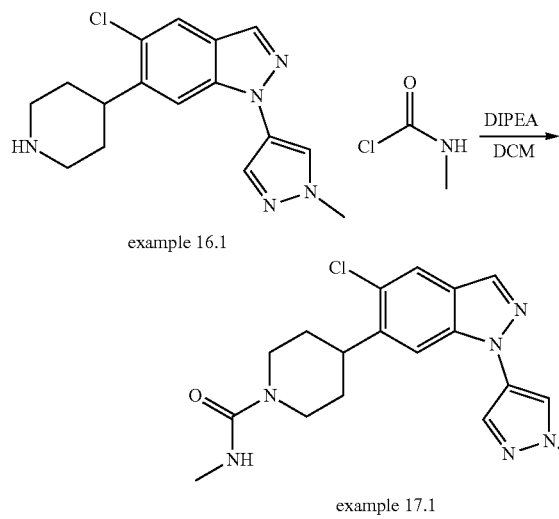

example 16.1 example 17.1

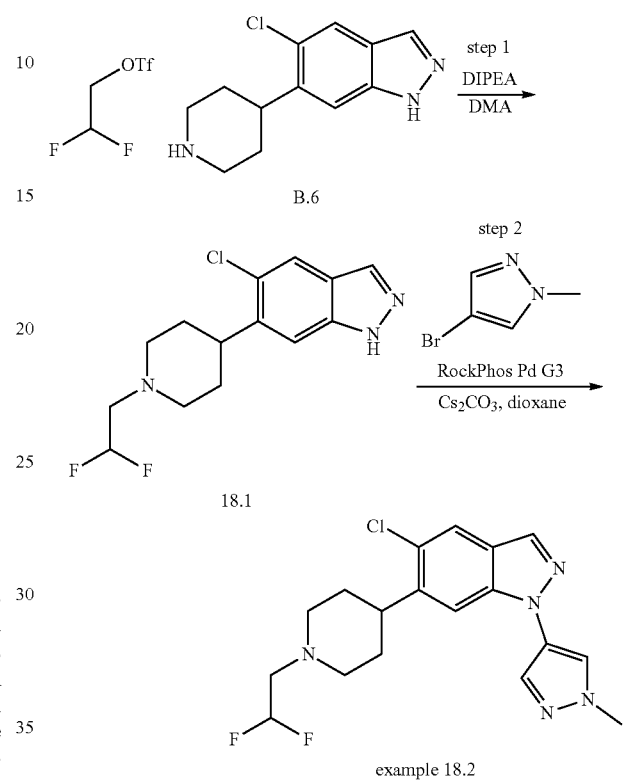

example 18.2

In a microwave vial, methylcarbamic chloride (11.9 mg, 0.128 mmol), DIPEA (0.037 ml, 0.213 mmol) and compound example 16.1 (15 mg, 0.043 mmol) were combined and dissolved in dichloromethane (1 ml). The vial was sealed, and stirred at room temperature for 3 hours. Upon completion, the reaction was diluted in iPrOH/chloroform (1:3 v/v) and saturated aqueous sodium bicarbonate. The separated organic layer was filtered through a phase separator, concentrated and purified by reverse phase prep-HPLC (Method A) to afford example 17.1, 4-(5-chloro-1-(1-methyl-1H-pyrazol-4-yl)-1H-indazol-6-yl)-N-methyl piperidine-1-carboxamide. TFA salt. MS (ESI) m/z calc'd for $C_{18}H_{22}ClN_6O$ [M+H]$^+$ 373. found 373. $^1$HNMR (499 MHz, DMSO-d$_6$) δ 8.35 (s, 1H), 8.20 (s, 1H), 7.98 (s, 1H), 7.90 (s, 1H), 7.50 (s, 1H), 6.45 (br s, 1H), 4.15 (d, J=13 Hz, 2H), 3.90 (s, 3H) 3.18 (m, 1H), 2.82 (m, 2H), 2.61 (s, 3H), 1.80 (m, 2H), 1.65 (m, 2H). LRRK2 IC$_{50}$ 14.5 nM.

Compounds in Table 9 below were prepared from example 16.1 using the method described in Scheme 20.

Step 1—Synthesis of Intermediate 18.1, 5-chloro-6-(1-(2,2-difluoroethyl)piperidin-4-yl)-1H-indazole Common intermediate B.6 (300 mg, 1.273 mmol) and N-ethyl-N-isopropylpropan-2-amine (411 mg, 3.18 mmol) were combined in a dry 20 mL vial with stir bar and solvated in DMA (12 mL). Then, 2,2-difluoroethyl trifluoromethanesulfonate (327 mg, 1.527 mmol) was added via syringe. The reaction was stirred at room temperature overnight. The next

TABLE 9

| Example | Structure Name | Observed m/z [M + H]$^+$ | LRRK2 IC$_{50}$ (nM) |
|---|---|---|---|
| 17.2 | 5-chloro-1-(1-methyl-1H-pyrazol-4-yl)-6-(1-(methylsulfonyl)piperidin-4-yl)-1H-indazole, TFA salt | 394 | 27.8 | day, the crude reaction was diluted with EtOAc and saturated NaHCO$_3$. The organic layer was extracted and washed 5 times with a 1:1 mixture of brine:water. The organic layer was then dried over Na$_2$SO$_4$, filtered, and concentrated to afford intermediate 18.1, 5-chloro-6-(1-(2,2-difluoroethyl) piperidin-4-yl)-1H-indazole. The material was used as is without any further purification. MS (ESI) m/z calc'd for C$_{14}$H$_{17}$Cl F$_2$N$_3$ [M+H]$^+$ 300. found 300.

Step 2—Synthesis of Example 18.2, 5-chloro-6-(1-(2,2-difluoroethyl)piperidin-4-yl)-1-(1-methyl-1H-pyrazol-4-yl)-1H-indazole Intermediate 18.1 (50 mg, 0.167 mmol), cesium carbonate (190 mg, 0.584 mmol), 4-bromo-1-methyl-1H-pyrazole (53.7 mg, 0.334 mmol), and RockPhos Pd G3 (20.98 mg, 0.025 mmol) were combined in a dry microwave vial with stir bar. The vial was sealed and purged with nitrogen gas. Then, 1,4-dioxane (2.5 mL) was added and the solution was heated to 105° C., and stirred overnight. The next day, the crude reaction was filtered through a plug of Celite® (diatomaceous earth) using EtOAc as eluent. The filtrate was purified by reverse phase prep-HPLC (Method A) to afford example 18.2, 5-chloro-6-(1-(2,2-difluoroethyl)piperidin-4-yl)-1-(1-methyl-1H-pyrazol-4-yl)-1H-indazole, TFA salt. MS (ESI) m/z calc'd for C$_{18}$H$_{21}$Cl F$_2$N$_5$ [M+H]$^+$ 380. found 380. $^1$H NMR (499 MHz, DMSO-d$_6$) δ 8.32 (s, 1H), 8.25 (s, 1H), 8.02 (s, 1H), 7.94-7.88 (m, 1H), 7.45 (s, 1H), 6.72-6.44 (m, 1H), 3.95 (s, 3H), 3.79-3.17 (m, 7H), 2.14-1.94 (m, 4H). LRRK2 IC$_{50}$ 23.2 nM.

Compounds in Table 10 below were prepared using the method described in Scheme 21.

Preparation of Example 19.7-1, (S,S or R,R)-5-chloro-6-(3-fluoro-1-methylpiperidin-4-yl)-1-(1-methyl-1H-pyrazol-4-yl)-1H-indazole and 19.7-2, (S,S or R,R)-5-chloro-6-(3-fluoro-1-methylpiperidin-4-yl)-1-(1-methyl-1H-pyrazol-4-yl)-1H-indazole

TABLE 10

| Example | Structure Name | Observed m/z [M + H]$^+$ | LRRK2 IC$_{50}$ (nM) |
|---|---|---|---|
| 18.3 | 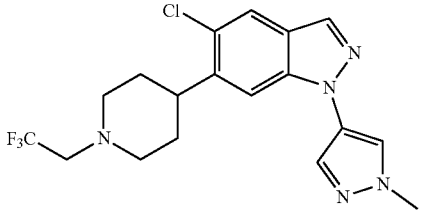 5-chloro-1-(1-methyl-1H-pyrazol-4-yl)-6-(1-(2,2,2-trifluoroethyl)piperidin-4-yl)-1H-indazole, TFA salt | 398 | 324 |
| 18.4 | 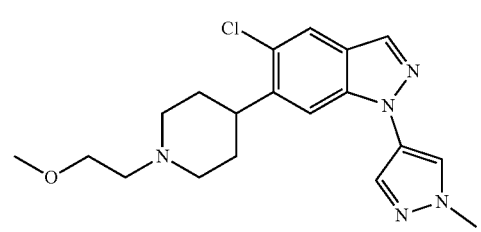 5-chloro-6-(1-(2-methoxyethyl)piperidin-4-yl)-1-(1-methyl-1H-pyrazol-4-yl)-1H-indazole, TFA salt | 374 | 11.3 |

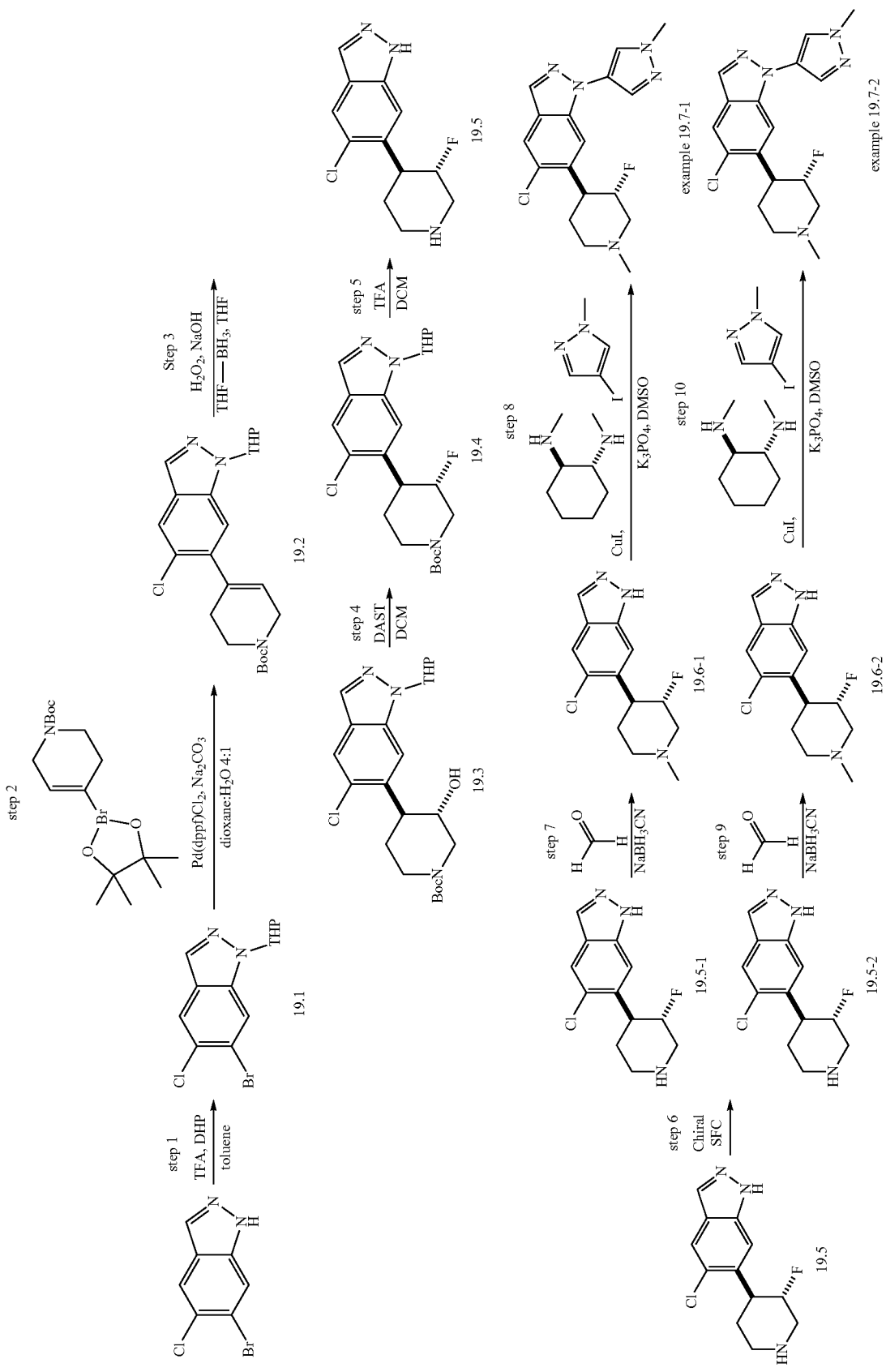

Step 1—Synthesis of Intermediate 19.1, 6-bromo-5-chloro-1-(tetrahydro-2H-pyran-2-yl)-1H-indazole To a solution of 6-bromo-5-chloro-1H-indazole (2.8 g, 12.10 mmol) in anhydrous toluene (70 ml) was added 3,4-dihydro-2H-pyran (1.526 g, 18.14 mmol) and 2,2,2-trifluoroacetic acid (0.093 ml, 1.210 mmol), and the resulting mixture was stirred at 80° C. for 3 hours. Afterward, the reaction mixture was concentrated, the residue was purified by silica gel column chromatography (gradient eluent of 0% to 80% EtOAc/Petroleum ether) to give intermediate 19.1, 6-bromo-5-chloro-1-(tetrahydro-2H-pyran-2-yl)-1H-indazole. MS (ESI) m/z calc'd for $C_{12}H_{13}BrClN_2O$ [M+H]$^+$ 317. found 317.

Step 2—Synthesis of Intermediate 19.2, tert-butyl 4-(5-chloro-1-(tetrahydro-2H-pyran-2-yl)-1H-indazol-6-yl)-3,6-dihydropyridine-1(2H)-carboxylate To a solution of intermediate 19.1 (3.5 g, 11.09 mmol), $Na_2CO_3$ (3.53 g, 33.3 mmol), and tert-butyl 4-(4,4,5,5-tetramethyl-1,3,2-dioxaborolan-2-yl)-5,6-dihydropyridine-1(2H)-carboxylate (3.60 g, 11.64 mmol) in 1,4-Dioxane (40 ml) and Water (10 ml) was added $PdCl_2(dppf)$ (0.406 g, 0.555 mmol). The resulting mixture was stirred at 100° C. under $N_2$ protection for 12 hours. Afterward, the reaction mixture was poured into water (60 mL) and extracted with EtOAc (100 mL×3). The organic layer was washed with brine (60 mL), dried over $Na_2SO_4$. After filtration and concentration in vacuo, the residue was purified by silica gel column chromatography (eluent of 0% to 80% EtOAc/Petroleum ether) to give intermediate 19.2, tert-butyl 4-(5-chloro-1-(tetrahydro-2H-pyran-2-yl)-1H-indazol-6-yl)-5,6-dihydropyridine-1(2H)-carboxylate. MS (ESI) m/z calc'd for $C_{22}H_{29}Cl N_3O_3$ [M+H]$^+$ 418. found 418.

Step 3—Synthesis of Intermediate 19.3, (R,R and S,S)-tert-butyl 4-(5-chloro-1-(tetrahydro-2H-pyran-2-yl)-1H-indazol-6-yl)-3-hydroxypiperidine-1-carboxylate To a solution of intermediate 19.2 (1.9 g, 4.55 mmol) in THF (30 ml) was added $BH_3 \cdot THF$ (18.18 ml, 18.18 mmol) dropwise at 0° C., then the resulting mixture was warmed to room temperature and was stirred at 18° C. for 12 hours. The reaction was cooled to 0° C. and NaOH (6.82 ml, 13.64 mmol) was added to the reaction at 0° C. Then $H_2O_2$ (3.98 ml, 45.5 mmol) was added dropwise at 0° C. The mixture was stirred at 18° C. for 1 hour. The solvent was evaporated and the resulting material was extracted with EtOAc (100 mL×3). The combined organic layers were washed with brine and dried over $Na_2SO_4$. After evaporation, the residue was purified by silica gel column chromatography (gradient eluent of 0% to 80% EtOAc/Petroleum ether) to give intermediate 19.3, (R,R and S,S)-tert-butyl 4-(5-chloro-1-(tetrahydro-2H-pyran-2-yl)-1H-indazol-6-yl)-3-hydroxypiperidine-1-carboxylate. MS (ESI) m/z calc'd for $C_{22}H_{31}Cl N_3O_4$ [M+H]$^+$ 436. found 436.

Step 4—Synthesis of Intermediate 19.4, (R,R and S,S)-tert-butyl 4-(5-chloro-1-(tetrahydro-2H-pyran-2-yl)-1H-indazol-6-yl)-3-fluoropiperidine-1-carboxylate To a solution of intermediate 19.3 (2 g, 4.59 mmol) in anhydrous DCM (30 ml) was added diethylaminosulfur trifluoride (2.425 ml, 18.35 mmol) at −78° C., and the resulting mixture was stirred at 30° C. under $N_2$ protection for 1 hour. Afterward, the mixture was poured into a saturated $NaHCO_3$ solution (60 mL). DCM (150 mL) was added into the mixture. The aqueous layer was extracted with DCM (150 mL×2). The combined layers were concentrated to afford the crude product, which was purified by prep-TLC (eluent 33% EtOAc/petroleum ether) to give intermediate 19.4, (R,R and S,S)-tert-butyl 4-(5-chloro-1-(tetrahydro-2H-pyran-2-yl)-1H-indazol-6-yl)-3-fluoropiperidine-1-carboxylate. MS (ESI) m/z calc'd for $C_{22}H_{30}ClFN_3O_3$ [M+H]$^+$ 438. found 438.

Step 5—Synthesis of Intermediate 19.5, (R,R and S,S)-5-chloro-6-(3-fluoropiperidin-4-yl)-1H-indazole To a solution of intermediate 19.4 (1.1 g, 2.51 mmol) in anhydrous DCM (20 ml) was added 2,2,2-trifluoroacetic acid (5 ml, 2.51 mmol) and the resulting mixture was stirred at 30° C. for 12 hours. The solvent was removed to afford intermediate 19.5, (R,R and S,S)-5-chloro-6-(3-fluoropiperidin-4-yl)-1H-indazole, TFA salt. The crude material was used as is without additional purification. MS (ESI) m/z calc'd for $C_{12}H_{14}ClFN_3$ [M+H]$^+$ 254. found 254.

Step 6—Resolution of Intermediate 19.5 (R,R and S,S)-5-chloro-6-(3-fluoropiperidin-4-yl)-1H-indazole into Intermediates 19.5-1, (R,R or S,S)-5-chloro-6-(3-fluoropiperidin-4-yl)-1H-indazole and 19.5-2, (R,R or S,S)-5-chloro-6-(3-fluoropiperidin-4-yl)-1H-indazole Intermediate 19.5 was resolved by chiral SFC (Chiralpak IC-3 150×4.6 mm I.D., 3 um. Mobile phase: A: $CO_2$ B: ethanol (0.05% DEA). Gradient: from 5% to 40% of B in 5.5 min and hold at 40% B for 3 min, then 5% B for 1.5 min. Flow rate: 2.5 mL/min Column, temperature: 35° C.). RT: 4.62 min (19.5-1), 5.05 min (19.5-2).

Intermediate 19.5-1, (R,R or S,S)-5-chloro-6-(3-fluoropiperidin-4-yl)-1H-indazole MS (ESI) m/z calc'd for $C_{12}H_{14}ClFN_3$ [M+H]$^+$ 254. found 254. $^1$H NMR (400 MHz, $CD_3OD$) δ 7.98 (s, 1H), 7.83 (s, 1H), 7.57 (s, 1H), 4.78 (m, 1H), 3.49 (m, 1H), 3.39 (m, 1H), 3.03 (m, 1H), 2.69 (m, 2H), 2.03 (m, 1H), 1.60 (m, 1H).

Intermediate 19.5-2, (R,R or S,S)-5-chloro-6-(3-fluoropiperidin-4-yl)-1H-indazole MS (ESI) m/z calc'd for $C_{12}H_{14}ClFN_3$ [M+H]$^+$ 254. found 254. $^1$H NMR (400 MHz, $CD_3OD$) δ 7.99 (s, 1H), 7.84 (s, 1H), 7.61 (s, 1H), 4.82 (m, 1H), 3.53 (m, 1H), 3.39 (m, 1H), 3.01 (m, 1H), 2.69 (m, 2H), 2.02 (m, 1H), 1.61 (m, 1H).

Step 7—Synthesis of Intermediate 19.6-1, (R,R or S,S)-5-chloro-6-(3-fluoro-1-methylpiperidin-4-yl)-1H-indazole To a solution of intermediate 19.5-1 (150 mg, 0.591 mmol) in anhydrous MeOH (10 ml) was added formaldehyde (35.5 mg, 1.182 mmol) and sodium cyanotrihydroborate (74.3 mg, 1.182 mmol), the resulting mixture was stirred at 25° C. for 12 hours. After filtration and concentration, the crude product was purified by pre-HPLC (TFA) to give intermediate 19.6-1, (R,R or S,S)-5-chloro-6-(3- fluoro-1-methylpiperidin-4-yl)-1H-indazole, TFA salt. MS (ESI) m/z calc'd for $C_{13}H_{16}ClFN_3$ [M+H]$^+$ 268. found 268.

Step 8—Synthesis of Example 19.7-1, (R,R or S,S)-5-chloro-6-(3-fluoro-1-methylpiperidin-4-yl)-1-(1-methyl-1H-pyrazol-4-yl)-1H-indazole To a solution of 4-iodo-1-methyl-1H-pyrazole (23.31 mg, 0.112 mmol) in anhydrous DMSO (5 ml) was added intermediate 19.6-1 (20 mg, 0.075 mmol), (trans)-N1,N2-dimethylcyclohexane-1,2-diamine (2.125 mg, 0.015 mmol), potassium phosphate (47.6 mg, 0.224 mmol) and CuI (1.423 mg, 7.47 μmol). The resulting mixture was stirred at 90° C. under $N_2$ protection for 12 hours. After filtration and concentration, the crude product was purified by pre-HPLC (TFA) to give example 19.7-1, (R,R or S,S)-5-chloro-6-(3-fluoro-1-methylpiperidin-4-yl)-1-(1-methyl-1H-pyrazol-4-yl)-1H-indazole, TFA salt. MS (ESI) m/z calc'd for $C_{17}H_{20}ClFN_5$ [M+H]$^+$ 348. found 348. $^1$H NMR (400 MHz, $CD_3OD$) δ 8.12-8.25 (m, 2H), 7.96 (s, 1H), 7.88 (br s, 1H), 7.67 (s, 1H), 7.63-7.67 (m, 1H), 5.22-5.48 (m, 1H), 5.22-5.48 (m, 1H), 4.00 (s, 3H), 3.92 (br s, 1H), 3.82 (m, 1H), 3.60 (br s, 1H), 3.16-3.30 (m, 2H), 3.03 (s, 3H), 2.27 (br s, 1H), 2.02-2.20 (m, 1H). LRRK2 IC$_{50}$ 3.9 nM.

Step 9—Synthesis of Intermediate 19.6-2, (R,R or S,S)-5-chloro-6-(3-fluoro-1-methylpiperidin-4-yl)-1H-indazole To a solution of intermediate 19.5-2 (150 mg, 0.591 mmol) in anhydrous MeOH (10 ml) was added formaldehyde (35.5 mg, 1.182 mmol) and sodium cyanotrihydroborate (74.3 mg, 1.182 mmol), the resulting mixture was stirred at 25° C. for 12 hours. Afterward, the reaction solution was filtered and concentrated. The crude residues was purified by prep-HPLC (TFA) to give intermediate 19.6-2, (R,R or S,S)-5-chloro-6-(3-fluoro-1-methylpiperidin-4-yl)-1H-indazole. TFA salt. MS (ESI) m/z calc'd for $C_{13}H_{16}ClFN_3$ [M+H]$^+$ 268. found 268.

Step 10—Synthesis of Example 19.7-2, (R,R or S,S)-5-chloro-6-(3-fluoro-1-methylpiperidin-4-yl)-1-(1-methyl-1H-pyrazol-4-yl)-1H-indazole To a solution of 4-iodo-1-methyl-1H-pyrazole (23.31 mg, 0.112 mmol) in anhydrous DMSO (5 ml) was added intermediate 19.6-2 (20 mg, 0.075 mmol), (trans)-N1,N2-dimethylcyclohexane-1,2-diamine (2.125 mg, 0.015 mmol), potassium phosphate (47.6 mg, 0.224 mmol), and CuI (1.423 mg, 7.47 μmol). The resulting mixture was stirred at 90° C. under $N_2$ protection for 12 hours. Afterward, the crude reaction solution was filtered and concentrated. The crude material was purified by pre-HPLC (TFA) to give example 19.7-2, (R,R or 52V)-5-chloro-6-(3-fluoro-1-methylpiperidin-4-yl)-1-(1-methyl-1H-pyrazol-4-yl)-1H-indazole, TFA salt. MS (ESI) m/z calc'd for $C_{17}H_{20}ClFN_5$ [M+H]$^+$ 348. found 348. $^1$H NMR (400 MHz, $CD_3OD$) δ 8.12-8.22 (m, 2H), 7.94 (s, 1H), 7.87 (s, 1H), 7.66 (s, 1H), 5.22-5.48 (m, 1H), 3.75-4.03 (m, 5H), 3.60 (m, 1H), 3.15-3.31 (m, 1H), 3.15-3.31 (m, 1H), 3.03 (s, 3H), 2.26 (br s, 1H), 2.10 (m, 1H). LRRK2 IC$_{50}$ 3.0 nM.

Compounds in Table 11 below were prepared from intermediate 19.6-1 or intermediate 19.6-2 using the method described in step 8 or step 10 of Scheme 22.

TABLE 11

| Example | Structure Name | Observed m/z [M + H]$^+$ | LRRK2 IC$_{50}$ (nM) |
| --- | --- | --- | --- |
| 19.8-1 | (R,R or S,S)-5-(5-chloro-6-(3-fluoro-1-methylpiperidin-4-yl)-1H-indazol-1-yl)-3-methylisothiazole | 365 | 8.3 |
| 19.8-2 | (R,R or S,S)-5-(5-chloro-6-(3-fluoro-1-methylpiperidin-4-yl)-1H-indazol-1-yl)-3-methylisothiazole, TFA salt | 365 | 5.9 |

Preparation of Examples 20.2-1, (R,R or S,S)-5-chloro-6-(3-fluoro-1-(oxetan-3-yl)piperidin-4-yl)-1-(1-methyl-1H-pyrazol-4-yl)-1H-indazole and 20.2-2, (R,R or S,S)-5-chloro-6-(3-fluoro-1-(oxetan-3-yl)piperidin-4-yl)-1-(1-methyl-1H-pyrazol-4-yl)-1H-indazole

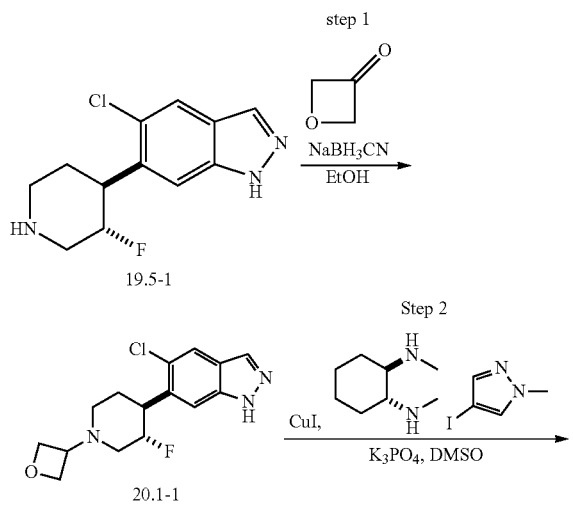

Scheme 23

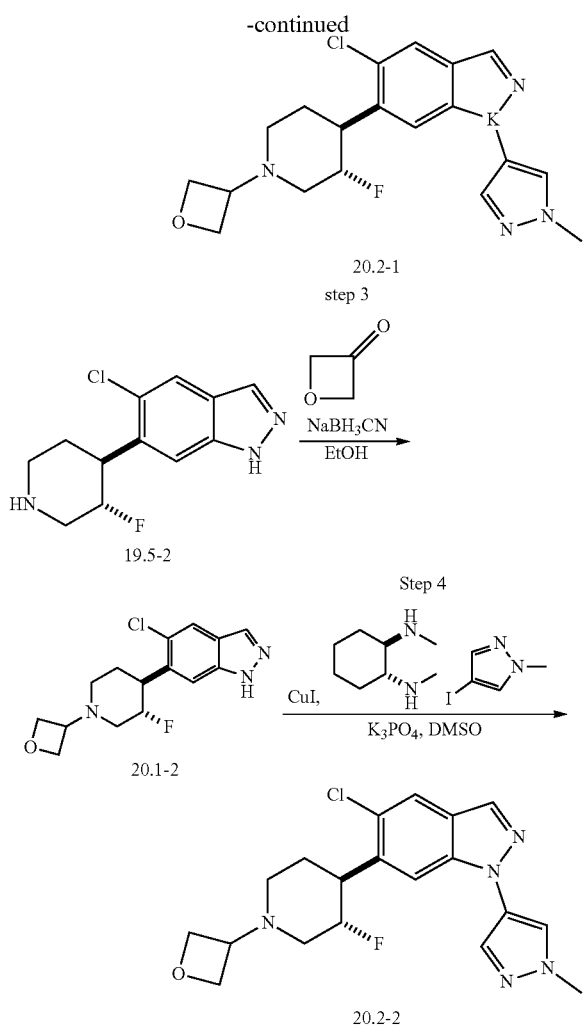

Step 1—Synthesis of Intermediate 20.1-1, (R,R or S,S)-5-chloro-6-(3-fluoro-1-(oxetan-3-yl)piperidin-4-yl)-1H-indazole To a solution of intermediate 19.5-1 (300 mg, 1.182 mmol) in anhydrous EtOH (20 ml) was added oxetan-3-one (170 mg, 2.365 mmol) and acetic acid (142 mg, 2.365 mmol), the pH was adjusted to 6~7. Then magnesium sulfate (285 mg, 2.365 mmol) and sodium cyanotrihydroborate (149 mg, 2.365 mmol) were added portion-wise, and the resulting mixture was stirred at 90° C. for 1 hours. Afterward, the reaction solution was filtered and concentrated. The crude material was purified by prep-TLC (EtOAc:MeOH=20:1) to give intermediate 20.1-1, (R,R or S,S)-5-chloro-6-(3-fluoro-1-(oxetan-3-yl)piperidin-4-yl)-1H-indazole. MS (ESI) m/z calc'd for $C_{15}H_{18}ClFN_5O$ [M+H]$^+$ 310. found 310.

Step 2—Synthesis of Example 20.2-1, (R,R or S,S)-5-chloro-6-(3-fluoro-1-(oxetan-3-yl)piperidin-4-yl)-1-(1-methyl-1H-pyrazol-4-yl)-1H-indazole To a solution of 4-iodo-1-methyl-1H-pyrazole (153 mg, 0.736 mmol) in anhydrous DMSO (15 ml) was added intermediate 20.1-1 (190 mg, 0.613 mmol), (trans)-N1,N2-dimethylcyclohexane-1,2-diamine (34.9 mg, 0.245 mmol), potassium phosphate (391 mg, 1.840 mmol) and CuI (23.36 mg, 0.123 mmol). The resulting mixture was stirred at 90° C. under $N_2$ protection for 12 hours. After cooling to room temperature, filtering and concentrating, the crude material was purified by pre-HPLC (TFA) to give example 20.2-1, (R,R or S,S)-5-chloro-6-(3-fluoro-1-(oxetan-3-yl)piperidin-4-yl)-1-(1-methyl-1H-pyrazol-4-yl)-1H-indazole, TFA salt. MS (ESI) m/z calc'd for $C_{19}H_{22}ClFN_5O$ [M+H]$^+$ 390. found 390. $^1$H NMR (400 MHz, CD$_3$OD) δ 8.17 (s, 2H), 7.96 (s, 1H), 7.88 (s, 1H), 7.65 (s, 1H), 5.16-5.41 (m, 1H), 4.76-4.86 (m, 4H), 4.36 (q, J=6.36 Hz, 1H), 4.01 (s, 3H), 3.69-3.85 (m, 2H), 3.41 (m, 1H), 2.85-3.03 (m, 2H), 2.27 (m, 1H), 1.95-2.11 (m, 1H). LRRK2 IC$_{50}$ 1.7 nM.

Step 3—Synthesis of Intermediate 20.1-2, (R,R or S,S)-5-chloro-6-(3-fluoro-1-(oxetan-3-yl)piperidin-4-yl)-1H-indazole To a solution of intermediate 19.5-2 (50 mg, 0.197 mmol) in anhydrous EtOH (10 ml) was added oxetan-3-one (28.4 mg, 0.394 mmol) and acetic acid (23.67 mg, 0.394 mmol), and the pH was adjusted to 6~7. Then, magnesium sulfate (47.4 mg, 0.394 mmol) and sodium cyanotrihydroborate (24.77 mg, 0.394 mmol) were both added portion-wise, and the resulting mixture was stirred at 90° C. for 1 hour. After filtration and concentration, the crude product was purified by pre-HPLC (TFA) to give intermediate 20.1-2, (R,R or S,S)-5-chloro-6-(3-fluoro-1-(oxetan-3-yl)piperidin-4-yl)-1H-indazole, TFA salt. MS (ESI) m/z calc'd for $C_{15}H_{18}ClFN_5O$ [M+H]$^+$ 310. found 310.

Step 4—Synthesis of Example 20.2-2, (R,R or S,S)-5-chloro-6-(3-fluoro-1-(oxetan-3-yl)piperidin-4-yl)-1-(1-methyl-1H-pyrazol-4-yl)-1H-indazole To a solution of 4-iodo-1-methyl-1H-pyrazole (20.14 mg, 0.097 mmol) in anhydrous DMSO (5 ml) was added intermediate 20.1-2 (20 mg, 0.065 mmol), (trans)-N1,N2-dimethylcyclohexane-1,2-diamine (1.837 mg, 0.013 mmol), potassium phosphate (41.1 mg, 0.194 mmol) and CuI (1.230 mg, 6.46 μmol). The resulting mixture was stirred at 90° C. under $N_2$ protection for 12 hours. After filtration and concentration, the crude product was purified by pre-HPLC (TFA) to give example 20.2-2, (R,R or 52V)-5-chloro-6-(3-fluoro-1-(oxetan-3-yl)piperidin-4-yl)-1-(1-methyl-1H-pyrazol-4-yl)-1H-indazole, TFA salt. MS (ESI) m/z calc'd for $C_{19}H_{22}ClFN_5O$ [M+H]$^+$ 390. found 390. $^1$H NMR (400 MHz, CD$_3$OD) δ 8.27 (s, 1H), 8.17 (s, 1H), 7.95 (s, 1H), 7.89 (s, 1H), 7.65-7.85 (m, 1H), 5.39-5.62 (m, 1H), 5.39-5.62 (m, 1H), 4.95-5.05 (m, 4H), 4.59 (m, 1H), 4.02 (s, 3H), 3.81-4.00 (m, 2H), 3.56 (m, 1H), 3.11-3.26 (m, 2H), 2.20-2.37 (m, 2H). LRRK2 IC$_{50}$ 5.8 nM.

Preparation of Example 21.6-1, (R,R or S,S)-6-(3-fluoro-1-methylpiperidin-4-yl)-5-methyl-1-(1-methyl-1H-pyrazol-4-yl)-1H-indazole and Example 21.6-2, (R,R or S,S)-6-(3-fluoro-1-methylpiperidin-4-yl)-5-methyl-1-(1-methyl-1H-pyrazol-4-yl)-1H-imidazole

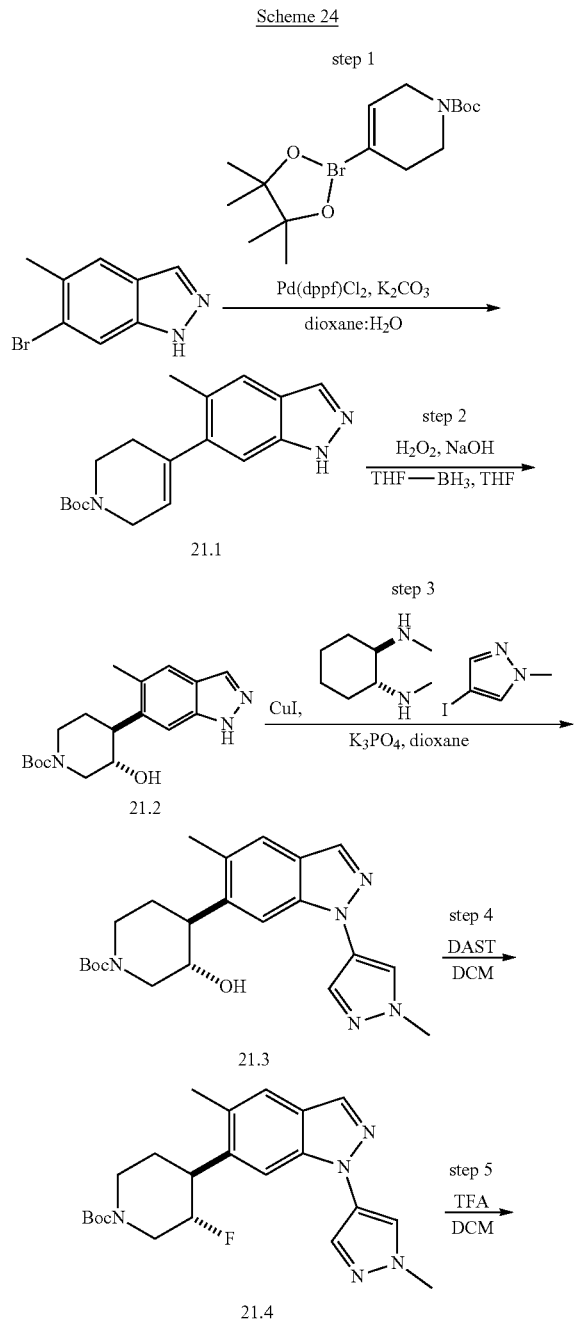

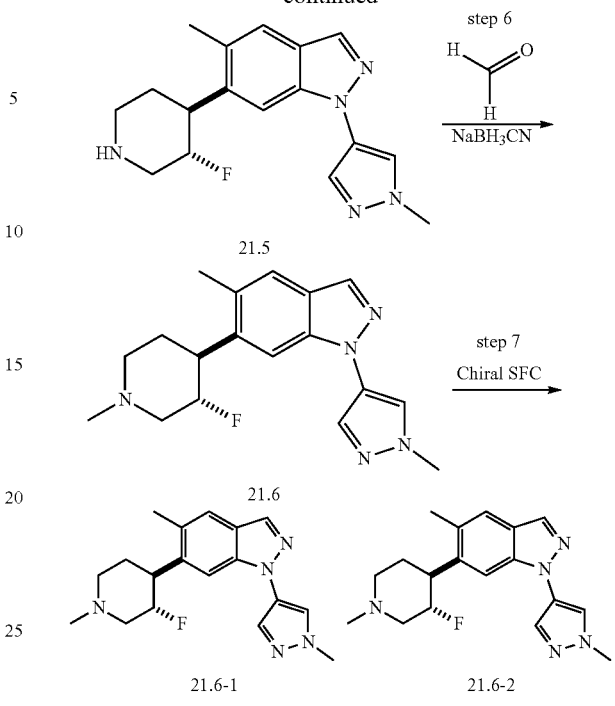

Step 1—Synthesis of Intermediate 21.1, tert-butyl 4-(5-methyl-1H-indazol-6-yl)-3,6-dihydropyridine-1(2H)-carboxylate To a solution of 6-bromo-5-methyl-1H-indazole (1.5 g, 7.11 mmol), $K_2CO_3$ (2.95 g, 21.32 mmol) and tert-butyl 4-(4,4,5,5-tetramethyl-1,3,2-dioxaborolan-2-yl)-5,6-dihydropyridine-1(2H)-carboxylate (2.64 g, 8.53 mmol) in 1,4-Dioxane (40 mL) and Water (15 mL) was added $PdCl_2(dppf)$ (0.520 g, 0.711 mmol). The resulting mixture was stirred at 80° C. under $N_2$ protection for 16 hours. Afterward, the reaction mixture was poured into water (20 mL) and extracted with EtOAc (50 mL×3). The organic layer was washed with brine (50 mL×3), dried over $Na_2SO_4$, filtered, and concentrated in vacuo. The crude residue was purified by silica gel column chromatography (gradient eluent of 0% to 25% EtOAc/Petroleum ether) to give intermediate 21.1, tert-butyl 4-(5-methyl-1H-indazol-6-yl)-3,6-dihydropyridine-1(2H)-carboxylate. MS (ESI) in z calc'd for $C_{18}H_{24}N_3O_2$ $[M+H]^+$ 314. found 314.

Step 2—Synthesis of Intermediate 21.2, (R,R and S,S)-tert-butyl 3-hydroxy-4-(5-methyl-1H-indazol-6-yl)piperidine-1-carboxylate To a solution of intermediate 21.1 (1.9 g, 6.06 mmol) in THF (20 ml) was added $BH_3$·THF (24.25 ml, 24.25 mmol) dropwise at 0° C., then the resulting mixture was warmed to room temperature and stirred at 18° C. for 16 hours. The reaction was cooled to 0° C. and 2 M NaOH aq. (11.1 mL) was added to the reaction at 0° C. Then $H_2O_2$ (5.31 mL, 60.6 mmol) was added dropwise at 0° C. The mixture was stirred at 18° C. for 1 hour. The reaction mixture was poured into water (20 mL) and extracted with EtOAc (50 mL×3). The organic layer was washed with brine (50 mL×3), dried over $Na_2SO_4$, filtered, and concentrated. The crude residue was purified by prep-HPLC (TFA) to give intermediate 21.2, (R,R and S,S)-tert-butyl 3-hydroxy-4-(5-methyl-1H-indazol-6-yl)piperidine-1-carboxylate, TFA salt. MS (ESI) m/z calc'd for $C_{18}H_{26}N_3O_3$ [M+H]$^+$ 276. found 276.

Step 3—Synthesis of Intermediate 21.3, (R,R and S,S)-tert-butyl 3-hydroxy-4-(5-methyl-1-(1-methyl-1H-pyrazol-4-yl)-1H-indazol-6-yl)piperidine-1-carboxylate To a solution of intermediate 21.2 (250 mg, 0.754 mmol) and 4-iodo-1-methyl-1H-pyrazole (204 mg, 0.981 mmol) in anhydrous Dioxane (3 mL) was added (trans)-N1,N2-dimethylcyclohexane-1,2-diamine (42.9 mg, 0.302 mmol), potassium phosphate (480 mg, 2.263 mmol) and CuI (28.7 mg, 0.151 mmol). The resulting mixture was stirred at 90° C. for 16 hours under N$_2$ protection. After filtration and evaporation, the crude residue was purified by silica gel column chromatography (gradient eluent of 0% to 21% EtOAc/Petroleum ether) to give intermediate 21.3, (R,R and S,S)-tert-butyl 3-hydroxy-4-(5-methyl-1-(1-methyl-1H-pyrazol-4-yl)-1H-indazol-6-yl)piperidine-1-carboxylate. MS (ESI) m/z calc'd for $C_{22}H_{30}N_5O_3$ [M+H]$^+$ 412. found 412.

Step 4—Synthesis of Intermediate 21.4, (R,R and S,S)-tert-butyl 3-fluoro-4-(5-methyl-1-(1-methyl-1H-pyrazol-4-yl)-1H-indazol-6-yl)piperidine-1-carboxylate To a solution of intermediate 21.3 (200 mg, 0.486 mmol) in DCM (10 mL) was added diethylaminosulfur trifluoride (0.128 mL, 0.972 mmol) under N$_2$ protection at −78° C. The reaction was warmed to 20° C. and was stirred at 20° C. for 1 hour. The reaction was quenched with saturated NaHCO$_3$ solution (10 mL) and was extracted with DCM (15 mL×3). The combined organic layer was washed with brine (25 mL), dried over Na$_2$SO$_4$. After filtration and evaporation, the crude residue was purified by silica gel column chromatography (gradient elution of 0% to 15% EtOAc/Petroleum ether) to give intermediate 21.4, (R,R and S,S)-tert-butyl 3-fluoro-4-(5-methyl-1-(1-methyl-1H-pyrazol-4-yl)-1H-indazol-6-yl)piperidine-1-carboxylate. MS (ESI) m/z calc'd for $C_{22}H_{29}FN_5O_2$ [M+H]$^+$ 414. found 414.

Step 5—Synthesis of Intermediate 21.5, (R,R and S,S)-6-(3-fluoropiperidin-4-yl)-5-methyl-1-(1-methyl-1H-pyrazol-4-yl)-1H-indazole A solution of intermediate 21.4 (150 mg, 0.363 mmol) in DCM (6 mL) was added TFA (2 mL) and the solution was stirred at 20° C. for 0.5 hours. Then, the pH of the reaction was adjusted to 7 using NH$_3$·H$_2$O. Next, the reaction solution was extracted with EtOAc (15 mL×3). The combined organic layer was washed with brine (20 mL×2) and dried over Na$_2$SO$_4$. Filtration and evaporation afforded intermediate 21.5, (R,R and S,S)-6-(3-fluoropiperidin-4-yl)-5-methyl-1-(1-methyl-1H-pyrazol-4-yl)-1H-indazole. The crude residue was used directly for the next step without further workup and purification. MS (ESI) m/z calc'd for $C_{17}H_{21}FN_5$ [M+H]$^+$ 314. found 314.

Step 6—Synthesis of Intermediate 21.6, (R,R and S,S)-6-(3-fluoro-1-methylpiperidin-4-yl)-5-methyl-1-(1-methyl-1H-pyrazol-4-yl)-1H-indazole To a solution of intermediate 21.5 (50 mg, 0.160 mmol) in MeOH (5 mL) was added formaldehyde (0.036 ml, 0.479 mmol). The resulting mixture was stirred at 18° C. for 0.5 hours. Then NaCNBH$_3$ (100 mg, 1.596 mmol) was added. The reaction mixture was stirred at 18° C. for 1 hour. Then the reaction was quenched with water (8 mL) and was extracted with EtOAc (20 mL×3). The combined organic layer was washed with brine (20 mL), dried over Na$_2$SO$_4$. After filtration and evaporation, the crude residue was purified by prep-HPLC (TFA) to give 21.6, (R,R and S,S)-6-(3-fluoro-1-methylpiperidin-4-yl)-5-methyl-1-(1-methyl-1H-pyrazol-4-yl)-1H-indazole, TFA salt. MS (ESI) m/z calc'd for $C_{18}H_{23}FN_5$ [M+H]$^+$ 328. found 328.

Step 7—Chiral Resolution of Intermediate 21.6 to Afford Examples 21.6-1, (R,R or S,S)-6-(3-fluoro-1-methylpiperidin-4-yl)-5-methyl-1-(1-methyl-1H-pyrazol-4-yl)-1H-indazole and Example 21.6-2, (R,R or S,S)-6-(3-Fluoro-1-Methylpiperidin-4-Yl)-5-Methyl-1-(1-Methyl-1H-pyrazol-4-yl)-1H-indazole Intermediate 21.6 was resolved by chiral SFC (Column: Daicel Chiralpak AD-H (250 mm×30 mm, 5 um). Mobile phase: A: CO$_2$ B: iPrOH (0.1% NH$_3$·H$_2$O). Gradient: 25% B to 100% B. Flow rate: 50 mL/min) RT: 1.495 min (21.6-1), 1.595 min (21.6-2).

Example 21.6-1, (R,R or S,S)-6-(3-fluoro-1-methylpiperidin-4-yl)-5-methyl-1-(1-methyl-1H-pyrazol-4-yl)-1H-indazole MS (ESI) m/z calc'd for $C_{18}H_{23}FN_5$ [M+H]$^+$ 328. found 328. $^1$H NMR (500 MHz, CDCl$_3$) δ 8.09 (s, 1H), 8.03 (s, 1H), 7.91 (s, 1H), 7.70 (s, 1H), 7.58 (s, 1H), 5.39-5.58 (m, 1H), 4.02 (s, 3H), 3.86 (m, 1H), 3.61 (m, 1H), 3.23-3.34 (m, 1H), 2.92 (s, 2H), 2.91-2.94 (m, 1H), 2.80-2.89 (m, 2H), 2.57 (m, 1H), 2.47 (s, 3H), 2.09 (m, 1H). LRRK2 IC$_{50}$ 13.7 nM.

Example 21.6-2, (R,R or S,S)-6-(3-fluoro-1-methylpiperidin-4-yl)-5-methyl-1-(1-methyl-1H-pyrazol-4-yl)-1H-indazole MS (ESI) m/z calc'd for $C_{18}H_{23}FN_5$ [M+H]$^+$ 328. found 328. $^1$H NMR (500 MHz, CDCl$_3$) δ 8.09 (s, 1H), 8.03 (s, 1H), 7.91 (s, 1H), 7.70 (s, 1H), 7.58 (s, 1H), 5.39-5.58 (m, 1H), 4.02 (s, 3H), 3.86 (m, 1H), 3.61 (m, 1H), 3.23-3.34 (m, 1H), 2.91-2.94 (m, 1H), 2.92 (s, 2H), 2.80-2.89 (m, 2H), 2.57 (q, 0.7=12.46 Hz, 1H), 2.47 (s, 3H), 2.09 (m, 1H). LRRK2 IC$_{50}$ 3.8 nM.

Preparation of Examples 22.1-1, (R,R or S,S)-6-(3-fluoro-1-(oxetan-3-yl)piperidin-4-yl)-5-methyl-1-(1-methyl-1H-pyrazol-4-yl)-1H-indazole and Example 22.1-2, (R,R or S,S)-6-(3-fluoro-1-(oxetan-3-yl)piperidin-4-yl)-5-methyl-1-(1-methyl-1H-pyrazol-4-yl)-1H-indazole Scheme 25

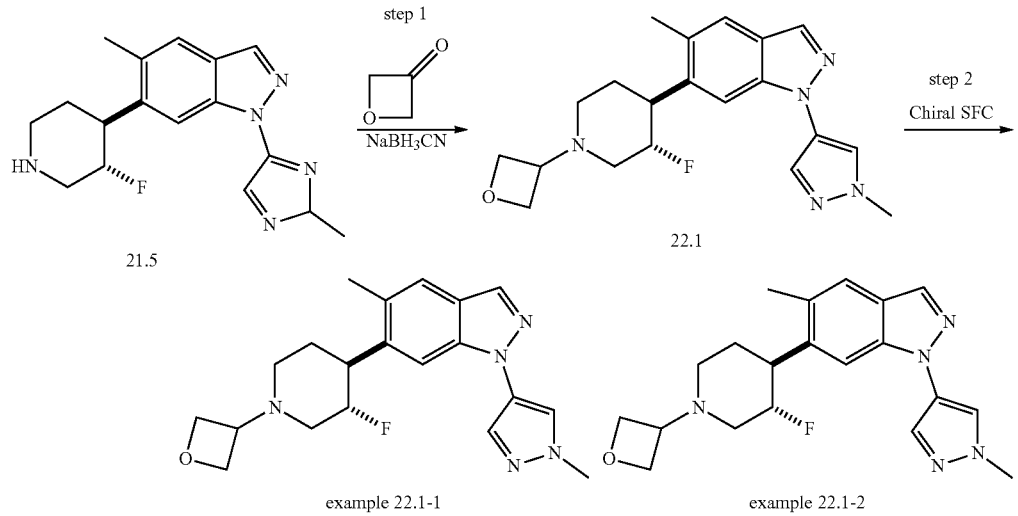

example 22.1-1 example 22.1-2

Step 1—Synthesis of Compound 22.1, (R,R and S,S)-6-(3-fluoro-1-(oxetan-3-yl)piperidin-4-yl)-5-methyl-1-(1-methyl-1H-pyrazol-4-yl)-1H-indazole To a solution of intermediate 21.5 (50 mg, 0.160 mmol) in MeOH (10 mL) was added oxetan-3-one (23.00 mg, 0.319 mmol) and NaCNBH$_3$ (30.1 mg, 0.479 mmol). The resulting mixture was stirred at 90° C. for 16 hours. The reaction was poured into water (20 mL) and was extracted with EtOAc (30 mL×3). The organic layer was washed with brine (25 mL), dried over MgSO$_4$ and filtered. The filtrate was concentrated in vacuo and the crude residue was purified by prep-HPLC (TFA) to give compound 22.1, (R,R and S,S)-6-(3-fluoro-1-(oxetan-3-yl)piperidin-4-yl)-5-methyl-1-(1-methyl-1H-pyrazol-4-yl)-1H-indazole, TFA salt. MS (ESI) m/z calc'd for $C_{20}H_{25}FN_5O$ [M+H]$^+$ 370. found 370. $^1$HNMR (500 MHz, CDCl$_3$) δ 8.04 (s, 1H), 7.98 (s, 1H), 7.88 (s, 1H), 7.59 (d, 0.7=11.60 Hz, 2H), 5.23-5.42 (m, 1H), 5.11 (br s, 1H), 4.94-5.02 (m, 2H), 4.76-4.85 (m, 2H), 4.10 (m, 1H), 4.02 (s, 3H), 3.64 (m, 1H), 2.51-2.61 (m, 2H), 2.47 (s, 3H), 2.31-2.41 (m, 1H).

Step 2—Chiral Resolution of Compound 22.1, (R,R and S,S)-6-(3-fluoro-1-(oxetan-3-yl)piperidin-4-yl)-5-methyl-1-(1-methyl-1H-pyrazol-4-yl)-1H-indazole to Afford Examples 22.1-1, (R,R or S,S)-6-(3-fluoro-1-(oxetan-3-yl)piperidin-4-yl)-5-methyl-1-(1-methyl-1H-pyrazol-4-yl)-1H-indazole and 22.1-2, (R,R or S,S)-6-(3-fluoro-1-(oxetan-3-yl)piperidin-4-yl)-5-methyl-1-(1-methyl-1H-pyrazol-4-yl)-1H-indazole Intermediate 22.1 was resolved by chiral SFC (Column: Daicel Chiralpak AS-H (250 mm×30 mm, 5 um). Mobile phase: A: CO$_2$ B: ethanol (0.1% NH$_3$·H$_2$O). Gradient: 45% B to 100% B. Flow rate: 60 mL/min). RT: 3.096 min (22.1-1), 3.984 min (22.1-2).

Example 22.1-1, (R,R or S,S)-6-(3-fluoro-1-(oxetan-3-yl)piperidin-4-yl)-5-methyl-1-(1-methyl-1H-pyrazol-4-yl)-1H-indazole MS (ESI) m/z calc'd for $C_{20}H_{25}FN_5O$ [M+H]$^+$ 370. found 370. $^1$H NMR (500 MHz, CDCl$_3$) δ 8.03 (br s, 1H), 7.84 (br s, 1H), 7.76 (br s, 1H), 7.58 (br s, 1H), 7.48 (br s, 1H), 4.77-4.96 (m, 1H), 4.69-4.76 (m, 2H), 4.60-4.68 (m, 2H), 4.01-4.05 (m, 3H), 3.60-3.69 (m, 1H), 3.24 (br s, 1H), 3.12 (m, 1H), 2.83 (br s, 1H), 2.48 (m, 3H), 1.90-2.14 (m, 4H). LRRK2 IC$_{50}$ 8.4 nM.

Example 22.1-2, (R,R or S,S)-6-(3-fluoro-1-(oxetan-3-yl)piperidin-4-yl)-5-methyl-1-(1-methyl-1H-pyrazol-4-yl)-1H-indazole MS (ESI) m/z calc'd for $C_{20}H_{25}FN_5O$ [M+H]$^+$ 370. found 370. $^1$H NMR (500 MHz, CDCl$_3$) δ 8.03 (s, 1H), 7.84 (s, 1H), 7.76 (s, 1H), 7.57 (s, 1H), 7.47 (s, 1H), 4.77-4.94 (m, 1H), 4.70-4.77 (m, 2H), 4.58-4.68 (m, 2H), 4.04 (s, 3H), 3.61-3.69 (m, 1H), 3.21-3.28 (m, 1H), 3.06-3.18 (m, 1H), 2.84 (m, 1H), 2.48 (s, 3H), 1.86-2.14 (m, 4H). LRRK2 IC$_{50}$ 4.3 nM.

Preparation of Example 23.5, 5-chloro-6-((2S,4R)-2-methyl-1-(3-methyloxetan-3-yl)piperidin-4-yl)-1-(1-methyl-1H-pyrazol-4-yl)-1H-indazole Scheme 26

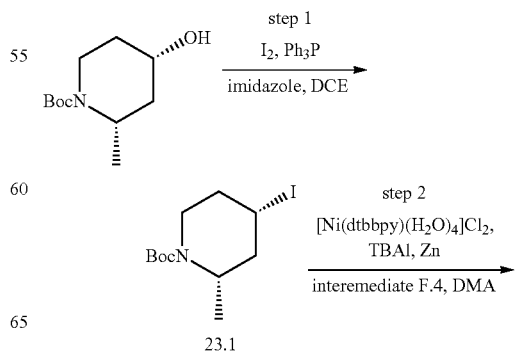

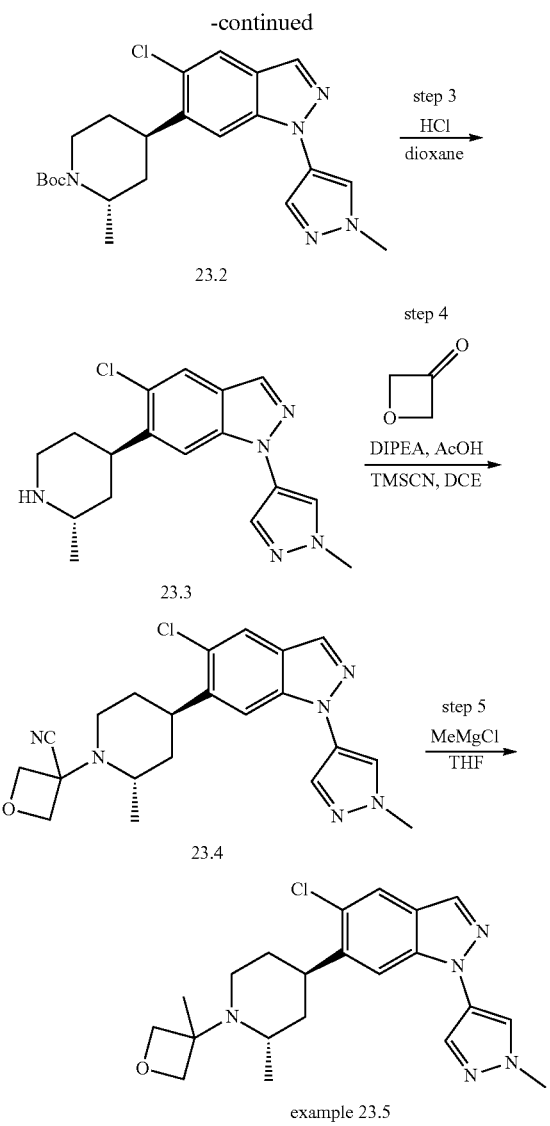

Step 1—Synthesis of Intermediate 23.1, tert-butyl (2S,4R or 2S,4S)-4-iodo-2-methylpiperidine-1-carboxylate Iodine (0.707 g, 2.79 mmol) was dissolved in DCE (10 ml). The reaction was cooled to 0° C., and then triphenylphosphine (0.792 g, 3.02 mmol) was added portionwise. After 90 minutes imidazole (0.237 g, 3.48 mmol) was added, followed by tert-butyl (2S,4S)-4-hydroxy-2-methylpiperidine-1-carboxylate (0.500 g, 2.32 mmol). The reaction was stirred at 0° C. with slow warming to room temperature overnight. Crude material was then partitioned between diethyl ether and water. The ether layer was washed a second time with water, then dried over MgSO$_4$, filtered and evaporated. The crude solid was triturated with hexanes and then filtered. The hexane filtrate was purified by silica gel column chromatography eluting with DCM to give intermediate 23.1, tert-butyl (2S,4R or 2S,4S)-4-iodo-2-methylpiperidine-1-carboxylate. MS (ESI) m/z calc'd for $C_{11}H_{20}INO_2$ [M+H-tBu]$^+$ 270. found 270.

Step 2—Synthesis of Intermediate 23.2, tert-butyl (2S,4R)-4-(5-chloro-1-(1-methyl-1H-pyrazol-4-yl)-1H-indazol-6-yl)-2-methylpiperidine-1-carboxylate Intermediate 23.1 (238 mg, 0.73 mmol), common intermediate F.4 (228 mg, 0.73 mmol), [Ni(dtbbpy)(H$_2$O)$_4$]Cl$_2$ (34.0 mg, 0.073 mmol), TBAI (67.6 mg, 0.18 mmol), and zinc (96 mg, 1.46 mmol) were placed in a reaction vial with a stir bar. The vial was evacuated and back-filled with nitrogen 3×, then DMA was added (3.7 mL). The vial was evacuated and charged 3× again with nitrogen, then heated to 60° C. Once the reaction had ceased to progress, it was cooled to room temperature and partitioned between EtOAc and water. The organic layer was washed with water, then dried over sodium sulfate, filtered and evaporated. The crude residue was purified by silica gel column chromatography (gradient elution 35-75% EtOAc in hexanes) to afford intermediate 23.2, tert-butyl (2S,4R)-4-(5-chloro-1-(1-methyl-1H-pyrazol-4-yl)-1H-indazol-6-yl)-2-methylpiperidine-1-carboxylate. MS (ESI) m/z calc'd for $C_{22}H_{28}ClN_5O_2$ [M+H-tBu]$^+$374. found 374.

Step 3—Synthesis of Intermediate 23.3, 5-chloro-1-(1-methyl-1H-pyrazol-4-yl)-6-((2S,4R)-2-methylpiperidin-4-yl)-1H-indazole Intermediate 23.3 (95 mg, 0.22 mmol) was dissolved in dioxane (1 mL). Then, 4M HCl in dioxane (1.1 mL, 4.40 mmol) was added. The reaction was allowed to stir overnight. The dioxane was evaporated and the crude material was reconstituted in diethyl ether and filtered to afford intermediate 23.3, 5-chloro-1-(1-methyl-1H-pyrazol-4-yl)-6-((2S,4R)-2-methylpiperidin-4-yl)-1H-indazole. MS (ESI) m/z calc'd for $C_{17}H_{20}ClN_5$ [M+H]$^+$ 330. found 330. $^1$H NMR (500 MHz, CD$_3$OD): δ 8.16 (s, 1H), 8.14 (s, 1H), 7.94 (s, 1H), 7.88 (s, 1H), 7.48 (s, 1H), 4.02 (s, 3H), 3.89 (m, 1H), 3.73 (m, 1H), 3.46 (m, 1H) 3.37 (m, 1H), 3.32 (m, 1H), 2.17 (m, 1H), 2.08 (m, 3H), 1.57 (d, J=7 Hz, 3H).

Step 4—Synthesis of Intermediate 23.4, 3-((2S,4R)-4-(5-chloro-1-(1-methyl-1H-pyrazol-4-yl)-1H-indazol-6-yl)-2-methylpiperidin-1-yl)oxetane-3-carbonitrile Intermediate 23.3 (85 mg, 0.23 mmol) was suspended in DCE (1 mL) and DIPEA (81 μl, 0.46 mmol) was added. Then 85 mg of 4 A molecular sieves (ground, activated in oven) and AcOH (20 μl, 0.35 mmol) were added. After stirring for ~ 5 minutes added 3-oxetanone (22 μl, 0.35 mmol) and heated to 50° C. After 120 minutes of stirring, TMS-CN (47 μl, 0.35 mmol) was carefully added via syringe. The reaction was heated to 70° C. for 1 hour. Once complete, the crude reaction mixture was partitioned between DCM and saturated aq. NaHCO$_3$. The organic layer was washed a second time with aq. NaHCO$_3$, dried over sodium sulfate, filtered and evaporated. The crude residue was purified silica gel column chromatography (gradient elution 20-75% (3:1 EtOAc:EtOH) in hexanes) to afford intermediate 23.4, 3-((2S,4R)-4-(5-chloro-1-(1-methyl-1H-pyrazol-4-yl)-1H-indazol-6-yl)-2-methylpiperidin-1-yl)oxetane-3-carbonitrile. MS (ESI) in z calc'd for $C_{21}H_{23}ClN_6O$ [M+H]$^+$ 411. found 411.

Step 5—Synthesis of Example 23.5, 5-chloro-6-((2S,4R)-2-methyl-1-(3-methyloxetan-3-yl)piperidin-4-yl)-1-(1-methyl-1H-pyrazol-4-yl)-1H-indazole Intermediate 23.4 (52.7 mg, 0.13 mmol) was solvated in THF (750 μl) under a nitrogen atmosphere and cooled to 0°

C. Methylmagnesium chloride (214 μl, 0.64 mmol) was added slowly via syringe. The reaction was then warmed to 50° C. After 90 minutes, the crude reaction was carefully quenched with saturated NaHCO₃ and EtOAc (gas evolution). The organic layer was washed again with saturated NaHCO₃, dried over Na₂SO₄, filtered, and concentrated. The crude material was then purified silica gel column chromatography (gradient elution of 30-100% (3:1 EtOAc: EtOH) in hexanes) to afford example 23.5, 5-chloro-6-((2S, 4R)-2-methyl-1-(3-methyloxetan-3-yl)piperidin-4-yl)-1-(1-methyl-1H-pyrazol-4-yl)-1H-indazole. MS (ESI) m/z calc'd for $C_{21}H_{26}ClN_5O$ [M+H]⁺ 400. found 400. ¹H NMR (500 MHz, DMSO-d6): δ 8.37 (s, 1H), 8.20 (s, 1H), 7.95 (s, 1H), 7.88 (s, 1H), 7.51 (s, 1H), 4.67 (m, 2H), 4.09 (m, 2H) 3.93 (s, 3H), 3.33 (m, 2H), 2.87 (m, 2H), 1.81 (m, 2H) 1.68 (m, 2H), 1.48 (s, 3H), 0.98 (d, J=8 Hz, 3H). LRRK2 IC₅₀ 1.2 nM.

Preparation of Example 24.6, (R,R and S,S)-5-methyl-6-(3-methyl-1-(3-methyloxetan-3-yl)piperidin-4-yl)-1-(1-methyl-1H-pyrazol-4-yl)-1H-indazole

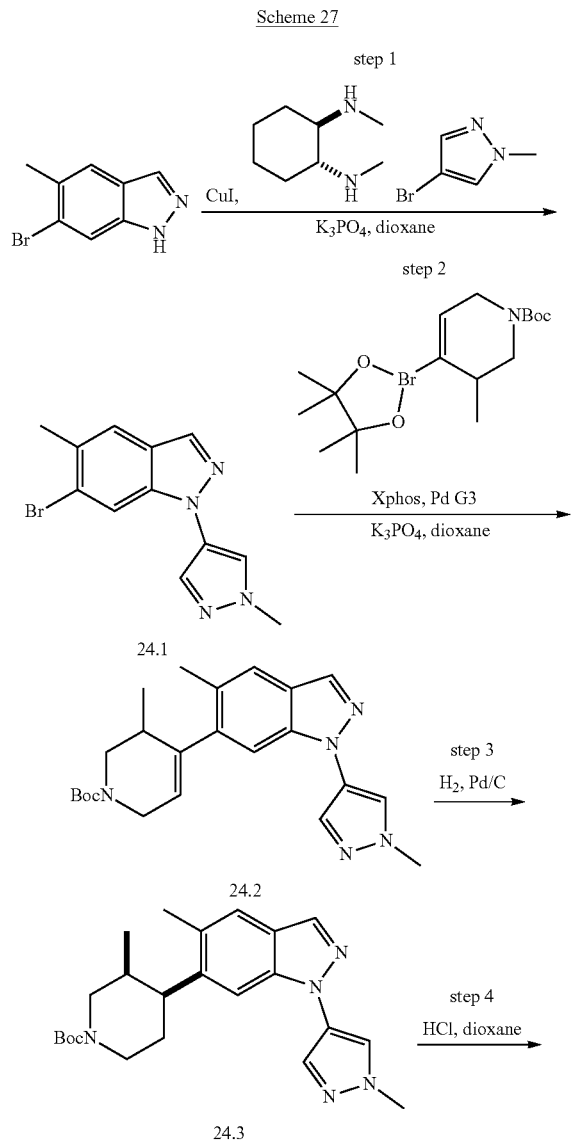

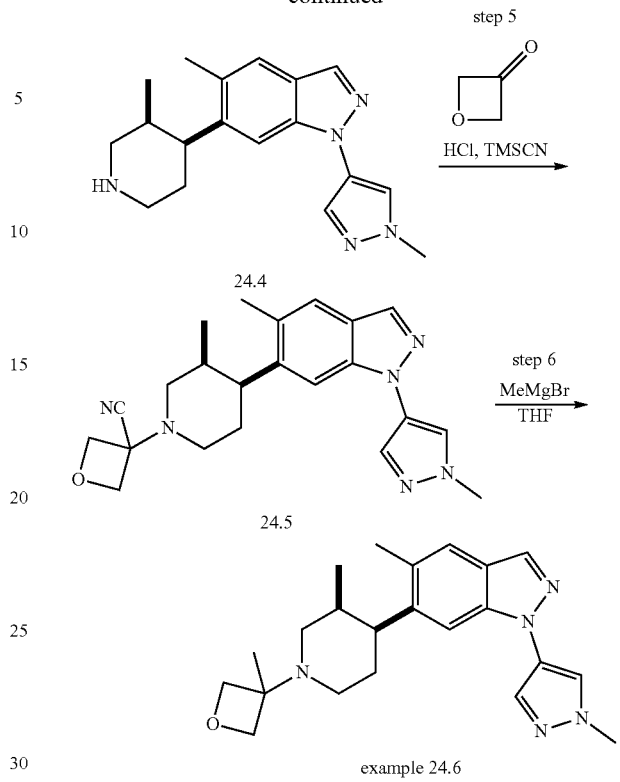

Step 1—Synthesis of Intermediate 24.1, 6-bromo-5-methyl-1-(1-methyl-1H-pyrazol-4-yl)-1H-indazole 6-bromo-5-methyl-1h-indazole (400 mg, 1.895 mmol), 4-bromo-1-methyl-1H-pyrazole (0.392 mL, 3.79 mmol), cuprous iodide (36.1 mg, 0.190 mmol), trans-N,N'-dimethylcyclohexane-1,2-diamine (0.060 mL, 0.379 mmol), and potassium phosphate (1207 mg, 5.69 mmol) were combined in a 20 mL microwave vial and dissolved in 1,4-dioxane (9 mL). The vial was sealed and stirred at 110° C. overnight. Next day, the reaction was cooled to room temperature and loaded directly onto a silica gel column. The material was purified by silica gel column chromatography (gradient of 25-100% ethyl acetate in hexanes) to give intermediate 24.1, 6-bromo-5-methyl-1-(1-methyl-1H-pyrazol-4-yl)-1H-indazole. MS (ESI) m/z calc'd for $C_{12}H_{11}BrN_4$ [M+H]⁺ 291. found 291.

Step 2—Synthesis of Intermediate 24.2, tert-butyl 3-methyl-4-(5-methyl-1-(1-methyl-1H-pyrazol-4-yl)-1H-indazol-6-yl)-3,6-dihydropyridine-1(2H)-carboxylate Intermediate 24.1 (90 mg, 0.309 mmol), tert-butyl 3-methyl-4-(tetramethyl-1,3,2-dioxaborolan-2-yl)-1,2,3,6-tetrahydropyridine-1-carboxylate (100 mg, 0.309 mmol), methanesulfonato(2-dicyclohexylphosphino-2',4',6'-tri-i-propyl-1,1'-biphenyl)(2'-amino-1,1'-biphenyl-2-yl)palladium(II) (26.2 mg, 0.031 mmol), and potassium phosphate (197 mg, 0.927 mmol) were combined in a 5 mL microwave vial and dissolved in 1,4-dioxane (1200 μl) and water (300 μl). The vial was sealed and flushed with argon and stirred at 65° C. overnight. The next day, the crude reaction was directly purified using silica gel column chromatography (gradient elution of 10-75% ethyl acetate in hexanes) to give intermediate 24.2, tert-butyl 3-methyl-4-(5-methyl-1-(1-methyl-1H-pyrazol-4-yl)-1H-indazol-6-yl)-3,6-dihydropyridine-1(2H)-carboxylate. MS (ESI) m/z calc'd for $C_{23}H_{29}N_5O_2$ [M+H]$^+$ 408. found 408.

Step 3—Synthesis of Intermediate 24.3, (R,R and S,S)-tert-butyl 3-methyl-4-(5-methyl-1-(1-methyl-1H-pyrazol-4-yl)-1H-indazol-6-yl)piperidine-1-carboxylate Intermediate 24.2 (120 mg, 0.294 mmol) was dissolved in Ethyl acetate (10 ml) in a 100 mL round bottom flask. 10% palladium on carbon (30 mg, 0.282 mmol) was then added to the solution. The flask was sealed with a septum, evacuated, and charged with a balloon of hydrogen and then stirred at room temperature overnight. Some ethanol was added to push the reaction to completion. The reaction was filtered through Celite® (diatomaceous earth) using ethyl acetate and concentrated to give intermediate 24.3, (R,R and S,S)-tert-butyl 3-methyl-4-(5-methyl-1-(1-methyl-1H-pyrazol-4-yl)-1H-indazol-6-yl)piperidine-1-carboxylate. MS (ESI) m/z calc'd for $C_{23}H_{31}N_5O_2$ [M+H]$^+$ 410. found 410.

Step 4—Synthesis of Intermediate 24.4, (R,R and S,S)-5-methyl-1-(1-methyl-1H-pyrazol-4-yl)-6-(3-methylpiperidin-4-yl)-1H-indazole Intermediate 24.3 (90 mg, 0.220 mmol) was dissolved in 1,4-dioxane (1000 μL) followed by addition of HCl, 4M in 1,4-dioxane (1000 μL, 4.00 mmol). The reaction was stirred at room temperature for 30 minutes, and then concentrated to give intermediate 24.4, (R,R and S,S)-5-methyl-1-(1-methyl-1H-pyrazol-4-yl)-6-(3-methylpiperidin-4-yl)-1H-indazole, HCl salt. The crude material was used for the next step without additional purification. MS (ESI) m/z calc'd for $C_{18}H_{23}N_5$ [M+H]$^+$ 310. found 310].

Step 5—Synthesis of Intermediate 24.5, (R,R and S,S)-3-(3-methyl-4-(5-methyl-1-(1-methyl-1H-pyrazol-4-yl)-1H-indazol-6-yl)piperidin-1-yl)oxetane-3-carbonitrile Intermediate 24.4, HCl salt (76 mg, 0.220 mmol) was suspended in 1,2-Dichloroethane (750 μl) with 76 mg of 4 angstrom molecular sieves, and acetic acid (18.87 μl, 0.330 mmol) was added. Then, 3-oxetanone (19 μl, 0.330 mmol) was added. After 10 minutes of stirring at room temp, trimethylsilyl cyanide (41 μl, 0.330 mmol) was added carefully. The reaction was then heated to 55° C. overnight. The crude reaction was quenched with saturated NaHCO$_3$ (aq) and DCM. The organic layer was extracted 2×, then dried over MgSO$_4$, filtered, and concentrated. The crude material was purified by silica gel column chromatography (gradient of 10-100% ethyl acetate in hexanes) to afford intermediate 24.5, (R,R and S,S)-3-(3-methyl-4-(5-methyl-1-(1-methyl-1H-pyrazol-4-yl)-1H-indazol-6-yl)piperidin-1-yl)oxetane-3-carbonitrile. MS (ESI) m/z calc'd for $C_{22}H_{26}N_6O$ [M+H]$^+$ 391. found 391.

Step 6—Synthesis of Example 24.6, (R,R and S,S)-5-methyl-6-(3-methyl-1-(3-methyloxetan-3-yl)piperidin-4-yl)-1-(1-methyl-1H-pyrazol-4-yl)-1H-indazole Intermediate 24.5 (35 mg, 0.090 mmol) was dissolved in tetrahydrofuran (299 μl) followed by the addition of methylmagnesium bromide (149 μl, 0.448 mmol). The reaction was stirred at 65° C. overnight and then cooled to room temperature and quenched with water. The crude solution was extracted using 3:1 CHCl$_3$:IPA and a phase separator. The organic layer was concentrated and the crude material was purified using reverse phase prep-HPLC (Method B) to afford example 24.6, (R,R and S,S)-5-methyl-6-(3-methyl-1-(3-methyloxetan-3-yl)piperidin-4-yl)-1-(1-methyl-1H-pyrazol-4-yl)-1H-indazole. MS (ESI) m/z calc'd for $C_{24}H_{29}N_5O$ [M+H]$^+$ 380. found 380. $^1$H NMR (500 MHz, DMSO-d$_6$) δ 8.31 (s, 1H), 8.25 (s, 1H), 7.92 (s, 1H), 7.60 (s, 1H), 7.29 (s, 1H), 4.48-4.47 (d, 1H), 4.34-4.32 (d, 1H), 4.16-4.13 (m, 2H), 3.97 (s, 3H), 3.08-3.04 (m, 1H), 2.70-2.68 (m, 1H), 2.45-2.32 (m, 4H), 2.42 (s, 3H), 2.24-2.19 (m, 1H), 1.52-1.50 (m, 1H), 1.31 (s, 3H), 0.81-0.80 (d, 3H). LRRK2 IC$_{50}$ 0.9 nM.

Preparation of Example 25.5, (4-(5-chloro-1-(1-methyl-1H-pyrazol-4-yl)-1H-indazol-6-yl)-1-methylpiperidin-2-yl)methanol

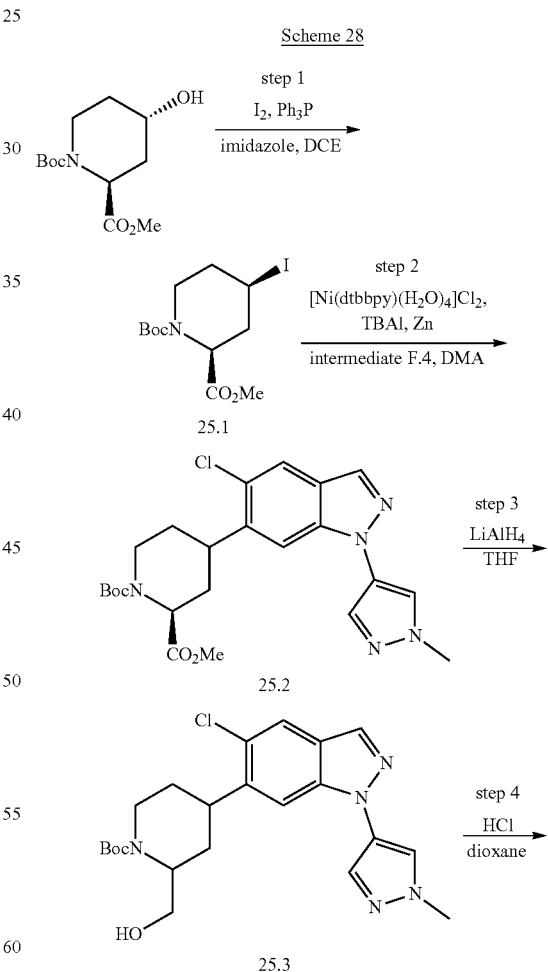

Scheme 28

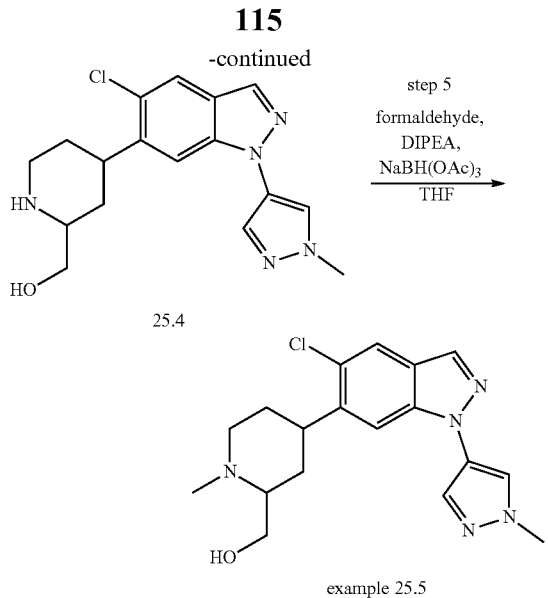

25.4 example 25.5

Step 1—Synthesis of Intermediate 25.1, 1-(tert-butyl) 2-methyl (2S,4R or 2S,4S)-4-iodopiperidine-1,2-dicarboxylate Iodine (1.175 g, 4.63 mmol) was dissolved in 16 mL DCE. The solution was cooled to 0° C., then triphenylphosphine (1.315 g, 5.01 mmol) was added portion wise. After 90 minutes imidazole (0.394 g, 5.78 mmol) was added, followed by 1-(tert-butyl) 2-methyl (2S,4S)-4-hydroxypiperidine-1,2-dicarboxylate (1.00 g, 3.86 mmol) in 4 mL DCM. The reaction was stirred at 0° C. with slow warming to room temperature overnight. The crude reaction was partitioned between diethyl ether and water. The ether layer was washed a second time with water, then dried over $MgSO_4$, filtered, and evaporated. The crude material was triturated with hexanes and then filtered. The hexane filtrate was evaporated and purified by silica gel column chromatography (eluting with 10-40% EtOAc in hexanes) to give intermediate 25.1, 1-(tert-butyl) 2-methyl (2S,4R or 2S,4S)-4-iodopiperidine-1,2-dicarboxylate. MS (ESI) m/z calc'd for $C_{12}H_{20}INO_4$ [M+H-Boc]$^+$ 270. found 270.

Step 2—Synthesis of Intermediate 25.2, 1-(tert-butyl) 2-methyl (2S)-4-(5-chloro-1-(1-methyl-1H-pyrazol-4-yl)-1H-indazol-6-yl)piperidine-1,2-dicarboxylate Intermediate 25.1 (0.583 g, 1.58 mmol), common intermediate F.4 (0.410 g, 1.32 mmol), [Ni(dtbbpy)(H$_2$O)$_4$]Cl$_2$ (0.061 g, 0.13 mmol), TBAI (0.122 g, 0.33 mmol), and zinc (0.172 g, 2.63 mmol) were placed in a round bottom flask with a stir bar. The vessel was evacuated and charged with nitrogen 3×, then DMA (6.6 mL) was added. The vessel was evacuated and charged 3× again with nitrogen, then heated to 60° C. and monitored by LCMS. After 2 hours, the reaction solution was partitioned between EtOAc and water. The organic layer was washed with water, then dried over sodium sulfate, filtered, and evaporated. The crude material was purified by silica gel column chromatography (eluting with 35-75% EtOAc in hexanes) to afford intermediate 25.2, 1-(tert-butyl) 2-methyl (2S)-4-(5-chloro-1-(1-methyl-1H-pyrazol-4-yl)-1H-indazol-6-yl)piperidine-1,2-dicarboxylate. MS (ESI) m/z calc'd for $C_{19}H_{21}Cl\,N_5O_4$ [M-tBu+H]$^+$ 418. found 418.

Step 3—Synthesis of Intermediate 25.3, tert-butyl 4-(5-chloro-1-(1-methyl-1H-pyrazol-4-yl)-1H-indazol-6-yl)-2-(hydroxymethyl)piperidine-1-carboxylate Intermediate 25.2 (275 mg, 0.58 mmol) was dissolved in THF (2.3 mL) and cooled to 0° C. Then, 1N lithium aluminum hydride (580 µl, 0.58 mmol) in THF was added dropwise and stirred for 10-15 minutes. The reaction was then quenched with 4-5 drops of 5N NaOH followed by EtOAc. To the mixture was added MgSO$_4$ and it was stirred 15 minutes, then filtered and concentrated. The crude was purified by silica gel column chromatography (gradient elution with 20-75% 3:1 EtOAc:EtOH in hexanes) to give intermediate 25.3, tert-butyl 4-(5-chloro-1-(1-methyl-1H-pyrazol-4-yl)-1H-indazol-6-yl)-2-(hydroxymethyl)piperidine-1-carboxylate. MS (ESI) m/z calc'd for $C_{18}H_{21}Cl\,N_5O_3$ [M+H-tBu]$^+$ 390. found 390.

Step 4—Synthesis of Intermediate 25.4, (4-(5-chloro-1-(1-methyl-1H-pyrazol-4-yl)-1H-indazol-6-yl)piperidin-2-yl)methanol Intermediate 25.3 (132 mg, 0.30 mmol) was dissolved in dioxane (1 mL). To the solution was added 4M HCl in dioxane (1.1 ml, 4.4 mmol). After 45 minutes, the reaction was evaporated and reconstituted in ether. The solid was filtered off and dried to afford intermediate 25.4, (4-(5-chloro-1-(1-methyl-1H-pyrazol-4-yl)-1H-indazol-6-yl)piperidin-2-yl)methanol. MS (ESI) m/z calc'd for $C_{17}H_{21}ClN_5O$ [M+H]$^+$ 346. found 346. $^1$HNMR (500 MHz, CD$_3$OD): δ 8.16 (s, 1H), 8.13 (s, 1H), 7.94 (s, 1H), 7.87 (s, 1H), 7.48 (s, 1H), 4.15 (m, 1H), 4.01 (s, 3H), 3.84 (m, 1H), 3.64 (m, 2H), 3.40 (m, 1H), 2.16 (m, 2H), 2.05 (m, 3H).

Step 5—Synthesis of Example 25.5, (4-(5-chloro-1-(1-methyl-1H-pyrazol-4-yl)-1H-indazol-6-yl)-1-methylpiperidin-2-yl)methanol Intermediate 25.4 (30 mg, 0.072 mmol) was suspended in THF (720 µl). To the mixture was added DIPEA (25 µl, 0.14 mmol) and it was allowed to stir until all solid is in solution. Then formaldehyde (43 µl, 0.57 mmol) was added. After 15-20 minutes sodium triacetoxyborohydride (30.4 mg, 0.14 mmol) was added and the reaction was allowed to stir overnight. The reaction was quenched with aq. NaHCO$_3$, diluted with water and extracted with EtOAc. The organic layer was dried over sodium sulfate, filtered, and evaporated. The crude material was purified by reverse phase prep-HPLC (Method B) to afford example 25.5, (4-(5-chloro-1-(1-methyl-1H-pyrazol-4-yl)-1H-indazol-6-yl)-1-methylpiperidin-2-yl)methanol. Absolute and relative stereochemistry was not determined. MS (ESI) m/z calc'd for $C_{18}H_{23}ClN_5O$ [M+H]$^+$ 360. found 360. $^1$H NMR (500 MHz, CDCl$_3$): δ 8.03 (s, 1H), 7.82 (s, 1H), 7.78 (s, 1H), 7.77 (s, 1H), 7.40 (s, 1H), 4.02 (m, 4H), 3.65 (m, 1H), 3.39 (m, 1H), 3.09 (m, 2H), 2.82 (m, 1H), 2.66 (s, 3H), 1.93 (m, 2H), 1.80 (d, J=13.5 Hz, 1H), 1.71 (m, J=13 Hz, 1H). LRRK2 IC$_{50}$ 9.7 nM

Preparation of Example 26.7-2, (R,R or S,S)-6-(3-methyl-1-(oxetan-3-yl)piperidin-4-yl)-1-(1-methyl-1H-pyrazol-4-yl)-1H-indazole

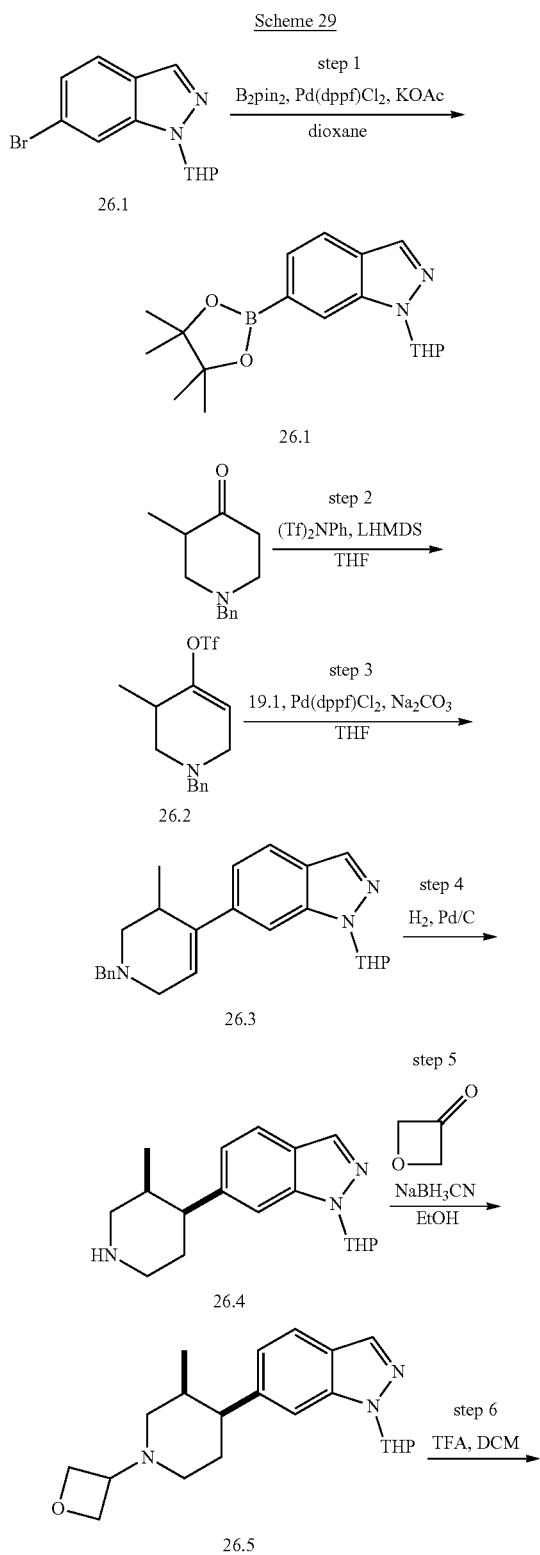

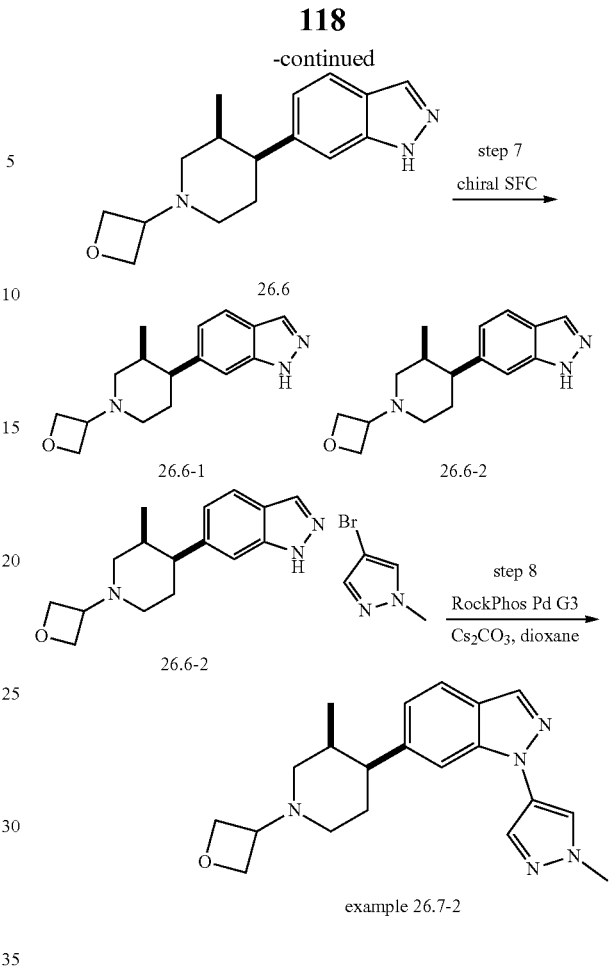

example 26.7-2

Step 1—Synthesis of Intermediate 26.1, 1-(tetrahydro-2H-pyran-2-yl)-6-(4,4,5,5-tetramethyl-1,3,2-dioxaborolan-2-yl)-1H-indazole To a solution of 6-bromo-1-(tetrahydro-2H-pyran-2-yl)-1H-indazole (20 g, 71.1 mmol) in anhydrous 1,4-Dioxane (100 mL) was added 4,4,4',4',5,5,5',5'-octamethyl-2,2'-bi(1,3,2-dioxaborolane) (21.68 g, 85 mmol), KOAc (20.94 g, 213 mmol) and $PdCl_2$(dppf)-$CH_2Cl_2$ Adduct (5.81 g, 7.11 mmol), and the resulting mixture was stirred at 110° C. under $N_2$ protection for 2 hours. Then, the reaction mixture was filtered through a pad of Celite® (diatomaceous earth) and the pad was washed with EtOAc (50 mL×3). The filtrate was concentrated and the crude residue was purified by silica gel column chromatography (eluting with 0% to 18% EtOAc/Petroleum ether) to give intermediate 26.1, 1-(tetrahydro-2H-pyran-2-yl)-6-(4,4,5,5-tetramethyl-1,3,2-dioxaborolan-2-yl)-1H-indazole.

Step 2—Synthesis of Intermediate 26.2, 1-benzyl-3-methyl-1,2,3,6-tetrahydropyridin-4-yl trifluoromethanesulfonate To a solution of 1-benzyl-3-methylpiperidin-4-one (10 g, 49.2 mmol) in THF (100 mL) was added LiHMDS (59.0 mL, 59.0 mmol) at −78° C., the resulting mixture was stirred at −78° C. for 2 hours, then 1,1,1-trifluoro-N-phenyl-N-((trifluoromethyl)sulfonyl)methanesulfonamide (19.33 g, 54.1 mmol) in THF (80 mL) was added dropwise over a period of 20 min and the temperature was maintained under −60° C. The reaction was warmed to 20° C. and was stirred at 20° C. for 3 horns. Then the reaction was quenched with saturated NH₄Cl (20 mL) and extracted with EtOAc (80 mL×3). The combined organic layer was washed with brine (60 mL) and dried over Na₂SO₄. After filtration and evaporation, the crude residue was purified by silica gel column chromatography (eluting with 0% to 11% EtOAc/Petroleum ether) to give intermediate 26.2, 1-benzyl-3-methyl-1,2,3,6-tetrahydropyridin-4-yl trifluoromethanesulfonate.

Step 3—Synthesis of Intermediate 26.3, 6-(1-benzyl-3-methyl-1,2,3,6-tetrahydropyridin-4-yl)-1-(tetrahydro-2H-pyran-2-yl)-1H-indazole To a solution of intermediate 26.2 (20 g, 59.6 mmol), and intermediate 26.1 (23.49 g, 71.6 mmol) in Dioxane (160 mL) and Water (50 mL) was added Na₂CO₃ (18.96 g, 179 mmol) and PdCl₂(dppf) (4.36 g, 5.96 mmol). The resulting mixture was stirred at 80° C. for 2 hours under N₂ protection. Then the reaction was poured into water (40 mL) and extracted with EtOAc (120 mL×3). The combined organic layer was washed with brine (130 mL) and dried over Na₂SO₄. After filtration and evaporation, the residue was purified by silica gel column chromatography (Eluent of 0% to 9% EtOAc/Petroleum ether) to give intermediate 26.3, 6-(1-benzyl-3-methyl-1,2,3,6-tetrahydropyridin-4-yl)-1-(tetrahydro-2H-pyran-2-yl)-1H-indazole. MS (ESI) m/z calc'd for $C_{25}H_{30}N_3O$ [M+H]⁺ 388. found 388.

Step 4—Synthesis of Intermediate 26.4, (R,R and S,S)-6-(3-methylpiperidin-4-yl)-1-(tetrahydro-2H-pyran-2-yl)-1H-indazole To a solution of intermediate 26.3 (5.5 g, 14.19 mmol) in EtOAc (20 mL) was added Pd/C (1.510 g, 1.419 mmol, 10%). The mixture was degassed under vacuum and purged with H₂ three times. Then the solution was stirred under 50 psi at 50° C. for 16 hours. Then the suspension was filtered through a pad of Celite® (diatomaceous earth) and the pad was washed with MeOH (35 mL×3). The filtrate was concentrated to give intermediate 26.4, (R,R and S,S)-6-(3-methylpiperidin-4-yl)-1-(tetrahydro-2H-pyran-2-yl)-1H-indazole which was used directly for next step without additional purification. MS (ESI) m/z calc'd for $C_{18}H_{26}N_3O$ [M+H]⁺ 300. found 300.

Step 5—Synthesis of Intermediate 26.5, (R,R and S,S)-6-(3-methyl-1-(oxetan-3-yl)piperidin-4-yl)-1-(tetrahydro-2H-pyran-2-yl)-1H-indazole To a solution of intermediate 26.4 (2.7 g, 9.02 mmol) and oxetan-3-one (1.950 g, 27.1 mmol) and MgSO₄ (1.085 g, 9.02 mmol) in EtOH (10 mL) was added NaCNBH₃ (1.133 g, 18.04 mmol). The resulting mixture was stirred at 90° C. for 5 hours. Then the reaction mixture was poured into water (10 mL) and extracted with EtOAc (20 mL*3). The organic layer was washed with brine (15 mL), dried over MgSO₄ and filtered. The filtrate was concentrated in vacuo and purified by silica gel column chromatography (eluent of 0% to 20% EtOAc/Petroleum ether) to give intermediate 26.5, (R,R and S,S)-6-(3-methyl-1-(oxetan-3-yl)piperidin-4-yl)-1-(tetrahydro-2H-pyran-2-yl)-1H-indazole. MS (ESI) m/z calc'd for $C_{21}H_{30}N_3O_2$ [M+H]⁺ 356. found 356.

Step 6—Synthesis of Intermediate 26.6, (R,R and S,S)-6-(3-methyl-1-(oxetan-3-yl)piperidin-4-yl)-1H-indazole To a solution of intermediate 26.5 (4 g, 11.25 mmol) in DCM (20 mL) was added TFA (4 mL) dropwise. The resulting mixture was stirred at 30° C. for 3 hours. Then, triethylamine (8 mL) was added and the pH was adjusted to 7. After evaporation, the residue was purified by prep-HPLC (Neutral) to give intermediate 26.6, (R,R and S,S)-6-(3-methyl-1-(oxetan-3-yl)piperidin-4-yl)-1H-indazole. MS (ESI) m/z calc'd for $C_{16}H_{22}N_3O$ [M+H]⁺ 272. found 272. ¹H NMR (400 MHz, CD₃OD) δ 7.97 (s, 1H), 7.68 (d, J=8.56 Hz, 1H), 7.31 (s, 1H), 7.05 (m, 1H), 4.64-4.73 (m, 3H), 4.58 (t, 0.7=6.11 Hz, 1H), 3.47 (m, 1H), 2.92-3.04 (m, 2H), 2.71 (m, 1H), 2.13-2.33 (m, 3H), 1.97 (m, 1H), 1.74 (m, 1H), 0.83 (d, 0.7=7.09 Hz, 3H).

Step 7—Chiral Resolution of Intermediate 26.6, (R,R and S,S)-6-(3-methyl-1-(oxetan-3-yl)piperidin-4-yl)-1H-indazole Intermediate 26.6 resolved via chiral SFC (Column: Daicel Chiralcel OJ (250 mm×50 mm, 10 um). Mobile phase: A: CO₂ B: ethanol (0.1% NH₃·H₂O). Isocratic 40% B. Flow rate: 200 mL/min). RT: 3.121 min (26.6-1), 3.890 (26.6-2).

Intermediate 26.6-1, (R,R or S,S)-6-(3-methyl-1-(oxetan-3-yl)piperidin-4-yl)-1H-indazole MS (ESI) m/z calc'd for $C_{16}H_{22}N_3O$ [M+H]⁺ 272. found 272. ¹H NMR (400 MHz, CD₃OD) δ 7.96 (s, 1H), 7.67 (d, 7=8.33 Hz, 1H), 7.30 (s, 1H), 7.04 (dd, 7=8.33, 0.88 Hz, 1H), 4.61-4.76 (m, 3H), 4.56 (t, 7=6.14 Hz, 1H), 3.39-3.52 (m, 1H), 2.87-3.05 (m, 2H), 2.69 (m, 1H), 2.11-2.33 (m, 3H), 1.94 (m, 1H), 1.72 (m, 1H), 0.81 (d, 7=7.02 Hz, 3H).

Intermediate 26.6-2, (R,R or S,S)-6-(3-methyl-1-(oxetan-3-yl)piperidin-4-yl)-1H-indazole MS (ESI) m/z calc'd for $C_{16}H_{22}N_3O$ [M+H]⁺ 272. found 272. ¹H NMR (400 MHz, CD₃OD) δ 7.96 (s, 1H), 7.67 (d, 7=8.33 Hz, 1H), 7.30 (s, 1H), 6.96-7.10 (m, 1H), 4.68 (m, 3H), 4.50-4.62 (m, 1H), 3.46 (m, 1H), 2.88-3.04 (m, 2H), 2.69 (m, 1H), 2.13-2.32 (m, 3H), 1.95 (m, 1H), 1.73 (m, 1H), 0.81 (d, 0.7=7.02 Hz, 3H).

Step 8—Synthesis of Example 26.7-2, (R,R or S,S)-6-(3-methyl-1-(oxetan-3-yl)piperidin-4-yl)-1-(1-methyl-1H-pyrazol-4-yl)-1H-indazole Intermediate 26.6-2 (35 mg, 0.129 mmol), 4-bromo-1-methyl-1H-pyrazole (50 mg, 0.311 mmol), Rockphos Pd G3 (10.81 mg, 0.013 mmol), and cesium carbonate (126 mg, 0.387 mmol) were combined in a 5 mL microwave vial and dissolved in 1,4-dioxane (800 μl). The vial was sealed, flushed with argon, and stirred at 95° C. overnight. The reaction was cooled to room temperature and partitioned between water and 3:1 CHCl₃:IPA. The mixture was separated using a phase separator and concentrated. The residue was purified by reverse phase prep-HPLC (Method A) followed by base-mediated neutralization of the resulting TFA salt to give example 26.7-2, (R,R or S,S)-6-(3-methyl-1-(oxetan-3-yl)piperidin-4-yl)-1-(1-methyl-1H-pyrazol-4-yl)-1H-indazole. MS (ESI) m/z calc'd for $C_{20}H_{25}N_5O$ [M+H]⁺ 352. found 352. ¹H NMR (500 MHz, DMSO-d₆) δ 8.31 (s, 1H), 8.25 (s, 1H), 7.92 (s, 1H), 7.83-7.81 (d, J=8.3 Hz, 1H), 7.42 (s, 1H), 7.15-7.14 (d, J=8.3 Hz, 1H), 4.88-4.85 (m, 1H), 4.79-4.75 (m, 3H), 4.49-4.43 (m, 1H), 3.57-3.54 (m, 3H), 3.19-3.15 (m, 1H), 3.00-2.95 (m, 1H), 2.57-2.52 (m, 1H), 2.50 (s, 3H), 2.31-2.25 (m, 1H), 2.06-2.03 (m, 1H), 0.80-0.79 (d, 3H). LRRK2 IC₅₀ 36.2 nM.

Preparation Examples 27.5-1, (R,S or S,R)-5-chloro-6-(3-methyl-1-(3-methyloxetan-3-yl)piperidin-4-yl)-1-(1-methyl-1H-pyrazol-4-yl)-1H-indazole and Example 27.5-2, (R,S or S,R)-5-chloro-6-(3-methyl-1-(3-methyloxetan-3-yl)piperidin-4-yl)-1-(1-methyl-1H-pyrazol-4-yl)-1H-indazole Scheme 30

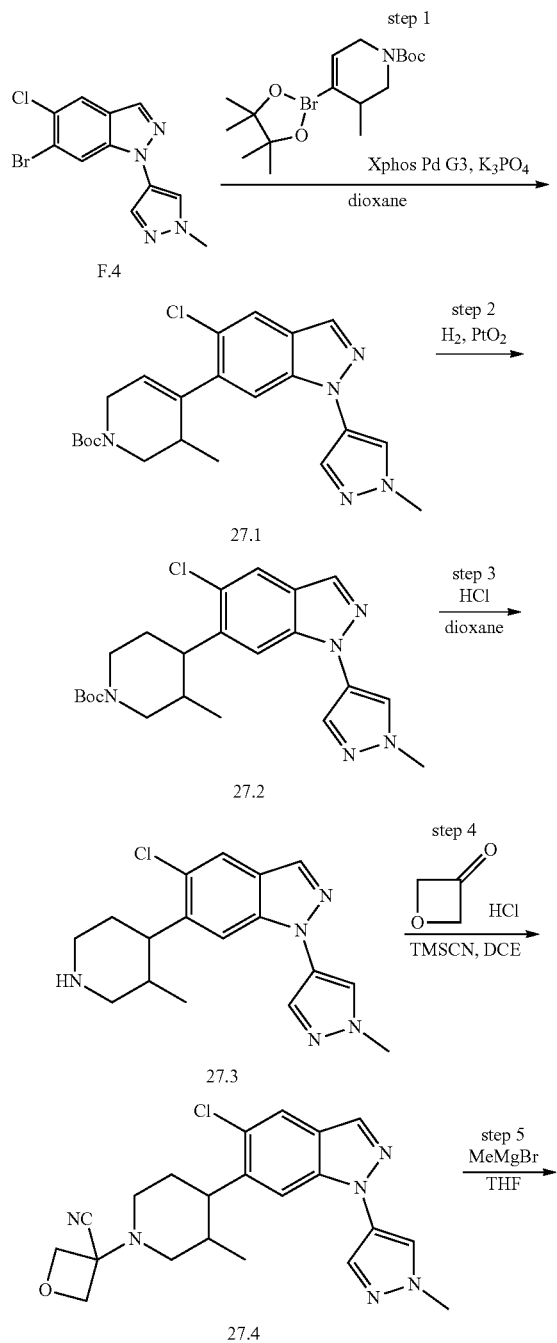

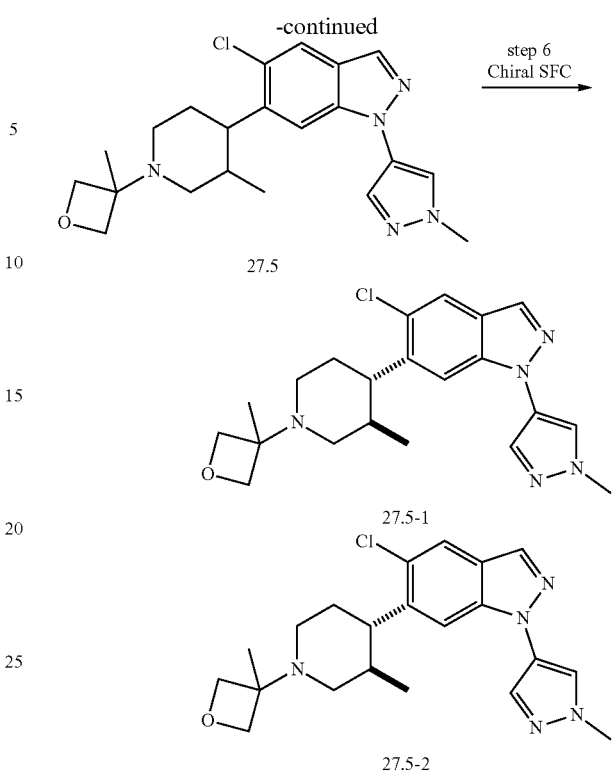

Step 1—Synthesis of Intermediate 27.1, tert-butyl 4-(5-chloro-1-(1-methyl-1H-pyrazol-4-yl)-1H-indazol-6-yl)-3-methyl-3,6-dihydropyridine-1(2H)-carboxylate Common intermediate F.4 (480 mg, 1.541 mmol), tert-butyl 3-methyl-4-(tetramethyl-1,3,2-dioxaborolan-2-yl)-1,2,3,6-tetrahydropyridine-1-carboxylate (550 mg, 1.702 mmol), methanesulfonato(2-dicyclohexylphosphino-2',4',6'-tri-i-propyl-1,1'-biphenyl)(2'-amino-1,1'-biphenyl-2-yl)palladium(II) (130 mg, 0.154 mmol), and potassium phosphate (981 mg, 4.62 mmol) were combined in a 20 mL microwave vial and dissolved in 1,4-dioxane (6000 µl) and water (1500 µl). The vial was sealed, flushed with argon, and stirred at 65° C. overnight. Then, the reaction was cooled to room temperature and diluted with ethyl acetate and washed with water and then brine. The organic layer was dried using $MgSO_4$, filtered, and concentrated. The crude material was purified by silica gel column chromatography (gradient elution of 25-100% ethyl acetate in hexanes) to give intermediate 27.1, tert-butyl 4-(5-chloro-1-(1-methyl-1H-pyrazol-4-yl)-1H-indazol-6-yl)-3-methyl-3,6-dihydropyridine-1(2H)-carboxylate. MS (ESI) m/z calc'd for $C_{22}H_{26}ClN_5O_2$ [M+H]$^+$ 428. found 428.

Step 2—Synthesis of Intermediate 27.2, tert-butyl 4-(5-chloro-1-(1-methyl-1H-pyrazol-4-yl)-1H-indazol-6-yl)-3-methylpiperidine-1-carboxylate Intermediate 27.1 (400 mg, 0.935 mmol) and platinum (IV) oxide (21.23 mg, 0.093 mmol) was dissolved in methanol (3500 µl) and ethyl acetate (1200 µl) in a 100 mL round bottom flask. The flask was sealed with a septum, evacuated, and charged with a balloon of hydrogen. The reaction was stirred at room temperature overnight. Then the reaction was filtered through Celite® (diatomaceous earth) using ethyl acetate and concentrated. The crude material was purified by silica gel column chromatography (gradient elution of 25-100% ethyl acetate in hexanes) to give intermediate 27.2, tert-butyl 4-(5-chloro-1-(1-methyl-1H-pyrazol-4-yl)-1H-indazol-6-yl)-3-methylpiperidine-1-carboxylate. MS (ESI) m/z calc'd for $C_{22}H_{28}ClN_5O_2$ [M+H]$^+$ 430. found 430.

Step 3—Synthesis of Intermediate 27.3, 5-chloro-1-(1-methyl-1H-pyrazol-4-yl)-6-(3-methylpiperidin-4-yl)-1H-indazole Intermediate 27.2 (315 mg, 0.733 mmol) was dissolved in 1,4-Dioxane (2000 μL) and HCl, 4M in 1,4-dioxane (2000 μL, 8.00 mmol) and stirred at room temperature for two hours. The crude material was then concentrated to give intermediate 27.3, 5-chloro-1-(1-methyl-1H-pyrazol-4-yl)-6-(3-methylpiperidin-4-yl)-1H-indazole, HCl salt, which was used for the next steps without additional purification. MS (ESI) m/z calc'd for $C_{17}H_{20}ClN_5$ [M+H]$^+$ 330. found 330.

Step 4—Synthesis of Intermediate 27.4, 3-(4-(5-chloro-1-(1-methyl-1H-pyrazol-4-yl)-1H-indazol-6-yl)-3-methylpiperidin-1-yl)oxetane-3-carbonitrile Intermediate 27.3, HCl salt (268 mg, 0.661 mmol) was suspended in 1,2-dichloroethane (2200 μl) with 268 mg of 4 angstrom molecular sieves, and acetic acid (57 μl, 0.991 mmol) was added. 3-oxetanone (58 μl, 0.991 mmol) was added. After 10 minutes of stirring at room temp, trimethylsilyl cyanide (124 μl, 0.991 mmol) was added carefully. The reaction was then heated to 55° C. overnight. The crude reaction was quenched with saturated NaHCO$_3$ (aq) and DCM. The organic layer was extracted with 3:1 CHCl$_3$:IPA using a phase separator. The crude material was purified by silica gel column chromatography (gradient elution of 10-100% ethyl acetate in hexanes) to give intermediate 27.4, 3-(4-(5-chloro-1-(1-methyl-1H-pyrazol-4-yl)-1H-indazol-6-yl)-3-methylpiperidin-1-yl)oxetane-3-carbonitrile. MS (ESI) m/z calc'd for $C_{21}H_{23}ClN_6O$ [M+H]$^+$ 411. found 411.

Step 5—Synthesis of Intermediate 27.5, 5-chloro-6-(3-methyl-1-(3-methyloxetan-3-yl)piperidin-4-yl)-1-(1-methyl-1H-pyrazol-4-yl)-1H-indazole Intermediate 27.4 (260 mg, 0.730 mmol) was dissolved in tetrahydrofuran (2500 μl) followed by addition of methylmagnesium bromide (1200 μl, 3.60 mmol). The reaction was stirred at 65° C. overnight. Then, the solution was cooled to room temperature and quenched with water. The crude mixture was extracted using 3:1 CHCl$_3$:IPA and a phase separator. The organic solution was concentrated and the resulting crude material was purified silica gel column chromatography (gradient elution of 10-100% ethyl acetate in hexanes) to give intermediate 27.5, 5-chloro-6-(3-methyl-1-(3-methyloxetan-3-yl)piperidin-4-yl)-1-(1-methyl-1H-pyrazol-4-yl)-1H-indazole. MS (ESI) m/z calc'd for $C_{21}H_{26}ClN_5O$ [M+H]$^+$ 400. found 400.

Step 6—Chiral Resolution of Intermediate 27.5, 5-chloro-6-(3-methyl-1-(3-methyloxetan-3-yl)piperidin-4-yl)-1-(1-methyl-1H-pyrazol-4-yl)-1H-indazole Intermediate 27.5 was purified by chiral SFC (Column: AS-H, 21 mm×250 mm; Eluent: 15% (2-Propanol w/0.1% NH$_4$OH)/CO$_2$; Flow rate: 70 mL/min; 220 nm; RT: 4.1 minutes (27.5-1), 6.0 min (27.5-2).

Example 27.5-1, (R,S or S,R)-5-chloro-6-(3-methyl-1-(3-methyloxetan-3-yl)piperidin-4-yl)-1-(1-methyl-1H-pyrazol-4-yl)-1H-indazole MS (ESI) m/z calc'd for $C_{21}H_{26}ClN_5O$ [M+H]$^+$ 400. found 400. $^1$H NMR (500 MHz, DMSO-d$_6$) δ 8.41 (s, 1H), 8.23 (s, 1H), 7.98 (s, 1H), 7.91 (s, 1H), 7.56 (s, 1H), 4.48-4.43 (m, 2H), 4.18-4.15 (m, 2H), 3.97 (s, 1H), 2.85-2.80 (m, 1H), 2.65-2.61 (m, 2H), 2.24-2.08 (m, 3H), 1.92-1.88 (m, 2H), 1.77-1.69 (m, 2H), 1.32 (s, 3H), 0.65-0.64 (d, 3H). LRRK2 IC$_{50}$ 10.1 nM.

Example 27.5-2, (R,S or S,R)-5-chloro-6-(3-methyl-1-(3-methyloxetan-3-yl)piperidin-4-yl)-1-(1-methyl-1H-pyrazol-4-yl)-1H-indazole MS (ESI) m/z calc'd for $C_{21}H_{26}ClN_5O$ [M+H]$^+$ 400. found 400. $^1$H NMR (500 MHz, DMSO-d$_6$) δ 8.41 (s, 1H), 8.23 (s, 1H), 7.98 (s, 1H), 7.91 (s, 1H), 7.56 (s, 1H), 4.48-4.43 (m, 2H), 4.18-4.15 (m, 2H), 3.97 (s, 1H), 2.85-2.80 (m, 1H), 2.65-2.61 (m, 2H), 2.24-2.10 (m, 3H), 1.92-1.88 (m, 2H), 1.77-1.70 (m, 2H), 1.32 (s, 3H), 0.65-0.64 (d, 3H). LRRK2 IC$_{50}$ 12.6 nM.

Preparation of Example 28.4, 5-chloro-1-(1-methyl-1H-pyrazol-4-yl)-6-(2-(oxetan-3-yl)-2-azaspiro[3.3]heptan-6-yl)-1H-indazole

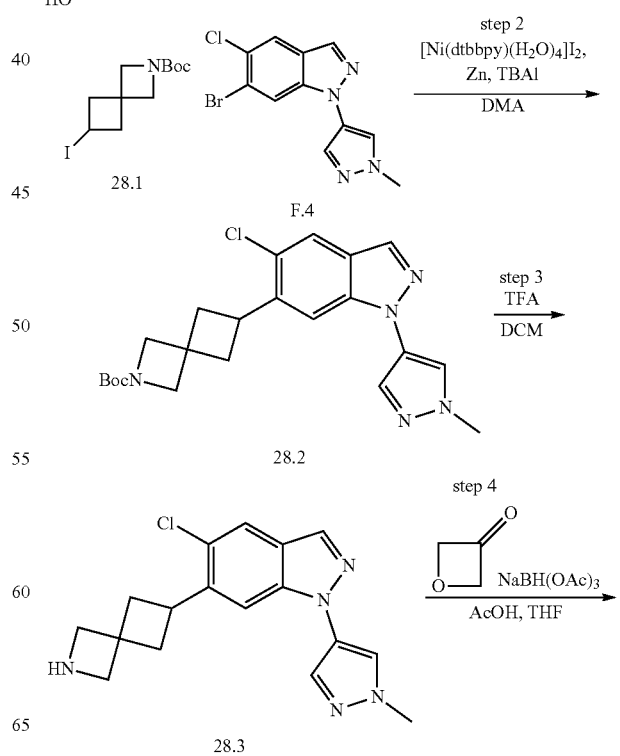

Scheme 31

-continued

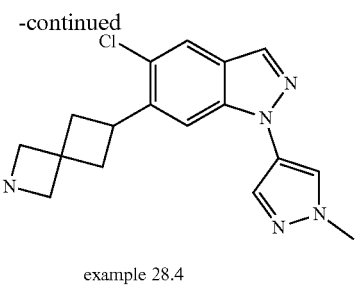

example 28.4

Step 1—Synthesis of Intermediate 28.1, tert-butyl 6-iodo-2-azaspiro[3.3]heptane-2-carboxylate Tert-butyl 6-hydroxy-2-azaspiro[3.3]heptane-2-carboxylate (1.0 g, 4.69 mmol), iodine (1.547 g, 6.10 mmol), triphenylphosphine (1.6 g, 6.10 mmol) and imidazole (638 mg, 9.38 mmol) were stirred at room temperature overnight. The reaction was diluted with DCM/hexanes, filtered and concentrated. The crude material was purified via silica gel column chromatography (gradient elution: 0% to 40% (3:1 EtOAC:EtOH)/hexanes) to provide intermediate 28.1, tert-butyl 6-iodo-2-azaspiro[3.3]heptane-2-carboxylate. MS (ESI) m/z calc'd for $C_7H_{11}INO_2$ [M-tBu+H]$^+$ 268. found 268.

Step 2—Synthesis of Intermediate 28.2, tert-butyl 6-(5-chloro-1-(1-methyl-1H-pyrazol-4-yl)-1H-indazol-6-yl)-2-azaspiro[3.3]heptane-2-carboxylate Common intermediate F.4 (75 mg, 0.241 mmol), intermediate 28.1 (93 mg, 0.289 mmol), [Ni(dtbbpy)(H$_2$O)$_4$]I$_2$ (15.72 mg, 0.024 mmol), tetrabutylammonium iodide (22.23 mg, 0.060 mmol), and zinc dust (47.2 mg, 0.722 mmol) were added to a 5 mL vial. The vial was capped and purged with N$_2$. DMA (2 mL) was added and the reaction was stirred at 60° C. for 1 hour. The reaction was cooled then diluted with H$_2$O (10 mL) and extracted with EtOAc (2×15 mL). The organic extract was washed 4× with 1:1 water:brine, dried over Na$_2$SO$_4$, filtered and concentrated. The residue was purified via silica gel column chromatography (gradient elution: 0% to 100% (3:1 EtOAC/EtOH) in DCM) to provide intermediate 28.2, tert-butyl 6-(5-chloro-1-(1-methyl-1H-pyrazol-4-yl)-1H-indazol-6-yl)-2-azaspiro[3.3]heptane-2-carboxylate. MS (ESI) m/z calc'd for $C_{18}H_{19}ClN_5O_2$ [M-tBu+H]$^+$ 372. found 372.

Step 3—Synthesis of Intermediate 28.3, 5-chloro-1-(1-methyl-1H-pyrazol-4-yl)-6-(2-azaspiro[3.3]heptan-6-yl)-1H-indazole Intermediate 28.2 (90 mg, 0.210 mmol) was dissolved in DCM (1 ml) and trifluoroacetic acid (784 µL, 10.18 mmol) was added dropwise via syringe. The reaction was allowed to stir at room temperature for 3 hours. The reaction was diluted with DCM (10 mL) and slowly neutralized with saturated aqueous NaHCO$_3$ (5 mL). Once neutralized, the mixture was extracted with DCM (3×10 mL). The combined organic extract was dried over Na$_2$SO$_4$, filtered and concentrated to provide intermediate 28.3, 5-chloro-1-(1-methyl-1H-pyrazol-4-yl)-6-(2-azaspiro[3.3]heptan-6-yl)-1H-indazole. MS (ESI) m/z calc'd for $C_{17}H_{19}ClN_5$ [M+H]$^+$ 328. found 328.

Step 4—Synthesis of Example 28.4, 5-chloro-1-(1-methyl-1H-pyrazol-4-yl)-6-(2-(oxetan-3-yl)-2-azaspiro[3.3]heptan-6-yl)-1H-indazole Intermediate 28.3 (46 mg, 0.104 mmol) was dissolved in THF (1 mL) in a 1 dram vial under N$_2$. Acetic acid (7.15 µl, 0.125 mmol) and oxetan-3-one (0.020 ml, 0.312 mmol) were added via syringes. The reaction was allowed to stir for 10 minutes, then sodium triacetoxyborohydride (66.2 mg, 0.312 mmol) was added in one portion. The reaction was quenched after 45 minutes by the careful addition of saturated aqueous NaHCO$_3$ (5 mL) and extracted with 3:1 CHCl$_3$:IPA (3×5 mL). The phases were separated and the organic extract was concentrated. The reaction mixture was purified by reverse phase prep-HPLC (Method A). The resulting salt was further purified via Achiral-Prep-SFC [Column: Phenomenex diol, 21 mm×250 mm; 15% (MeOH/ 0.1% NH$_4$OH)/CO$_2$; Flow rate: 70 mL/min; 220 nm; RT: 2.38 min] to provide example 28.4, 5-chloro-1-(1-methylpyrazol-4-yl)-6-[2-(oxetan-3-yl)-2-azaspiro[3.3]heptan-6-yl]indazole. MS (ESI) in z calc'd for $C_{20}H_{23}ClN_5O$ [M+H]$^+$ 384. found 384. $^1$H NMR (499 MHz, DMSO-d$_6$) δ 8.34 (s, 1H), 8.21 (s, 1H), 7.92 (s, 2H), 7.47 (s, 1H), 4.53 (m, 2H), 4.42-4.28 (m, 2H), 3.96 (s, 3H), 3.65 (m, 2H), 3.36 (s, 2H), 3.12 (s, 2H), 2.59 (m, 2H), 2.30 (m, 2H). LRRK2 IC$_{50}$ 187.3 nM.

Preparation of Examples 29.3-1, (R or S)-5-chloro-1-(1-methyl-1H-pyrazol-4-yl)-6-(1-(oxetan-3-yl)azepan-4-yl)-1H-indazole and 29.3-2, (R or S)-5-chloro-1-(1-methyl-1H-pyrazol-4-yl)-6-(1-(oxetan-3-yl)azepan-4-yl)-1H-indazole

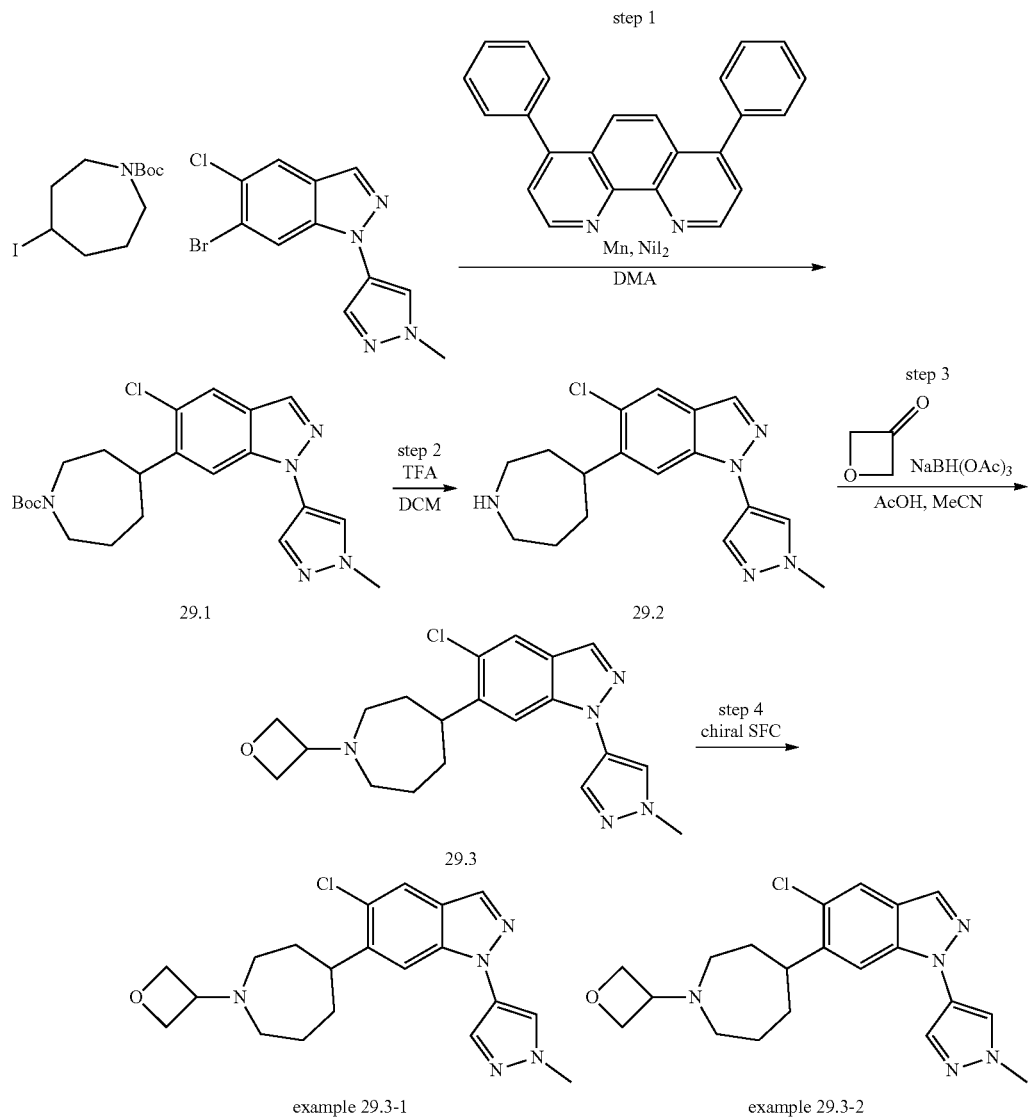

Scheme 32

Step 1—Synthesis of Intermediate 29.1, (R and S)-tert-butyl 4-(5-chloro-1-(1-methyl-1H-pyrazol-4-yl)-1H-indazol-6-yl)azepane-1-carboxylate A mixture of 4,7-diphenyl-1,10-phenanthroline (34.8 mg, 0.105 mmol) and nickel(II) iodide (32.7 mg, 0.105 mmol) in DMA (3488 μl) was stirred for 0.5 h at 23° C. To the solution is then added manganese (46.0 mg, 0.837 mmol), tertbutyl 4-iodoazepane-1-carboxylate (170 mg, 0.523 mmol), and common intermediate F.4 (65.2 mg, 0.209 mmol) in one portion. The mixture was deoxygenated by sparging with nitrogen gas for 10 min. The reaction was stirred at 40° C. for 5 hours. The reaction mixture was cooled to room temperature and filtered through a pad of Celite® (diatomaceous earth). DMA was removed under reduced pressure. The crude residue was purified by silica gel column chromatography (gradient elution: 0-45% EtOAc:Hexanes) to afford intermediate 29.1, (R and S)-tert-butyl 4-(5-chloro-1-(1-methyl-1H-pyrazol-4-yl)-1H-indazol-6-yl)azepane-1-carboxylate. MS (ESI) m/z calc'd for $C_{22}H_{29}ClN_5O_2$ [M+H]$^+$ 430. found 430.

Step 2—Synthesis of Intermediate 29.2, (R and S)-6-(azepan-4-yl)-5-chloro-1-(1-methyl-1H-pyrazol-4-yl)-1H-indazole To a solution of intermediate 29.1 (46.4 mg, 0.108 mmol) in DCM (1079 μl) was added trifluoroacetic acid (700 μl, 9.21 mmol). The reaction was allowed to stir at 23° C. for 60 min. The reaction was concentrated to dryness to afford intermediate 29.2, (R and S)-6-(azepan-4-yl)-5-chloro-1-(1-methyl-1H-pyrazol-4-yl)-1H-indazole. TFA sat. The material was used directly for the next step without further purification. MS (ESI) m/z calc'd for $C_{17}H_{21}ClN_5$ [M+H]$^+$ 330. found 330.

Step 3—Synthesis of Intermediate 29.3, (R and S)-5-chloro-1-(1-methyl-1H-pyrazol-4-yl)-6-(1-(oxetan-3-yl)azepan-4-yl)-1H-indazole To a solution of intermediate 29.2, TFA salt (133 mg, 0.300 mmol) in MeCN (2996 μl) was added acetic acid (20.58 μl, 0.360 mmol), 300 mg 4 Å-MS, and 3-oxetanone (57.8 μl, 0.899 mmol). After stirring at 23° C. for 10 min, sodium triacetoxyborohydride (318 mg, 1.498 mmol) was added to the heterogeneous mixture. The reaction was allowed to stir at 23° C. for 60 min. The reaction was diluted with MeCN, filtered and concentrated to dryness under reduced pressure. The residue was purified via silica gel column chromatography (gradient elution of 0-50% EtOAc:Hexanes) to give intermediate 29.3, (R and S)-5-chloro-1-(1-methyl-1H-pyrazol-4-yl)-6-(1-(oxetan-3-yl)azepan-4-yl)-1H-indazole. MS (ESI) m/z calc'd for $C_{20}H_{25}ClN_5O$ [M+H]$^+$ 386. found 386.

Step 4—Chiral Resolution of Intermediate 29.3, (R and S)-5-chloro-1-(1-methyl-1H-pyrazol-4-yl)-6-(1-(oxetan-3-yl)azepan-4-yl)-1H-indazole Intermediate 29.3 was resolved by chiral SFC (Column: OJ-H, 21 mm×250 mm; Eluent: 10% (MeOH/0.1% NH$_4$OH)/CO$_2$; Flow rate: 70 mL/min; 220 nm; RT 5.3 min (29.3-1), 6.4 min (29.3-2).

Example 29.3-1, (R or S)-5-chloro-1-(1-methyl-1H-pyrazol-4-yl)-6-(1-(oxetan-3-yl)azepan-4-yl)-1H-indazole MS (ESI) m/z calc'd for $C_{20}H_{25}ClN_5O$ [M+H]$^+$ 386. found 386. $^1$H NMR (499 MHz, Methanol-d4) δ 8.15 (s, 1H), 8.13 (s, 1H), 7.89 (s, 2H), 7.54 (s, 1H), 4.76 (t, J=6.7 Hz, 2H), 4.65 (t, J=5.1 Hz, 2H), 4.04 (s, 3H), 3.96 (s, 1H), 3.54 (t, J=10.4 Hz, 1H), 2.85-2.74 (m, 4H), 2.16-1.79 (m, 6H). LRRK2 IC$_{50}$ 0.7 nM.

Example 29.3-2, (R or S)-5-chloro-1-(1-methyl-1H-pyrazol-4-yl)-6-(1-(oxetan-3-yl)azepan-4-yl)-1H-indazole MS (ESI) m/z calc'd for $C_{20}H_{25}ClN_5O$ [M+H]$^+$ 386. found 386. $^1$H NMR (499 MHz, Methanol-d4) δ 8.15 (s, 1H), 8.13 (s, 1H), 7.89 (s, 2H), 7.54 (s, 1H), 4.76 (t, J=6.7 Hz, 2H), 4.65 (t, J=5.1 Hz, 2H), 4.04 (s, 3H), 3.96 (s, 1H), 3.56-3.53 (m, 1H), 2.85-2.74 (m, 4H), 2.16-1.79 (m, 6H). LRRK2 IC$_{50}$ 1.7 nM.

Preparation of Examples 30.5-1, (R or S)-5-chloro-1-(1-methyl-1H-pyrazol-4-yl)-6-(1-(oxetan-3-yl)pyrrolidin-3-yl)-1H-indazole and example 30.5-2, (R or S)-5-chloro-1-(1-methyl-1H-pyrazol-4-yl)-6-(1-(oxetan-3-yl)pyrrolidin-3-yl)-1H-indazole

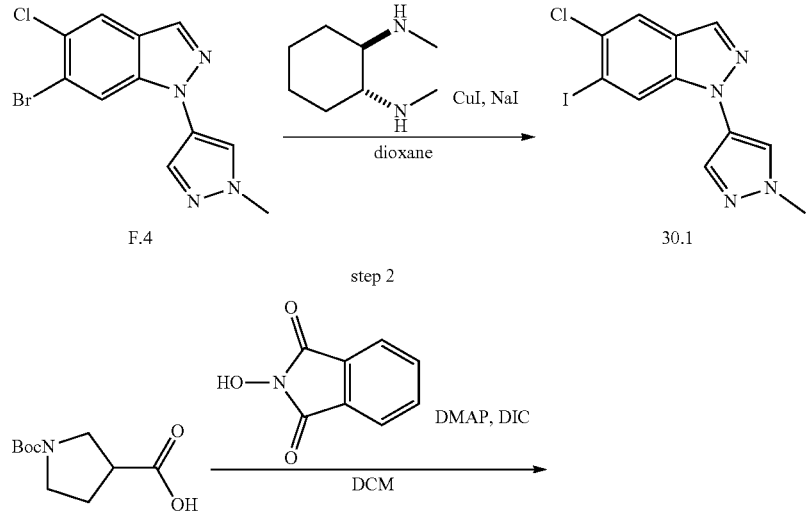

Scheme 33

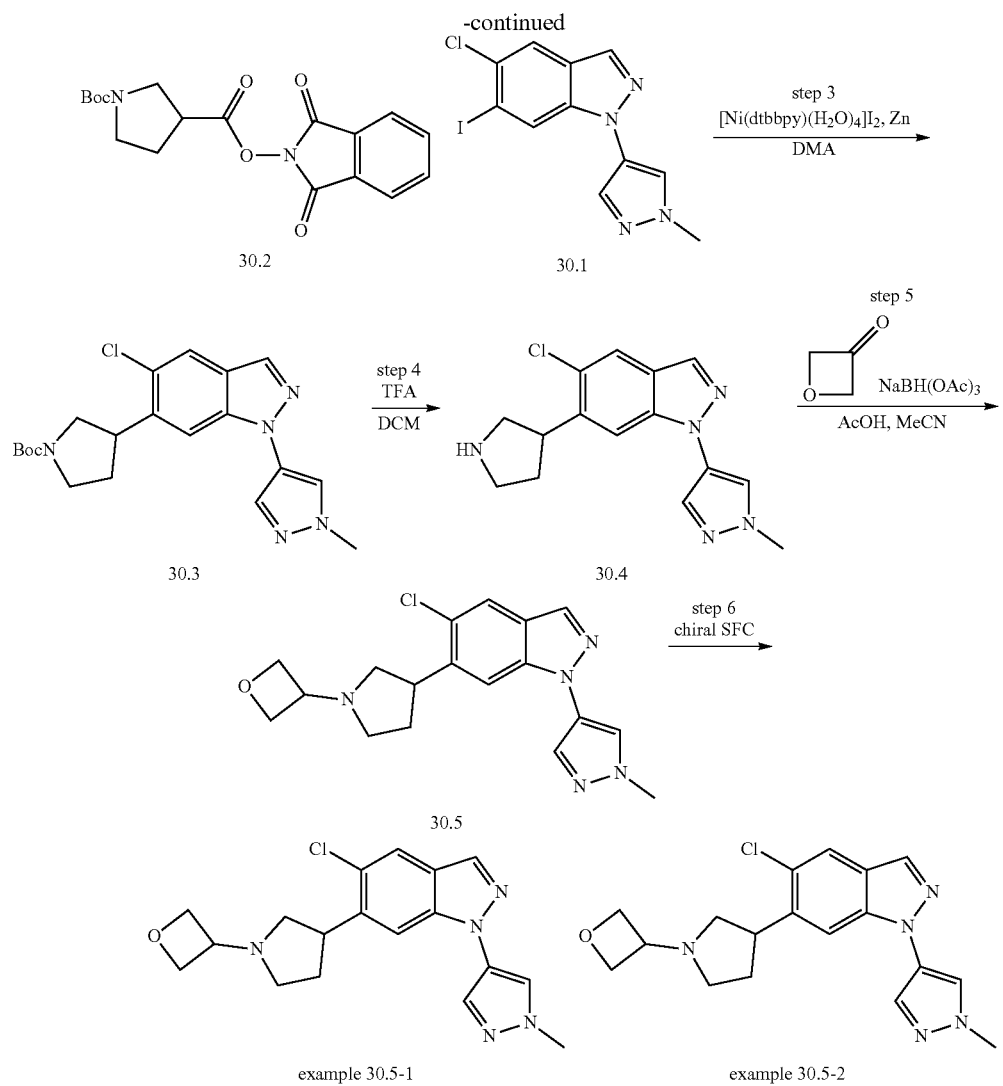

Step 1—Synthesis of Intermediate 30.1, 5-chloro-6-iodo-1-(1-methyl-1H-pyrazol-4-yl)-1H-indazole To a vial charged with a stir bar was added common intermediate F.4 (297 mg, 0.953 mmol), (trans)-N,N'-dimethylcyclohexane-1,2-diamine (40.7 mg, 0.286 mmol), cuprous iodide (27.2 mg, 0.143 mmol), and sodium iodide (429 mg, 2.86 mmol). To the solids were added 1,4-dioxane (1589 μl) and then the solution was degassed and backfilled with nitrogen gas. The mixture was heated to 100° C. for 36 hours. The reaction was cooled to room temperature and then diluted with EtOAc and quenched with water. The aqueous layer was extracted with EtOAc (3×50 mL). The combined organic layer was washed with brine and then dried over $Na_2SO_4$. The organic layer was filtered and then concentrated. The crude material was purified via silica gel column chromatography (gradient elution of 0-40% EtOAc: Hexanes) to afford intermediate 30.1, 5-chloro-6-iodo-1-(1-methyl-1H-pyrazol-4-yl)-1H-indazole. MS (ESI) m/z calc'd for $C_{11}H_9ClIN_4$ $[M+H]^+$ 359. found 359.

Step 2—Synthesis of Intermediate 30.2, 1-(tert-butyl) 3-(1,3-dioxoisoindolin-2-yl) pyrrolidine-1,3-dicarboxylate To a solution of 1-(tert-butoxycarbonyl)pyrrolidine-3-carboxylic acid (300 mg, 1.394 mmol), N-hydroxyphthalimide (250 mg, 1.533 mmol), and 4-dimethylaminopyridine (17.03 mg, 0.139 mmol) in DCM (6969 μl) was added N,N'-diisopropylcarbodiimide (240 μl, 1.533 mmol). The reaction was allowed to stir at 23° C. for 16 hours. The reaction was diluted with DCM, filtered and concentrated to dryness. The residue was purified via silica gel column chromatography (gradient elution of 0-40% EtOAc:Hexanes) to afford intermediate 30.2, 1-(tert-butyl) 3-(1,3-dioxoisoindolin-2-yl) pyrrolidine-1,3-dicarboxylate. MS (ESI) m/z calc'd for $C_{18}H_{21}N_2O_6$ $[M+H]^+$ 361. found 305. $^1$H NMR (499 MHz, DMSO-$d_6$) δ 7.92 (dd, J=5.5, 3.1 Hz, 2H), 7.83 (dd, J=5.5, 3.1 Hz, 2H), 3.80 (m, J=9.3 Hz, 2H), 3.47 (m, J=14.6, 7.7 Hz, 3H), 2.37 (m, 2H), 1.50 (s, 9H).

Step 3—Synthesis of Intermediate 30.3, tert-butyl 3-(5-chloro-1-(1-methyl-1H-pyrazol-4-yl)-1H-indazol-6-yl)pyrrolidine-1-carboxylate To a solution of intermediate 30.2 (178.7 mg, 0.496 mmol) in DMA (1340 µl) was added intermediate 30.1 (96.1 mg, 0.268 mmol), zinc (70.1 mg, 1.072 mmol), and [Ni(dtbbpy)(H$_2$O)$_4$]I$_2$ (21.99 mg, 0.054 mmol). The green heterogeneous mixture was degassed and backfilled with nitrogen gas. The reaction mixture was allowed to stir at 23° C. The reaction was filtered through a pad of Celite® (diatomaceous earth) and DMA was removed under reduced pressure. The crude oil was purified via silica gel column chromatography (gradient elution of 0-50% EtOAc:Hexanes) to afford intermediate 30.3, tert-butyl 3-(5-chloro-1-(1-methyl-1H-pyrazol-4-yl)-1H-indazol-6-yl)pyrrolidine-1-carboxylate. MS (ESI) m/z calc'd for C$_{20}$H$_{24}$ClN$_5$O$_2$ [M+H]$^+$ 402. found 402.

Step 4—Synthesis of Intermediate 30.4, 5-chloro-1-(1-methyl-1H-pyrazol-4-yl)-6-(pyrrolidin-3-yl)-1H-indazole To a solution of intermediate 30.3 (42.9 mg, 0.107 mmol) in DCM (534 µl) was added trifluoroacetic acid (500 µl, 6.58 mmol). The homogeneous solution was allowed to stir at 23° C. for 30 min. The reaction was concentrated to dryness to afford intermediate 30.4, 5-chloro-1-(1-methyl-1H-pyrazol-4-yl)-4-yl)-6-(pyrrolidin-3-yl)-1H-indazole. TFA salt. The material was used directly for the next step without further purification. MS (ESI) m/z calc'd for C$_{15}$H$_{17}$ClN$_5$ [M+H]$^+$ 302. found 302.

Step 5—Synthesis of Intermediate 30.5, (R and S)-5-chloro-1-(1-methyl-1H-pyrazol-4-yl)-6-(1-(oxetan-3-yl)pyrrolidin-3-yl)-1H-indazole To a solution of intermediate 30.4, TFA salt (32.2 mg, 0.107 mmol) in MeCN (1067 µl) was added acetic acid (7.33 µl, 0.128 mmol), 300 mg 4 Å-MS, and 3-oxetanone (20.60 µl, 0.320 mmol). After stirring at 23° C. for 10 min, sodium triacetoxyborohydride (113 mg, 0.534 mmol) was added. The reaction was allowed to stir at 23° C. for 60 min. The mixture was diluted with MeCN, filtered and concentrated to dryness. The crude material was purified via silica gel column chromatography (gradient elution of 0-50% EtOAc:Hexanes) to afford intermediate 30.5, (R and <S)-5-chloro-1-(1-methyl-1H-pyrazol-4-yl)-6-(1-(oxetan-3-yl)pyrrolidin-3-yl)-1H-indazole. MS (ESI) m/z calc'd for C$_{18}$H$_{21}$ClN$_5$O [M+H]$^+$ 358. found 358.

Step 6—Chiral Resolution of Intermediate 30.5, (R and S)-5-chloro-1-(1-methyl-1H-pyrazol-4-yl)-6-(1-(oxetan-3-yl)pyrrolidin-3-yl)-1H-indazole Intermediate 30.5 was resolved by chiral SFC (Column: OD-H, 21×250 mm; 25% (MeOH/0.1% NH$_4$OH)/CO$_2$; Flow rate: 70 mL/min; 220 nm; RT: 3.9 min (30.5-1), 5.9 min (30.5-2).

Example 30.5-1, (R or S)-5-chloro-1-(1-methyl-1H-pyrazol-4-yl)-6-(1-(oxetan-3-yl)pyrrolidin-3-yl)-1H-indazole MS (ESI) m/z calc'd for C$_{18}$H$_{21}$ClN$_5$O [M+H]$^+$ 358. found 358. $^1$H NMR (499 MHz, DMSO-d$_6$) δ 8.32 (s, 1H), 8.28-8.16 (m, 1H), 7.96 (s, 1H), 7.92 (s, 1H), 7.80 (s, 1H), 4.62 (q, J=6.3 Hz, 2H), 4.57-4.48 (m, 2H), 3.95 (s, 3H), 3.88-3.75 (m, 1H), 3.72-3.59 (m, 1H), 2.88-2.73 (m, 3H), 2.59-2.52 (m, 1H), 2.43-2.31 (m, 1H), 1.91-1.72 (m, 1H). LRRK2 IC$_{50}$ 190.3 nM.

Example 30.5-2, (R or S)-5-chloro-1-(1-methyl-1H-pyrazol-4-yl)-6-(1-(oxetan-3-yl)pyrrolidin-3-yl)-1H-indazole MS (ESI) m/z calc'd for C$_{18}$H$_{21}$ClN$_5$O [M+H]$^+$ 358. found 358. $^1$H NMR (499 MHz, DMSO-d$_6$) δ 8.32 (s, 1H), 8.23 (s, 1H), 7.97 (s, 1H), 7.92 (s, 1H), 7.79 (s, 1H), 4.63-4.62 (d, J=5.5 Hz, 2H), 4.53 (s, 2H), 3.95 (s, 3H), 3.81 (s, 1H), 2.82 (s, 3H), 2.37 (s, 1H), 1.85 (s, 1H). LRRK2 IC$_{50}$ 202.2 nM.

Preparation of Example 31.3, 5-chloro-1-(1-methyl-1H-pyrazol-4-yl)-6-(1-(oxetan-3-yl)azetidin-3-yl)-1H-indazole

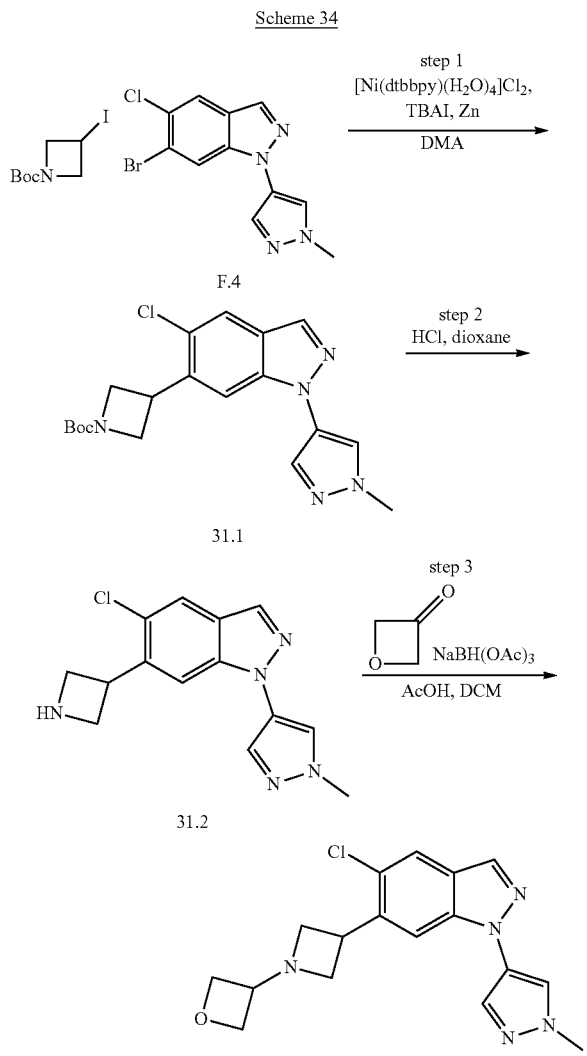

Scheme 34 example 31.3

Step 1—Synthesis of Intermediate 31.1, tert-butyl 3-(5-chloro-1-(1-methyl-1H-pyrazol-4-yl)-1H-indazol-6-yl)azetidine-1-carboxylate In the glove box, to a vial were added common intermediate F.4 (100 mg, 0.321 mmol), tetrabutylammonium iodide (30 mg, 0.080 mmol), [Ni(dtbbpy)(H$_2$O)$_4$]Cl$_2$ (16.8 mg, 0.0320 mmol), zinc (63.0 mg, 0.963 mmol), tert-butyl 3-iodoazetidine-1-carboxylate (91 mg, 0.32 mmol) and DMA (1600 μl). The vial was sealed, removed from the glove box and heated at 60° C. for 30 min. The solvent was removed in vacuo. The residue was purified by column chromatography on silica gel (gradient: EtOAc in hexane, 0-50%) to afford intermediate 31.1, tert-butyl 3-(5-chloro-1-(1-methyl-1H-pyrazol-4-yl)-1H-indazol-6-yl)azetidine-1-carboxylate. MS (ESI) m/z calc'd for C$_{15}$H$_{15}$ClN$_5$O$_2$ [M-tBu+H]$^+$ 332. found 332.

Step 2—Synthesis of Intermediate 31.2, 6-(azetidin-3-yl)-5-chloro-1-(1-methyl-1H-pyrazol-4-yl)-1H-indazole To a slurry of intermediate 31.1 (78 mg, 0.20 mmol) in dioxane (500 μl) was added HCl (4 M in dioxane, 500 μl, 2.0 mmol). The mixture was stirred at rt for 1 hour. The solvent was removed in vacuo to afford intermediate 31.2, 6-(azetidin-3-yl)-5-chloro-1-(1-methyl-1H-pyrazol-4-yl)-1H-indazole, HCl salt. The crude material was used directly for the next step without additional purification. MS (ESI) m/z calc'd for C$_{14}$H$_{15}$Cl N$_5$ [M+H]$^+$ 288. found 288.

Step 3—Synthesis of Example 31.3, 5-chloro-1-(1-methyl-1H-pyrazol-4-yl)-6-(1-(oxetan-3-yl)azetidin-3-yl)-1H-indazole To a stirred mixture of oxetan-3-one (15 mg, 0.21 mmol) and intermediate 31.2, HCl salt (20 mg, 0.070 mmol) in 1,2-dichloroethane (500 μl) and acetic acid (10 μl) was added sodium triacetoxyborohydride (44.2 mg, 0.209 mmol). The mixture was stirred at rt for 18 hours. The mixture was quenched with MeOH/water, concentrated, dissolved into MeOH and purified by reverse phase prep-HPLC (Method A) to afford example 31.3, 5-chloro-1-(1-methyl-1H-pyrazol-4-yl)-6-(1-(oxetan-3-yl)azetidin-3-yl)-1H-indazole, TFA salt. MS (ESI) m/z calc'd for C$_{17}$H$_{19}$ClN$_5$O [M+H]$^+$ 344. found 344. $^1$H NMR (600 MHz, DMSO-d$_6$) δ 8.51-8.22 (m, 2H), 8.14-7.91 (m, 2H), 7.59 (s, 1H), 4.92-4.25 (m, 5H), 3.96 (s, 3H), 3.91-3.36 (m, 5H). LRRK2 IC$_{50}$ 2362 nM.

Preparation of Example 32.1, (cis or trans)-6-(3-oxabicyclo[3.1.0]hexan-6-yl)-5-chloro-1-(1-methyl-1H-pyrazol-4-yl)-1H-indazole

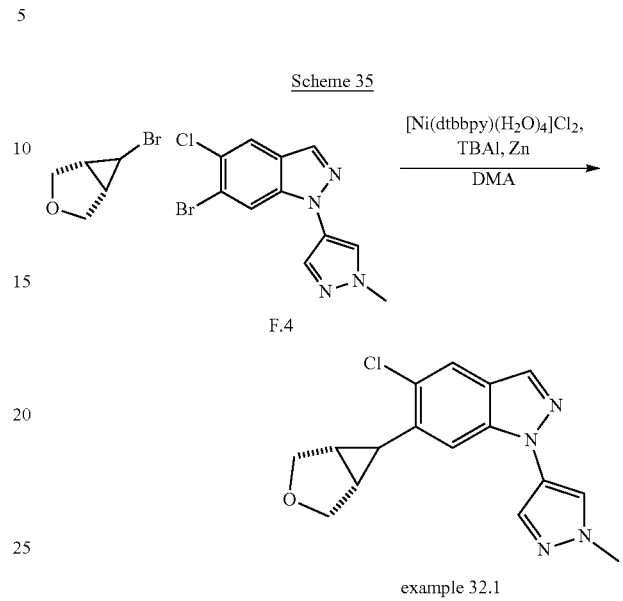

example 32.1

To a vial was added common intermediate F.4 (50 mg, 0.16 mmol), tetrabutylammonium iodide (11 mg, 0.030 mmol), [Ni(dtbbpy)(H$_2$O)$_4$]Cl$_2$ (8.39 mg, 0.0160 mmol), zinc (31.5 mg, 0.481 mmol), 6-bromo-3-oxabicyclo[3.1.0]hexane (26.2 mg, 0.160 mmol) and DMA (800 μl). The mixture was evacuated and backfilled with N$_2$ 4 times and heated at 60° C. for 3 hours. The mixture was filtered and purified by reverse phase prep-HPLC (Method B) to afford example 32.1, (cis or trans)-6-(3-oxabicyclo[3.1.0]hexan-6-yl)-5-chloro-1-(1-methyl-1H-pyrazol-4-yl)-1H-indazole. MS (ESI) m/z calc'd for C$_{16}$H$_{16}$Cl N$_4$O [M+H]$^+$ 315. found 315. $^1$H NMR (600 MHz, DMSO-d$_6$) δ 8.36 (s, 1H), 8.22 (d, J=0.8 Hz, 1H), 7.97 (s, 1H), 7.95-7.89 (m, 1H), 7.35 (s, 1H), 4.10-3.84 (m, 5H), 3.74 (d, J=8.2 Hz, 2H), 2.29-2.15 (m, 2H), 2.06 (t, J=3.8 Hz, 1H). LRRK2 IC$_{50}$ 69.2 nM.

Preparation of Example 33.1, methyl 3-(5-chloro-1-(1-methyl-1H-pyrazol-4-yl)-1H-indazol-6-yl)bicyclo[1.1.1]pentane-1-carboxylate

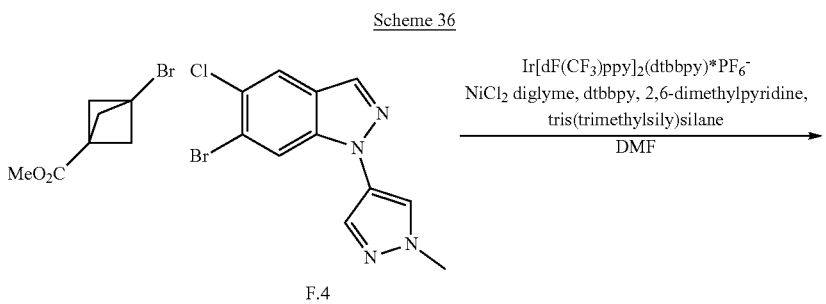

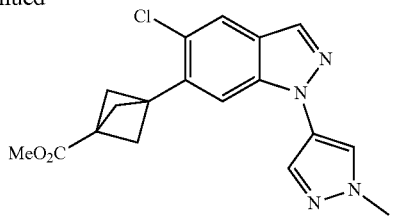

example 33.1

To vial #1 was added common intermediate F.4 (50 mg, 0.16 mmol), methyl 3-bromobicyclo[1.1.1]pentane-1-carboxylate (49.4 mg, 0.241 mmol), Ir[dF(CF$_3$)ppy]$_2$(dtbbpy)$^+$ PF$_6^-$ (1.627 mg, 1.605 µmol), 2,6-dimethylpyridine (37.4 µl, 0.321 mmol), tris(trimethylsilyl)silane (39.9 mg, 0.160 mmol), and DME (800 µl). To vial #2 was added 4,4'-di-tert-butyl-2,2'-bipyridine (dtbbpy) (4.3 mg, 0.016 mmol), NiCl$_2$ diglyme (3.5 mg, 0.016 mmol), and DME (800 µl). The mixture was stirred at room temperature for 15 min to get a light green solution. Then the solution in vial #2 was added to vial #1. The resulting mixture in vial #1 was bubbled with nitrogen for 15 min. The reaction mixture was sealed and irradiated in Merck Photo reactor (Fan: 9783 rpm; stir at 1000 rpm; LED: 50%) for 3 hours. The mixture was concentrated in vacuo, diluted with MeOH, filtered, and purified by reverse phase prep-HPLC (Method A) to afford example 33.1, methyl 3-(5-chloro-1-(1-methyl-1H-pyrazol-4-yl)-1H-indazol-6-yl)bicyclo[1.1.1]pentane-1-carboxylate, TFA salt. MS (ESI) m/z calc'd for C$_{18}$H$_{18}$ClN$_4$O$_2$ [M+H]$^+$ 357. found 357. $^1$H NMR (600 MHz, DMSO-d$_6$) δ 8.33 (s, 1H), 8.25 (s, 1H), 7.93 (s, 1H), 7.92 (s, 1H), 7.40 (s, 1H), 3.95 (s, 3H), 3.66 (s, 3H), 2.52 (s, 6H). LRRK2 IC$_{50}$ 796.5 nM.

Preparation of Example 34.2, (R and S)-5-chloro-1-(1-methyl-1H-pyrazol-4-yl)-6-(spiro[2.2]pentan-1-yl)-1H-indazole Scheme 37

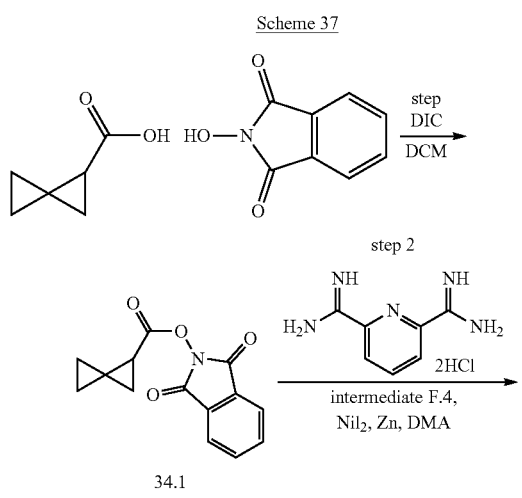

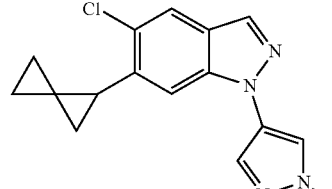

example 34.2

Step 1—Synthesis of Intermediate 34.1, 1,3-dioxoisoindolin-2-yl spiro[2.2]pentane-1-carboxylate To a mixture of spiro[2.2]pentane-1-carboxylic acid (300 mg, 2.68 mmol), 2-hydroxyisoindoline-1,3-dione (480 mg, 2.94 mmol) and DMAP (32.7 mg, 0.268 mmol) in anhydrous DCM (10 mL) was added N,N'-Diisopropylcarbodiimide (371 mg, 2.94 mmol), and the resulting mixture was stirred at 20° C. for 2 hours. The reaction mixture was filtered through a pad of Celite® (diatomaceous earth) and the pad was washed with DCM (10 mL×3). The filtrate was concentrated in vacuo. The crude product was purified by silica gel column chromatography (eluent of 0% to 10% EtOAc/Petroleum ether) to give intermediate 34.1, 1,3-dioxoisoindolin-2-yl spiro[2.2]pentane-1-carboxylate.

Step 2—Synthesis of Example 34.2, (R and S)-5-chloro-1-(1-methyl-1H-pyrazol-4-yl)-6-(spiro[2.2]pentan-1-yl)-1H-indazole To a solution of pyridine-2,6-bis(carboximidamide) dihydrochloride (10 mg, 0.042 mmol) in anhydrous DMA (2 mL) was added common intermediate F.4 (30 mg, 0.096 mmol), intermediate 34.1 (37.2 mg, 0.144 mmol), zinc (20 mg, 0.306 mmol) and nickel(II) iodide (10 mg, 0.032 mmol). The resulting mixture was stirred at 60° C. under N$_2$ protection for 16 hours. The reaction mixture was poured into water (10 mL) and extracted with EtOAc (10 mL×3). The organic layer was washed with water (10 mL), dried over Na$_2$SO$_4$. After filtration and concentration, the crude product was purified by pre-HPLC (TFA) to give example 34.2, (R and S)-5-chloro-1-(1-methyl-1H-pyrazol-4-yl)-6-(spiro[2.2]pentan-1-yl)-1H-indazole, TFA salt. MS (ESI) m/z calc'd for C$_{16}$H$_{16}$ClN$_4$ [M+H]+ 299. found 299. $^1$H NMR (500 MHz, CD$_3$OD) δ 8.12 (d, 0.7=0.92 Hz, 1H), 8.12 (s, 1H), 7.86 (s, 2H), 7.36 (s, 1H), 4.03 (s, 3H), 2.74 (m, 1H), 1.58 (m, 1H), 1.35 (m, 1H), 1.09 (m, 1H), 0.95-1.00 (m, 1H), 0.83 (m, 1H), 0.73 (m, 1H). LRRK2 IC$_{50}$ 35.6 nM.

Preparation of Example 35.9, 5-chloro-4-fluoro-1-(1-methyl-1H-pyrazol-4-yl)-6-(1-(oxetan-3-yl)piperidin-4-yl)-1H-indazole

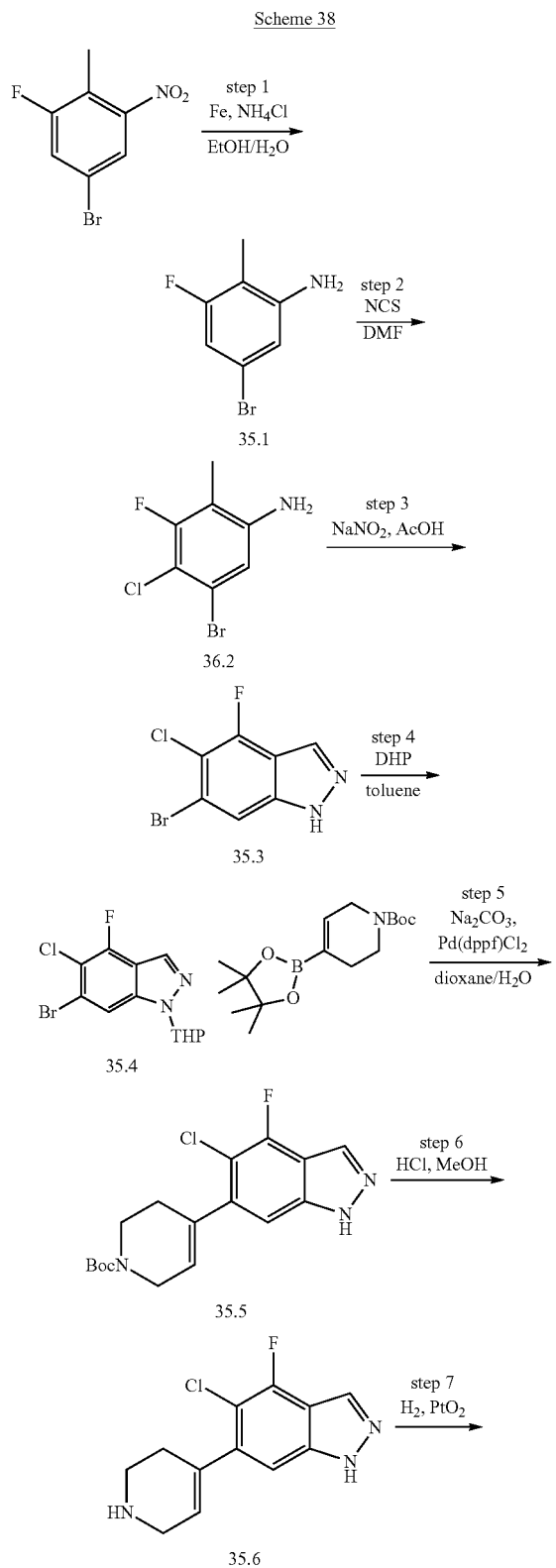

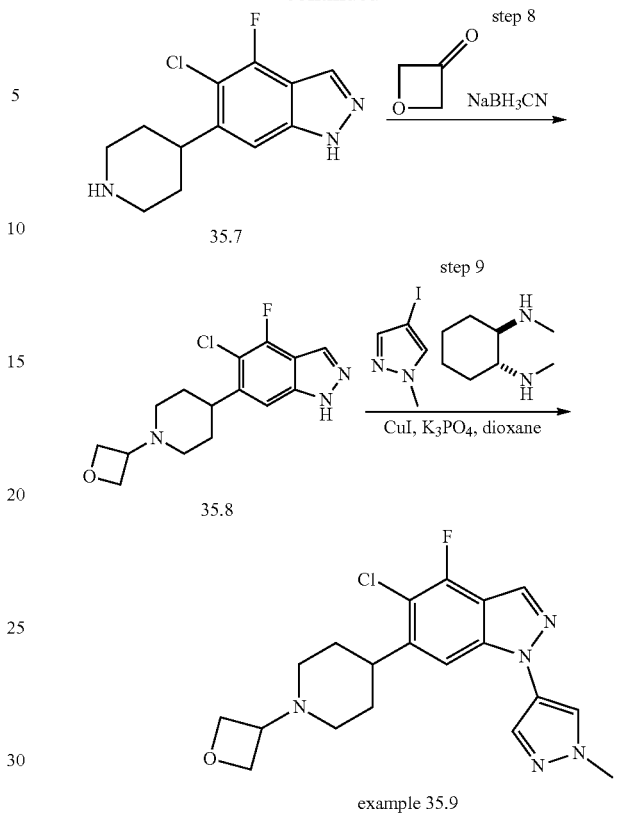

Step 1—Synthesis of Intermediate 35.1, 5-bromo-3-fluoro-2-methylaniline

To a solution of 5-bromo-1-fluoro-2-methyl-3-nitrobenzene (2.4 g, 10.26 mmol) into EtOH (30 mL) and Water (6 mL) was added iron (2.86 g, 51.3 mmol) and NH₄Cl (2.74 g, 51.3 mmol). The reaction mixture was stirred at 90° C. for 1 hour. After Alteration and concentration, the mixture was poured into 20 mL water and extracted with EA (30 mL×3). The organic layer was washed with water (10 mL×3), dried over Na₂SO₄. The organic layer was concentrated to give intermediate 35.1, 5-bromo-3-fluoro-2-methylaniline which was used for the next step directly without further purification. MS (ESI) m/z calc'd for C₇H₈BrFN [M+H]⁺ 203.9. found 203.9.

Step 2—Synthesis of Intermediate 35.2, 5-bromo-4-chloro-3-fluoro-2-methylaniline To a solution of intermediate 35.1 (500 mg, 2.451 mmol) in anhydrous DMF (15 ml) was added NCS (295 mg, 2.205 mmol). The mixture was stirred at 30° C. for 16 hours. The reaction mixture was poured into water (10 mL) and extracted with EtOAc (30 mL×3). The organic layer was washed with water (10 mL×3), dried over Na₂SO₄. After filtration and concentration, the crude product was purified by silica gel column chromatography (eluent of 5% EtOAc/Petroleum ether) to give intermediate 35.2, 5-bromo-4-chloro-3-fluoro-2-methylaniline. MS (ESI) m/z calc'd for C₇H₇BrClFN [M+H]⁺ 238. found 238.

Step 3—Synthesis of Intermediate 35.3, 6-bromo-5-chloro-4-fluoro-1H-indazole

To a solution of intermediate 35.2 (900 mg, 3.77 mmol) in anhydrous AcOH (10 mL) was added sodium nitrite (286 mg, 4.15 mmol) and Water (1 mL), and the resulting mixture was stirred at 30° C. for 1 hour. Then, the AcOH was removed by vacuum. Then, the reaction mixture was adjusted to pH=7~8 with NaHCO₃ (50 mL), extracted with EtOAc (50 mL×3) and dried over Na₂SO₄. After filtration, the solvent was concentrated to give intermediate 35.3, 6-bromo-5-chloro-4-fluoro-1H-indazole which was used to next step directly without further purification. MS (ESI) m/z calc'd for $C_7H_4BrClFN_2$ [M+H]⁺ 250. found 250.

Step 4—Synthesis of Intermediate 35.4, 6-bromo-5-chloro-4-fluoro-1-(tetrahydro-2H-pyran-2-yl)-1H-indazole To a solution of intermediate 35.3 (250 mg, 1.002 mmol) in anhydrous toluene (5 mL) was added 3,4-dihydro-2H-pyran (101 mg, 1.203 mmol) and 2,2,2-trifluoroacetic acid (0.05 mL, 0.649 mmol), and the resulting mixture was stirred at 80° C. for 5 hours. Then the reaction mixture was concentrated, and the residue was purified by silica gel column chromatography (eluent of 0% to 10% EtOAc/Petroleum) to give intermediate 35.4, 6-bromo-5-chloro-4-fluoro-1-(tetrahydro-2H-pyran-2-yl)-1H-indazole. MS (ESI) m/z calc'd for $C_{12}H_{12}BrClFN_2O$ [M+H]⁺ 333. found 333.

Step 5—Synthesis of Intermediate 35.5, tert-butyl 4-(5-chloro-4-fluoro-1-(tetrahydro-2H-pyran-2-yl)-1H-indazol-6-yl)-3,6-dihydropyridine-1(2H)-carboxylate To a solution of intermediate 35.4 (250 mg, 0.749 mmol) in 1,4-Dioxane (5 mL) and Water (1 mL) was added (2-(1-(tert-butoxycarbonyl)-1,2,3,6-tetrahydropyridin-4-yl)-4,5,5-trimethyl-1,3,2-dioxaborolan-4 yl)methylium (254 mg, 0.824 mmol), Na₂CO₃ (238 mg, 2.248 mmol) and PdCl₂(dppf) (54.8 mg, 0.075 mmol). The resulting mixture was stirred at 100° C. under N₂ protection for 2 hours. After filtration, the reaction mixture was poured into water (20 mL) and extracted with EtOAc (20 mL×3). The organic layer was washed with water (10 mL), dried over Na₂SO₄. After filtration and concentration, the crude product was purified by silica gel column chromatography (eluent of 0% to 20% EtOAc/Petroleum ether) to give intermediate 35.5, tert-butyl 4-(5-chloro-4-fluoro-1-(tetrahydro-2H-pyran-2-yl)-1H-indazol-6-yl)-5,6-dihydropyridine-1(2H)-carboxylate. MS (ESI) m/z calc'd for $C_{22}H_{28}Cl FN_3O_3$ [M+H]⁺ 436. found 436.

Step 6—Synthesis of Intermediate 35.6, 5-chloro-4-fluoro-6-(1,2,3,6-tetrahydropyridin-4-yl)-1H-indazole Intermediate 35.5 (200 mg, 0.459 mmol) was added into 4M HCl/MeOH (5 mL). The resulting mixture was stirred at 30° C. for 2 hours. Then the solvent was concentrated to give intermediate 35.6, 5-chloro-4-fluoro-6-(1,2,3,6-tetrahydropyridin-4-yl)-1H-indazole, HCl salt, which was used to next step directly without further purification. MS (ESI) m/z calc'd for $C_{12}H_{12}Cl FN_3$ [M+H]⁺ 252. found 252.

Step 7—Synthesis of Intermediate 35.7, 5-chloro-4-fluoro-6-(piperidin-4-yl)-1H-indazole To a solution of intermediate 35.6 (100 mg, 0.397 mmol) in anhydrous EtOAc (5 mL) was added platinum (IV) oxide (20 mg, 0.088 mmol), and the resulting mixture was stirred at 30° C. under H₂ (15 psi) pressure for 16 hours. Afterward, the reaction was filtered, and the solvent was concentrated to give intermediate 35.7, 5-chloro-4-fluoro-6-(piperidin-4-yl)-1H-indazole. MS (ESI) m/z calc'd for $C_{12}H_{14}ClFN_3$ [M+H]⁺ 254. found 254.

Step 8—Synthesis of Intermediate 35.8, 5-chloro-4-fluoro-6-(1-(oxetan-3-yl)piperidin-4-yl)-1H-indazole To a solution of intermediate 35.7 (50 mg, 0.197 mmol) and oxetan-3-one (45 mg, 0.624 mmol) in anhydrous EtOH (2 mL) was added NaBH₃CN (30 mg, 0.477 mmol). The mixture was stirred at 9° C. for 1 hour. LCMS showed the reaction was complete. After filtration and concentration, the crude product was purified by pre-HPLC (TFA) to give intermediate 35.8, 5-chloro-4-fluoro-6-(1-(oxetan-3-yl)piperidin-4-yl)-1H-indazole, TFA salt. MS (ESI) m/z calc'd for $C_{15}H_{17}ClFN_3O$ [M+H]⁺ 310. found 310.

Step 9—Synthesis of Example 35.9, 5-chloro-4-fluoro-1-(1-methyl-1H-pyrazol-4-yl)-6-(1-(oxetan-3-yl)piperidin-4-yl)-1H-indazole To a solution of intermediate 35.8 (30 mg, 0.097 mmol) in anhydrous 1,4-Dioxane (3 mL) was added 4-iodo-1-methyl-1H-pyrazole (40.3 mg, 0.194 mmol), K₃PO₄ (61.7 mg, 0.291 mmol), (trans)-N1,N2-dimethylcyclohexane-1,2-diamine (10 mg, 0.070 mmol) and CuI (5 mg, 0.026 mmol), and the resulting mixture was stirred at 90° C. under N₂ protection for 16 hours. Afterward, the reaction was filtered and concentrated. The crude residue was purified by pre-HPLC (TFA) to give example 35.9, 5-chloro-4-fluoro-1-(1-methyl-1H-pyrazol-4-yl)-6-(1-(oxetan-3-yl)piperidin-4-yl)-1H-indazole, TFA salt. MS (ESI) m/z calc'd for $C_{19}H_{22}ClFN_5O$ [M+H]⁺ 390. found 390. ¹H NMR (500 MHz, CDCl₃): δ 8.17 (s, 1H), 8.03 (s, 1H), 7.86 (s, 1H), 7.40 (s, 1H), 5.13 (t, J=1.17 Hz, 2H), 4.81 (m, 2H), 4.18 (m, 1H), 4.03 (s, 3H), 3.59 (m, 2H), 3.43 (m, 1H), 2.78 (m, 2H), 2.46-2.54 (m, 2H), 2.13 (m, 2H). LRRK2 IC₅₀ 6.9 nM.

Preparation of Example 36.2, (R,R or S,S)-1-(1-(bicyclo[1.1.1]pentan-1-yl)-1H-pyrazol-4-yl)-5-chloro-6-(3-fluoro-1-(3-methyloxetan-3-yl)piperidin-4-yl)-1H-indazole Scheme 39

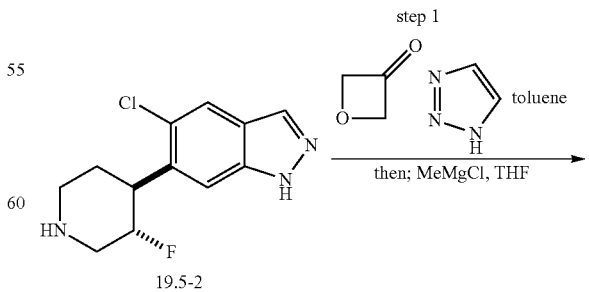

19.5-2

-continued step 2

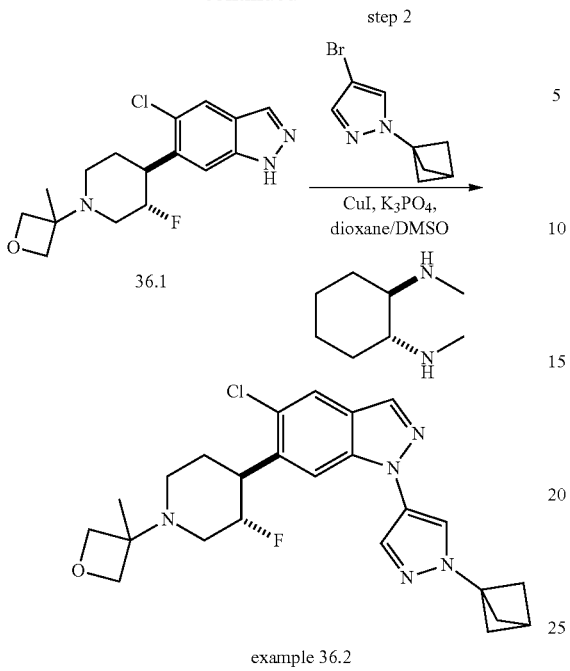

example 36.2

Step 1—Synthesis of Intermediate 36.1, (R,R or S,S)-5-chloro-6-(3-fluoro-1-(3-methyloxetan-3-yl)piperidin-4-yl)-1H-indazole Intermediate 19.5-2 (300 mg, 1.182 mmol) was dissolved in toluene (5 mL) in a 20 mL microwave vial under an atmosphere of nitrogen. 3-oxetanone (0.076 mL, 1.301 mmol) and 1H-1,2,3-triazole (0.082 mL, 1.419 mmol) were added via syringe and the reaction was heated to 120° C. in an aluminum heating block and allowed to stir for 2 hours. The reaction was then allowed to cool to room temperature then transferred via syringe to a 50 mL RBF and diluted with THF (11 mL). The solution was cooled to 0° C. in an ice bath. Then methylmagnesium chloride (3.0M in THF) (1.967 mL, 5.90 mmol) was added dropwise via syringe. The reaction was allowed to stir at 0° C. for 15 min then removed from the ice bath and allowed to warm to room temp and stir for 18 hours. The reaction was cooled back to 0° C. in an ice bath then carefully quenched with sat. $NH_4Cl$ (aq). The quenched solution was extracted 4× with 3:1 $CHCl_3$:IPA. The combined organic extract was dried over $Na_2SO_4$, filtered and concentrated. The reaction mixture was purified via column chromatography on silica gel (gradient: 0% to 100% EtOAc in DCM) to provide intermediate 36.1, (R,R or SB)-5-chloro-6-(3-fluoro-1-(3-methyloxetan-3-yl)piperidin-4-yl)-1H-indazole. MS (ESI) m/z calc'd for $C_{16}H_{20}ClFN_3O$ [M+H]$^+$ 324 found 324.

Step 2—Synthesis of Example 36.2, (R,R or S,S)-1-(1-(bicyclo[1.1.1]pentan-1-yl)-1H-pyrazol-4-yl)-5-chloro-6-(3-fluoro-1-(3-methyloxetan-3-yl)piperidin-4-yl)-1H-indazole Potassium phosphate tribasic (197 mg, 0.927 mmol), copper (I) iodide (29.4 mg, 0.154 mmol), and intermediate 36.1 (100 mg, 0.309 mmol) were weighed into a 2-5 mL microwave vial and placed under an atmosphere of nitrogen. Degassed dioxane (1.5 ml), DMSO (1.0 ml), 1-(bicyclo[1.1.1]pentan-1-yl)-4-bromo-1H-pyrazole (76 mg, 0.355 mmol) and N,N'-dimethyl-1,2-cyclohexanediamine (0.029 ml, 0.185 mmol) were added successively via syringes. The reaction was allowed to stir at 90° C. for 18 hours. The reaction was cooled to room temperature, diluted with water and extracted 3× with 3:1 $CHCl_3$:IPA. The organic extract was dried over $Na_2SO_4$, filtered, and concentrated. The reaction mixture was purified by reverse phase HPLC (Method A) and the resulting material was free-based with $NaHCO_3$ to obtain example 36.2, (R,R or S,S)-1-(1-(bicyclo[1.1.1]pentan-1-yl)-1H-pyrazol-4-yl)-5-chloro-6-(3-fluoro-1-(3-methyloxetan-3-yl)piperidin-4-yl)-1H-indazole. MS (ESI) m/z calc'd for $C_{24}H_{28}ClFN_5O$ [M+H]$^+$ 456 found 456. $^1$H NMR (500 MHz, DMSO-$d_6$) δ 8.39 (s, 1H), 8.25 (s, 1H), 8.06 (s, 1H), 7.99 (s, 1H), 7.77 (s, 1H), 5.17 (dtd, J=49.1, 9.8, 4.7 Hz, 1H), 4.48 (m, 1H), 4.41 (m, 1H), 4.16 (m, 2H), 3.29 (m, 1H), 3.01 (m, 1H), 2.66 (s, 1H), 2.63 (m, 1H), 2.32 (s, 6H), 2.28-2.11 (m, 2H), 1.89 (m, 1H), 1.76 (m, 1H), 1.33 (s, 3H). LRRK2 IC$_{50}$<0.625 nM Preparation of Example 37.1, 3-(4-(1-(1-(bicyclo[1.1.1]pentan-1-yl)-1H-pyrazol-4-yl)-5-chloro-1H-indazol-6-yl)piperidin-1-yl)thietane 1,1-dioxide Scheme 40

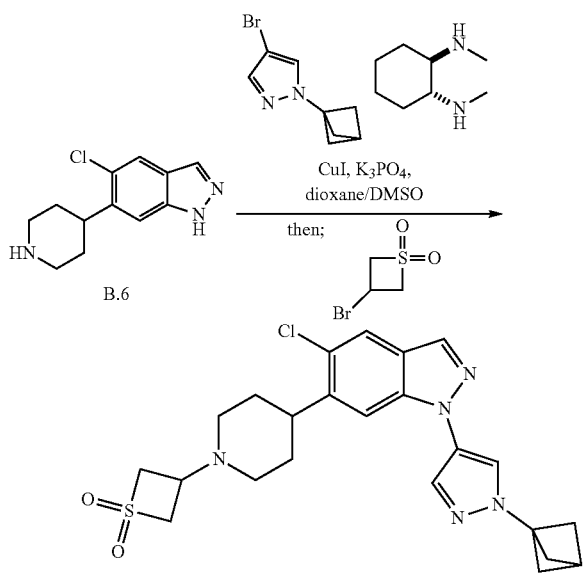

example 37.1

Potassium phosphate (135 mg, 0.636 mmol), copper (I) iodide (16.16 mg, 0.085 mmol), 1-(bicyclo[1.1.1]pentan-1-yl)-4-bromo-1H-pyrazole (54.2 mg, 0.255 mmol), and intermediate B.6 (50 mg, 0.212 mmol) were weighed into a 2-5 mL microwave vial and placed under an atmosphere of nitrogen. Degassed dioxane (0.5 ml), DMSO (0.5 ml) and trans-N,N'-dimethyl-1,2-cyclohexanediamine (0.015 ml, 0.095 mmol) were added via syringes. The reaction was allowed to stir at 90° C. overnight. LCMS after 16 h showed mostly unreacted starting material. A second addition of copper (I) iodide (16.16 mg, 0.085 mmol) premixed with N,N'-dimethyl-1,2-cyclohexanediamine (0.015 ml, 0.095 mmol) in degassed DMSO (0.1 mL) was added to the cooled reaction and it was reheated to 90° C. and stirred for an additional 20 h. The reaction was cooled to room temperature and 3-bromothietane 1,1 dioxide (78 mg, 0.424 mmol) was added. The reaction was heated to 90° C. for 1.5 hours. The reaction was cooled, diluted with water and extracted 4× with 3:1 CHCl$_3$:IPA. The organic extract was filtered through a phase separator and concentrated. The reaction mixture was purified by reverse phase HPLC (Method A) and the resulting solution was free-based with NaHCO$_3$ to obtain example 37.1, 3-(4-(1-(1-(bicyclo[1.1.1]pentan-1-yl)-1H-pyrazol-4-yl)-5-chloro-1H-indazol-6-yl)piperidin-1-yl)thietane 1,1-dioxide. MS (ESI) m/z calc'd for C$_{23}$H$_{27}$Cl FN$_5$O$_2$S [M+H]$^+$ 472 found 472. $^1$HNMR (500 MHz, DMSO-d$_6$) δ 8.40 (s, 1H), 8.23 (s, 1H), 8.00 (s, 1H), 7.97 (s, 1H), 7.54 (s, 1H), 4.33-4.20 (m, 2H), 4.09 (m, 2H), 3.28-3.17 (m, 1H), 3.00 (m, 4H), 2.67 (s, 1H), 2.31 (s, 6H), 2.08 (m, 2H), 1.82 (m, 3H). LRRK2 IC$_{50}$<0.625 nM Preparation of Example 38.2, (R and S)-3-(4-(1-(1-(bicyclo[1.1.1]pentan-1-yl)-1H-pyrazol-4-yl)-5-chloro-1H-indazol-6-yl)piperidin-1-yl)tetrahydrothiophene 1,1-dioxide

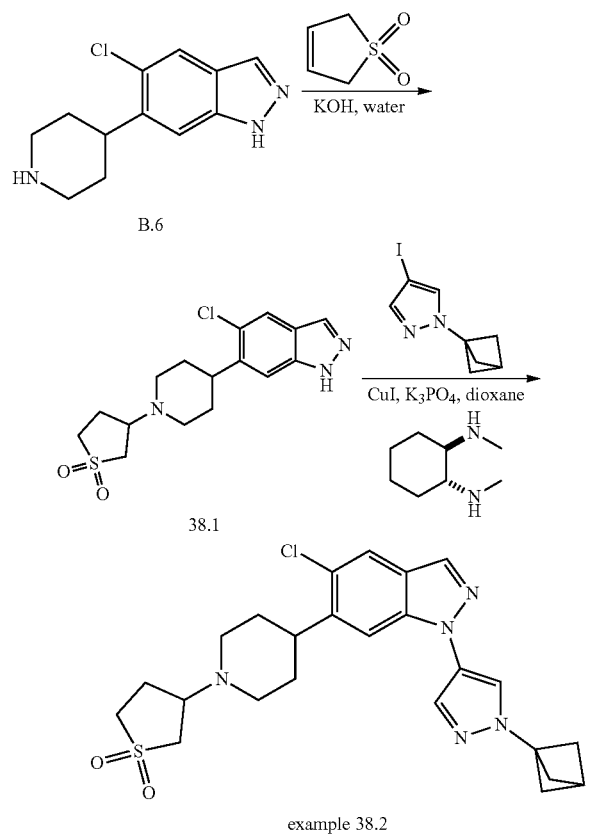

Step 1—Synthesis of Intermediate 38.1, (R and S)-3-(4-(5-chloro-1H-indazol-6-yl)piperidin-1-yl)tetrahydrothiophene 1,1-dioxide To a vial was added intermediate B.6 (250 mg, 1.06 mmol), 2,5-dihydrothiophene 1,1-dioxide (150 mg, 1.27 mmol), KOH (1M, 4.2 mL, 4.2 mmol), EtOH (3 mL) and Water (1.5 mL). The mixture was heated at 100° C. overnight. The mixture was extracted with EtOAc three times. The combined organic layers were washed with brine, dried over MgSO$_4$, filtered, and concentrated in vacuo. The residue was purified by reversed phase HPLC (method B) to afford intermediate 38.1, (R and S)-3-(4-(5-chloro-1H-indazol-6-yl)piperidin-1-yl)tetrahydrothiophene 1,1-dioxide. MS (ESI) m/z calc'd for C$_{16}$H$_{21}$Cl N$_3$O$_2$S [M+H]$^+$ 354 found 354.

Step 2—Synthesis of Example 38.2, (R and S)-3-(4-(1-(1-(bicyclo[1.1.1]pentan-1-yl)-1H-pyrazol-4-yl)-5-chloro-1H-indazol-6-yl)piperidin-1-yl)tetrahydrothiophene 1,1-dioxide To a vial was added trans-N,N'-dimethyl-1,2-cyclohexanediamine (8.0 mg, 0.056 mmol), copper(I) iodide (6.4 mg, 0.034 mmol), common intermediate G.2 (21 mg, 0.081 mmol), intermediate 38.1 (29.7 mg, 0.0840 mmol), K$_3$PO$_4$ (53.4 mg, 0.252 mmol) and dioxane (800 µL). The vessel was evacuated and back filled with N$_2$ 4 times, then heated at 80° C. for 16 h. The mixture was filtered and purified by reversed phase HPLC (method B) to afford example 38.2, (R and S)-3-(4-(1-(1-(bicyclo[1.1.1]pentan-1-yl)-1H-pyrazol-4-yl)-5-chloro-1H-indazol-6-yl)piperidin-1-yl)tetrahydrothiophene 1,1-dioxide. MS (ESI) m/z calc'd for C$_{24}$H$_{29}$Cl N$_5$O$_2$S [M+H]$^+$ 486 found 486. $^1$H NMR (600 MHz, DMSO-d$_6$) δ 8.40 (s, 1H), 8.23 (s, 1H), 8.01 (s, 1H), 7.97 (s, 1H), 7.54 (s, 1H), 3.32-3.23 (m, 1H), 3.16-2.95 (m, 6H), 2.67 (s, 1H), 2.39-2.30 (m, 1H), 2.32 (s, 6H), 2.28-2.17 (m, 2H), 2.07-1.98 (m, 2H), 1.90-1.72 (m, 4H). LRRK2 IC$_{50}$<0.625 nM Preparation of Example 39.3, (R,R or S,S)-3-(4-(1-(1-(bicyclo[1.1.1]pentan-1-yl)-1H-pyrazol-4-yl)-5-chloro-1H-indazol-6-yl)-3-fluoropiperidin-1-yl)thietane 1,1-dioxide

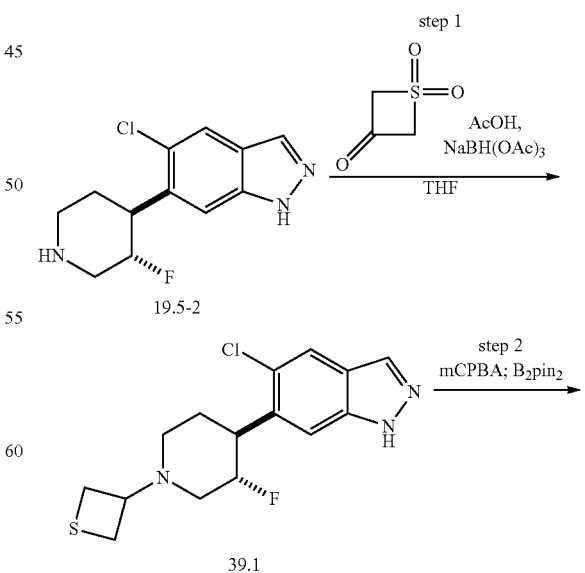

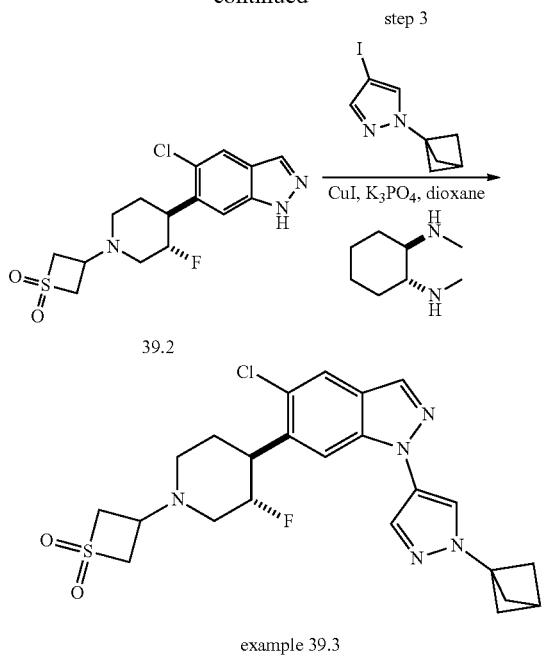

example 39.3

Step 1—Synthesis of Intermediate 39.1, (R,R or S,S)-5-chloro-6-((3S,4S)-3-fluoro-1-(thietan-3-yl)piperidin-4-yl)-1H-indazole Intermediate 19.5-2 (500 mg, 1.97 mmol), acetic acid (59.2 mg, 0.985 mmol), thietan-3-one (434 mg, 4.93 mmol) were combined in a dry 50 mL RBF with stir bar and then solvated in THF (15 mL). The mixture was stirred at 40° C. for 10 min. Then, sodium triacetoxyborohydride (1462 mg, 6.90 mmol) was added and the reaction was stirred at room temperature for 2 hours. The mixture was then diluted with DCM and saturated NaHCO$_3$. The organic layer was extracted, dried over Na$_2$SO$_4$, filtered, and concentrated. The resulting residue was purified by silica gel chromotography using a gradient of 0-100% 3:1 (EtOAc:EtOH) in hexanes to afford intermediate 39.1, (R,R or S,S)-5-chloro-6-((3S,4S)-3-fluoro-1-(thietan-3-yl)piperidin-4-yl)-1H-indazole. MS (ESI) m/z calc'd for C$_{15}$H$_{18}$Cl FN$_3$S [M+H]$^+$ 326 found 326.

Step 2—Synthesis of Intermediate 39.2, (R,R or S,S)-3-((3S,4S)-4-(5-chloro-1H-indazol-6-yl)-3-fluoropiperidin-1-yl)thietane 1,1-dioxide Intermediate 39.1 (700 mg, 2.15 mmol), 3-chlorobenzoperoxoic acid (989 mg, 4.30 mmol) were combined in a dry 100 mL RBF with stir bar and solvated in DCM (20 mL). The mixture was stirred at room temperature overnight. The resulting material was washed with 10% solution of aqeuous sodium thiosulfate. The organic layer was collected, dried over Na$_2$SO$_4$, filtered, and concentrated. This material was then redissolved in MeCN (10 mL) and bis(pinacolato)diboron (285 mg, 1.124 mmol) was added. The mixture was stirred at room temperature for 1 hour. Then, ethane-1,2-diamine (1125 mg, 18.73 mmol) was added and stirred was continued for 2 hours. Next, the mixture was diluted with 3:1 CHCl$_3$:IPA and brine. The organic layer was extracted, dried over Na$_2$SO$_4$, filtered, and concentrated. The residue was then purified by silica gel chromotography using a gradient of 0-100% of 3:1 EtOAc:EtOH in hexanes to afford intermediate 39.2, (R,R or S,S)-3-((3S,4S)-4-(5-chloro-1H-indazol-6-yl)-3-fluoropiperidin-1-yl)thietane 1,1-dioxide. MS (ESI) m/z calc'd for C$_{15}$H$_{18}$ClFN$_3$O$_2$S [M+H]$^+$ 358 found 358.

Step 3—Synthesis of Example 39.3, (R,R or S,S)-3-(4-(1-(1-(bicyclo[1.1.1]pentan-1-yl)-1H-pyrazol-4-yl)-5-chloro-1H-indazol-6-yl)-3-fluoropiperidin-1-yl)thietane 1,1-dioxide Intermediate 39.2 (100 mg, 0.279 mmol), copper (I) iodide (26.6 mg, 0.140 mmol), potassium phosphate tribasic (208 mg, 0.978 mmol), trans-N,N'-dimethyl-1,2-cyclohexanediamine (31.8 mg, 0.224 mmol), and common intermediate G.2 (71.5 mg, 0.335 mmol) were combined in a dry 30 mL vial with stir bar. The vessel was purged with N$_2$ gas, and then dioxane (6 mL) was added. The reaction was stirred at 75° C. overnight. Then, the crude material was filtered through celite, concentrated, and purified by reverse phase HPLC (method A) to afford example 39.3, (R,R or S,S)-3-(4-(1-(1-(bicyclo[1.1.1]pentan-1-yl)-1H-pyrazol-4-yl)-5-chloro-1H-indazol-6-yl)-3-fluoropiperidin-1-yl)thietane 1,1-dioxide. MS (ESI) m/z calc'd for C$_{23}$H$_{26}$Cl FN$_5$O$_2$S [M+H]$^+$ 490 found 490. $^1$H NMR (499 MHz, DMSO-d$_6$) δ 8.40 (s, 1H), 8.26 (s, 1H), 8.05 (s, 1H), 8.01 (s, 1H), 7.76 (s, 1H), 5.18 (m, 1H), 4.32 (m, 2H), 4.20 (m, 2H), 3.36 (m, 4H), 2.92 (m, 1H), 2.54-2.46 (m, 4H), 2.31 (s, 6H), 2.24-2.09 (m, 2H), 1.97-1.86 (m, 1H), 1.78 (m, 1H). LRRK2 IC$_{50}$<0.625 nM Preparation of Example 40.4-1, (R,R or S,S)-4-(4-(1-(1-(bicyclo[1.1.1]pentan-1-yl)-1H-pyrazol-4-yl)-5-chloro-1H-indazol-6-yl)piperidin-1-yl)-4-methyl-tetrahydrofuran-3-ol Scheme 43
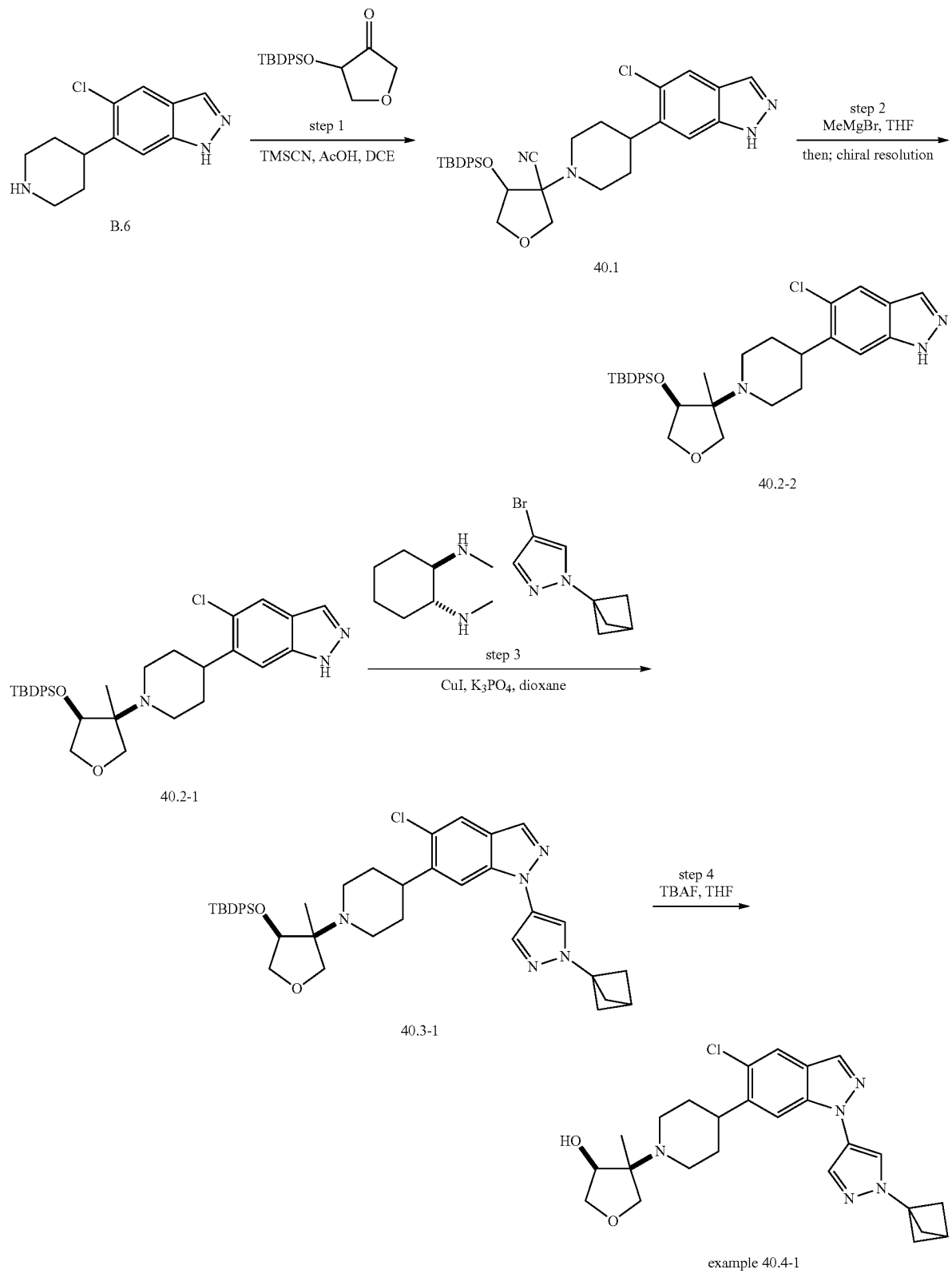

Step 1—Synthesis of Intermediate 40.1, 4-((tert-butyldiphenylsilyl)oxy)-3-(4-(5-chloro-1H-indazol-6-yl)piperidin-1-yl)tetrahydrofuran-3-carbonitrile Into a 500-mL 4-necked round-bottom flask purged and maintained with an inert atmosphere of nitrogen, was placed intermediate B.6 (75.00 g, 318.174 mmol), AcOH (28.66 g, 477.261 mmol), 4-[(tert-butyldiphenylsilyl)oxy]oxolan-3-one (130.00 g, 381.809 mmol), and DCE (200.00 mL). The resulting solution was stirred for 30 min at room temperature. To this was added TMSCN (47.35 g, 477.261 mmol). The resulting solution was allowed to react, with stirring, overnight at 60° C. The reaction was then quenched by the addition of water. The resulting solution was extracted 3 times with 1 L of dichloromethane, the combined organic phase was washed with 200 mL of salt water, dried over anhydrous sodium sulfate and concentrated to afford intermediate 40.1, 4-((tert-butyldiphenylsilyl)oxy)-3-(4-(5-chloro-1H-indazol-6-yl)piperidin-1-yl)tetrahydrofuran-3-carbonitrile. MS (ESI) m/z calc'd for $C_{33}H_{38}ClN_4O_2Si$ $[M+H]^+$ 585 found 585.

Step 2—Synthesis of Intermediates 40.2-1, (R,R or S,S)-6-(1-(4-((tert-butyldiphenylsilyl)oxy)-3-methyltetrahydrofuran-3-yl)piperidin-4-yl)-5-chloro-1H-indazole and 40.2-2, (R,R or S,S)-6-(1-(4-((tert-butyldiphenylsilyl)oxy)-3-methyltetrahydrofuran-3-yl)piperidin-4-yl)-5-chloro-1H-indazole Into a 2-L 4-necked round-bottom flask purged and maintained with an inert atmosphere of nitrogen, was placed intermediate 40.1 (100.00 g, 170.876 mmol), THF (1.00 L), and MeMgBr (203.76 g, 1708.765 mmol). The resulting solution was stirred for 5 h at 60° C. The reaction was then quenched by the addition of 2 L of NH₄Cl. The resulting solution was extracted with 3 times with 2 L of ethyl acetate, the organic phase was washed with 1 L of salt water. The mixture was dried over anhydrous sodium sulfate and concentrated. The residue was purified by silica gel chromotography using 1:3 EtOAc:petroleum ether. The resulting material was then purified by prep-SFC using the following conditions: (Column: CHIRAL ART Cellulose-SB, 5*25*5 um; mobile phase: CO₂/(MeOH:DCM=5:1)=50/50; Detector 220 nm, flow rate: 150 g/min). This resulted in intermediates 40.2-1, (R,R or S,S)-6-(1-(4-((tert-butyldiphenylsilyl)oxy)-3-methyltetrahydrofuran-3-yl)piperidin-4-yl)-5-chloro-1H-indazole and 40.2-2, (R,R or S,S)-6-(1-(4-((tert-butyldiphenylsilyl)oxy)-3-methyltetrahydrofuran-3-yl)piperidin-4-yl)-5-chloro-1H-indazole.

Intermediate 40.2-1

MS (ESI) m/z calc'd for $C_{33}H_{41}ClN_3O_2Si$ $[M+H]^+$ 574 found 574. ¹H NMR (400 MHz, DMSO-d₆, ppm): δ 13.15 (s, 1H), 8.00 (d, J=1.2 Hz, 1H), 7.86-7.77 (m, 3H), 7.72-7.65 (m, 2H), 7.57-7.39 (m, 6H), 7.22 (s, 1H), 4.13 (d, J=3.3 Hz, 1H), 3.92 (d, J=6.9 Hz, 1H), 3.85 (dd, J=10.0, 3.4 Hz, 1H), 3.72-3.62 (m, 2H), 2.87 (t, J=11.6 Hz, 1H), 2.59 (s, 2H), 2.28-2.16 (m, 1H), 1.83 (d, J=12.0 Hz, 1H), 1.75-1.62 (m, 1H), 1.49 (d, J=12.2 Hz, 1H), 1.36 (q, J=11.4, 10.8 Hz, 1H), 1.23 (s, 1H), 1.04 (s, 8H), 1.03 (s, 1H), 0.91 (s, 3H).

Step 3—Synthesis of Intermediate 40.3-1, (R,R or S,S)-1-(1-(bicyclo[1.1.1]pentan-1-yl)-1H-pyrazol-4-yl)-6-(1-(4-((tert-butyldiphenylsilyl)oxy)-3-methyltetrahydrofuran-3-yl)piperidin-4-yl)-5-chloro-1H-indazole Intermediate 40.2-1, (170 mg, 0.296 mmol), 1-(bicyclo[1.1.1]pentan-1-yl)-4-bromo-1H-pyrazole (76 mg, 0.355 mmol), copper (I) iodide (28.2 mg, 0.148 mmol), potassium phosphate tribasic (220 mg, 1.04 mmol), and trans-N,N'-dimethyl-1,2-cyclohexanediamine (33.7 mg, 0.237 mmol) were combined in a vial. The vessel was purged with N₂ gas, and then dioxane (2.5 mL) was added. The resulting mixture was stirred at 80° C. overnight. The crude reaction was then filtered through a pad of celite using excess EtOAc. The filtrate was then concentrated to provide crude intermediate 40.3-1, (R,R or S,S)-1-(1-(bicyclo[1.1.1]pentan-1-yl)-1H-pyrazol-4-yl)-6-(1-(4-((tert-butyldiphenylsilyl)oxy)-3-methyltetrahydrofuran-3-yl)piperidin-4-yl)-5-chloro-1H-indazole. MS (ESI) m/z calc'd for $C_{41}H_{49}ClN_5O_2Si$ $[M+H]^+$ 706 found 706.

Step 4—Synthesis of Example 40.4-1, (R,R or S,S)-4-(4-(1-(1-(bicyclo[1.1.1]pentan-1-yl)-1H-pyrazol-4-yl)-5-chloro-1H-indazol-6-yl)piperidin-1-yl)-4-methyltetrahydrofuran-3-ol Crude intermediate 40.3-1 (200 mg, 0.283 mmol) was solvated in THF (4 mL) in a vial. Then, tetrabutylammonium fluoride (1 M solution in THF, 1.416 mL) was added. The mixture was stirred at 50° C. for 4 hours. Then, the reaction was diluted with diethyl ether and washed 3 times with saturated ammonium chloride solution. The organic layer was extracted, dried over sodium sulfate, filtered, and concentrated. The crude material was purified by reverse phase HPLC (method A) to afford example 40.4-1, (R,R or S,S)-4-(4-(1-(1-(bicyclo[1.1.1]pentan-1-yl)-1H-pyrazol-4-yl)-5-chloro-1H-indazol-6-yl)piperidin-1-yl)-4-methyltetrahydrofuran-3-ol. MS (ESI) m/z calc'd for $C_{25}H_{31}ClN_5O_2$ $[M+H]^+$ 468 found 468. ¹H NMR (499 MHz, DMSO-d₆) δ 8.37 (s, 1H), 8.27 (s, 1H), 8.02 (s, 1H), 7.97 (s, 1H), 7.44 (s, 1H), 4.21-4.11 (m, 3H), 3.91-3.78 (m, 3H), 3.56-3.34 (m, 5H), 3.04 (d, J=11.4 Hz, 1H), 2.30 (s, 6H), 1.99 (dd, J=59.9, 9.7 Hz, 3H), 1.37 (s, 3H). LRRK2 $IC_{50}<0.625$ nM Preparation of Example 41.6, (R,R or S,S)-4-(4-(5-chloro-1-(1-cyclopropyl-1H-pyrazol-4-yl)-1H-indazol-6-yl)piperidin-1-yl)-4-methyltetrahydrofuran-3-ol Scheme 44

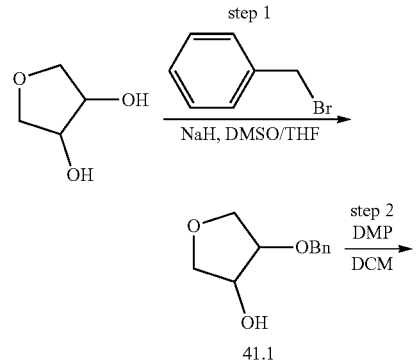

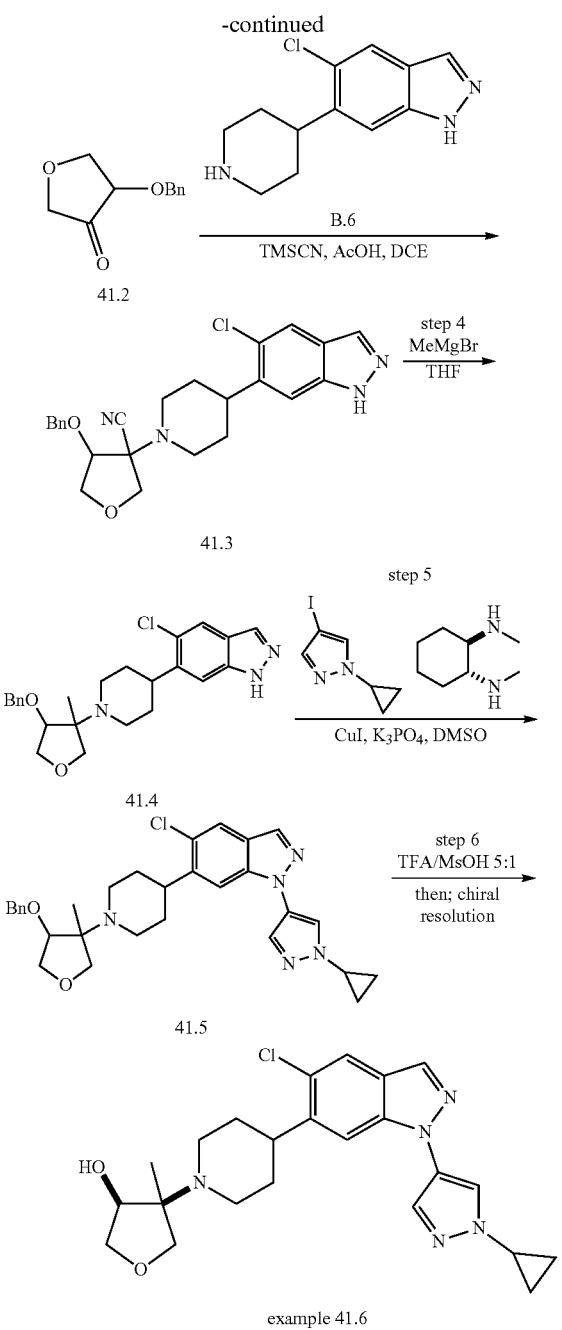

and filtered. The filtrate was concentrated in vacuo to give the residue, which was purified by silica gel column chromotography using EtOAc:petroleum ether ~20% gradient to give intermediate 41.1, 4-(benzyloxy)tetrahydrofuran-3-ol. $^1$H NMR (400 MHz, CDCl$_3$) δ 7.42-7.30 (m, 5H), 4.68-4.58 (m, 2H), 4.26-4.28 (m, 1H), 4.06-4.10 (m, 1H), 3.88-0.93 (m, 2H), 3.84-3.71 (m, 2H), 2.75 (d, J=5.5 Hz, 1H).

Step 2—Synthesis of Intermediate 41.2, 4-(benzyloxy)dihydrofuran-3(2H)-one

A solution of intermediate 41.1 (4.7 g, 24.20 mmol) in DCM (120 mL) was cooled to 0° C. and Dess-Martin periodinane (30.8 g, 72.6 mmol) was added. The reaction was stirred for 2 h at 25° C. TLC showed the reaction was complete. This reaction was poured into ice-water (100 mL) and filtered. The filtrate was quenched with saturated NaHCO$_3$ (50 mL) and extracted with DCM (50 mL×3). The combined organic layers were washed with brine (200 mL), dried over anhydrous Na$_2$SO$_4$ and filtered. The filtrate was concentrated in vacuo to give the residue, which was purified by silica gel chromatography using 0-15% EtOAc: petroleum ether gradient to give intermediate 41.2, 4-(benzyloxy)dihydrofuran-3(2H)-one. $^1$H NMR (400 MHz, CDCl3) δ 7.40-7.28 (m, 5H), 4.92 (d, J=11.7 Hz, 1H), 4.68 (d, J=11.7 Hz, 1H), 4.29 (m, 1H), 4.07-3.94 (m, 3H), 3.87 (m, 1H).

Step 3—Synthesis of Intermediate 41.3, 4-(benzyloxy)-3-(4-(5-chloro-1H-indazol-6-yl)piperidin-1-yl) tetrahydrofuran-3-carbonitrile To a solution of intermediate B.6 (700 mg, 2.97 mmol) in DCE (35 mL) were added intermediate 41.2 (1712 mg, 8.91 mmol), and AcOH (0.850 mL, 14.85 mmol). The mixture was stirred for 30 min at 50° C., then TMS-CN (3.98 mL, 29.7 mmol) was added to the mixture. The mixture was stirred at 50° C. for 54 h. LCMS showed the reaction was complete. Water (20 mL) was added to the mixture and the mixture was extracted with DCM (20 mL×2). The combined organic layers were washed with brine (50 mL), dried over anhydrous Na$_2$SO$_4$ and filtered. The filtrate was concentrated in vacuo to give the residue, which was purified by silica gel chromatography using EtOAc:petroleum ether 0-50% gradient to give intermediate 41.3, 4-(benzyloxy)-3-(4-(5-chloro-1H-indazol-6-yl)piperidin-1-yl)tetrahydrofuran-3-carbonitrile. MS (ESI) m/z calc'd for C$_{24}$H$_{26}$Cl N$_4$O$_2$ [M+H]$^+$ 437 found 437.

Step 4—Synthesis of Intermediate 41.4, 6-(1-(4-(benzyloxy)-3-methyltetrahydrofuran-3-yl)piperidin-4-yl)-5-chloro-1H-indazole To a solution of intermediate 41.3 (630 mg, 1.442 mmol) in THF (12 mL) was added methylmagnesium bromide (2.403 mL, 7.21 mmol) at 0° C. The mixture was stirred for 1 h at 60° C. under MW. The mixture was quenched with saturated NH$_4$Cl (25 mL) and extracted with EtOAc (25 mL×3). The combined organic layers were washed with brine (50 mL), dried over anhydrous Na$_2$SO$_4$ and filtered. The filtrate was concentrated in vacuo to give a residue. The residue was washed with petroleum ether and the precipitate to collect to afford intermediate 41.4, 6-(1-(4-(benzyloxy)-3-methyltetrahydrofuran-3-yl)piperidin-4-yl)-5-chloro-1H-indazole. MS (ESI) in z calc'd for C$_{24}$H$_{29}$Cl N$_3$O$_2$ [M+H]$^+$ 426 found 426.

Step 5—Synthesis of Intermediate 41.5, 6-(1-(4-(benzyloxy)-3-methyltetrahydrofuran-3-yl)piperidin-4-yl)-5-chloro-1-(1-cyclopropyl-1H-pyrazol-4-yl)-1H-indazole To a solution of potassium phosphate tribasic (792 mg, 3.73 mmol) and 1-cyclopropyl-4-iodo-1H-pyrazole (437 mg, 1.866 mmol) in DMSO (10 mL) were added intermediate 41.4 (530 mg, 1.244 mmol), trans-N1,N2-dimethylcyclohexane-1,2-diamine (35.4 mg, 0.249 mmol) and copper (I) iodide (237 mg, 1.244 mmol) at room temperature. The mixture was stirred for 36 h at 90° C. under $N_2$ atmosphere. 16% $NH_3$ aqueous (20 mL) was added to the mixture and this mixture was extracted with EtOAc (10 mL×3). The combined organic layers were washed with brine (20 mL), dried over $Na_2SO_4$ and filtered. The filtrate was concentrated in vacuo to give intermediate 41.5, 6-(1-(4-(benzyloxy)-3-methyltetrahydrofuran-3-yl)piperidin-4-yl)-5-chloro-1-(1-cyclopropyl-1H-pyrazol-4-yl)-1H-indazole. MS (ESI) m/z calc'd for $C_{30}H_{35}ClN_5O_2$ $[M+H]^+$ 532 found 532.

Step 6—Synthesis of Example 41.6, (R,R or S,S)-4-(4-(5-chloro-1-(1-cyclopropyl-1H-pyrazol-4-yl)-1H-indazol-6-yl)piperidin-1-yl)-4-methyltetrahydrofuran-3-ol To a solution of intermediate 41.5 (660 mg, 1.240 mmol) in TFA (3.3 mL, 42.8 mmol) was added MsOH (0.66 mL, 10.16 mmol) at room temperature. The mixture was stirred for 1 h at 60° C. The mixture was concentrated in vacuo to give a residue, which was purified by prep-HPLC (TFA) to give 4-(4-(5-chloro-1-(1-cyclopropyl-1H-pyrazol-4-yl)-1H-indazol-6-yl)piperidin-1-yl)-4-methyltetrahydrofuran-3-ol as a mixture of isomer. This material was then purified by prep-SFC to give the cis ((R,R and S,S)-4-(4-(5-chloro-1-(1-cyclopropyl-1H-pyrazol-4-yl)-1H-indazol-6-yl)piperidin-1-yl)-4-methyltetrahydrofuran-3-ol) and tram ((R,S and S,R)-4-(4-(5-chloro-1-(1-cyclopropyl-1H-pyrazol-4-yl)-1H-indazol-6-yl)piperidin-1-yl)-4-methyltetrahydrofuran-3-ol) isomers. The cis isomer was then further purified by chiral prep-SFC using the following conditions: Chiralpak AD-3 50×4.6 mm I.D., 3 um Mobile phase: A: $CO_2$ B: ethanol (0.05% DEA) Gradient: from 5% to 40% of B in 2 min and hold 40% for 1.2 min, then 5% of B for 0.8 min Flow rate: 4 mL/min Column temp.: 35° C. ABPR: 1500 psi. This provided (second peak) example 41.6, (R,R or S,S)-4-(4-(5-chloro-1-(1-cyclopropyl-1H-pyrazol-4-yl)-1H-indazol-6-yl)piperidin-1-yl)-4-methyltetrahydrofuran-3-ol. MS (ESI) m/z calc'd for $C_{23}H_{29}ClN_5O_2$ $[M+H]^+$ 442 found 442. $^1$H NMR (400 MHz, $CDCl_3$): δ 8.03 (d, J=0.8 Hz, 1H), 7.83 (s, 1H), 7.82-7.80 (m, 1H), 7.79-7.77 (m, 1H), 7.43 (s, 1H), 4.37 (s, 1H), 4.21 (m, 1H), 3.82-3.75 (m, 2H), 3.72 (m, 1H), 3.65 (m, 1H), 3.26-3.09 (m, 2H), 2.72 (d, J=11.5 Hz, 1H), 2.61-2.43 (m, 2H), 2.12-1.91 (m, 2H), 1.78-1.68 (m, 2H), 1.27-1.22 (m, 2H), 1.21 (s, 3H), 1.16-1.09 (m, 2H). LRRK2 $IC_{50}$<0.625 nM Preparation of Example 42.3, (R,R or S,S)-4-(4-(1-(1-(bicyclo[1.1.1]pentan-1-yl)-1H-pyrazol-4-yl)-5-chloro-1H-indazol-6-yl)piperidin-1-yl)tetrahydrofuran-3-ol

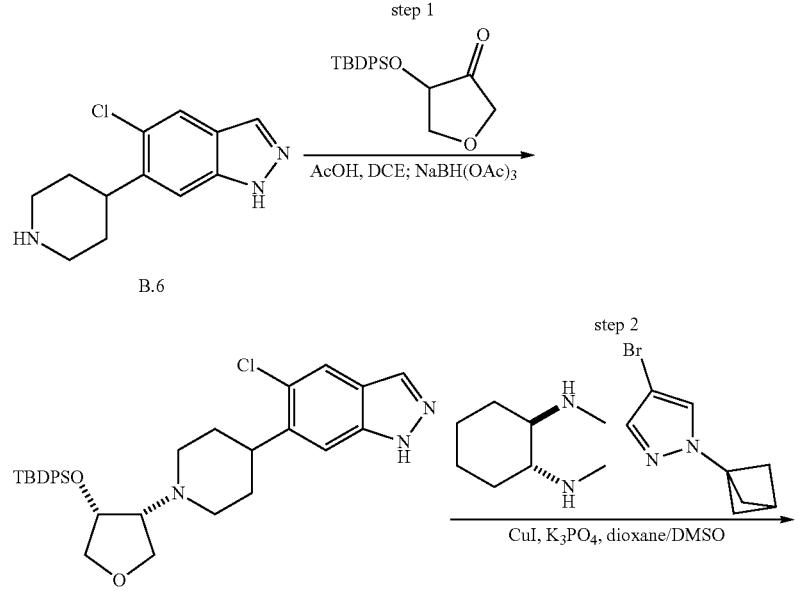

Scheme 45

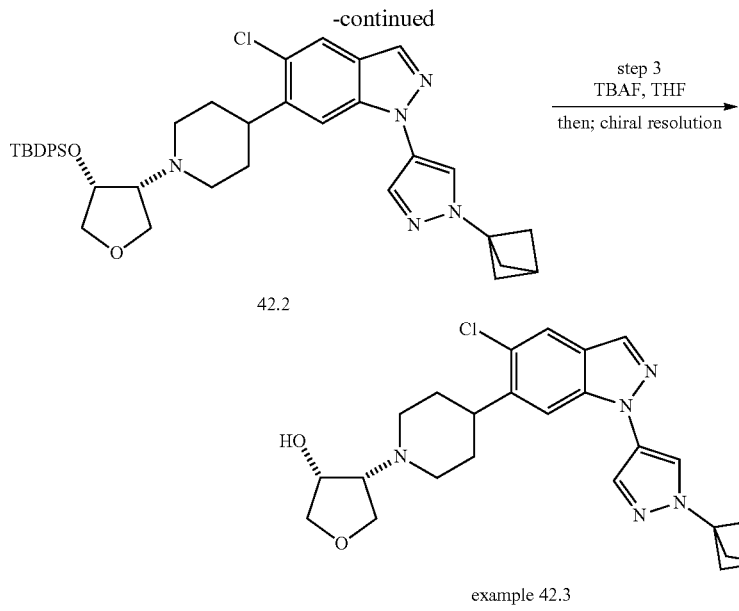

42.2 example 42.3

Step 1—Synthesis of Intermediate 42.1, (R,R and S,S)-6-(1-(4-(((tert-butyldiphenylsilyl)oxy)tetrahydrofuran-3-yl)piperidin-4-yl)-5-chloro-1H-indazole Intermediate B.6 (200 mg, 0.848 mmol) and 4-((tert-butyldiphenylsilyl)oxy)dihydrofuran-3(2H)-one (867 mg, 2.55 mmol) in a mixture of acetic acid (243 μL, 4.24 mmol) and DCE (8485 μL) was stirred at RT for 30 mins, then sodium triacetoxyborohydride (539 mg, 2.55 mmol) was added. The reaction mixture was stirred at 50° C. for 5 h. The reaction mixture was then cooled to RT, diluted with DCM, quenched with aq. sat. NaHCO₃ solution. Two layers were separated. The organic layer was collected, dried over Na₂SO₄, filtered, and concentrated under reduced pressure. The residue was purified by silica gel chromatography (0 to 100% EtOAc in hexanes) to give intermediate 42.1, (R,R and S,S)-6-(1-(4-(((tert-butyldiphenylsilyl)oxy)tetrahydrofuran-3-yl)piperidin-4-yl)-5-chloro-1H-indazole. MS (ESI) m/z calc'd for $C_{32}H_{39}ClN_3O_2Si$ [M+H]⁺ 560 found 560.

Step 2—Synthesis of Intermediate 42.2, (R,R and S,S)-1-(1-(bicyclo[1.1.1]pentan-1-yl)-1H-pyrazol-4-yl)-6-(1-(4-((tert-butyldiphenylsilyl)oxy)tetrahydrofuran-3-yl)piperidin-4-yl)-5-chloro-1H-indazole A mixture of CuI (45.9 mg, 0.241 mmol), K₃PO₄ (307 mg, 1.446 mmol), intermediate 42.1 (270 mg, 0.482 mmol), and 1-(bicyclo[1.1.1]pentan-1-yl)-4-bromo-1H-pyrazole (103 mg, 0.482 mmol) was evacuated and back filled with N₂ for 3 times. Dioxane (2410 μL), DMSO (2410 μL) and trans-N1,N2-dimethylcyclohexane-1,2-diamine (45.6 μL, 0.289 mmol) was added. The mixture was stirred at 80° C. for 2 days. The mixture was cooled to RT, diluted with EtOAc (100 mL) and sat. aq. NH₄Cl solution. The organic layer was washed with brine, dried over Na₂SO₄, filtered and concentrated under reduced pressure. The residue was purified by silica gel chromatography (0 to 100% EtOAc in hexanes) to give intermediate 42.2, (R,R and S,S)-1-(1-(bicyclo[1.1.1]pentan-1-yl)-1H-pyrazol-4-yl)-6-(1-(4-((tert butyldiphenylsilyl)oxy)tetrahydrofuran-3-yl)piperidin-4-yl)-5-chloro-1H-indazole. MS (ESI) m/z calc'd for $C_{40}H_{47}ClN_5O_2Si$ [M+H]⁺ 692 found 692.

Step 3—Synthesis of Example 42.3, (R,R or S,S)-4-(4-(1-(1-(bicyclo[1.1.1]pentan-1-yl)-1H-pyrazol-4-yl)-5-chloro-1H-indazol-6-yl)piperidin-1-yl)tetrahydrofuran-3-ol To a solution of intermediate 42.2 (190 mg, 0.274 mmol) in THF (915 μL) were added TBAF (1.0 M in THF, 933 μL, 0.933 mmol). The mixture was stirred at RT for 4 h. The reaction is quenched with sat. NH₄Cl solution (15 mL) and extracted with EtOAc (100 mL). The organic layer was washed with brine, dried over Na₂SO₄. After filtration and concentration under reduce pressure, the residue was purified by silica gel chromatography eluting with acetone in hexanes to give (R,R and S,S)-4-(4-(1-(1-(bicyclo[1.1.1]pentan-1-yl)-1H-pyrazol-4-yl)-5-chloro-1H-indazol-6-yl)piperidin-1-yl)tetrahydrofuran-3-ol. This material was then resolved using the following chiral SFC conditions: [Column: DAICEL CHIRALPAK OJ-H (250 mm*21 mm, 10 um), Mobile phase: A: CO₂, B: MeOH (0.1% NH₃·H₂O), Gradient: 10% of B, Flow Rate (mL/min) 70] to afford (peak 1) example 42.3, (RR or S,S)-4-(4-(1-(1-(bicyclo[1.1.1]pentan-1-yl)-1H-pyrazol-4-yl)-5-chloro-1H-indazol-6-yl)piperidin-1-yl)tetrahydrofuran-3-ol. MS (ESI) m/z calc'd for $C_{24}H_{29}Cl N_5O_2$ [M+H]⁺ 454 found 454. ¹H NMR (499 MHz, DMSO-d6) δ 8.39 (d, J=0.8 Hz, 1H), 8.24 (d, J=0.9 Hz, 1H), 8.00 (d, J=0.8 Hz, 1H), 7.97 (s, 1H), 7.55 (s, 1H), 4.30 (s, 1H), 4.18 (s, 1H), 3.91-3.83 (m, 2H), 3.69 (d, J=9.5 Hz, 1H), 3.60 (dd, J=10.3, 7.4 Hz, 1H), 3.23-3.18 (m, 1H), 3.08-2.99 (m, 1H), 2.76 (d, J=11.2 Hz, 1H), 2.71-2.63 (m, 1H), 2.67 (s, 1H), 2.32 (s, 6H), 2.27 (m, 1H), 2.21-2.12 (m, 1H), 1.96-1.79 (m, 4H). LRRK2 IC₅₀<0.625 nM The compounds of the invention, surprisingly and advantageously, exhibit good potency as inhibitors of LRRK2 kinase. The IC₅₀ values reported herein were measured as follows.

Biological Assay: LRRK2 Km ATP LanthaScreen™ Assay

The LRRK2 kinase activity reported herein as IC₅₀ values was determined with LanthaScreen™ technology from Life Technologies Corporation (Carlsbad, CA) using GST-tagged truncated human mutant G2019S LRRK2 in the presence of the fluorescein-labeled peptide substrate LRRKtide, also from Life Technologies. The data presented for the Km ATP LanthaScreen™ Assay represents mean IC$_{50}$ values based on several test results and may have reasonable deviations depending on the specific conditions and reagents used. Assays were performed in the presence of 134 μM ATP (Km ATP). Upon completion, the assay was stopped and phosphorylated substrate detected with a terbium (Tb)-labeled anti-pERM antibody (cat. no. PV4898). The compound dose response was prepared by diluting a 10 mM stock of compound to a maximum concentration of 9.99 μM in 100% dimethylsulfoxide followed by custom fold serial dilution in dimethylsulfoxide nine times. Twenty nanoliters of each dilution was spotted via a Labcyte Echo onto a 384-well black-sided plate (Corning 3575) followed by 15 μl of a 1.25 nM enzyme solution in 1× assay buffer (50 mM Tris pH 8.5, 10 mM MgCl2, 0.01% Brij-35, 1 mM EGTA, 2 mM dithiothreitol, 0.05 mM sodium orthovanadate). Following a 15-minute incubation at room temperature, the kinase reaction was started with the addition of 5 μl of 400 nM fluorescein-labeled LRRKtide peptide substrate and 134 μM ATP solution in 1× assay buffer. The reaction was allowed to progress at ambient temperature for 90 minutes. The reaction was then stopped by the addition of 20 μl of TR-FRET Dilution Buffer (Life Technologies, Carlsbad, CA) containing 2 nM Tb-labeled anti-phospho LRRKtide antibody and 10 mM EDTA (Life Technologies, Carlsbad, CA). After an incubation of 1 hour at room temperature, the plate was read on an EnVision multimode plate reader (Perkin Elmer, Waltham, MA) with an excitation wavelength of 337 nm (Laser) and a reading emission at both 520 and 495 nm. Compound IC$_{50}$s were interpolated from nonlinear regression best fits of the log of the final compound concentration, plotted as a function of the 520/495-nm emission ratio using Activity base. Abase uses a 4 parameter (4P) logistic fit based on the Levenberg-Marquardt algorithm.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. A compound having a structural Formula (I):

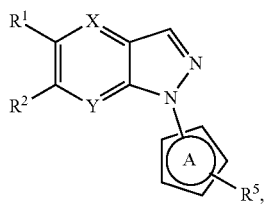

or a pharmaceutically acceptable salt thereof, wherein:
X is selected from N, C—H, C—F, and C—Cl;
Y is selected from N, C—H, C—F, and C—Cl;
R$^1$ is selected from H, F, Cl, CN, —(C$_1$-C$_3$)alkyl, —O(C$_1$-C$_3$)alkyl, —(C$_1$-C$_3$)haloalkyl, —O(C$_1$-C$_3$)haloalkyl, and —(C$_3$-C$_6$)cycloalkyl;
R$^2$ is a moiety selected from:

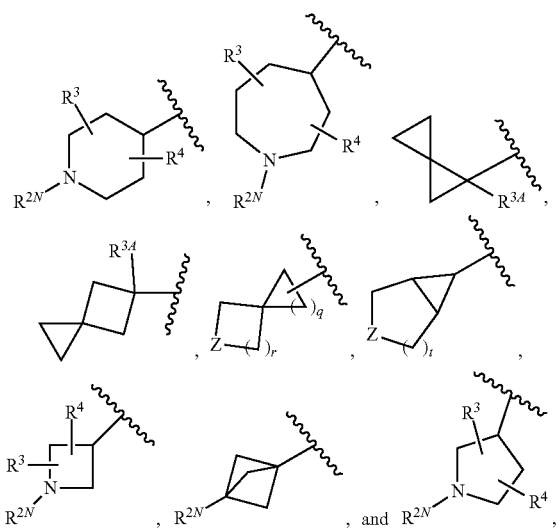

wherein:
q is 1, 2, or 3;
r is 1 or 2;
t is 1 or 2;
Z is selected from O and N(R$^{2N}$);
R$^{2N}$ is selected from H, (C$_1$-C$_6$)alkyl, —(C$_1$-C$_6$)haloalkyl, (C$_1$-C$_6$)alkyl-OH, (C$_1$-C$_6$)alkyl-CN, —S(O)$_2$(C$_1$-C$_6$)alkyl, —(C$_1$-C$_6$)alkyl-S(O)$_2$(C$_1$-C$_6$)alkyl, C(O)O(C$_1$-C$_6$)alkyl, C(O)NH$_2$, C(O)NH(C$_1$-C$_6$)alkyl, —C(O)N((C$_1$-C$_6$)alkyl)$_2$, (C$_1$-C$_6$)alkyl-O—(C$_1$-C$_6$)alkyl, oxetanyl which is optionally substituted with R$^{2A}$, furanyl which is optionally substituted with 1 or 2 groups selected from OH and R$^{2A}$, pyranyl which is optionally substituted with 1 or 2 groups selected from OH and R$^{2A}$, and

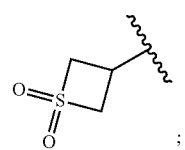 [SMILES: *C1CS(=O)(=O)C1]

each R$^{2A}$ is independently selected from H and —(C$_1$-C$_4$)alkyl;

$R^3$ is selected from H, F, Cl, $(C_1-C_4)$alkyl, $(C_1-C_6)$haloalkyl, and $(C_1-C_6)$alkyl-OH;

$R^{3A}$ is selected from H and CN;

$R^4$ is selected from H, F, Cl, $(C_1-C_4)$alkyl, $(C_1-C_6)$haloalkyl, and $(C_1-C_6)$alkyl-OH;

ring A is 5-membered heteroaryl group comprising 1, 2, or 3 ring heteroatoms selected from N, O, and S;

$R^5$ is selected from H, $(C_1-C_6)$alkyl, $(C_1-C_6)$haloalkyl, $(C_3-C_6)$cycloalkyl, $(C_3-C_6)$cycloalkyl substituted with $(C_1-C_4)$alkyl, $S(O)_2(C_3-C_6)$cycloalkyl, $C(O)N(R^{5A})_2$, $C(O)OR^{5A}$, phenyl, heteroaryl, heterocycloalkyl and

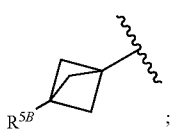

and each $R^{5A}$ is independently selected from H and $-(C_1-C_4)$alkyl; and $R^{5B}$ is selected from H, $(C_1-C_4)$alkyl, $(C_1-C_4)$haloalkyl, $(C_1-C_4)$alkyl-O-$(C_1-C_4)$alkyl, CN, $S(O)_2(C_3-C_6)$cycloalkyl, $C(O)N(R^{5A})_2$, and $C(O)OR^{5A}$.

2. The compound of claim 1, or a pharmaceutically acceptable salt thereof, wherein ring A is selected from pyrazolyl, triazolyl, thiazolyl, oxazolyl, and oxadiazolyl;

$R^5$ is selected from H, $(C_1-C_6)$alkyl, $(C_1-C_6)$haloalkyl, $(C_3-C_6)$cycloalkyl, $(C_3-C_6)$cycloalkyl substituted with $(C_1-C_4)$alkyl, $S(O)_2(C_3-C_6)$cycloalkyl, $C(O)N(R^{5A})_2$, $C(O)OR^{5A}$, phenyl, heteroaryl, heterocycloalkyl, and

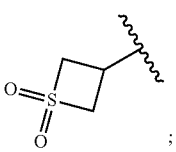

$R^{5A}$ is selected from H and $-(C_1-C_4)$alkyl; and $R^{5B}$ is selected from H, $(C_1-C_4)$alkyl, $(C_1-C_4)$haloalkyl, $(C_1-C_4)$alkyl-O-$(C_1-C_4)$alkyl, CN, $C(O)N(R^{5A})_2$, and $C(O)OR^{5A}$.

3. The compound of claim 1, or a pharmaceutically acceptable salt thereof, wherein $R^2$ is:

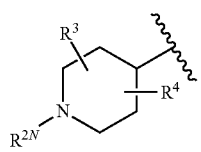

wherein:

$R^{2N}$ is selected from H,

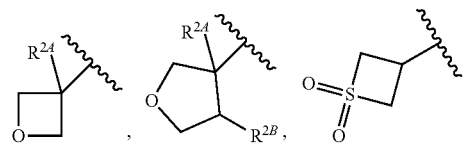

$-(C_1-C_6)$alkyl, $-(C_1-C_6)$haloalkyl, $-(C_1-C_6)$alkyl-OH, $-(C_1-C_6)$alkyl-CN, $-S(O)_2(C_1-C_6)$alkyl, $-(C_1-C_6)$alkyl-$S(O)_2(C_1-C_6)$alkyl, $-C(O)NH_2$, $-C(O)NH(C_1-C_6)$alkyl, $-C(O)N((C_1-C_6)$alkyl$)_2$, and $-(C_1-C_6)$alkyl-O-$(C_1-C_6)$alkyl;

$R^{2A}$ is selected from H and $-(C_1-C_4)$alkyl;

$R^{2B}$ is selected from H and OH;

$R^3$ is selected from H, F, Cl, $(C_1-C_4)$alkyl, $(C_1-C_6)$haloalkyl, and $(C_1-C_6)$alkyl-OH; and $R^4$ is selected from H, F, Cl, $-(C_1-C_4)$alkyl, $-(C_1-C_6)$haloalkyl, and $-(C_1-C_6)$alkyl-OH.

4. The compound according to claim 1, or a pharmaceutically acceptable salt thereof, wherein:

$R^2$ is a moiety selected from:

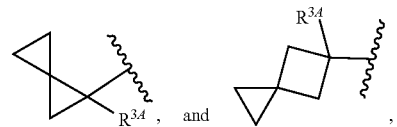

wherein $R^{3A}$ is selected from H and CN.

5. The compound according to claim 1, or a pharmaceutically acceptable salt thereof, wherein:

$R^2$ is:

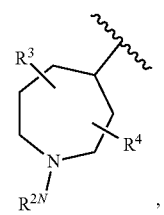

wherein:

$R^{2N}$ is selected from

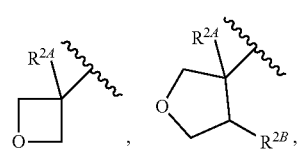

H, $-(C_1-C_6)$alkyl, $-(C_1-C_6)$haloalkyl, $-(C_1-C_6)$alkyl-OH, $-(C_1-C_6)$alkyl-CN, $-S(O)_2(C_1-C_6)$alkyl, $-(C_1-C_6)$alkyl-$S(O)_2(C_1-C_6)$alkyl, $-C(O)NH_2$, $-C(O)NH(C_1-C_6)$alkyl, $-C(O)N((C_1-C_6)$alkyl$)_2$, and $-(C_1-C_6)$alkyl-O-$(C_1-C_6)$alkyl;

$R^{2A}$ is selected from H and $-(C_1-C_4)$alkyl;

$R^{2B}$ is selected from H and OH;

$R^3$ is selected from H, F, Cl, $(C_1-C_4)$alkyl, $(C_1-C_6)$haloalkyl, and $(C_1-C_6)$alkyl-OH; and $R^4$ is selected from H, F, Cl, $-(C_1-C_4)$alkyl, $-(C_1-C_6)$haloalkyl, and $-(C_1-C_6)$alkyl-OH.

6. The compound according to claim 1, or a pharmaceutically acceptable salt thereof, wherein $R^2$ is a moiety selected from:

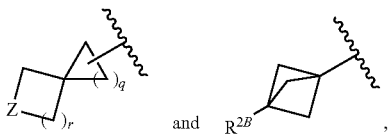

wherein:
q is 1, 2, or 3;
r is 1 or 2;
Z is O or $NR^{2N}$;
$R^{2N}$ is selected from

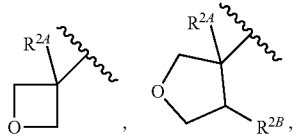

H, $-(C_1-C_6)$alkyl, $-(C_1-C_6)$haloalkyl, $-(C_1-C_6)$alkyl-OH, $-(C_1-C_6)$alkyl-CN, $-S(O)_2(C_1-C_6)$alkyl, $-(C_1-C_6)$alkyl-$S(O)_2(C_1-C_6)$alkyl, $C(O)O(C_1-C_6)$alkyl, $C(O)NH_2$, $-C(O)NH(C_1-C_6)$alkyl, $-C(O)N((C_1-C_6)$alkyl$)_2$, and $-(C_1-C_6)$alkyl-O$-(C_1-C_6)$alkyl;
$R^{2A}$ is selected from H and $-(C_1-C_4)$alkyl; and
$R^{2B}$ is selected from H and OH.

7. The compound according to claim 1, or a pharmaceutically acceptable salt thereof, wherein:
$R^2$ is a moiety selected from:

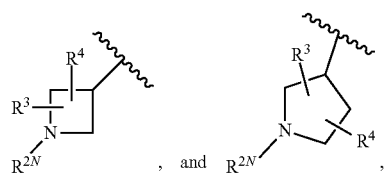

wherein:
$R^{2N}$ is selected from

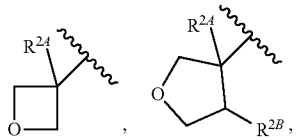

H, $-(C_1-C_6)$alkyl, $-(C_1-C_6)$haloalkyl, $-(C_1-C_6)$alkyl-CN, $-S(O)_2(C_1-C_6)$alkyl, $-(C_1-C_6)$alkyl-$S(O)_2(C_1-C_6)$alkyl, $-C(O)NH_2$, $-C(O)NH(C_1-C_6)$alkyl, $-C(O)N((C_1-C_6)$alkyl$)_2$, and $-(C_1-C_6)$alkyl-O$-(C_1-C_6)$alkyl;
$R^{2A}$ is selected from H and $-(C_1-C_4)$alkyl;
$R^{2B}$ is selected from H and OH;
$R^3$ is selected from H, F, Cl, $(C_1-C_4)$alkyl, $(C_1-C_6)$haloalkyl, and $(C_1-C_6)$alkyl-OH; and
$R^4$ is selected from H, F, Cl, $(C_1-C_4)$alkyl, $(C_1-C_6)$haloalkyl, and $(C_1-C_6)$alkyl-OH;

In an alternative of each of the preceding embodiments, in Formula (I):
$R^2$ is a moiety selected from:

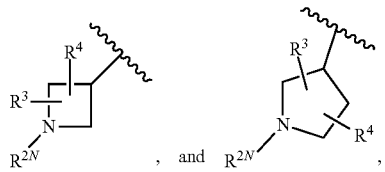

wherein:
$R^{2N}$ is selected from

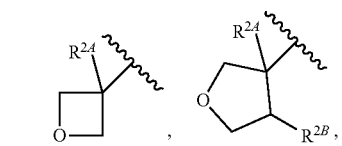

H, $-(C_1-C_6)$alkyl, $-(C_1-C_6)$haloalkyl, $-(C_1-C_6)$alkyl-CN, $-S(O)_2(C_1-C_6)$alkyl, $-(C_1-C_6)$alkyl-$S(O)_2$ $(C_1-C_6)$alkyl, $-C(O)NH_2$, $-C(O)NH(C_1-C_6)$alkyl, $-C(O)N((C_1-C_6)$alkyl$)_2$, and $-(C_1-C_6)$alkyl-O$-(C_1-C_6)$alkyl;
$R^{2A}$ is selected from H and $-(C_1-C_4)$alkyl;
$R^{2B}$ is selected from H and OH;
$R^3$ is selected from H, F, Cl, $(C_1-C_4)$alkyl, $(C_1-C_6)$haloalkyl, and $(C_1-C_6)$alkyl-OH; and
$R^4$ is selected from H, F, Cl, $(C_1-C_4)$alkyl, $(C_1-C_6)$haloalkyl, and $(C_1-C_6)$alkyl-OH.

8. The compound according to claim 1, or a pharmaceutically acceptable salt thereof, wherein:
$R^2$ is:

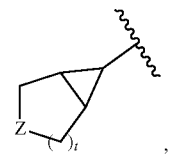

wherein:
t is 1 or 2;
Z is selected from O and $NR^{2N}$.

9. The compound according to claim 1, or a pharmaceutically acceptable salt thereof, wherein:
X is C—H;
Y is C—H; and
$R^1$ is selected from H, Cl, —$CH_3$, and CN.

10. The compound according to claim 1, or a pharmaceutically acceptable salt thereof, wherein:
X is N;
Y is selected from C—H, C—F, and C—Cl; and
$R^1$ is selected from H, Cl, —$CH_3$, and CN.

11. The compound according to claim 1, or a pharmaceutically acceptable salt thereof, wherein:
X is N;
Y is C—F; and
is selected from H, Cl, —$CH_3$, and CN.

12. The compound of claim 1, or a pharmaceutically acceptable salt thereof, wherein said compound is selected from:

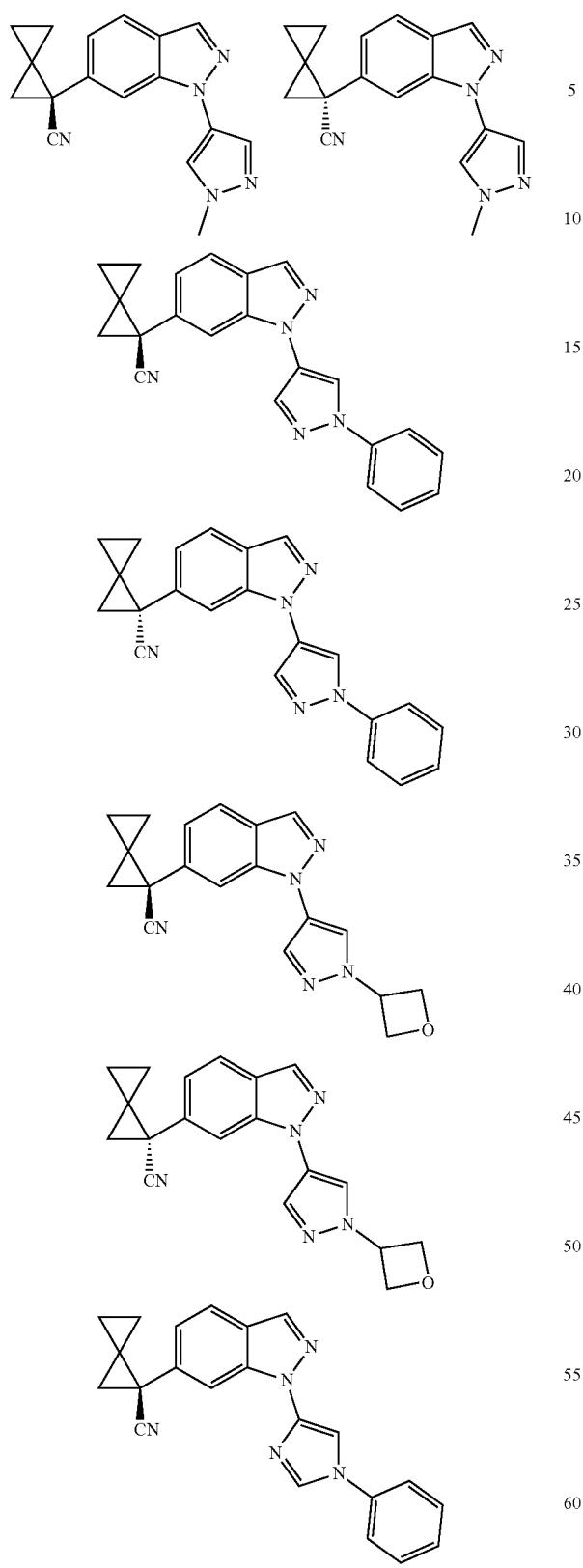
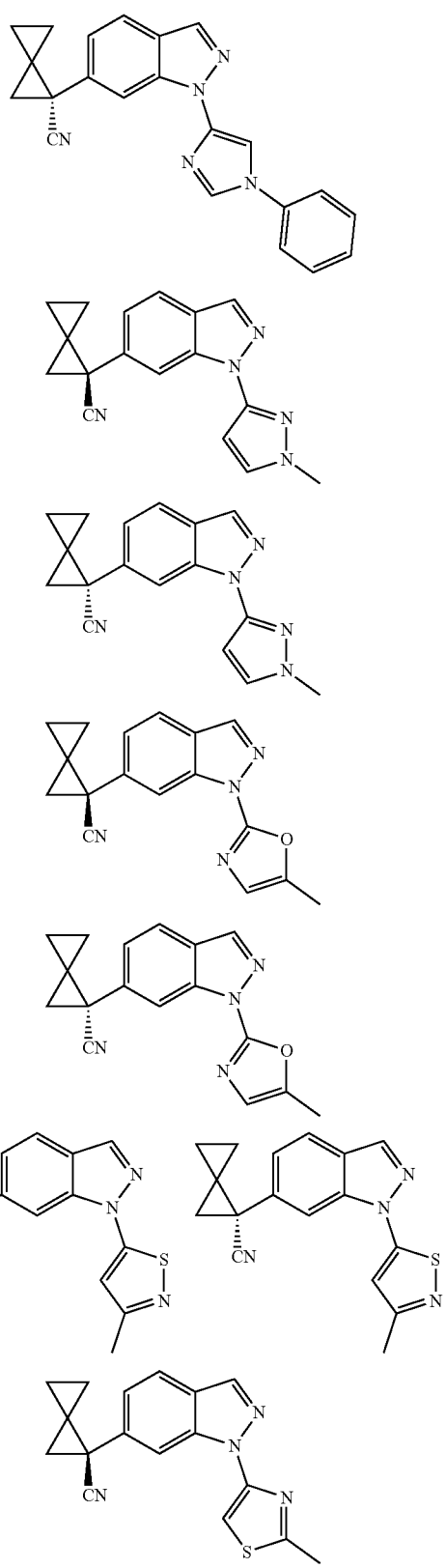

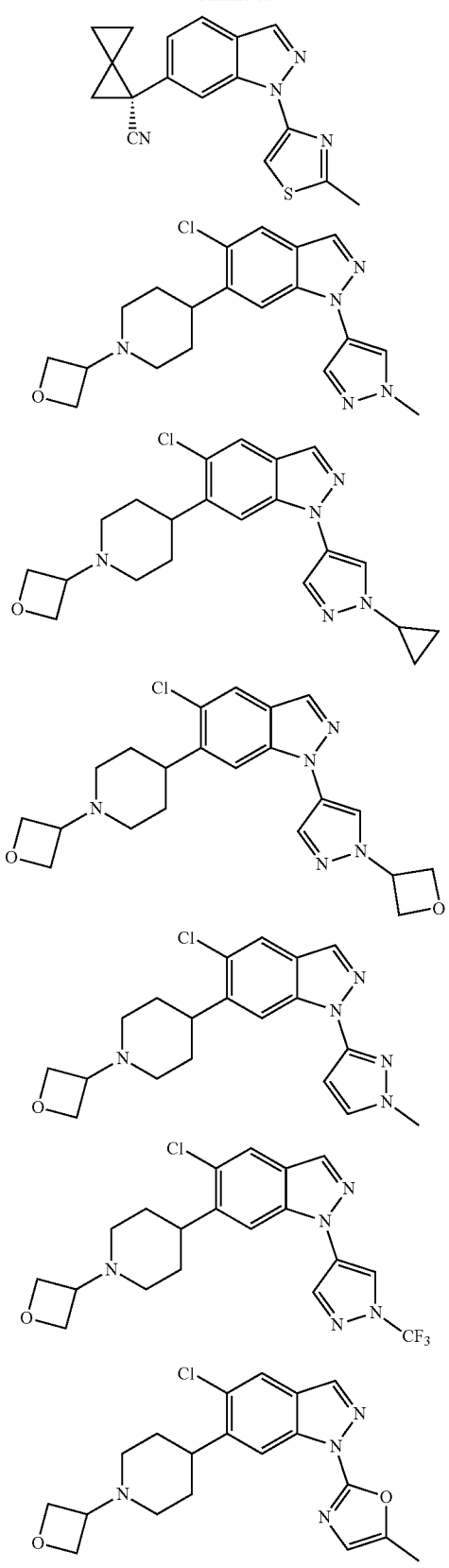
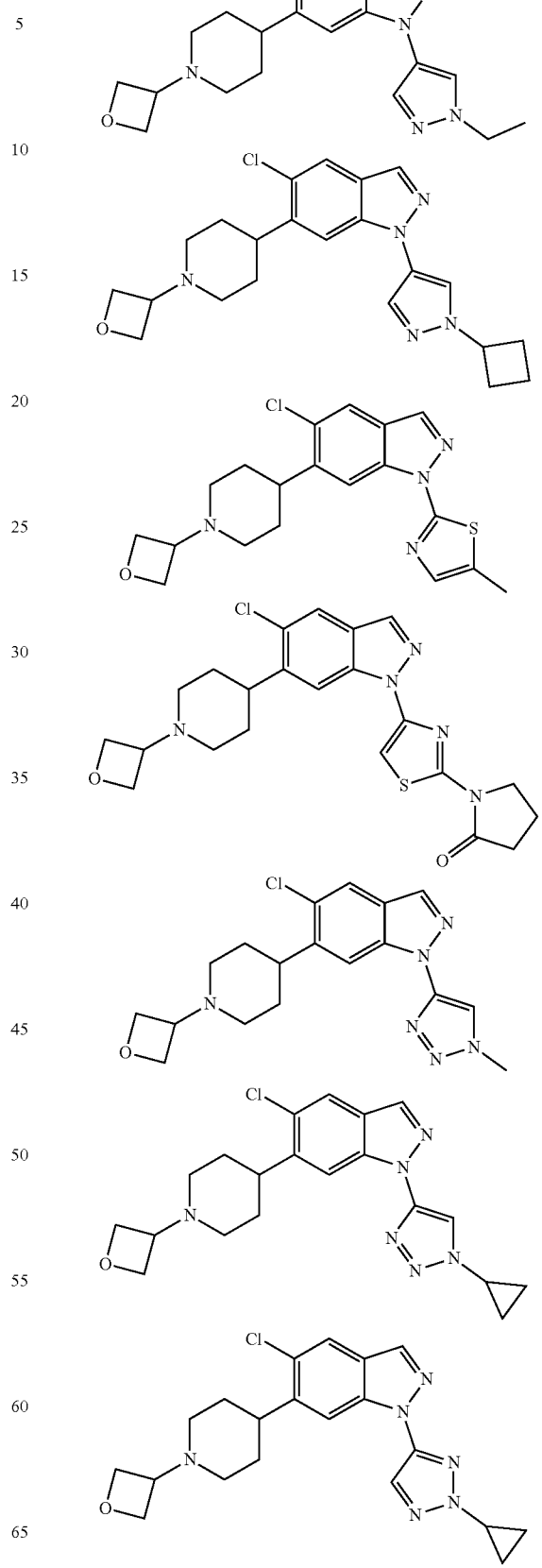

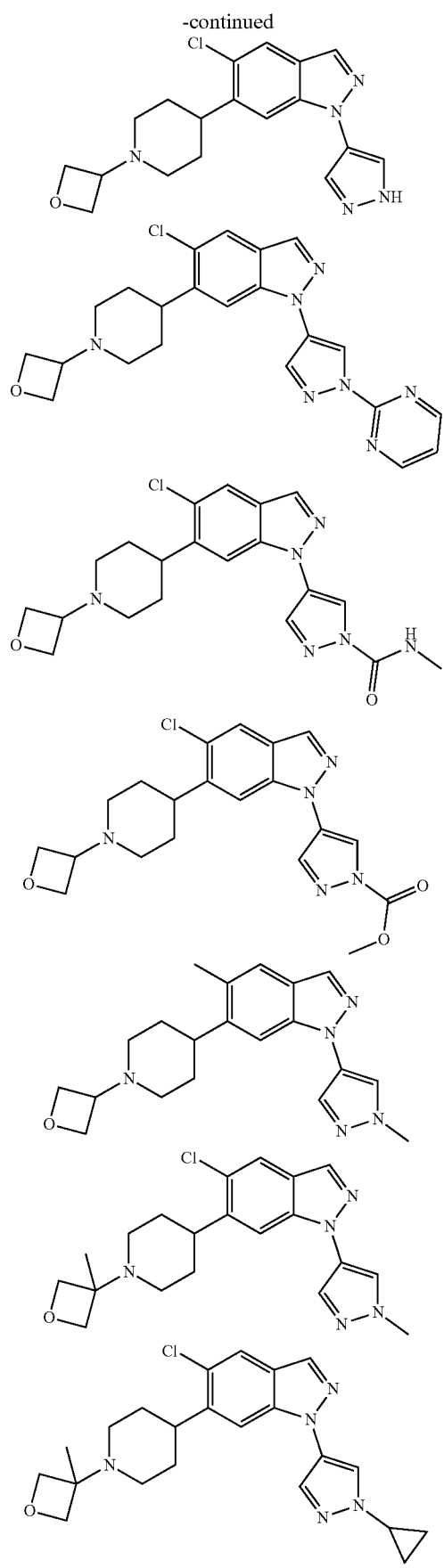

171
-continued
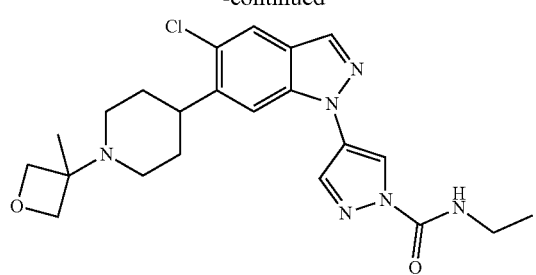
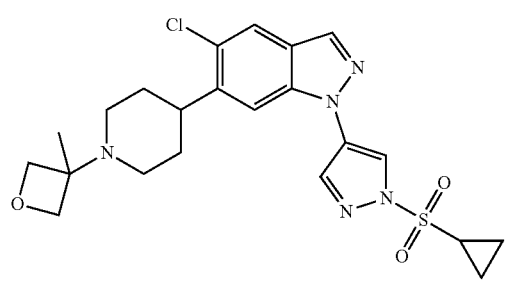
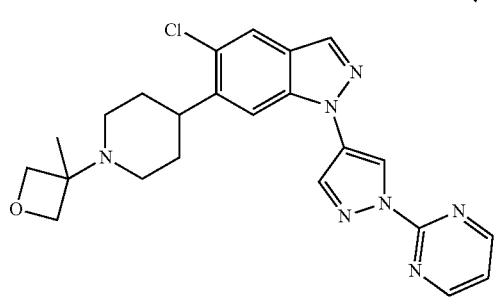
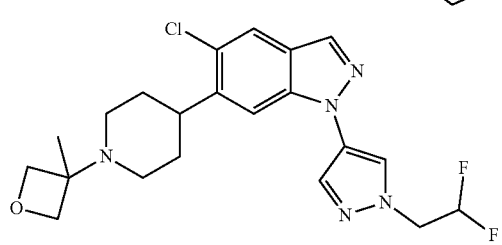
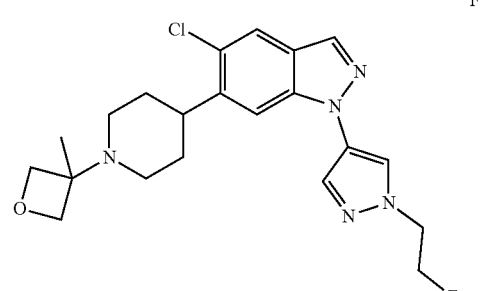
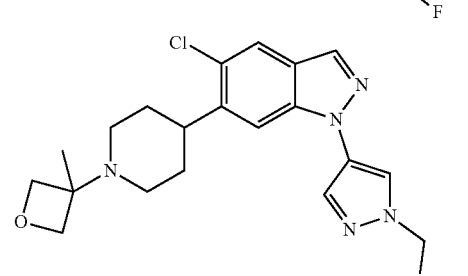
172
-continued
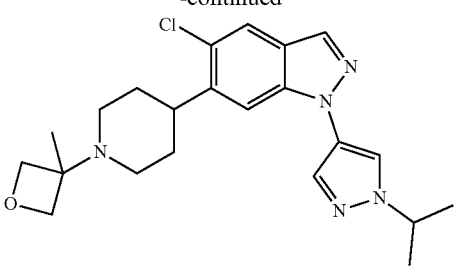
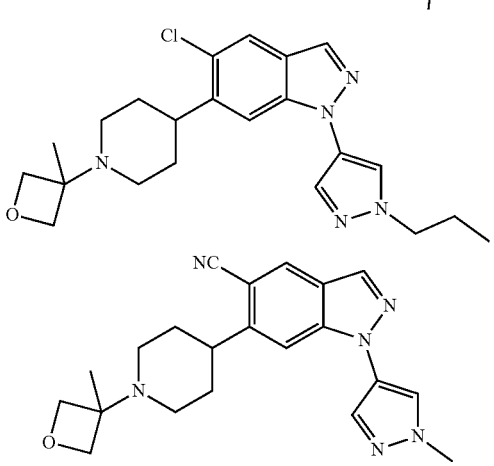
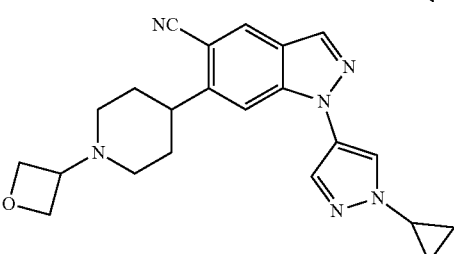
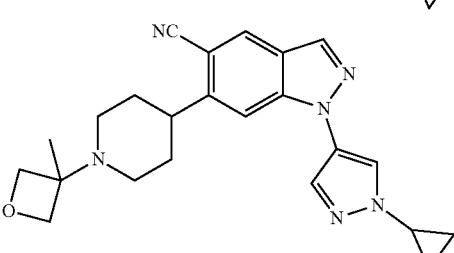
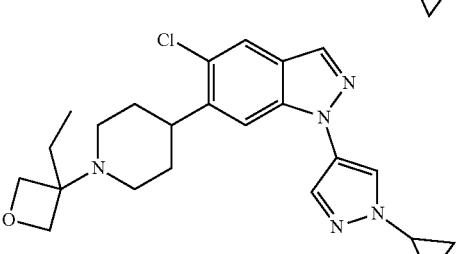
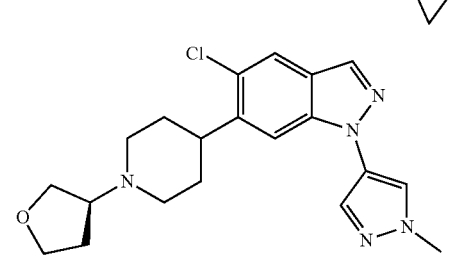

173
-continued
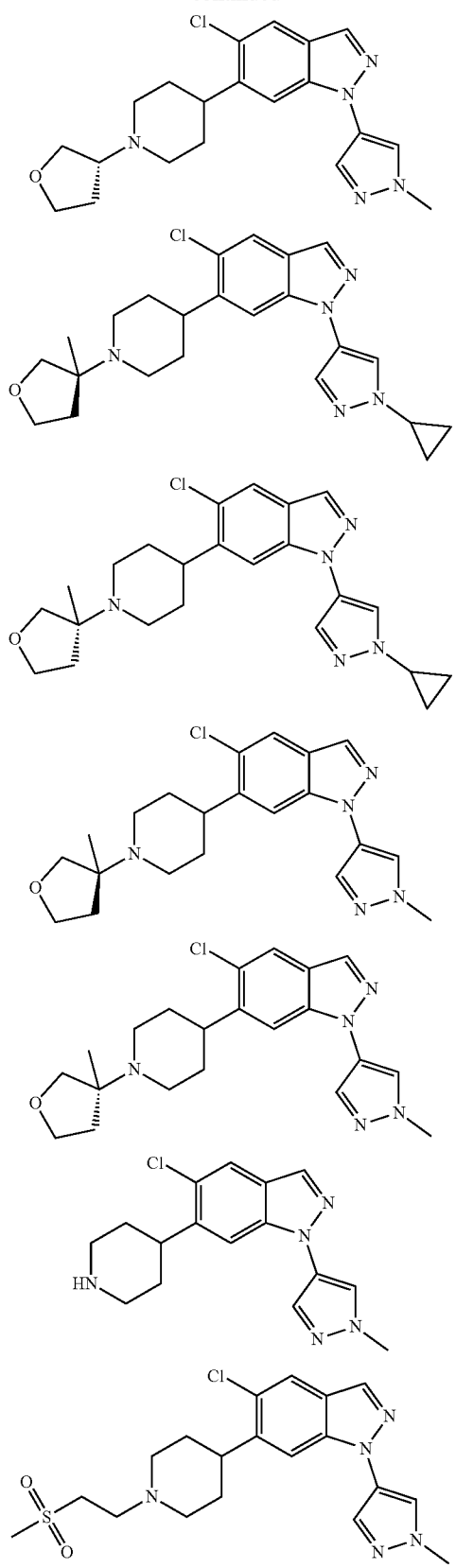
174
-continued
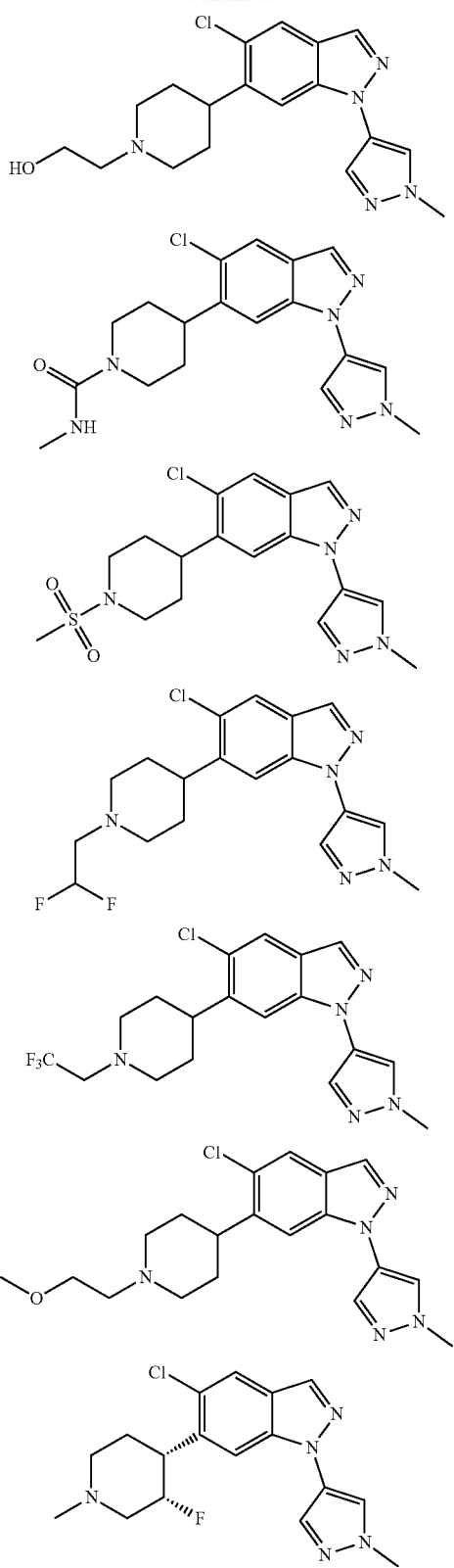

-continued
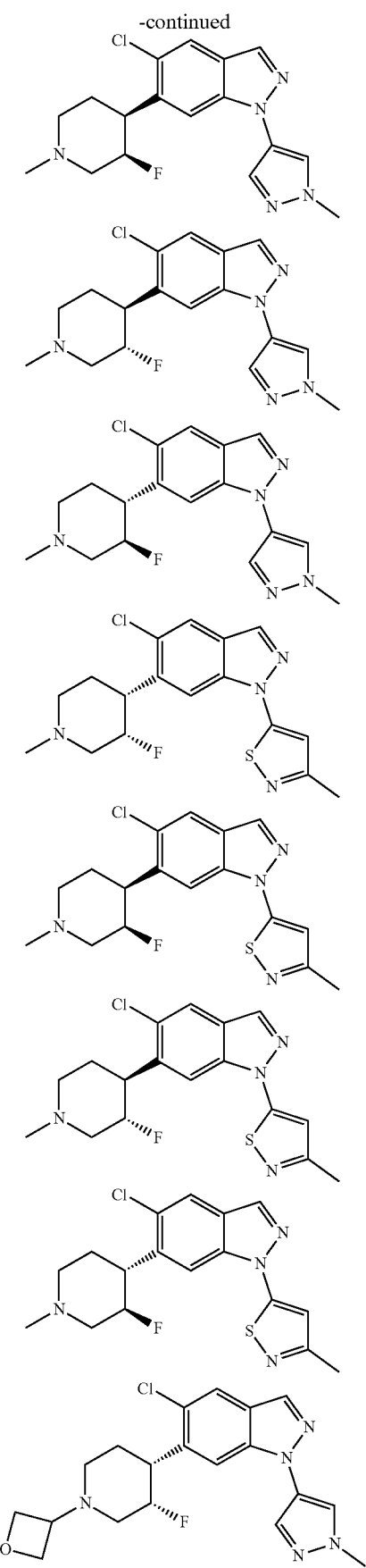
-continued
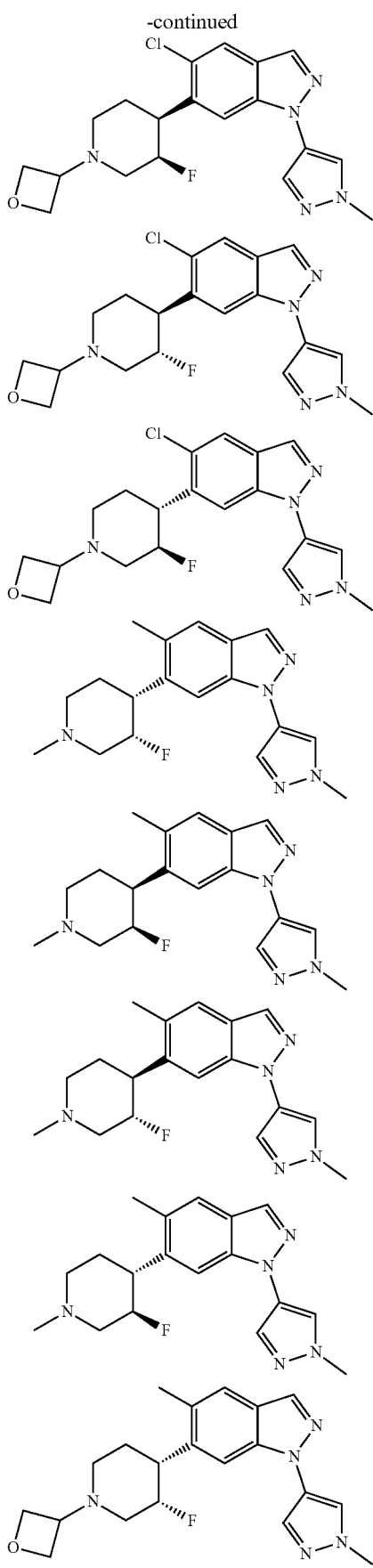

177
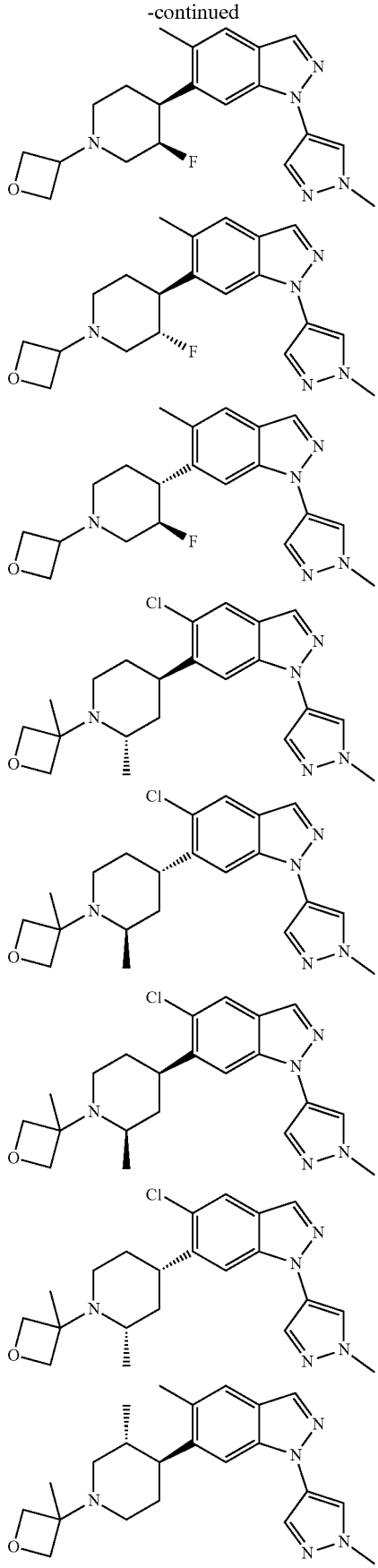
178
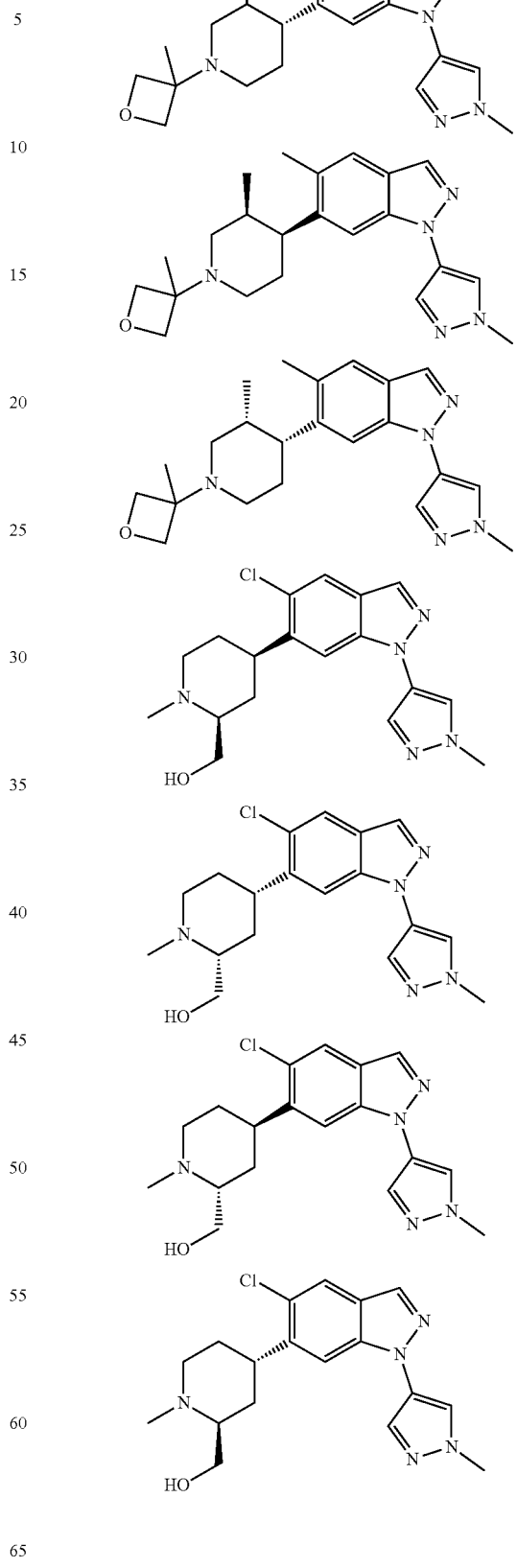

-continued
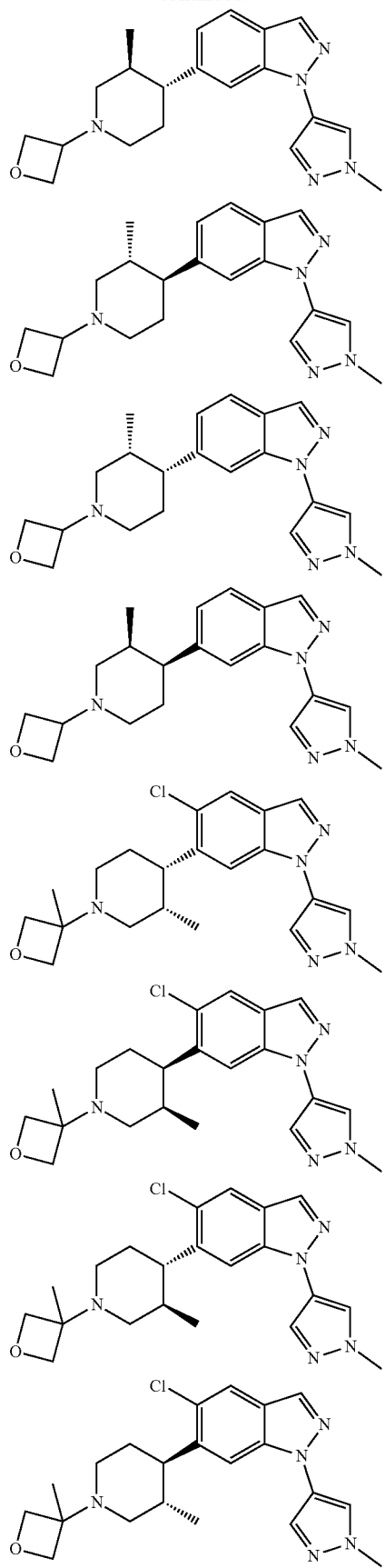
-continued
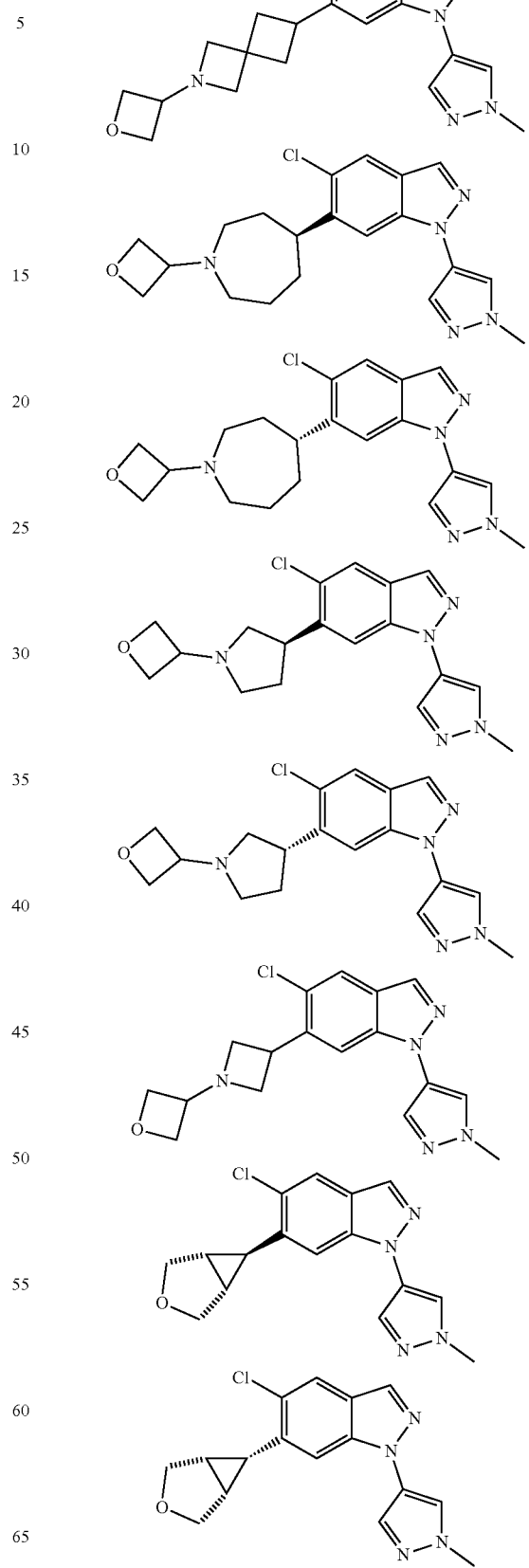

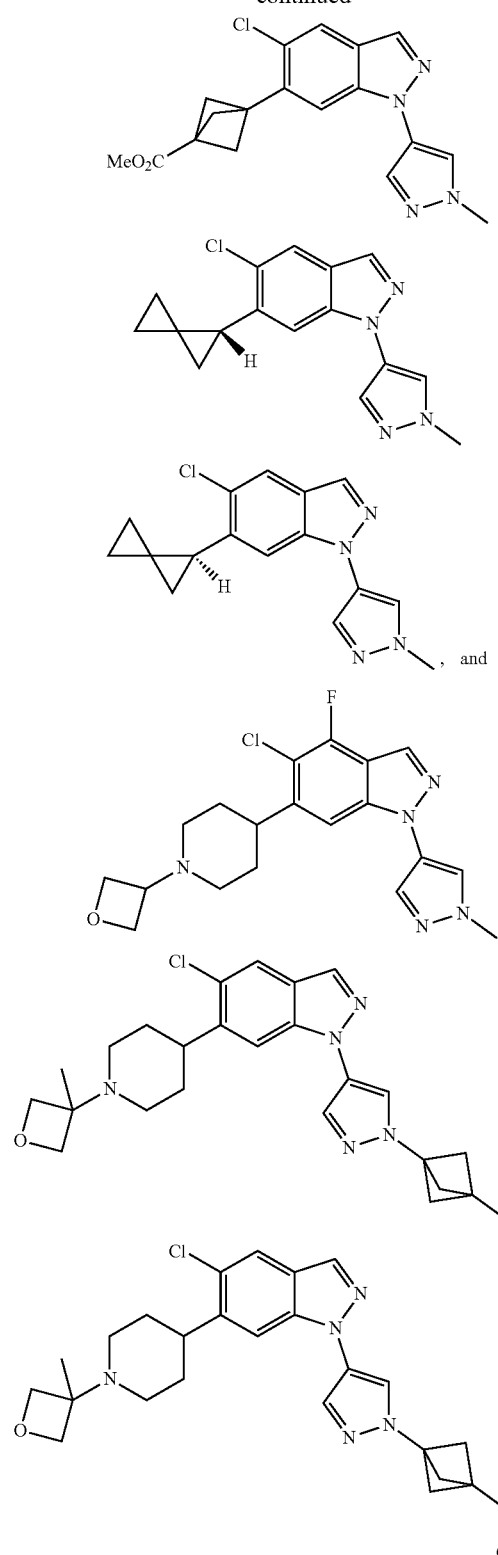
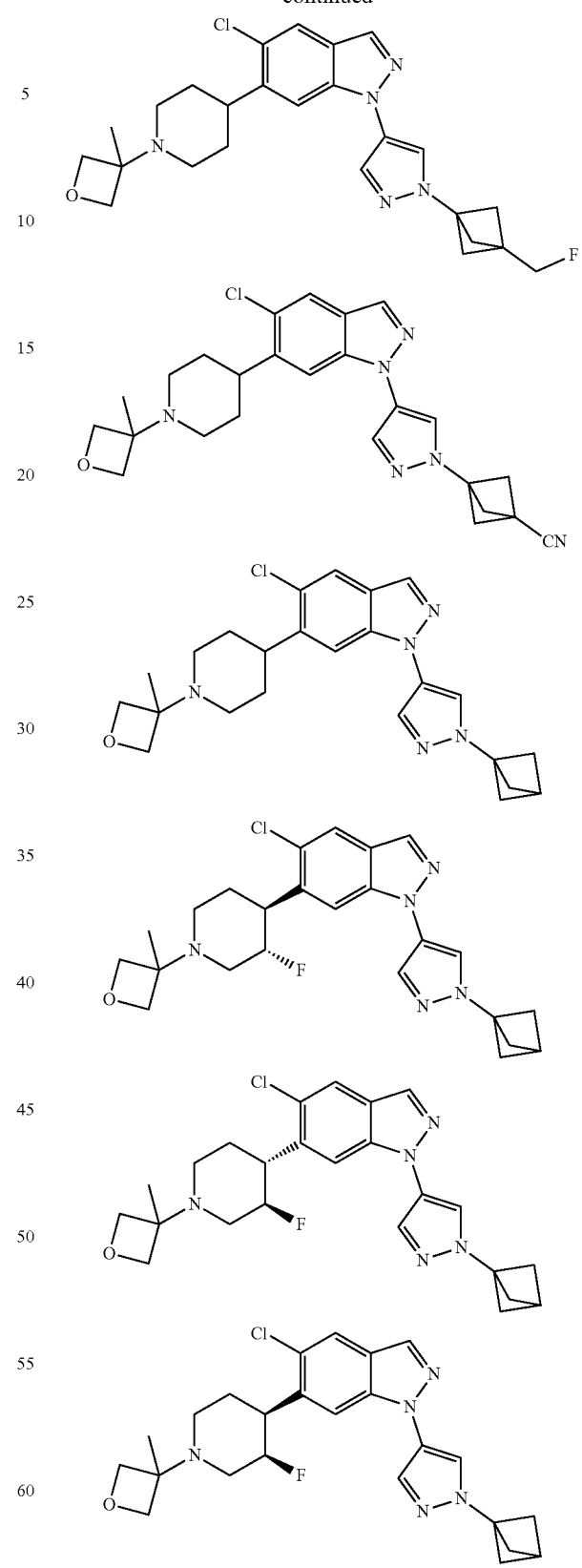

183
-continued
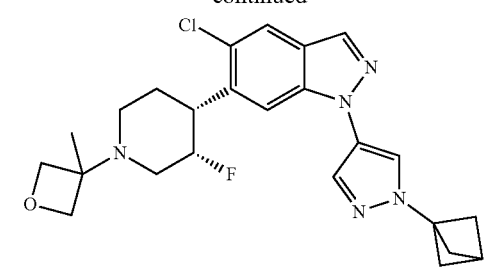
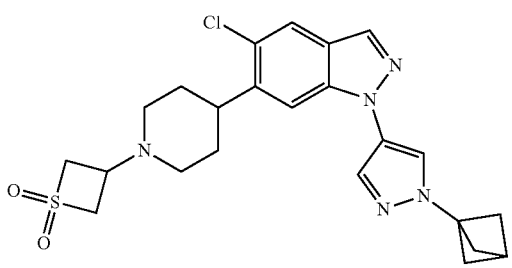
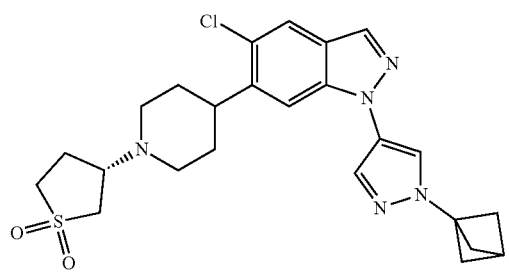
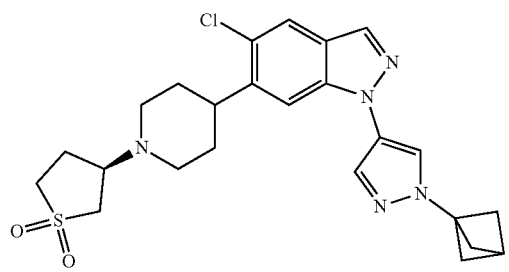
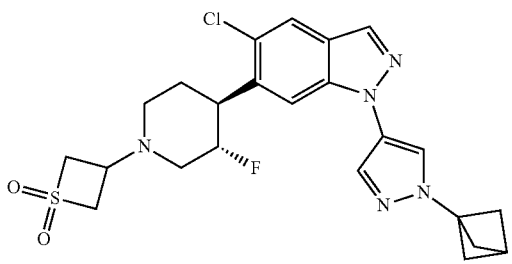
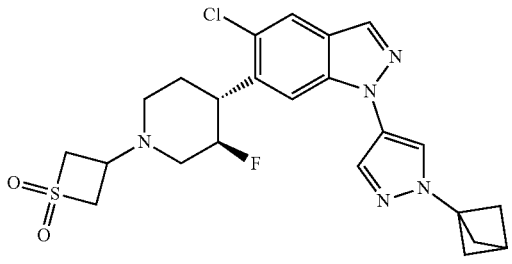
184
-continued
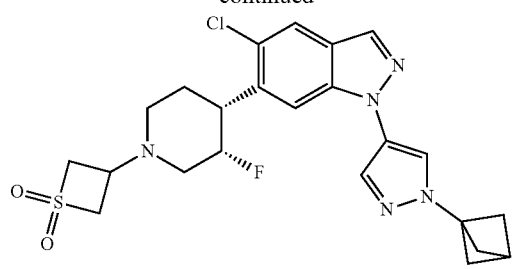
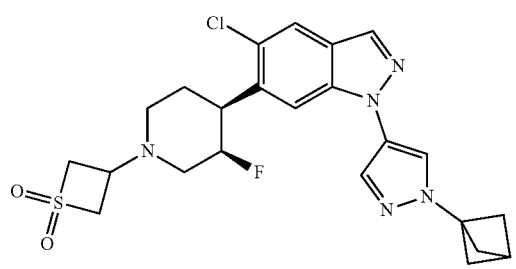
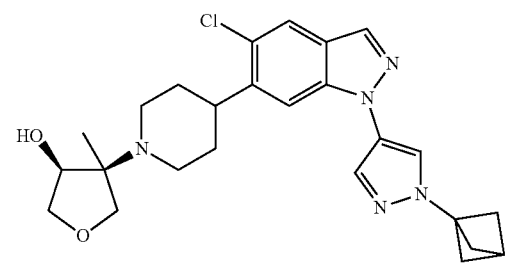
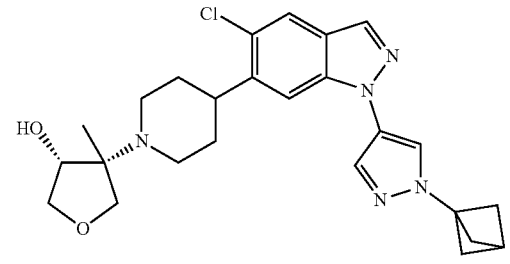
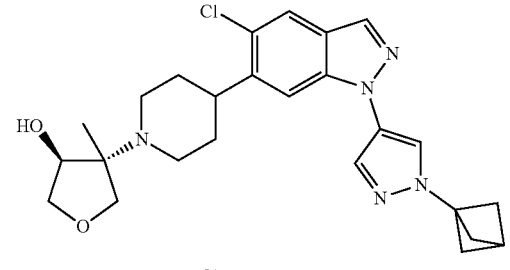
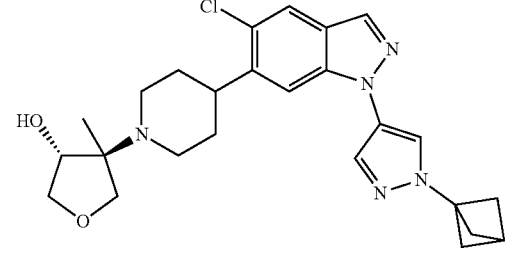

-continued

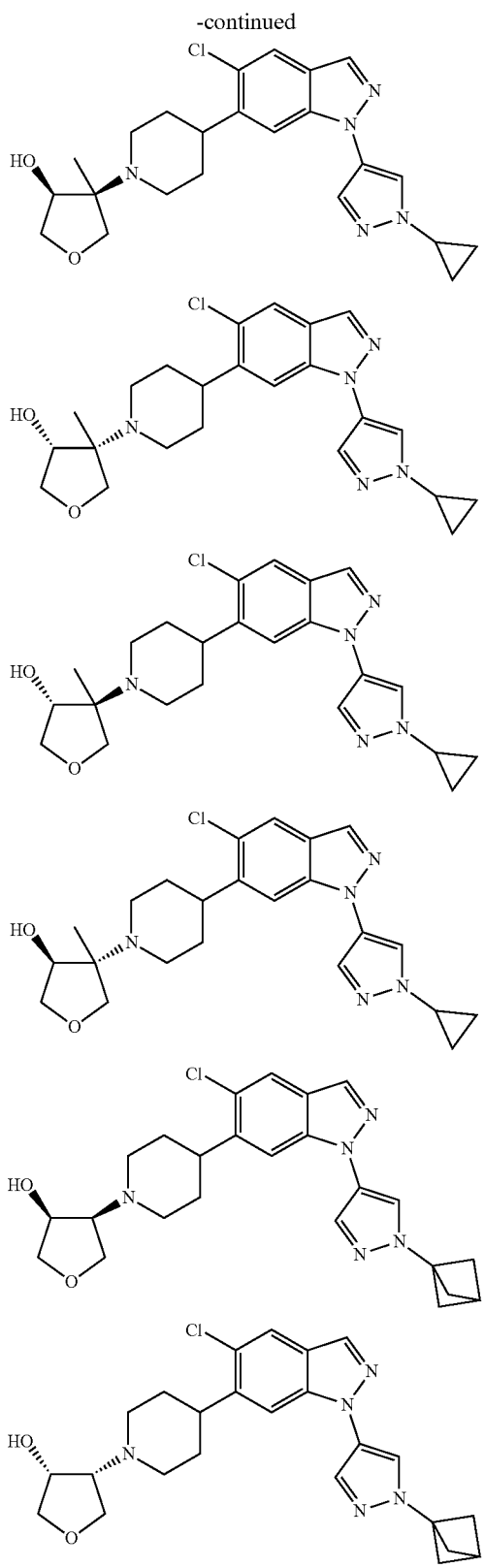

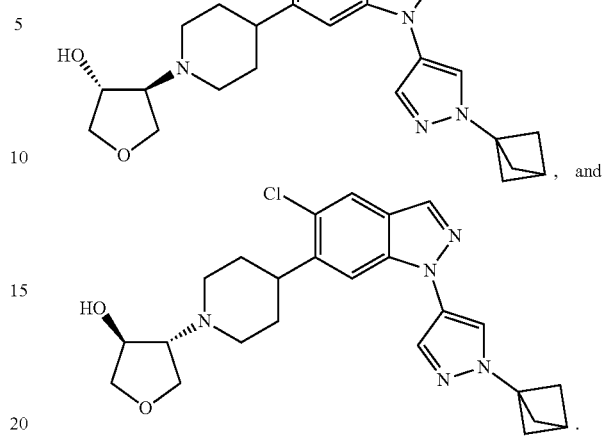

13. A pharmaceutical composition comprising a compound of claim 1, or a pharmaceutically acceptable salt thereof, and a pharmaceutically acceptable carrier.

14. A method of treating Parkinson's Disease comprising administering an effective amount of a compound of claim 1, or a pharmaceutically acceptable salt thereof, to a person in need thereof.

15. A method for the treatment or prophylaxis of an indication in which LRRK2 kinase is involved comprising administering to a subject in need thereof an effective amount of a compound according to claim 1, or a pharmaceutically acceptable salt thereof, said indication selected from:
  abnormal motor symptoms associated with Parkinson's disease, non-motor symptoms associated with Parkinson's disease, Lewy body dementia, L-Dopa induced dyskinesias,
  Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17,
  neuroinflammation associated with of microglial inflammatory responses associated with multiple sclerosis, HIV-induced dementia, ALS, ischemic stroke, traumatic brain injury and spinal cord injury,
  lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis,
  renal cancer, breast cancer, lung cancer, prostate cancer, and acute myelogenous leukemia (AML) in subjects expressing the LRRK2 G2019S mutation,
  papillary renal and thyroid carcinomas in a subject in whom LRRK2 is amplified or overexpressed, Crohn's disease and leprosy.

* * * * *